(12) United States Patent
Jiang et al.

(10) Patent No.: US 11,286,528 B2
(45) Date of Patent: Mar. 29, 2022

(54) METHODS OF REDUCING IMMUNOGENICITY AGAINST FACTOR VIII IN INDIVIDUALS UNDERGOING FACTOR VIII THERAPY

(71) Applicants: Bioverativ Therapeutics Inc., Waltham, MA (US); Puget Sound Blood Center, Seattle, WA (US)

(72) Inventors: Haiyan Jiang, Belmont, MA (US); Tongyao Liu, Lexington, MA (US); Sriram Krishnamoorthy, Medford, MA (US); Neil Josephson, Seattle, WA (US); Glenn Pierce, Cambridge, MA (US)

(73) Assignees: BIOVERATIV THERAPEUTICS INC., Waltham, MA (US); PUGET SOUND BLOOD CENTER, Seattle, WA (US)

( * ) Notice: Subject to any disclaimer, the term of this patent is extended or adjusted under 35 U.S.C. 154(b) by 0 days.

(21) Appl. No.: 16/246,225

(22) Filed: Jan. 11, 2019

(65) Prior Publication Data
US 2019/0241960 A1 Aug. 8, 2019

Related U.S. Application Data

(63) Continuation of application No. 14/371,931, filed as application No. PCT/US2013/021332 on Jan. 12, 2013, now Pat. No. 10,221,455.

(60) Provisional application No. 61/668,961, filed on Jul. 6, 2012, provisional application No. 61/586,103, filed on Jan. 12, 2012.

(51) Int. Cl.
| | |
|---|---|
| *C07K 14/755* | (2006.01) |
| *C12Q 1/6883* | (2018.01) |
| *A61K 38/21* | (2006.01) |
| *A61K 39/00* | (2006.01) |
| *A61K 38/37* | (2006.01) |
| *A61K 47/68* | (2017.01) |

(52) U.S. Cl.
CPC ............ *C12Q 1/6883* (2013.01); *A61K 38/21* (2013.01); *A61K 38/37* (2013.01); *A61K 39/0008* (2013.01); *A61K 47/6811* (2017.08); *A61K 47/6815* (2017.08); *C07K 14/755* (2013.01); *A61K 2039/6031* (2013.01); *A61K 2039/6056* (2013.01); *C07K 2319/30* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,695,199 A | 9/1987 | Goodacre et al. | |
| 4,757,006 A | 7/1988 | Toole et al. | |
| 4,868,112 A | 9/1989 | Toole et al. | |
| 4,994,371 A | 2/1991 | Davie et al. | |
| 5,004,803 A | 4/1991 | Kaufman et al. | |
| 5,112,950 A | 5/1992 | Meulien et al. | |
| 5,171,844 A | 12/1992 | Van et al. | |
| 5,364,771 A | 11/1994 | Lollar et al. | |
| 5,543,502 A | 8/1996 | Nordfang et al. | |
| 5,595,886 A | 1/1997 | Chapman et al. | |
| 5,610,278 A | 3/1997 | Nordfang et al. | |
| 5,789,203 A | 8/1998 | Chapman et al. | |
| 5,859,204 A | 1/1999 | Lollar et al. | |
| 5,972,885 A | 10/1999 | Spira et al. | |
| 6,048,720 A | 4/2000 | Dalborg et al. | |
| 6,060,447 A | 5/2000 | Chapman et al. | |
| 6,228,620 B1 | 5/2001 | Chapman et al. | |
| 6,251,632 B1 | 6/2001 | Lillicrap et al. | |
| 6,316,226 B1 | 11/2001 | Van et al. | |
| 6,346,513 B1 | 2/2002 | Van et al. | |
| 6,376,463 B1 | 4/2002 | Lollar et al. | |
| 6,458,563 B1 | 10/2002 | Lollar et al. | |
| 7,041,635 B2 | 5/2006 | Kim et al. | |
| 7,348,004 B2 * | 3/2008 | Peters ................. | C07K 14/745 424/178.1 |
| 7,381,408 B2 | 6/2008 | Mezo et al. | |
| 7,404,956 B2 | 7/2008 | Peters et al. | |
| 7,820,162 B2 | 10/2010 | Mezo et al. | |
| 7,862,820 B2 | 1/2011 | Peters et al. | |

(Continued)

FOREIGN PATENT DOCUMENTS

| | | |
|---|---|---|
| CA | 2863329 A1 | 7/2013 |
| EP | 0295597 A2 | 12/1988 |

(Continued)

OTHER PUBLICATIONS

Astermark, J. Haemophilia. Dec. 2006; 12 Suppl 6:8-13; discussion 13-4.*

(Continued)

*Primary Examiner* — Michael Szperka
(74) *Attorney, Agent, or Firm* — Lathrop GPM LLP; James H. Velema, Esq.

(57) ABSTRACT

The present disclosure provides methods of administering chimeric and hybrid Factor VIII (FVIII) polypeptides comprising FVIII and Fc to subjects at risk of developing inhibitory FVIII immune responses, including anti-FVIII antibodies and/or cell-mediated immunity. The administration is sufficient to promote coagulation and to induce immune tolerance to FVIII. The chimeric polypeptide can comprise full-length FVIII or a FVIII polypeptide containing a deletion, e.g., a full or partial deletion of the B domain.

14 Claims, 50 Drawing Sheets

Specification includes a Sequence Listing.

(56) References Cited

U.S. PATENT DOCUMENTS

| | | |
|---|---|---|
| 8,329,182 B2 | 12/2012 | Peters et al. |
| 8,759,293 B2 | 6/2014 | Barnett |
| 8,815,250 B2 * | 8/2014 | Rivera .................. C12N 9/644 |
| | | 424/192.1 |
| 8,932,830 B2 | 1/2015 | Peters et al. |
| 9,050,318 B2 * | 6/2015 | Dumont ................. C07K 16/46 |
| 9,233,145 B2 | 1/2016 | Pierce et al. |
| 9,241,978 B2 * | 1/2016 | Dumont ................. A61K 38/37 |
| 9,266,145 B2 * | 2/2016 | Maurer ................. A61L 31/022 |
| 9,623,091 B2 * | 4/2017 | Pierce ................... A61K 38/38 |
| 9,629,903 B2 * | 4/2017 | Pierce ...................... A61P 7/04 |
| 9,636,416 B2 | 5/2017 | Peters et al. |
| 9,670,475 B2 * | 6/2017 | Pierce ................ A61K 39/3955 |
| 9,675,676 B2 * | 6/2017 | Pierce ................... C07K 16/18 |
| 9,867,873 B2 * | 1/2018 | Pierce .............. A61K 39/39533 |
| 10,221,455 B2 * | 3/2019 | Jiang ......................... A61P 7/04 |
| 10,391,152 B2 * | 8/2019 | Jiang ................. A61K 38/4846 |
| 2002/0038002 A1 * | 3/2002 | Zaghouani ......... C07K 14/4713 |
| | | 530/388.22 |
| 2003/0211113 A1 | 11/2003 | Kakkis et al. |
| 2004/0096456 A1 * | 5/2004 | Conti-Fine ........... C07K 14/755 |
| | | 424/185.1 |
| 2004/0110929 A1 | 6/2004 | Bjorn et al. |
| 2005/0100990 A1 | 5/2005 | Saenko et al. |
| 2005/0147618 A1 | 7/2005 | Rivera et al. |
| 2005/0260194 A1 | 11/2005 | Peters et al. |
| 2009/0163699 A1 | 6/2009 | Chamberlain et al. |
| 2009/0264627 A1 | 10/2009 | Gillies et al. |
| 2011/0159540 A1 | 6/2011 | Mezo et al. |
| 2011/0182896 A1 | 7/2011 | Rivera et al. |
| 2011/0268737 A1 | 11/2011 | Favier et al. |
| 2012/0142593 A1 | 6/2012 | Zhao et al. |
| 2013/0108629 A1 | 5/2013 | Dumont et al. |
| 2013/0171175 A1 | 7/2013 | Pierce et al. |
| 2013/0202595 A1 | 8/2013 | Pierce et al. |
| 2013/0274194 A1 | 10/2013 | Dumont et al. |
| 2014/0370035 A1 | 12/2014 | Jiang et al. |
| 2015/0252345 A1 | 9/2015 | Pierce et al. |
| 2015/0266944 A1 | 9/2015 | Jiang et al. |
| 2016/0199455 A1 | 7/2016 | Dumont et al. |
| 2016/0257943 A1 | 9/2016 | Pierce et al. |
| 2016/0346365 A1 | 12/2016 | Pierce et al. |
| 2019/0241960 A1 | 8/2019 | Jiang et al. |

FOREIGN PATENT DOCUMENTS

| | | |
|---|---|---|
| EP | 2184070 A1 | 5/2010 |
| EP | 2802668 A1 | 11/2014 |
| EP | 3453402 A1 | 3/2019 |
| JP | 2005-530762 A | 10/2005 |
| JP | 2007-500744 A | 1/2007 |
| JP | 2011-505414 A | 2/2011 |
| JP | 2011-523663 A | 8/2011 |
| JP | 2012-507994 A | 4/2012 |
| JP | 2012-522490 A | 9/2012 |
| JP | 2013-510581 A | 3/2013 |
| JP | 2013-512678 A | 4/2013 |
| JP | 2017-149784 A | 8/2017 |
| WO | WO 8704187 A1 | 7/1987 |
| WO | WO 8800831 A1 | 2/1988 |
| WO | WO 8803558 A1 | 5/1988 |
| WO | WO 8808035 A1 | 10/1988 |
| WO | WO 9109122 A1 | 6/1991 |
| WO | WO 9320093 A1 | 10/1993 |
| WO | WO 9411503 A2 | 5/1994 |
| WO | WO 2004101739 A2 | 11/2004 |
| WO | WO 2004101740 A2 | 11/2004 |
| WO | WO 2005001025 A2 | 1/2005 |
| WO | WO 2006074199 A1 | 7/2006 |
| WO | WO 200914930 A1 | 1/2009 |
| WO | WO 2009/071886 A1 | 6/2009 |
| WO | WO 2009149303 A1 | 12/2009 |
| WO | WO 2010/006635 A1 | 1/2010 |
| WO | WO-2010006623 A2 * | 1/2010 ....... H01L 21/02617 |
| WO | WO 2010052228 A1 | 5/2010 |
| WO | WO 2010/111414 A1 | 9/2010 |
| WO | WO 2011/060242 A2 | 5/2011 |
| WO | WO 2011069164 A2 | 6/2011 |
| WO | WO 2012/006623 A2 | 1/2012 |
| WO | WO 2013/106789 A1 | 1/2013 |

OTHER PUBLICATIONS

Mariani et al., Semin Thromb Hemost. Feb. 2003;29(1):69-76.*
George et al,, J Blood Med. Apr. 24, 2015;6:131-41. doi: 10.2147/JBM.S54632. eCollection 2015.*
Kreuz et al,, Haemophilia. Jan. 1995;1(1):24-32. doi: 10.1111/j.1365-2516.1995.tb00036.x.*
Eigenbrot et al., Structure, vol. 9, Issue 7, Jul. 3, 2001, pp. 627-636.*
Akilesh, S., et al., "Neonatal FcR Expression in Bone Marrow-Derived Cells Functions to Protect Serum IgG from Catabolism," The Journal of Immunology 179(7):4580-4588, The American Association of Immunologists, Inc., United States (2007).
Aledort, L.M., et al., "A longitudinal study of orthopaedic outcomes for severe factor-VIII-deficient haemophiliacs," Journal of Internal Medicine 236(4):391-399, Blackwell Scientific Publications, England (1994).
Armour, K.L., et al., "Recombinant human IgG molecules lacking Fcγ receptor I binding and monocyte triggering activities," European Journal of Immunology 29(8):2613-2624, Wiley-VCH Verlag GmbH, Germany (1999).
Astermark, J., et al., "Polymorphisms in the CTLA-4 gene and inhibitor development in patients with severe hemophilia A," Journal of Thrombosis and Haemostasis 5(2):263-265, International Society on Thrombosis and Haemostasis, England (2007).
Astermark, J., et al., "Polymorphisms in the IL10 but not in the IL1beta and IL4 genes are associated with inhibitor development in patients with hemophilia A," Blood 107(8):3167-3172, The American Society of Hematology, United States (2006).
Astermark, J., et al., "Polymorphisms in the TNF A Gene and the Risk of Inhibitor Development in Patients with Hemophilia A," Blood 108(12):3739-3745, The American Society of Hematology, United States (2006).
Aznar, J.A., et al., "The orthopaedic status of severe haemophiliacs in Spain," Haemophilia 6(3):170-176, Blackwell Science, England (2000).
Bajaj, S.P., et al., "Redetermination of the Rate-Limiting Step in the Activation of Factor IX by Factor XIa and by Factor VIIa/Tissue Factor. Explanation for Different Electrophoretic Radioactivity Profiles Obtained on Activation of 3H- and 125I-Labeled Factor IX," Biochemistry 22(17):4047-4053, American Chemical Society, United States (1983).
Bi, L., et al., "Targeted Disruption of the Mouse Factor VIII Gene Produces a Model of Haemophilia A," Nature Genetics 10(1):119-121, Nature Publishing Co., United States (1995).
Bitonti, A.J., et al., "Pulmonary delivery of an erythropoietin Fc fusion protein in non-human primates through an immunoglobulin transport pathway," Proceedings of the National Academy of Sciences USA 101(26):9763-9768, The National Academy of Sciences, United States (2004).
Borvak, J., et al., "Functional Expression of the MHC Class I-related Receptor, FcRn, in Endothelial Cells of Mice," International Immunology 10(9):1289-1298, Oxford University Press, i England (1998).
Brandstetter, H., et al., "X-ray structure of clotting factor IXa: active site and module structure related to Xase activity and hemophilia B," Proceedings of the National Academy of Sciences USA 92(21):9796-9800, The National Academy of Sciences, United States (1995).
Brunetti-Pierri, N., et al., "Bioengineered factor IX molecules with increased catalytic activity improve the therapeutic index of gene therapy vectors for hemophilia B," Human Gene Therapy 20(5):479-485, Mary Ann Liebert. Inc., United States (2009).
Brutlag, D.L., et al., "Improved sensitivity of biological sequence database searches," Computer Applications in the Biosciences 6(3):237-245, Oxford University Press, England (1990).

(56) References Cited

OTHER PUBLICATIONS

Burmeister, W.P., et al., "Crystal structure of the complex of rat neonatal Fc receptor with Fc," Nature 372(6504):379-383, Nature Publishing Group, England (1994).
Butenas, S. and Mann, K.G., "Blood coagulation," Biochemistry (Moscow) 67(1):3-12, MAIK Nauka/Interperiodica, United States (2002).
Cameron, C., et al., "The canine factor VIII cDNA and 5' flanking sequence," Thrombosis and Haemostasis 79(2):317-322, Schattauer Verlag, Germany (1998).
Cao, O., et al., "Role of regulatory T cells in tolerance to coagulation factors," Journal of Thrombosis and Haemostasis 7(Suppl 1):88-91, Blackwell Publishing, England (2009).
Castaman, G., et al., "Pregnancy and Delivery in Women with Von Willebrand's Disease and Different Von Willebrand Factor Mutations," Haematologica 95(6):963-969, Ferrata Storti Foundation, Italy (2010).
Chang, J., et al., "Changing Residue 338 in Human Factor IX from Arginine to Alanine Causes an Increase in Catalytic Activity," The Journal of Biological Chemistry 273(20):12089-12094, The American Society for Biochemistry and Molecular Biology, Inc., United States (1998).
Co-pending U.S. Appl. No. 15/465,319, inventors Peters et al., filed Mar. 21, 2017 (Not Published).
Co-pending U.S. Appl. No. 15/491,742, inventors Peters et al., filed Apr. 19, 2017 (Not Published).
Coppola, A., et al., "Primary Prophylaxis in Children with Haemophilia," Blood Transfusion Prophylaxis in Congenital Coagulation Disorders 6(Suppl 2):s4-s11, Society of Transfusion Medicine and Immunohaematology, Italy (2008).
Cutler, J.A., et al., "The identification and classification of 41 novel mutations in the factor VIII gene (F8C)," Human Mutation 19(3):274-278, Wiley Liss, Inc., United States (2002).
De Groot, A.S., et al., "Activation of natural regulatory T cells by IgG Fc-derived peptide "Tregitopes"," Blood 112(8):3303-331 I, The American Society of Hematology, United States (2008).
Dobeli, H., et al., "Role of the carboxy-terminal sequence on the biological activity of human immune interferon (IFN-γ)," Journal of Biotechnology 7:199-216, Elsevier Science Publishers B.V., Netherlands (1998).
Dumont, J.A., et al., "Delivery of an Erythropoietin-Fc Fusion Protein by Inhalation in Humans through an Immunoglobulin Transport Pathway," Journal of Aerosol Medicine 18(3):294-303, May Ann Liebert, Inc., United States (2005).
Dumont, J.A., et al., "Factor VIII-Fc Fusion Protein Shows Extended Half-Life and Hemostatic Activity in Hemophilia A Dogs," ASH $51^{st}$ Annual Meeting Abstracts 114(22): Abstract 545, The American Society of Hematology, United States (2009).
Dumont, J.A., et al., "Monomeric Fc Fusion Technology: An Approach to Create Long-Lasting Clotting Factors," in: *Therapeutic Proteins—Strategies to Modulate Half-Life*, Kontermann R., ed., Chapter 10, pp. 189-206, Wiley Blackwell, Germany (Mar. 26, 2012).
Dumont, J.A., et al., "Monomeric Fc Fusion: Impact on Pharmacokinetic and Biological Activity of Protein Therapeutics," BioDrugs 20(3):151-160, Adis Data Information B.V., New Zealand (2006).
Dumont, J.A., et al., "Prolonged Activity of a Recombinant Factor VIII-Fc Fusion Protein in Hemophilia a Mice and Dogs," Blood 119(13):3024-3030, The American Society of Hematology, United States (Mar. 29, 2012).
Eaton, D.L., et al., "Construction and Characterization of an Active Factor VIII Variant Lacking the Central One-Third of the Molecule," Biochemistry 25(26):8343-8347, The American Chemical Society, United States (1986).
Eckhardt, C.L., et al., "Surgery and inhibitor development in hemophilia A: a systematic review," Journal of Thrombosis and Haemostasis 9(10):1948-1958, Blackwell Publishing, England (Oct. 2011).

English language Abstract of European Patent Publication No. EP 0295597 A2, European Patent Office, Espacenet database—Worldwide (1988).
Extended European Search Report for European Application No. 18183272.6, dated Feb. 13, 2019.
Fatouros, A., et al., "Recombinant factor VIII SQ influence of oxygen, metal ions, pH and ionic strength on its stability in aqueous solution," International Journal of Pharmaceutics 155(1):121-131, Elsevier, United States (1997).
Feldman, B.M., et al., "Tailored prophylaxis in severe hemophilia A: interim results from the first 5 years of the Canadian Hemophilia Primary Prophylaxis Study," Journal of Thrombosis and Haemostasis 4(6):1228-1236, Blackwell Publishing, England (2006).
Foster, P.A., et al., "Synthetic factor VIII peptides with amino acid sequences contained within the C2 domain of factor VIII inhibit factor VIII binding to phosphatidylserine," Blood 75(10):1999-2004, The American Society of Hematology, United States (1990).
Friend, P.J., et al., "Phase 1 study of an engineered aglycosylated humanized CD3 antibody in renal transplant rejection," Transplantation 68(11):1632-1637, Lippincott Williams & Wilkins, Inc., United States (1999).
Gayle, R.B., III., et al., "Identification of Regions in Interleukin-lα Important for Activity," The Journal of Biological Chemistry 268(29):22105-22111, The American Society for Biochemistry and Molecular Biology, Inc., United States (1993).
GenBank, "*Homo sapiens* coagulation factor VIII, procoagulant component (F8), transcript variant 1, mRN A," Accession No. NM_000132.3, accessed at http://www.ncbi.nlm.nih.gov/nuccore/NM_000132.3, 2008, 12 pages.
GenBank, "*Homo sapiens* mRNA for immunoglobulin kappa heavy chain," Accession No. Y14735.1, accessed at http://www.ncbi.nlm.nih.gov/nuccore/Y14735, Aug. 19, 1998, 3 pages.
Geraghty, S., et al., "Practice patterns in haemophilia A therapy—global progress towards optimal care," Haemophilia 12(1):75-81, Blackwell Publishing Ltd., England (2006).
Gitschier, J., et al., "Characterization of the human factor VIII gene," Nature 312(5992):326-330, Nature Publishing Group, England (1984).
Graham, J.B., et al., "Canine Hemophilia: Observations on the Course, the Clotting Anomaly, and the Effect of Blood Transfusions," The Journal of Experimental Medicine 90(2):97-111, The Rockefeller University Press, United States (1949).
Green, D., "Factor VIII inhibitors: a 50-year perspective," Haemophilia 17(6):831-838, Blackwell Publishing Ltd., England (Nov. 2011).
Grubb, J.H., et al., "Infused Fc-tagged β-glucuronidase crosses the placenta and produces clearance of storage in utero in mucopolysaccharidosis VII mice," Proceedings of the National Academy of Sciences USA 105(24)8375-8380, The National Academy of Sciences, United States (2008).
Hacker, M.R., et al., "Barriers to compliance with prophylaxis therapy in haemophilia," Haemophilia 7(4):392-396, Blackwell Science, England (2001).
Hay, C.R.M., et al., "The diagnosis and management of factor VIII and IX inhibitors: a guideline from the United Kingdom Haemophilia Centre Doctors Organization," British Journal of Haematology 133(6):591-605, Blackwell Publishing, England (2006).
Healey, J.F., et al., "The cDNA and derived amino acid sequence of porcine factor VIII," Blood 88(11):4209-4214, The American Society of Hematology, United States (1996).
Herzog, R.W., et al., "Long-term correction of canine hemophilia B by gene transfer of blood coagulation factor IX mediated by adeno-associated viral vector," Nature Medicine 5(1):56-63, Nature Publishing Co., United States (1999).
Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, Inc., United States (1990).
Huang, C., "Receptor-Fc Fusion Therapeutics Traps, and MIMETIBODY™ Technology," Current Opinion in Biotechnology 20(6):692-699, Current Biology, England (2009).

(56) References Cited

OTHER PUBLICATIONS

International Search Report and Written Opinion for International Application No. PCT/US2013/021332, ISA/US, United States, dated Mar. 18, 2013.
Karpf, D.M., et al., "Preclinical pharmacokinetic (PK) evaluation of glycopegylated long acting RFVIII," Hemophilia 16(Suppl. 4):40 Blackwell Publishing Ltd., England (2010).
Kasper C.K., "Diagnosis and Management of Inhibitors to Factors VIII and IX: An Introductory Discussion for Physicians," Treatment of Hemophilia 34:1-22, World Federation of Hemophilia, Canada (2004).
Kempton, C.L., et al., "How we treat a hemophilia A patient with a factor VIII inhibitor," Blood 113(1):11-17, The American Society of Hematology, United States (2009).
Kreuz, W., et al., "When should prophylactic treatment in patients with haemophilia A and B start?—The German experience," Haemophilia 4(4):413-417, Blackwell Science Ltd., England (1998).
Langner, K.D., et al., "Synthesis of Biologically Active Deletion Mutants of Human Factor VIII:C," Behring Institute Mitteilungen 82:16-25, Behringwerke AG, Germany (1988).
Lee, C.A., et al., "Pharmacokinetics of Recombinant Factor VIII (Recombinate) Using One-Stage Clotting and Chromogenic Factor VIII Assay," Thrombosis and Haemostasis 82(6):1644-1647, Schattauer Verlag, Germany (1999).
Lei, T.C., "Induction of tolerance to factor VIII inhibitors by gene therapy with immunodominant A2 and C2 domains presented by B cells as Ig fusion proteins," Blood 105(12):4865-4870, The American Society of Hematology, United States (2005).
Lencer, W.I. and Blumberg, R.S., "A passionate kiss, then run: exocytosis and recycling of IgG by FcRn," Trends in Cell Biology 15(1):5-9, Elsevier Science Publishers, England (2005).
Lenting, P.J., et al., "Clearance mechanisms of von Willebrand factor and factor VIII," Journal of Thrombosis and Haemostasis 5(7):1353-1360, Blackwell Publishing, England (2007).
Liesner, R.J., et al., "The impact of prophylactic treatment on children with severe haemophilia," British Journal of Haematology 92(4):973-978, Blackwell Publishing, England (1996).
Lillicrap, D., "Improvements in factor concentrates," Current Opinion in Hematology 17(5):393-397, Lippincott Williams & Wilkins, United States (2010).
Liu, T. Z., et al. "Recombinant FVIII Fc fusion protein is fully active in treating acute injury and demonstrates prolonged prophylactic efficacy in hemophilia A mice," Journal of Thrombosis and Haemostasis 9(Supp.2):561, Abstract P-WE-131, Blackwell Publishing, United States (Jul. 2011).
Liu, T., et al., "Evaluation of antibody responses to rFVIIIFc compared to Xyntha® and Advate® in hemophilia A mice," Hemophilia 18(Suppl. 3):41, Blackwell Publishing Ltd., England (Jul. 9, 2012).
Liu, T., et al., "Site-Specific PEGylation of Factor VIII (PEG-FVIII) Preserves Full Clotting Activity and Extends Therapeutic Efficacy in Hemophilia A Dogs," 50$^{th}$ ASH Annual Meeting and Exposition Online Program and Abstracts:511, the American Society of Hematology, United States (2008).
Livak, K.J. and Schmittgen T.D., "Analysis of relative gene expression data using real-time quantitative PCR and the $2^{-\Delta\Delta C}$ Method," Methods 25(4):402-408, Academic Press, United States (2001).
Ljung, R.C.R., "Prophylactic treatment in Sweden—overtreatment or optimal model?" Haemophilia 4(4):409-412, Blackwell Science Ltd., England (1998).
Lollar, P. and Parker, E.T., "Structural Basis for the Decreased Procoagulant Activity of Human Factor VIII Compared to the Porcine Homolog," Journal of Biological Chemistry 266(19):12481-12486, The American Society for Biochemistry and Molecular Biology, Inc., United States (1991).
Lollar, P., et al., "Coagulant Properties of Hybrid Human/Porcine Factor VIII Molecules," Journal of Biological Chemistry 267(33):23652-23657, The American Society for Biochemistry and Molecular Biology, Inc., United States (1992).

Lozier, J.N., et al., "The Chapel Hill Hemophilia A Dog Colony Exhibits a Factor VIII Gene Inversion," Proceedings of the National Academy of Sciences USA 99(20):12991-12996, The National Academy of Sciences, United States (2002).
Löfqvist, T., et al., "Haemophilia prophylaxis in young patients—a long term follow-up," Journal of Internal Medicine 241(5):395-400, Blackwell Scientific Ltd., England (1997).
Manco-Johnson, M., et al., "Prophylaxis versus Episodic Treatment to Prevent Joint Disease in Boys with Severe Hemophilia," New England Journal of Medicine 357(6):535-544, Massachusetts Medical Society, United States (2007).
Manucci, P.M. and Tuddenham, E.G.D, "The hemophilias—from royal genes to gene therapy," The New England Journal of Medicine 344(23):1773-1779, Massachusetts Medical Society, United States (2001).
McCue, J.T., et al., "Applicants of a Novel Affinity Adsorbent for the Capture and Purification of Recombinant Factor VIII Compounds," Journal of Chromatography A 1216(45):7824-7830, Elsevier, Netherlands (2009).
Mei, B., et al., "Rational design of fully active, long lasting PEGylated factor VIII for hemophilia A Treatment," Blood 116(2):270-279, The American Society of Hematology, United States (2010).
Meslier, Y., et al., "Induction of Tolerance to Therapeutic FVIII by Materno-Fetal Transfer in a Hemophilia A mouse model," European Journal Immunology 2009: Tuesday, Poster Sessions, abstract PD11/26, p. S536, Wiley-VCI-1 Verlag Gmbh & Co. KGaA, Germany (2009).
Metzner, H.J., et al., "Characterization of factor VIII/von Willebrand factor concentrates using a modified method of von Willebrand factor multimer analysis," Haemophilia 4(Suppl. 3):25-32, Blackwell Science Ltd., England (1998).
Metzner, H.J., et al., "Genetic fusion to albumin improves the pharmacokinetic properties of factor IX," Journal of Thrombosis and Haemostasis 102(4):634-644, Stuttgart, Schattauer, Germany (2009).
Meulien, P., et al., "A new recombinant procoagulant protein derived from the cDNA encoding human factor VIII," Protein Engineering 2(4):301-306, IRL Press Ltd., England (1988).
Mikaelsson, M. and Oswaldsson, U., "Assaying the Circulating Factor VIII Activity in Hemophilia A Patients Treated with Recombinant Factor VIII Products," Seminars in Thrombosis and Hemostasis 28(3):257-264, Thieme, United States (2002).
Molho, P., et al., "Epidemiological survey of the orthopaedic status of severe hemophilia A and B patients in France," Haemophilia 6(1):23-32, Blackwell Science Ltd., England (2000).
Morfini, M., "Pharmacokinetics of factor VIII and factor IX," Hemophilia 9(Suppl. 1):94-100, Blackwell Publishing Ltd., England (2003).
Moss, J., et al., "Safety and pharmacokinetic of a glycoPEGylated recombinant activated factor VIII derivative: a randomized first human dose trial in healthy subjects," Journal of Thrombosis and Haemostasis 9(7):1368-1374, Blackwell Publishing Ltd., England (Jul. 2011).
Negrier, C., et al., "Enhanced pharmacokinetic properties of a glycoPEGylated recombinant factor IX: a first human dose trial in patients with hemophilia B," Blood 118(10):2695-2701, The American Society of Hematology, United States (Sep. 2011).
Ngo, J.C.K., et al., "Crystal structure of human factor VIII: implications for the formation of the factor IXa-factor VIIIa complex," Structure 16(4):597-606, Cell Press, United States (2008).
Nilsson, I.M., et al., "Twenty-five years' experience of prophylactic treatment in severe haemophilia A and B," Journal of Internal Medicine 232(1):25-32, Blackwell Scientific Publications, England (1992).
Oganesyan, V., et al., "Structural characterization of a human Fc fragment engineered for extended serum half-life," Molecular Immunology 46(8-9):1750-1755, Pergamon Press, England (2009).
Pan, J., et al., "Enhanced Efficacy of Recombinant FVIII in Noncovalent Complex with PEGylated Liposome in Hemophilia A Mice," Blood 114(13):2802-2811, The American Society of Hematology, United States (2009).
Pavlova, A., et al., "Impact of polymorphisms of the major histocompatibility complex class II, interleukin-10, tumor necrosis fac-

(56) References Cited

OTHER PUBLICATIONS tor-α and cytotoxic T-lymphocyte antigen-4 genes on inhibitor development in severe hemophilia A," Journal of Thrombosis and Haemostasis 7(12):2006-2015, Blackwell Publishing, England (2009).
Persson, E., et al., "Rational design of coagulation factor VIIa variant with substantially increased intrinsic activity," Proceedings of the National Academy of Sciences USA 98(24):13583-13588, The National Academy of Sciences, United States (2001).
Persson, E., et al., "Substitution of valine for leucine 305 in factor VIIa increases the intrinsic enzymatic activity," The Journal of Biological Chemistry 276(31):29195-29199, The American Society for Biochemistry and Molecular Biology, Inc., United States (2001).
Peters, R.T., et al., "Biochemical and Functional Characterization of a Recombinant Monomeric Factor VIII-Fc Fusion Protein," Journal of Thrombosis and Haemostasis 11(1):132-141, Blackwell Publishing, England (Published online: Jan. 27, 2013).
Peters, R.T., et al., "Prolonged Activity of Factor IX as a Monomeric Fc Fusion Protein," Blood 115(10): 2057-2064, The American Society of Hematology, United States (Mar. 2010; Prepub. Online Jan. 2010).
Petrini, P., et al., "Prophylaxis with factor concentrates in preventing hemophilic arthropathy," The American Journal of Pediatric Hematology/Oncology 13(3):280-287, Raven Press, United States, (1991).
Petrovan, R.J. and Ruf, W., "Residue Met[156] Contributes to the Labile Enzyme Conformation of Coagulation Factor VIIa," The Journal of Biological Chemistry 276(9):6616-6620, The American Society for Biochemistry and Molecular Biology, Inc., United States (2001).
Peyvandi, F., et al., "Genetic diagnosis of haemophilia and other inherited bleeding disorders," Haemophilia 12(Suppl. 3):82-89, Blackwell Publishing Ltd., England (2006).
Powell, J.S., et al., "Safety and prolonged activity of recombinant factor VIII Fc fusion protein in hemophilia A patients," Blood 119(13):3031-3037, The American Society of Hematology, United States (Mar. 29, 2012).
Qadura, M., et al., "Reduction of the immune response to factor VIII mediated through tolerogenic factor VIII presentation by immature dendritic cells," Journal of Thrombosis and Haemostasis 6(12):2095-2104, Blackwell Publishing Ltd., England (2008).
Report of Expert Meeting on FVIII Products and Inhibitor Development, European Medicines Agency, London, England, Feb. 28, 2006-Mar. 2, 2006.
Risebrough, N., et al., "Cost-utility analysis of Canadian tailored prophylaxis, primary prophylaxis and on-demand therapy in young children with severe haemophilia A," Haemophilia 14(4):743-752, Blackwell Publishing Ltd., England (2008).
Roberts, S.A., et al., "Engineering factor Viii for Hemophilia Gene Therapy," Genetic Syndrome Gene Therapy S1: 1-7, OMICS, India (2011).
Rodriguez-Merchan, E.C., "Management of Musculoskeletal Complications of Hemophilia," Seminars in Thrombosis and Hemostasis 25(1):87-95, Thieme, United States (2003).
Ron, D., et al., "Expression of Biologically Active Recombinant Keratinocyte Growth Factor: Structure/function analysis of aminoterminal truncation mutants," The Journal of Biological Chemistry 268(4):2984-2988, American Society for Biochemistry and Molecular Biology, United States (1993).
Roopenian, D.C., and Akilesh, S., "FcRn: the Neonatal Fc Receptor Comes of Age," Nature Reviews Immunology 7(9):715-725, Nature Publishing Group, England (2007).
Rosén, S., "Assay of Factor VIII:C with a Chromogenic Substrate," New Frontiers in Hemophilia Research, the XVth World Federation of Hemophilia Congress Stockholm, Sweden, Jun. 27-Jul. 1, 1983, published in Scandinavian Journal of Rheumatology Supplement 33(540):139-145, Munksgaard, Denmark (1984).
Routledge, E.G., et al., "The effect of aglycosylation on the immunogenicity of a humanized therapeutic CD3 monoclonal antibody," Transplantation 60(8):847-853, Williams & Wilkins, United States (1995).

Röstin, J., et al., "B-Domain Deleted Recombinant Coagulation Factor VIII Modified with Monotherapy Polyethylene Glycol," Bioconjugate Chemistry 11(3):387-396, American Chemical Society, United States (2000).
Salas, J., et al., "Enhanced pharmacokinetics of factor VIIA as a monomeric FC Fusion," Journal of Thrombosis and Haemostasis 9(Suppl. 2):268, Blackwell Publishing, England (Jul. 2011).
Sarver, N., et al., "Stable Expression of Recombinant Factor VIII Molecules Using a Bovine Papillomavirus Vector," DNA 6(6):553-564, Mary Ann Liebert, Inc., United States (1987).
Schmidt, S.R., "Fusion proteins as biopharmaceuticals—Applications and challenges," Current Opinion in Drug Discovery & Development 12(2):284-295, Thomson Reuters, England (2009).
Shen, B.W., et al., "The tertiary structure and domain organization of coagulation factor VIII," Blood 111(3):1240-1247, The American Society of Hematology, United States (2007).
Shields, R.L., et al., High Resolution Mapping of the Binding Site on Human IgG1 for FcγRI, FCγRII, FCγRIII, and FcRn and Design of IgG1 Variants with Improved Binding to the FcγR*, The Journal of Biological Chemistry 276(9):6591-6604, The American Society for Biochemistry and Molecular Biology, Inc., United States (2001).
Sichler, K., et al., "Physiological fIXa activation involves a cooperative conformational rearrangement of the 99-loop," The Journal of Biological Chemistry 278(6):4121-4126, The American Society for Biochemistry and Molecular Biology, Inc., United States (2003).
Simioni, P., et al., "X-linked thrombophilia with a mutant factor IX (factor IX Padua)," The New England Journal of Medicine 361(17):1671-1675, Massachusetts Medical Society, United States (2009).
Simister, N.E., "Placental transport of immunoglobulin G," Vaccine 21(24):3365-3369, Elsevier Science, Netherlands (2003).
Smith, N.L., et al., "Novel associations of multiple genetic loci with plasma levels of factor VII, factor VIII, and von Willebrand factor: The CHARGE (Cohorts for Heart and Aging Research in Genome Epidemiology) Consortium," Circulation 121(12):1382-1392, American Heart Association Inc., United States (2010).
Soejima, K., et al., "Factor VIIa modified in the 170 loop shows enhanced catalytic activity but does not change the zymogen-like property," The Journal of Biological Chemistry 276(20):17229-17235, The American Society for Biochemistry and Molecular Biology, Inc., United States (2001).
Soejima, K., et al., "The 99 and 170 loop-modifier factor VIIa mutants show enhanced catalytic activity without tissue factor," The Journal of Biological Chemistry 277(50):49027-49035, The American Society for Biochemistry and Molecular Biology, Inc., United States (2002).
Spitzer, S.G., et al., "Replacement of isoleucine-397 threonine in the clotting proteinase factor IXa (Los Angeles and Long Beach variants) affects macromolecular catalysis but not L-tosylarginine methyl ester hydrolysis. Lack of correlation between the ox brain prothrombin time and the mutation site in the variant proteins," The Journal of Biological Chemistry 265(1):219-225, The American Society for Biochemistry and Molecular Biology, Inc., United States (1990).
Story, C.M., et al., "A Major Histocompatibility Complex Class I-Like Fc Receptor Cloned from Human Placenta: Possible Role in Transfer of Immunoglobulin G from Mother to Fetus," The Journal of Experimental Medicine 180(6):2377-2381, The Rockefeller University Press, United States (1994).
Stroobants, A.K., et al., "Differences between one stage clotting and chromogenic factor VIII assay results," Journal of Thrombosis and Haemostasis 9(Suppl 2):381 (Abstract P-TU-230), Blackwell Publishing, England (Jul. 2011).
Strürzebecher, J., "Dramatic enhancement of the catalytic activity of coagulation factor IXa by alcohols," FEBS Letters 412(2):295-300, Federation of European Biochemical Societies, Netherlands (1997).
Toole, J.J., et al., "A large region (~95 kDa) of human factor VIII is dispensable for in vitro procoagulant activity," Proceedings of the National Academy of Sciences USA 83(16):5939-5942, National Academy of Sciences, United States (1986).
Toole, J.J., et al., "Molecular cloning of a cDNA encoding human antihaemophilic factor," Nature 312(5992):342-347, Nature Publishing Group, England (1984).

(56) References Cited

OTHER PUBLICATIONS

Vaccaro, C., et al., "Engineering the Fc region of immunoglobulin G to modulate in vivo antibody levels," Nature Biotechnology 23(10):1283-1288, Nature America Publishing, United States (2005).
Van Den Berg, H.M., et al., "Comparing outcomes of different treatment regimens for severe haemophilia," Haemophilia 9(1 Suppl):27-31, Blackwell Science, United States (2003).
Van Den Berg, H.M., et al., "Issues surrounding therapeutic choices for hemophilia patients," Haematologica 89(6):645-650, Ferrata Storti Foundation, Italy (2004).
Van Rooijen, N. et al., "Liposomes for specific depletion of macrophages from organs and tissues," Methods in Molecular Biology 605:189-203, Humana Press, United States (2010).
Van Schooten, C.J., et al., "Macrophages contribute to the cellular uptake of von Willebrand factor and factor VIII in vivo," Blood 112(5):1704-1712, The American Society of Hematology, United States (2008).
Vehar, G.A., et al., "Structure of human factor VIII," Nature 312(5992):337-342, Nature Publishing Group. England (1984).
Vysotchin, A., et al., "Domain structure and domain-domain interactions in human coagulation factor IX," The Journal of Biological Chemistry 268(12):8436-8446, The American Society for Biochemistry and Molecular Biology, Inc., United States (1993).
Wakabayashi, H., et al., "Residues 110-126 in the A1 Domain of Factor VIII Contain a Ca2+ Binding Site Required for Cofactor Activity," the Journal of Biological Chemistry 279(13):12677-12684, The American Society for Biochemistry and Molecular Biology, Inc., United States (2004).
Ward, E.S, and Ghetie, V., "The effector functions of immunoglobulins: implications for therapy," Therapeutic Immunology 2(2):77-94, Blackwell Science Ltd., England (1995).
Weimer, T., et al., "Prolonged in-vivo half-life of factor VIIa by fusion to albumin," Thrombosis and Haemostasis 99(4):659-667, Stuttgart, Schattauer, Germany (2008).
White, G.C., $2^{nd}$., et al., "A multicenter study of recombinant factor VIII (recombinate TM) in previously treated patients with hemophilia A. The Recombinate previously treated patient study group," Thrombosis and Haemostasis 77(4):660-667, Stuttgart, Schattauer, Germany (1997).
Wood., W.I., et al., "Expression of active human factor VIII from recombinant DNA clones," Nature 312(5992):330-337, Nature Publishing Group, England (1984).
Yoshida, M., et al., Human neonatal Fc receptor mediates transport of IgG into luminal secretions for delivery of antigens to mucosal dendritic cells, Immunity 20(6):769-783, Cell Press, United States (2004).
Zogg, T. and Brandstetter, H., "Structural basis of the cofactor—and substrate-assisted activation of human coagulation factor IXa," Structure 17(12):1669-1678, Cell Press, United States (2009).
Astermark et al., (2005) "The Malmö International Brother Study (MIBS): Genetic defects and inhibitor development in siblings with severe hemophilia A", Haematologica, 90(7): 924-931.
Astermark, et al., "Basic Aspects of Inhibitors to Factors VIII and IX and the Influence of Non-Genetic Risk Factors", vol. 12, Supplement 6, pp. 8-13, Dec. 2006.
Coppola et al., (2009) "Factor VIII gene (F8) mutations as predictors of outcome in immune tolerance induction of hemophilia A patients with high-responding inhibitors", J Thromb Haemost, 7(11): 1809-1815, doi:10.1111/j.1538-7836.2009.03615.x.
Damiano et al., (2000) "Immune tolerance for haemophilia patients with inhibitors: analysis of the western United States experience", The Tri-Regional Nursing Group, Haemophilia, 6(5): 526-532.
De Groot, et al., "Activation of Natural Regulatory T Cells by IgG Fc-Derived Peptide 'Tregitopes'", Blood, vol. 112, Nos. pp. 3303-3311, Oct. 15, 2008.
Delignant, "Transplacental Delivery of FC-Fused Recombinant Factor VIII (rFVIIIFC) In FVIII-Deficient Mice", Centre de Recherche Des Cordeliers, Presented at EAHAD 2021 Virtual Congress, Session 7, Feb. 5, 2021, 15 pages.

Dimichele et al., (2002) "The North American Immune Tolerance Registry: practices, outcomes, outcome predictors", Thromb Haemost, 87(1): 52-57.
Dimichele, (2009) "The North American Immune Tolerance Registry: contributions to the thirty-year experience with immune tolerance therapy", Haemophilia, 15(1): 320-328, doi:10.1111/j.1365-2516.2008.01880.x.
Eigenbrot, et al., "The Factor VII Zymogen Structure Reveals Reregistration of p. Strands during Activation", Structure, vol. 9, No. 7, pp. 627-636, Jul. 3, 2001.
Feagan, et al., "Ustekinumab as Induction and Maintenance Therapy for Crohn's Disease", New England Journal of Medicine, vol. 375, No. 20, pp. 1946-1960, Nov. 17, 2016.
Franchini et al., (2011), "Immune tolerance induction for patients with severe hemophilia A: a critical literature review", J Thromb Thrombolysis, 32(4): 439-447, doi: 10.1007/sl 1239-011 -0624-3.
Franchini et al., (2013) "Systematic review of the role of FVIII concentrates in inhibitor development in previously untreated patients with severe hemophilia A: a 2013 update", Semin Thromb Hemost, 39(7): 752-766, doi:10.1055/s-0033-1356715.
Freiburghaus, et al., "Tolerance Induction Using the Malmo Treatment Model 1982-1995", Haemophilia, vol. 5, No. 1, pp. 32-39, Jan. 1999.
Genbank, "Variation in lgG1 heavy chain allotype does not contribute to differences in biological activity of two human anti-Rhesus (D) monoclonal antibodies, Homo sapiens mRNA for immunoglobulin kappa heavy chain", GenBank accession No. Y14735, 3 Pages.
George, et al., "Profile of Efraloctocog Alfa and its Potential in the Treatment of Hemophilia A", Journal of Blood Medicine, vol. 6, pp. 131-141, Apr. 24, 2015.
Gouw et al., (2013), "Factor VIII products and inhibitor development in severe hemophilia A", N Engl J Med, 368(3): 231-239, doi:10.1056/NEJMoa1208024.
Gringeri, (2007) "VWF/FVIII concentrates in high-risk immunotolerance: the RESIST study", Haemophilia, 13(Suppl 5): 73-77, doi:10.1111/j.1365-2516.2007.01579.x.
Groomes et al., (2016) "Reduction of Factor VIII Inhibitor Titers During Immune Tolerance Induction With Recombinant Factor Vlll-Fc Fusion Protein", Pediatr Blood Cancer, 63(5): 922-924, doi:10.1002/pbc.25874.
Gupta et al., (2015) "Regulation of immune responses to protein therapeutics by transplacental induction of T cell tolerance", Sci Transl Med, 7(275): 275ra221, doi:10.1126/scitranslmed.aaa1957.
Hay et al., (2012) "The principal results of the International Immune Tolerance Study: a randomized dose comparison", Blood, 119(6): 1335-1344, doi:10.1182/blood-2011-08-369132.
Haya et al., (2001) "Immune tolerance treatment in haemophilia patients with inhibitors: the Spanish Registry", Haemophilia, 7(2): 154-159.
Ishiguro, "Immune Mechanisms Involved in the Development and Eradication of Anti-Factor VIII Alloantibodies in Hemophilia", Japanese Journal of Clinical Immunology, vol. 34, Issue 6, pp. 476-484, 2011.
Jimenez-Yuste et al., (2016) "Long-term outcome of haemophilia A patients after successful immune tolerance induction therapy using a single plasma-derived FVIII/VWF product: the long-term ITI study", Haemophilia, 22(6): 859-865, doi:10.1111/hae.12986.
Kau, et al., "Anti-Interleukin 4 and 13 for Asthma Treatment in the Era of Endotypes", Current Opinion in Allergy and Clinical Immunology, vol. 14, No. 6, pp. 570-575, Dec. 2014.
Kempton et al., (2014) "Toward optimal therapy for inhibitors in hemophilia", Blood, 124(23): 3365-3372, doi:10.1182/blood-2014-05-577643.
Kreuz et al., (2016) "First prospective report on immune tolerance in poor risk haemophilia A inhibitor patients with a single factor Vlll/von Willebrand factor concentrate in an observational immune tolerance induction study", Haemophilia, 22(1): 87-95, doi:10.1111/hae.12774.
Kreuz, et al., "Immune Tolerance Therapy in Paediatric Haemophiliacs with Factor VIII Inhibitors: 14 Years Follow-up", Haemophilia, vol. 1, No. 1, pp. 24-32, Jan. 1, 1995.

(56) References Cited

OTHER PUBLICATIONS

Krishnamoorthy et al., (2016) "Recombinant factor VIII Fc (rFVIIIFc) fusion protein reduces immunogenicity and induces tolerance in hemophilia A mice", Cell Immunol, 301: 30-39, doi:10.1016/j.cellimm.2015.12.008.
Kroner et al. (1999) "Comparison of the international immune tolerance registry and the North American immune tolerance registry", Vox Sang, 77(Suppl 1): 33-37.
Kurth et al., (2011) "The use of a single von Willebrand factor-containing, plasma-derived FVIII product in hemophilia A immune tolerance induction: the US experience", J Thromb Haemost, 9(11): 2229-2234, doi: 10.1111/j. 1538-7836.2011,04493.x.
Ling, et al., "Classification of the Kinetics of Factor VIII Inhibitors in Haemophilia A: Plasma Dilution Studies Are More Discriminatory Than Time-Course Studies", British Journal of Haematology, vol. 114, No. 4, pp. 861-867, Sep. 2001.
Lofqvist, et al., "Haemophilia Prophylaxis In Young Patients ± A Long-Term Follow-Up", Journal of Internal Medicine, vol. 241, pp. 395-400, 1997.
Malec et al., (2015) "Immune Tolerance Induction Using rFVIIIFc (Eloctate)", Blood, 126(23): 3531-3531.
Malec et al., (2016) "Extended half-life factor VIII for immune tolerance induction in haemophilia", Haemophilia, 22(6): e552-e554, doi:10.1111/hae.13064.
Mariani et al., (1994) "Immune tolerance in hemophilia-principal results from the International Registry - Report of the factor VIII and IX Subcommittee", Thromb Haemost, 72(1): 155-158.
Nakar et al., (2015) "Prompt immune tolerance induction at inhibitor diagnosis regardless of titre may increase overall success in haemophilia A complicated by inhibitors: experience of two U.S. centres", Haemophilia, 21(3): 365-373, doi:10.1111/hae.12608.
Noble, et al., "IL-12 and IL-4 Activate a CD39- Dependent Intrinsic Peripheral Tolerance Mechanism in Cd+ T Cells", European Journal of Immunology, vol. 46, No. 6, 11 Pages, Jun. 2016.
Oldenburg et al., (2006) "Genetic risk factors for inhibitors to factors VIII and IX", Haemophilia, 12(Suppl 6): 15-22, doi:10.1111/j.1365-2516.2006.01361 .x.
Oldenburg et al., (2014) "Primary and rescue immune tolerance induction in children and adults: a multicentre international study with a VWF-containing plasma-derived FVIII concentrate", Haemophilia, 20(1): 83-91, doi:10.1111/hae.12263.
Rocino, et al., "Successful Immune Tolerance Treatment with Monoclonal or Recombinant Factor VIII Concentrates in High Responding Inhibitor Patients", Vox Sanguinis, vol. 77, Supplement 1, pp. 65-69, Sep. 2001.
Rojas, et al., "IL-10: A Multifunctional Cytokine in Viral Infections", Review Article, Journal of Immunology Research, 15 Pages, Feb. 20, 2017.
Sakurai, et al., "Acquired Hemophilia A: A Frequently Overlooked Autoimmune Hemorrhagic Disorder", Journal of Immunology Research, vol. 2014, Article ID 320674, 10 Pages, Mar. 24, 2014.
Scalone et al., (2006) "Quality of life is associated to the orthopaedic status in haemophilic patients with inhibitors", Haemophilia, 12(2): 154-162, doi:10.1111/j. 1365-2516.2006.01204.x.
Simister, "Placental Transport of Immunoglobulin G", Vaccine, vol. 21, No. 24, pp. 3365-3369, Jul. 28, 2003.
Srivastava et al., (Jan. 2013) "Guidelines for the management of hemophilia", Haemophilia, 19(1): e1-47, doi:10.1111/j.1365-2516.2012.02909.x.
Supplementary European Search Report received for European Patent Application No. 13735995.6, dated Jul. 27, 2015.
Tagariello et al., (2013) "High rate of spontaneous inhibitor clearance during the long term observation study of a single cohort of 524 haemophilia A patients not undergoing immunotolerance", J Hematol Oncol, 6: 63, doi:10.1186/1756-8722-6-63.
Valentino et al., (2015) "US Guidelines for immune tolerance induction in patients with haemophilia A and inhibitors", Haemophilia, 21(5): 559-567, doi:10.1111/hae.12730.
Van Rooijen, et al., "Liposomes for Specific Depletion of Macrophages from Organs and Tissues", Methods of Molecular Biology, vol. 605, pp. 189-203, 2010.
Van Schooten, et al., "Macrophages Contribute to the Cellular Uptake of Von Willebrand Factor and Factor VIII in Vivo", Blood, vol. 112, Nos. pp. 1704-1712, Sep. 1, 2008.
Vasanthi, et al., "Role of Tumor Necrosis Factor-Alpha in Rheumatoid Arthritis: a Review", APLAR Journal of Rheumatology, vol. 10, No. 4, pp. 270-274, Dec. 2007.
Whelan et al., (2013) "Distinct characteristics of antibody responses against factor VIII in healthy individuals and in different cohorts of hemophilia A patients", Blood, 121(6): 1039-1048, doi:10.1182/blood-2012-07-444877.

\* cited by examiner

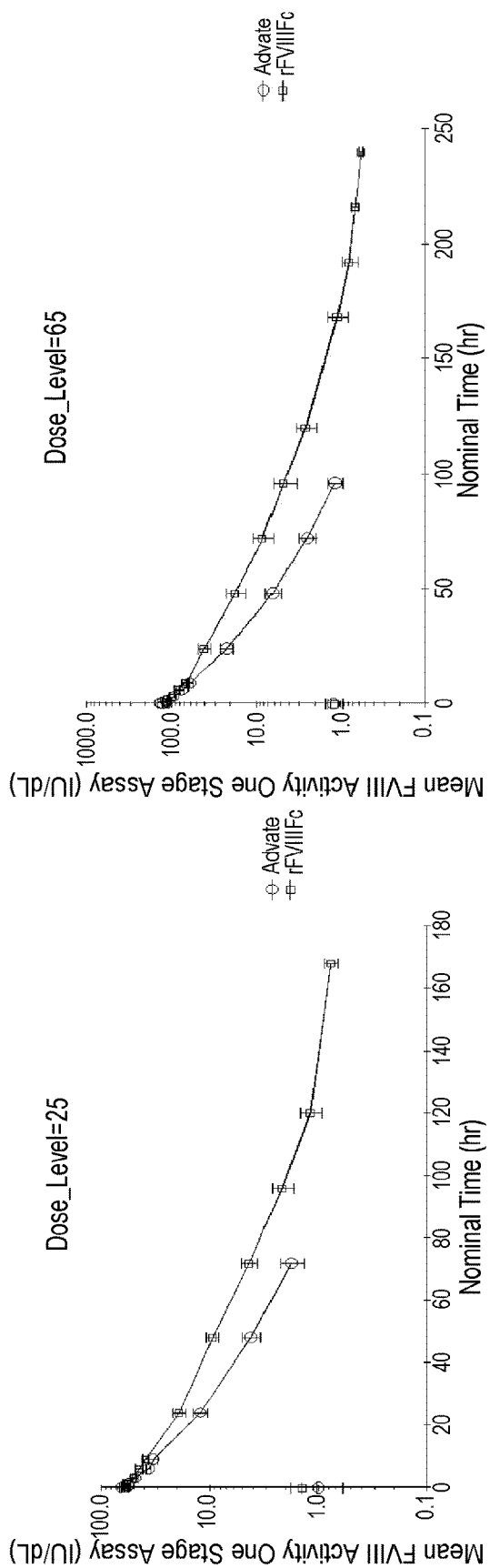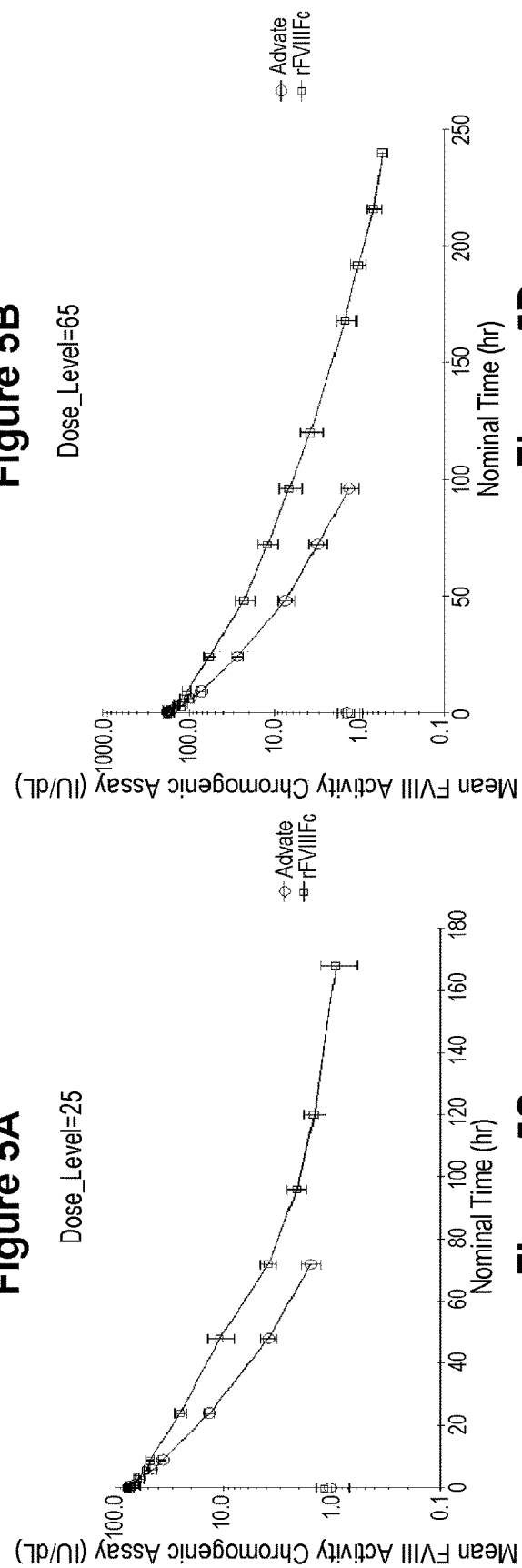

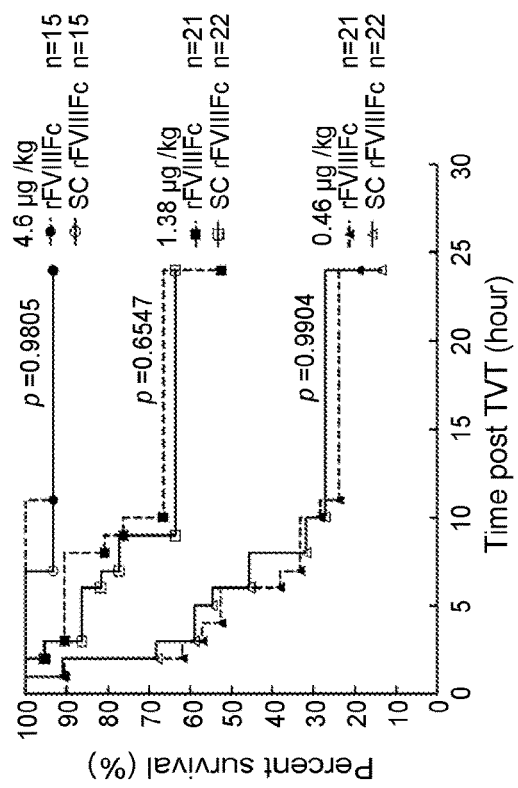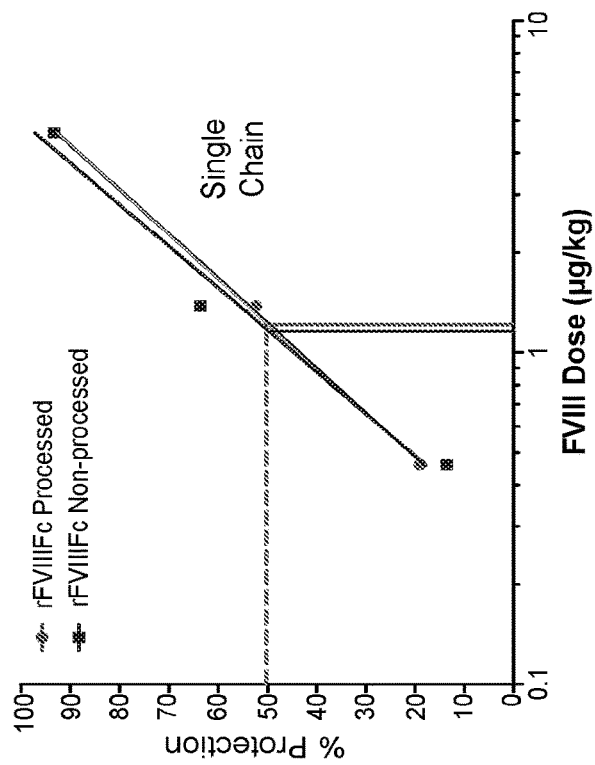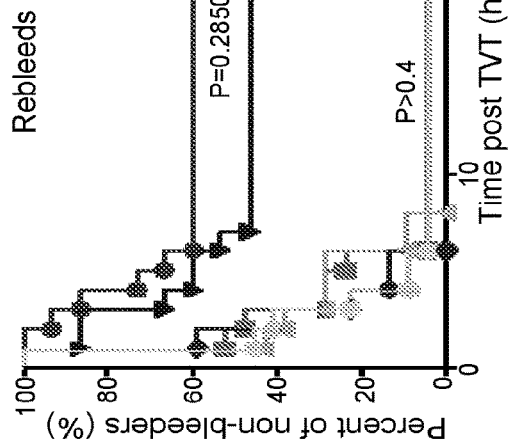
Figure 7A
Figure 7B
Figure 7C

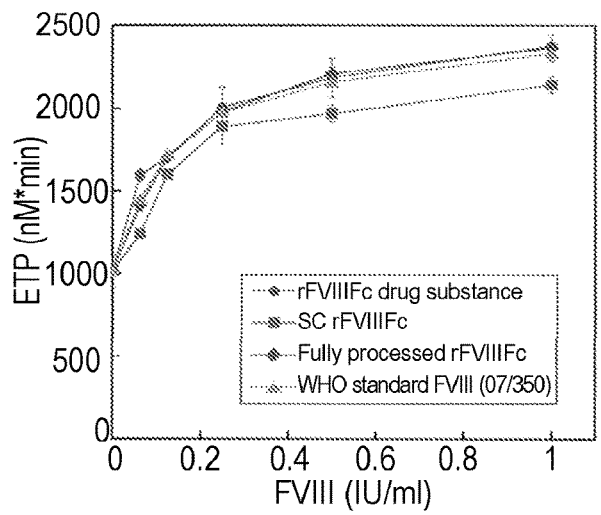
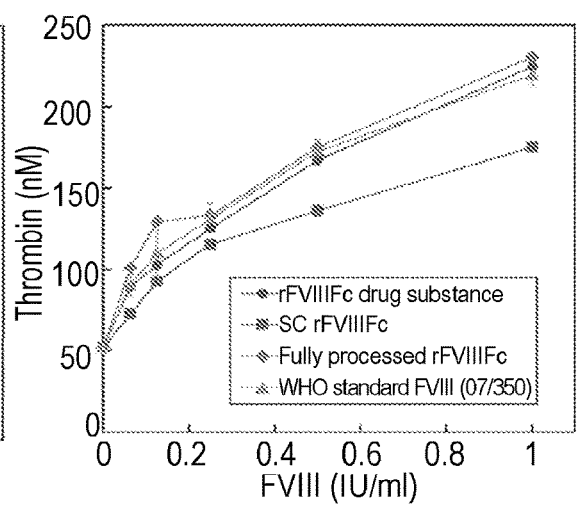
Figure 13A
Figure 13B
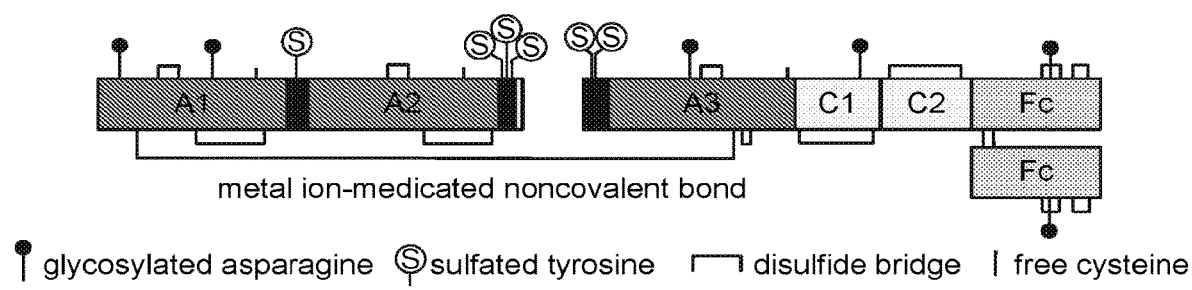
Figure 14

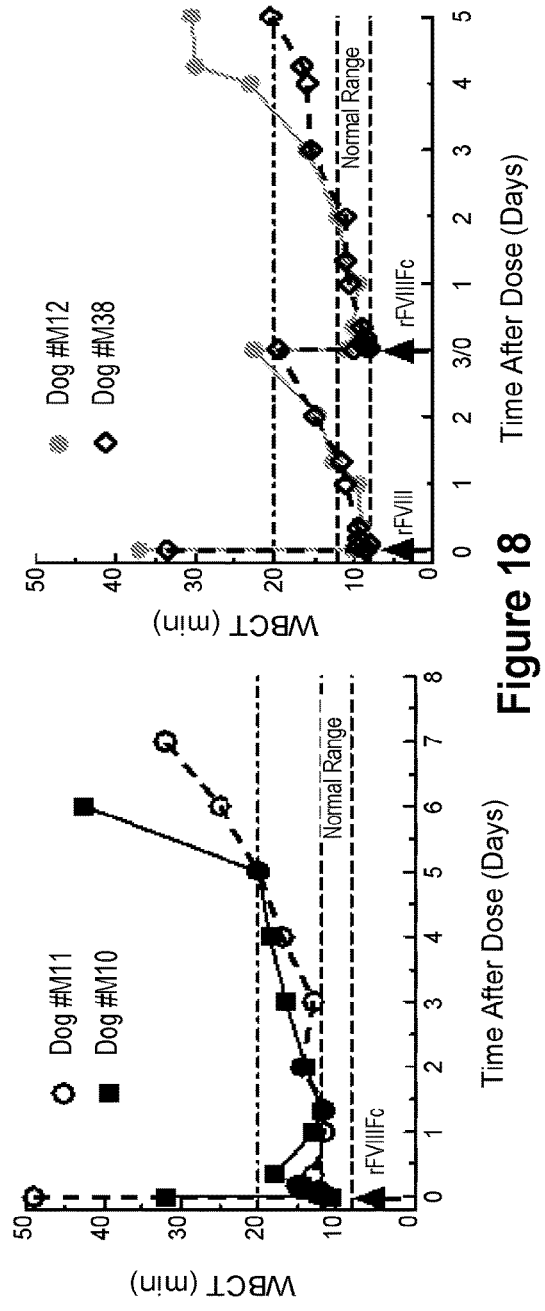
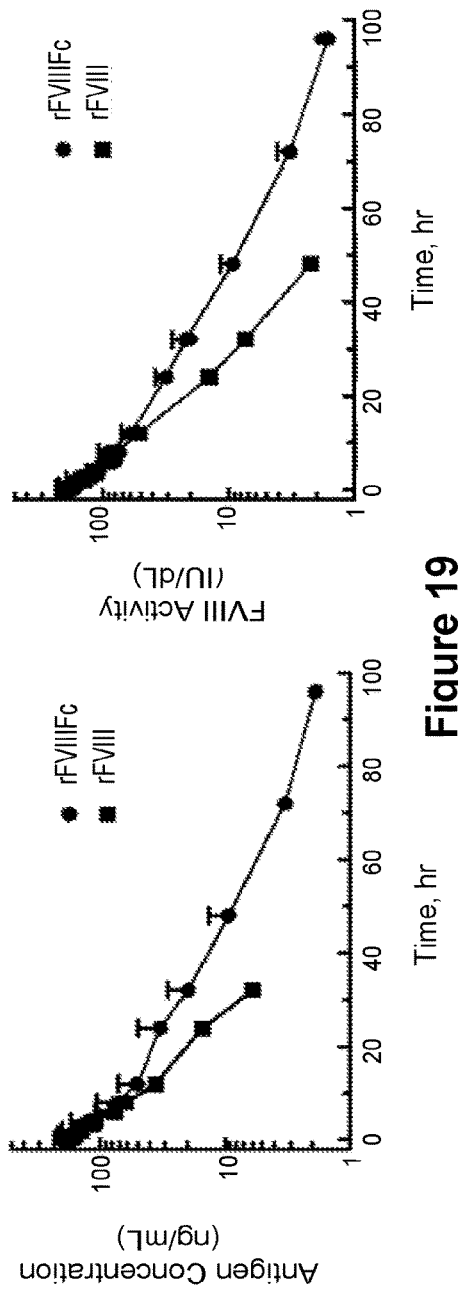
Figure 18
Figure 19

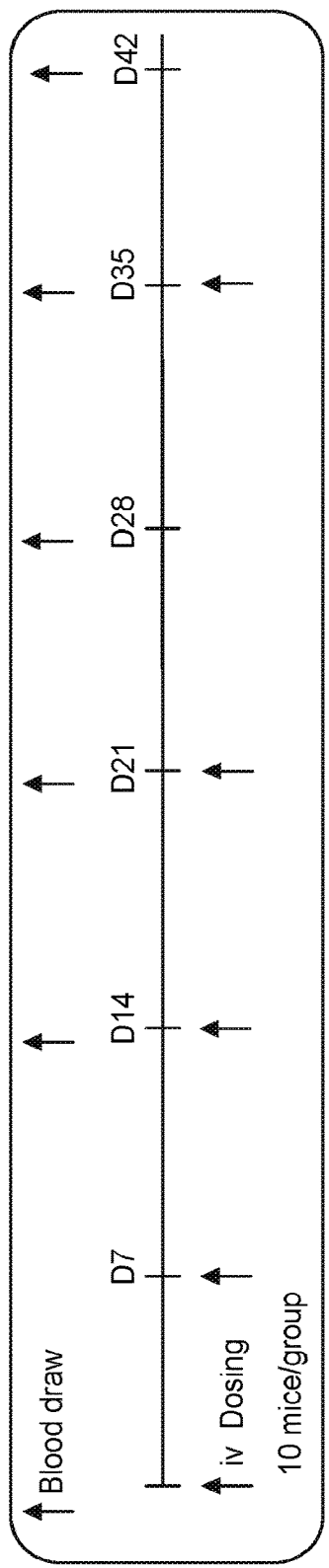
Figure 20
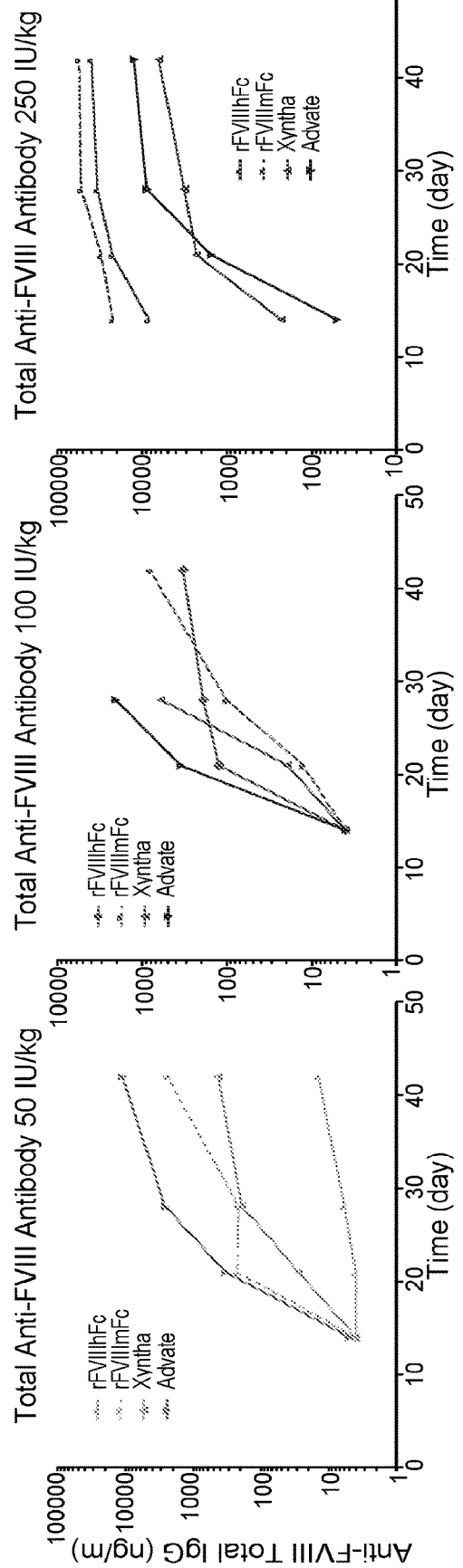
Figure 21A Figure 21B Figure 21C

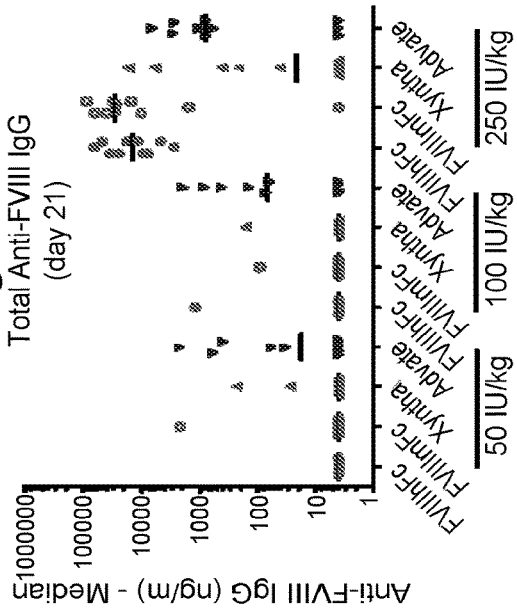
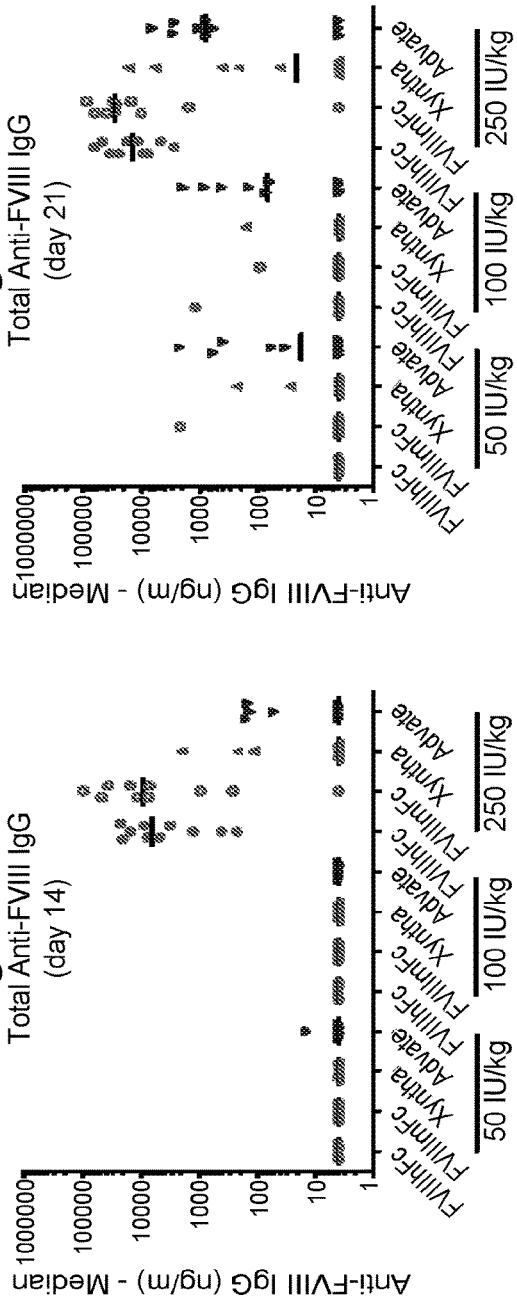
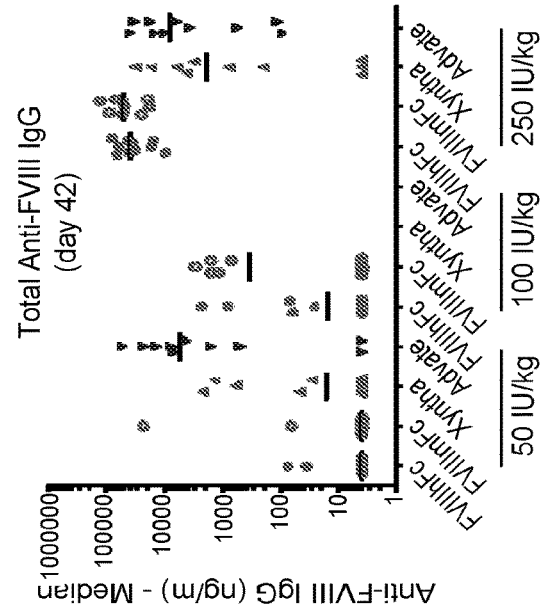
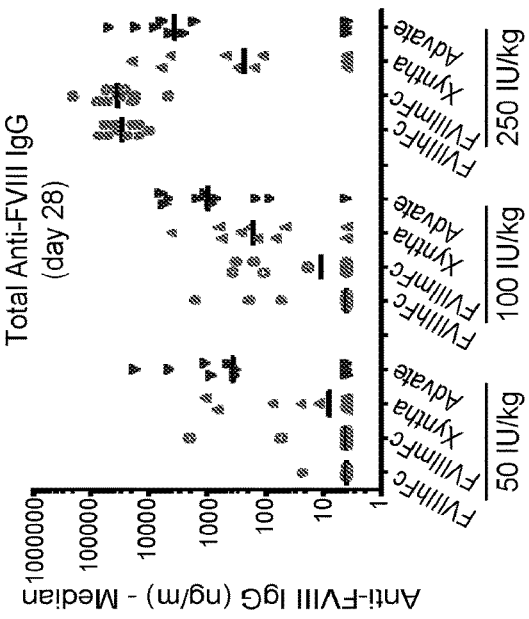

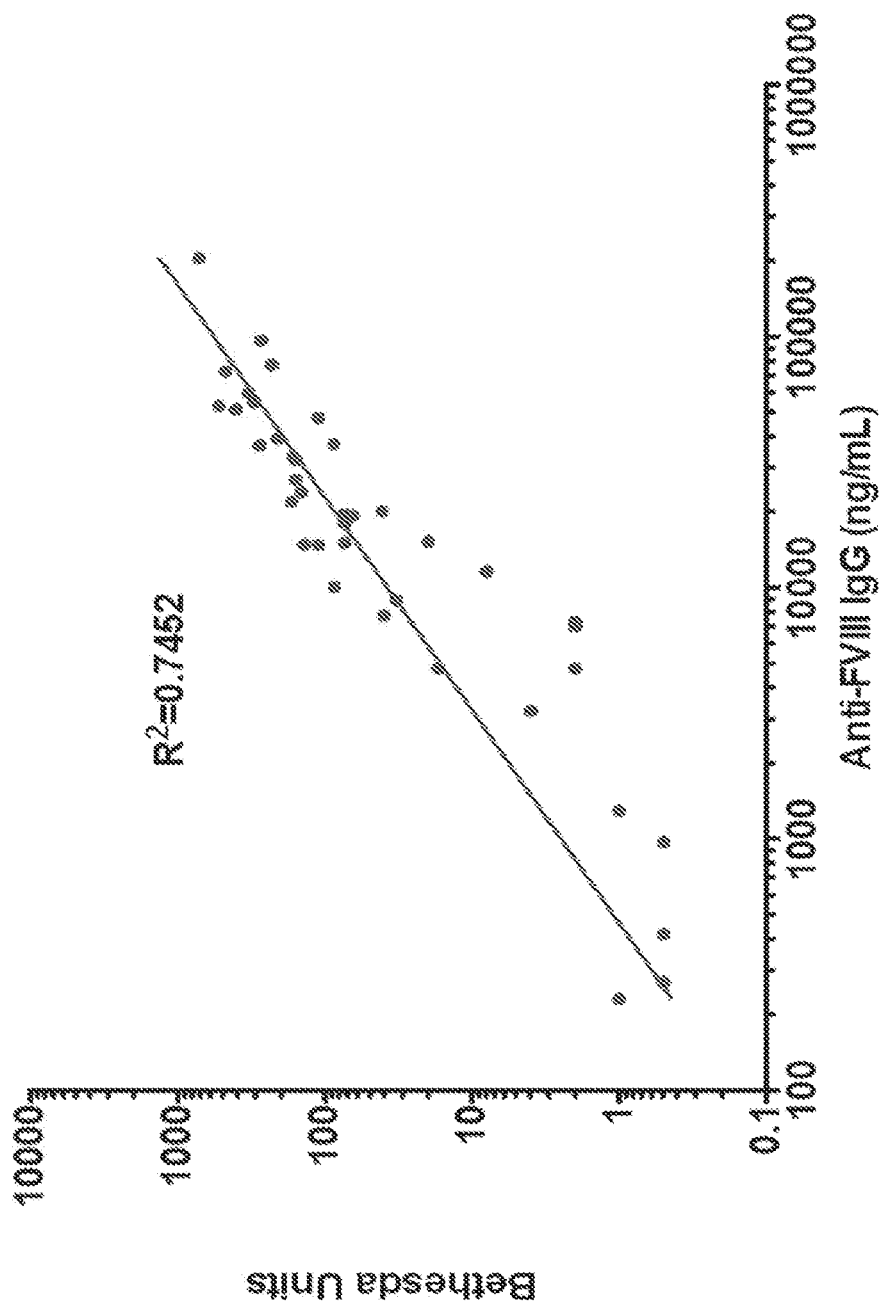

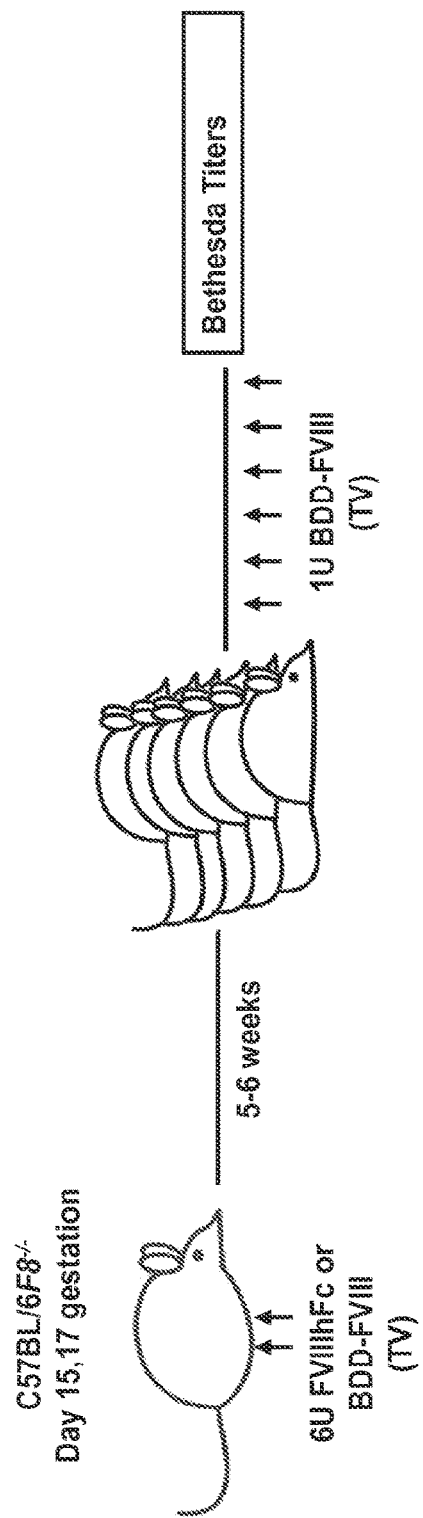
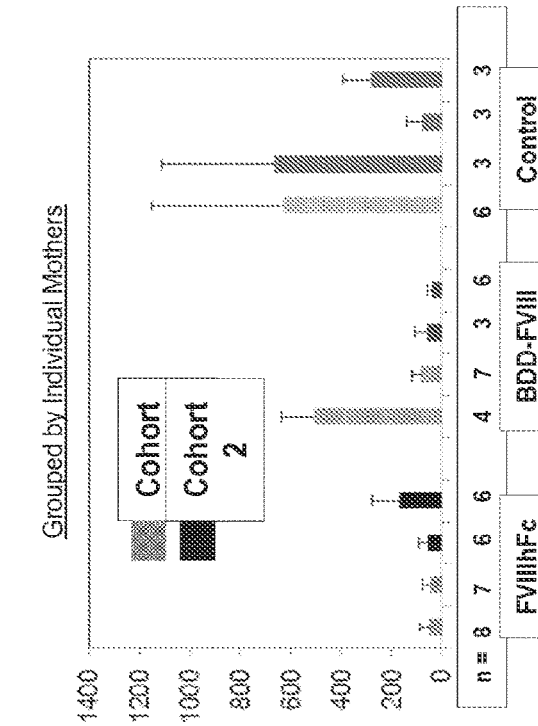
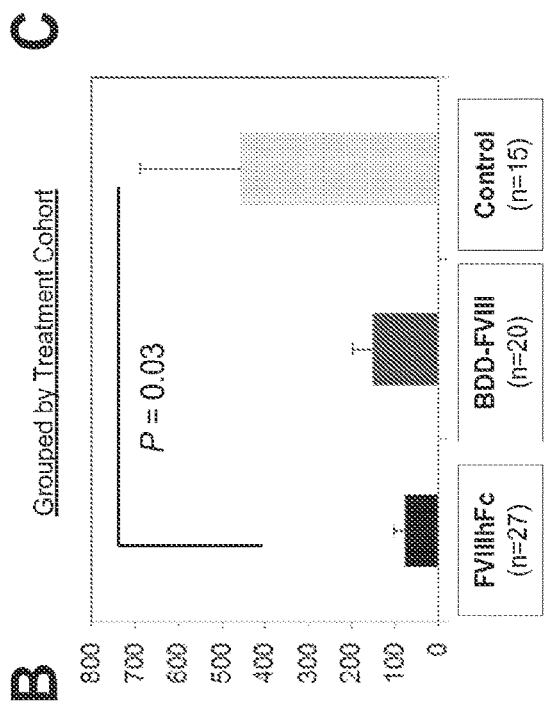
Figure 63

SEQUENCE LISTING

<160> NUMBER OF SEQ ID NOS: 6

<210> SEQ ID NO 1
<211> LENGTH: 5052
<212> TYPE: DNA
<213> ORGANISM: Homo sapiens

<400> SEQUENCE: 1

```
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc caaaatcttt tccattcaac     180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
```

```
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt cctggaaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag aacccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa agtcaatat ttgaacaatg ccctcagcg gattggtagg   1320 aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatataccct caaacacaaa   2040
atggtctatg aagacacact caccctattc ccattctcag agaaactgt cttcatgtcg   2100 atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc atcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagcttca aaagaaaaca   2460 cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
```

```
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggaccccctt   2940
ctggtctgcc acactaacac actgaaccct gctcatggga gacaagtgac agtacaggaa   3000
tttgctctgt ttttcaccat ctttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac acttttttctg   3420
gtgtacagca ataagtgtca gactcccctg ggaatggctt ctggacacat tagagatttt   3480
cagattacag cttcaggaca atatggacag tgggccccaa agctggccag acttcattat   3540
tccggatcaa tcaatgcctg gagcaccaag gagccctttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg gaagaagtg gcagacttat   3720
cgaggaaatt ccactggaac cttaatggtc ttctttggca atgtggattc atctgggata   3780
aaacacaata tttttaaccc tccaattatt gctcgataca tccgtttgca cccaactcat   3840
tatagcattc gcagcactct tcgcatggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga agtcacagg agtaactact cagggagtaa aatctctgct taccagcatg   4140
tatgtgaagg agttcctcat ctccagcagt caagatggcc atcagtggac tctctttttt   4200
cagaatggca aagtaaaggt ttttcaggga aatcaagact ccttcacacc tgtggtgaac   4260
tctctagacc caccgttact gactcgctac cttcgaattc accccagag ttgggtgcac   4320
cagattgccc tgaggatgga ggttctgggc tgcgaggcac aggacctcta cgacaaaact   4380
cacacatgcc caccgtgccc agctccagaa ctcctgggcg gaccgtcagt cttcctcttc   4440
cccccaaaac ccaaggacac cctcatgatc tcccggaccc ctgaggtcac atgcgtggtg   4500
gtggacgtga gccacgaaga ccctgaggtc aagttcaact ggtacgtgga cggcgtggag   4560
gtgcataatg ccaagacaaa gccgcgggag gagcagtaca acagcacgta ccgtgtggtc   4620
agcgtcctca ccgtcctgca ccaggactgg ctgaatggca aggagtacaa gtgcaaggtc   4680
tccaacaaag cctcccagc ccccatcgag aaaaccatct ccaaagccaa agggcagccc   4740
cgagaaccac aggtgtacac cctgccccca tcccgggatg agctgaccaa gaaccaggtc   4800
agcctgacct gcctggtcaa aggcttctat cccagcgaca tcgccgtgga gtgggagagc   4860
aatgggcagc cggagaacaa ctacaagacc acgcctcccg tgttggactc cgacggctcc   4920
ttcttcctct acagcaagct caccgtggac aagagcaggt ggcagcaggg gaacgtcttc   4980
tcatgctccg tgatgcatga ggctctgcac aaccactaca cgcagaagag cctctccctg   5040
tctccgggta aa                                                      5052
```

```
<210> SEQ ID NO 2
<211> LENGTH: 1684
<212> TYPE: PRT
<213> ORGANISM: Homo sapiens

<400> SEQUENCE: 2

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
```

```
            370                 375                 380
Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
            405                 410                 415

Leu Val Leu Ala Pro Asp Arg Ser Tyr Lys Ser Gln Tyr Leu Asn
            420                 425                 430

Asn Gly Pro Gln Arg Ile Gly Arg Lys Tyr Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
            485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
            565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Pro Pro Val Leu
            755                 760                 765

Lys Arg His Gln Arg Glu Ile Thr Arg Thr Thr Leu Gln Ser Asp Gln
            770                 775                 780

Glu Glu Ile Asp Tyr Asp Asp Thr Ile Ser Val Glu Met Lys Lys Glu
785                 790                 795                 800
```

```
Asp Phe Asp Ile Tyr Asp Glu Asp Glu Asn Gln Ser Pro Arg Ser Phe
            805                 810                 815

Gln Lys Lys Thr Arg His Tyr Phe Ile Ala Ala Val Glu Arg Leu Trp
        820                 825                 830

Asp Tyr Gly Met Ser Ser Ser Pro His Val Leu Arg Asn Arg Ala Gln
            835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
        915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
        995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200
```

```
Met Ile Ile His Gly Ile Lys Thr Gln Gly Ala Arg Gln Lys Phe
    1205              1210                1215
Ser Ser Leu Tyr Ile Ser Gln Phe Ile Ile Met Tyr Ser Leu Asp
    1220              1225                1230
Gly Lys Lys Trp Gln Thr Tyr Arg Gly Asn Ser Thr Gly Thr Leu
    1235              1240                1245
Met Val Phe Phe Gly Asn Val Asp Ser Ser Gly Ile Lys His Asn
    1250              1255                1260
Ile Phe Asn Pro Pro Ile Ile Ala Arg Tyr Ile Arg Leu His Pro
    1265              1270                1275
Thr His Tyr Ser Ile Arg Ser Thr Leu Arg Met Glu Leu Met Gly
    1280              1285                1290
Cys Asp Leu Asn Ser Cys Ser Met Pro Leu Gly Met Glu Ser Lys
    1295              1300                1305
Ala Ile Ser Asp Ala Gln Ile Thr Ala Ser Ser Tyr Phe Thr Asn
    1310              1315                1320
Met Phe Ala Thr Trp Ser Pro Ser Lys Ala Arg Leu His Leu Gln
    1325              1330                1335
Gly Arg Ser Asn Ala Trp Arg Pro Gln Val Asn Asn Pro Lys Glu
    1340              1345                1350
Trp Leu Gln Val Asp Phe Gln Lys Thr Met Lys Val Thr Gly Val
    1355              1360                1365
Thr Thr Gln Gly Val Lys Ser Leu Leu Thr Ser Met Tyr Val Lys
    1370              1375                1380
Glu Phe Leu Ile Ser Ser Ser Gln Asp Gly His Gln Trp Thr Leu
    1385              1390                1395
Phe Phe Gln Asn Gly Lys Val Lys Val Phe Gln Gly Asn Gln Asp
    1400              1405                1410
Ser Phe Thr Pro Val Val Asn Ser Leu Asp Pro Pro Leu Leu Thr
    1415              1420                1425
Arg Tyr Leu Arg Ile His Pro Gln Ser Trp Val His Gln Ile Ala
    1430              1435                1440
Leu Arg Met Glu Val Leu Gly Cys Glu Ala Gln Asp Leu Tyr Asp
    1445              1450                1455
Lys Thr His Thr Cys Pro Pro Cys Pro Ala Pro Glu Leu Leu Gly
    1460              1465                1470
Gly Pro Ser Val Phe Leu Phe Pro Pro Lys Pro Lys Asp Thr Leu
    1475              1480                1485
Met Ile Ser Arg Thr Pro Glu Val Thr Cys Val Val Val Asp Val
    1490              1495                1500
Ser His Glu Asp Pro Glu Val Lys Phe Asn Trp Tyr Val Asp Gly
    1505              1510                1515
Val Glu Val His Asn Ala Lys Thr Lys Pro Arg Glu Glu Gln Tyr
    1520              1525                1530
Asn Ser Thr Tyr Arg Val Val Ser Val Leu Thr Val Leu His Gln
    1535              1540                1545
Asp Trp Leu Asn Gly Lys Glu Tyr Lys Cys Lys Val Ser Asn Lys
    1550              1555                1560
Ala Leu Pro Ala Pro Ile Glu Lys Thr Ile Ser Lys Ala Lys Gly
    1565              1570                1575
Gln Pro Arg Glu Pro Gln Val Tyr Thr Leu Pro Pro Ser Arg Asp
    1580              1585                1590
Glu Leu Thr Lys Asn Gln Val Ser Leu Thr Cys Leu Val Lys Gly
```

```
                  1595                1600                1605
Phe  Tyr  Pro  Ser  Asp  Ile  Ala  Val  Glu  Trp  Glu  Ser  Asn  Gly  Gln
          1610                1615                1620

Pro  Glu  Asn  Asn  Tyr  Lys  Thr  Thr  Pro  Pro  Val  Leu  Asp  Ser  Asp
     1625                1630                1635

Gly  Ser  Phe  Phe  Leu  Tyr  Ser  Lys  Leu  Thr  Val  Asp  Lys  Ser  Arg
1640                1645                1650

Trp  Gln  Gln  Gly  Asn  Val  Phe  Ser  Cys  Ser  Val  Met  His  Glu  Ala
     1655                1660                1665

Leu  His  Asn  His  Tyr  Thr  Gln  Lys  Ser  Leu  Ser  Leu  Ser  Pro  Gly
1670                1675                1680

Lys

<210> SEQ ID NO 3
<211> LENGTH: 741
<212> TYPE: DNA
<213> ORGANISM: Homo sapiens

<400> SEQUENCE: 3
atggagacag acacactcct gctatgggta ctgctgctct ggttccagg ttccactggt    60
gacaaaactc acacatgccc accgtgccca gcacctgaac tcctgggagg accgtcagtc   120
ttcctcttcc ccccaaaacc caaggacacc ctcatgatct cccggacccc tgaggtcaca   180
tgcgtggtgg tggacgtgag ccacgaagac cctgaggtca agttcaactg gtacgtggac   240
ggcgtggagg tgcataatgc caagacaaag ccgcgggagg agcagtacaa cagcacgtac   300
cgtgtggtca gcgtcctcac cgtcctgcac caggactggc tgaatggcaa ggagtacaag   360
tgcaaggtct ccaacaaagc cctcccagcc cccatcgaga aaaccatctc caaagccaaa   420
gggcagcccc gagaaccaca ggtgtacacc ctgcccccat cccgcgatga gctgaccaag   480
aaccaggtca gcctgacctg cctggtcaaa ggcttctatc ccagcgacat cgccgtggag   540
tgggagagca atgggcagcc ggagaacaac tacaagacca cgcctcccgt gttggactcc   600
gacggctcct tcttcctcta cagcaagctc accgtggaca agagcaggtg gcagcagggg   660
aacgtcttct catgctccgt gatgcatgag gctctgcaca accactacac gcagaagagc   720
ctctccctgt ctccgggtaa a                                             741

<210> SEQ ID NO 4
<211> LENGTH: 247
<212> TYPE: PRT
<213> ORGANISM: Homo sapiens

<400> SEQUENCE: 4

Met  Glu  Thr  Asp  Thr  Leu  Leu  Leu  Trp  Val  Leu  Leu  Leu  Trp  Val  Pro
1                   5                   10                  15

Gly  Ser  Thr  Gly  Asp  Lys  Thr  His  Thr  Cys  Pro  Pro  Cys  Pro  Ala  Pro
               20                  25                  30

Glu  Leu  Leu  Gly  Gly  Pro  Ser  Val  Phe  Leu  Phe  Pro  Pro  Lys  Pro  Lys
           35                  40                  45

Asp  Thr  Leu  Met  Ile  Ser  Arg  Thr  Pro  Glu  Val  Thr  Cys  Val  Val  Val
50                  55                  60

Asp  Val  Ser  His  Glu  Asp  Pro  Glu  Val  Lys  Phe  Asn  Trp  Tyr  Val  Asp
65                  70                  75                  80

Gly  Val  Glu  Val  His  Asn  Ala  Lys  Thr  Lys  Pro  Arg  Glu  Glu  Gln  Tyr
                85                  90                  95
```

```
Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
                245

<210> SEQ ID NO 5
<211> LENGTH: 7734
<212> TYPE: DNA
<213> ORGANISM: Homo sapiens

<400> SEQUENCE: 5
atgcaaatag agctctccac ctgcttcttt ctgtgccttt tgcgattctg ctttagtgcc      60
accagaagat actacctggg tgcagtggaa ctgtcatggg actatatgca agtgatctc     120 ggtgagctgc ctgtggacgc aagatttcct cctagagtgc aaaatctttt ccattcaac     180 acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaaagactt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggatagggat     720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat ctcgccaata actttcctta ctgctcaaac actcttgatg     960
gaccttggac agtttctact gttttgtcat atctcttccc ccaacatga tggcatggaa    1020 gcttatgtca agtagacag ctgtccagag gaaccccaac tacgaatgaa aaataatgaa    1080
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctccctt agtcctcgcc    1260
```

```
cccgatgaca gaagttataa aagtcaatat ttgaacaatg gccctcagcg gattggtagg    1320
aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaagaatc tgtagatcaa    1740 agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccttt caaacacaaa    2040 atggtctatg aagacacact caccctattc ccattctcag agaaactgt cttcatgtcg    2100 atggaaaacc aggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcaagaca ccctagcact aggcaaaagc aatttaatgc caccacaatt    2340
ccagaaaatg acatagagaa gactgaccct tggtttgcac acagaacacc tatgcctaaa    2400
atacaaaatg tctcctctag tgatttgttg atgctcttgc gacagagtcc tactccacat    2460
gggctatcct tatctgatct ccaagaagcc aaatatgaga cttttctga tgatccatca    2520 cctggagcaa tagacagtaa taacagcctg tctgaaatga cacacttcag gccacagctc    2580
catcacagtg gggacatggt atttaccccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag acccccaag tatgccagtt cattatgata gtcaattaga taccactcta    2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaaagagc tcatggacct    3000
gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180 gtgacaccctt tgattcatga cagaatgctt atggacaaaa atgctacagc tttgaggcta    3240
aatcatatgt caaataaaac tacttcatca aaaaacatgg aaatggtcca acagaaaaaa    3300
gagggcccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
aatttcttgt ctgagaaaaa caagtggta gtaggaaagg gtgaatttac aaaggacgta    3540
ggactcaaag agatggtttt tccaagcagc agaaacctat ttcttactaa cttggataat    3600
```

```
ttacatgaaa ataatacaca caatcaagaa aaaaaaattc aggaagaaat agaaaagaag    3660
gaaacattaa tccaagagaa tgtagttttg cctcagatac atacagtgac tggcactaag    3720
aatttcatga agaaccttt cttactgagc actaggcaaa atgtagaagg ttcatatgac     3780
ggggcatatg ctccagtact tcaagatttt aggtcattaa atgattcaac aaatagaaca    3840
aagaaacaca cagctcattt ctcaaaaaaa ggggaggaag aaaacttgga aggcttggga    3900
aatcaaacca agcaaattgt agagaaatat gcatgcacca caaggatatc tcctaataca    3960
agccagcaga attttgtcac gcaacgtagt aagagagctt tgaaacaatt cagactccca    4020
ctagaagaaa cagaacttga aaaaggata attgtggatg acacctcaac ccagtggtcc     4080
aaaaacatga acatttgac cccgagcacc ctcacacaga tagactacaa tgagaaggag     4140
aaaggggcca ttactcagtc tcccttatca gattgcctta cgaggagtca tagcatccct    4200
caagcaaata gatctccatt acccattgca aaggtatcat catttccatc tattagacct    4260
atatatctga ccagggtcct attccaagac aactcttctc atcttccagc agcatcttat    4320
agaaagaaag attctggggt ccaagaaagc agtcatttct acaaggagc caaaaaaaat    4380
aacctttctt tagccattct aaccttggag atgactggtg atcaaagaga ggttggctcc    4440
ctggggacaa gtgccacaaa ttcagtcaca tacaagaaag ttgagaacac tgttctcccg    4500
aaaccagact tgcccaaaac atctggcaaa gttgaattgc ttccaaaagt tcacatttat    4560
cagaaggacc tattccctac ggaaactagc aatgggtctc ctggccatct ggatctcgtg    4620
gaagggagcc ttcttcaggg aacagaggga gcgattaagt ggaatgaagc aaacagacct    4680
ggaaaagttc cctttctgag agtagcaaca gaaagctctg caaagactcc ctccaagcta    4740
ttggatcctc ttgcttggga taaccactat ggtactcaga taccaaaaga agagtggaaa    4800
tcccaagaga agtcaccaga aaaaacagct tttaagaaaa aggataccat tttgtccctg    4860
aacgcttgtg aaagcaatca tgcaatagca gcaataaatg agggacaaaa taagcccgaa    4920
atagaagtca cctgggcaaa gcaaggtagg actgaaaggc tgtgctctca aaacccacca    4980
gtcttgaaac gccatcaacg ggaaataact cgtactactc ttcagtcaga tcaagaggaa    5040
attgactatg atgataccat atcagttgaa atgaagaagg aagattttga catttatgat    5100
gaggatgaaa atcagagccc ccgcagcttt caaaagaaaa cacgacacta ttttattgct    5160
gcagtggaga ggctctggga ttatgggatg agtagctccc cacatgttct aagaaacagg    5220
gctcagagtg gcagtgtccc tcagttcaag aaagttgttt ccaggaatt tactgatggc    5280
tcctttactc agcccttata ccgtggagaa ctaaatgaac atttgggact cctggggcca    5340
tatataagag cagaagttga agataatatc atggtaactt tcagaaatca ggcctctcgt    5400
ccctattcct tctattctag ccttatttct tatgaggaag atcagaggca aggagcagaa    5460
cctagaaaaa actttgtcaa gcctaatgaa accaaaactt acttttggaa agtgcaacat    5520
catatggcac ccactaaaga tgagtttgac tgcaaagcct gggcttattt ctctgatgtt    5580
gacctggaaa aagatgtgca ctcaggcctg attggacccc ttctggtctg ccacactaac    5640
acactgaacc ctgctcatgg gagacaagtg acagtacagg aatttgctct gttttttcacc    5700
atctttgatg agaccaaaag ctggtacttc actgaaaata tggaaagaaa ctgcagggct    5760
ccctgcaata tccagatgga agatcccact tttaagagaa attatcgctt ccatgcaatc    5820
aatggctaca taatggatac actacctggc ttagtaatgg ctcaggatca aaggattcga    5880
tggtatctgc tcagcatggg cagcaatgaa acatccatt ctattcattt cagtggacat    5940
gtgttcactg tacgaaaaaa agaggagtat aaaatggcac tgtacaatct ctatccaggt    6000
```

-continued

```
gttttttgaga cagtggaaat gttaccatcc aaagctggaa tttggcgggt ggaatgcctt      6060
attggcgagc atctacatgc tgggatgagc acactttttc tggtgtacag caataagtgt      6120
cagactcccc tgggaatggc ttctggacac attagagatt ttcagattac agcttcagga      6180
caatatggac agtgggcccc aaagctggcc agacttcatt attccggatc aatcaatgcc      6240
tggagcacca aggagccctt ttcttggatc aaggtggatc tgttggcacc aatgattatt      6300
cacggcatca agacccaggg tgcccgtcag aagttctcca gcctctacat ctctcagttt      6360
atcatcatgt atagtcttga tgggaagaag tggcagactt atcgaggaaa ttccactgga      6420
accttaatgg tcttctttgg caatgtggat tcatctggga taaaacacaa tattttaac      6480 cctccaatta ttgctcgata catccgtttg cacccaactc attatagcat tcgcagcact      6540
cttcgcatgg agttgatggg ctgtgattta aatagttgca gcatgccatt gggaatggag      6600
agtaaagcaa tatcagatgc acagattact gcttcatcct actttaccaa tatgtttgcc      6660
acctggtctc cttcaaaagc tcgacttcac ctccaaggga ggagtaatgc ctggagacct      6720
caggtgaata atccaaaaga gtggctgcaa gtggacttcc agaagacaat gaaagtcaca      6780
ggagtaacta ctcagggagt aaaatctctg cttaccagca tgtatgtgaa ggagttcctc      6840
atctccagca gtcaagatgg ccatcagtgg actctctttt ttcagaatgg caaagtaaag      6900 gttttcagg gaaatcaaga ctccttcaca cctgtggtga actctctaga cccaccgtta      6960
ctgactcgct accttcgaat tcaccccag agttgggtgc accagattgc cctgaggatg      7020
gaggttctgg gctgcgaggc acaggacctc tacgacaaaa ctcacacatg cccaccgtgc      7080
ccagctccag aactcctggg cggaccgtca gtcttcctct tccccccaaa acccaaggac      7140
accctcatga tctcccggac ccctgaggtc acatgcgtgg tggtggacgt gagccacgaa      7200
gaccctgagg tcaagttcaa ctggtacgtg gacggcgtgg aggtgcataa tgccaagaca      7260
aagccgcggg aggagcagta caacagcacg taccgtgtgg tcagcgtcct caccgtcctg      7320
caccaggact ggctgaatgg caaggagtac aagtgcaagg tctccaacaa agccctccca      7380
gcccccatcg agaaaaccat ctccaaagcc aaagggcagc cccgagaacc acaggtgtac      7440
accctgcccc catcccggga tgagctgacc aagaaccagg tcagcctgac ctgcctggtc      7500
aaaggcttct atcccagcga catcgccgtg gagtgggaga gcaatgggca gccggagaac      7560
aactacaaga ccacgcctcc cgtgttggac tccgacggct ccttcttcct ctacagcaag      7620
ctcaccgtgg acaagagcag gtggcagcag gggaacgtct tctcatgctc cgtgatgcat      7680
gaggctctgc acaaccacta cacgcagaag agcctctccc tgtctccggg taaa           7734
```

<210> SEQ ID NO 6
<211> LENGTH: 2578
<212> TYPE: PRT
<213> ORGANISM: Homo sapiens

<400> SEQUENCE: 6

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60
```

```
Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
```

```
                485                 490                 495
His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
                610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
            770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
            850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
                900                 905                 910
```

```
Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro  Ala Leu Leu Thr Lys  Asp Asn Ala
            995                 1000                1005

Leu Phe  Lys Val Ser Ile Ser  Leu Leu Lys Thr Asn  Lys Thr Ser
    1010                1015                1020

Asn Asn  Ser Ala Thr Asn Arg  Lys Thr His Ile Asp  Gly Pro Ser
    1025                1030                1035

Leu Leu  Ile Glu Asn Ser Pro  Ser Val Trp Gln Asn  Ile Leu Glu
    1040                1045                1050

Ser Asp  Thr Glu Phe Lys Lys  Val Thr Pro Leu Ile  His Asp Arg
    1055                1060                1065

Met Leu  Met Asp Lys Asn Ala  Thr Ala Leu Arg Leu  Asn His Met
    1070                1075                1080

Ser Asn  Lys Thr Thr Ser Ser  Lys Asn Met Glu Met  Val Gln Gln
    1085                1090                1095

Lys Lys  Glu Gly Pro Ile Pro  Pro Asp Ala Gln Asn  Pro Asp Met
    1100                1105                1110

Ser Phe  Phe Lys Met Leu Phe  Leu Pro Glu Ser Ala  Arg Trp Ile
    1115                1120                1125

Gln Arg  Thr His Gly Lys Asn  Ser Leu Asn Ser Gly  Gln Gly Pro
    1130                1135                1140

Ser Pro  Lys Gln Leu Val Ser  Leu Gly Pro Glu Lys  Ser Val Glu
    1145                1150                1155

Gly Gln  Asn Phe Leu Ser Glu  Lys Asn Lys Val Val  Val Gly Lys
    1160                1165                1170

Gly Glu  Phe Thr Lys Asp Val  Gly Leu Lys Glu Met  Val Phe Pro
    1175                1180                1185

Ser Ser  Arg Asn Leu Phe Leu  Thr Asn Leu Asp Asn  Leu His Glu
    1190                1195                1200

Asn Asn  Thr His Asn Gln Glu  Lys Lys Ile Gln Glu  Glu Ile Glu
    1205                1210                1215

Lys Lys  Glu Thr Leu Ile Gln  Glu Asn Val Val Leu  Pro Gln Ile
    1220                1225                1230

His Thr  Val Thr Gly Thr Lys  Asn Phe Met Lys Asn  Leu Phe Leu
    1235                1240                1245

Leu Ser  Thr Arg Gln Asn Val  Glu Gly Ser Tyr Asp  Gly Ala Tyr
    1250                1255                1260

Ala Pro  Val Leu Gln Asp Phe  Arg Ser Leu Asn Asp  Ser Thr Asn
    1265                1270                1275

Arg Thr  Lys Lys His Thr Ala  His Phe Ser Lys Lys  Gly Glu Glu
    1280                1285                1290

Glu Asn  Leu Glu Gly Leu Gly  Asn Gln Thr Lys Gln  Ile Val Glu
    1295                1300                1305
```

```
Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser His Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser His Leu Pro Ala Ala Ser Tyr Arg Lys Lys
1430                1435                1440

Asp Ser Gly Val Gln Glu Ser Ser His Phe Leu Gln Gly Ala Lys
1445                1450                1455

Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser
1520                1525                1530

Pro Gly His Leu Asp Leu Val Glu Gly Ser Leu Leu Gln Gly Thr
1535                1540                1545

Glu Gly Ala Ile Lys Trp Asn Glu Ala Asn Arg Pro Gly Lys Val
1550                1555                1560

Pro Phe Leu Arg Val Ala Thr Glu Ser Ser Ala Lys Thr Pro Ser
1565                1570                1575

Lys Leu Leu Asp Pro Leu Ala Trp Asp Asn His Tyr Gly Thr Gln
1580                1585                1590

Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
```

-continued

```
            1700            1705            1710
Thr Arg His Tyr Phe Ile Ala Ala Val Glu Arg Leu Trp Asp Tyr
    1715            1720            1725

Gly Met Ser Ser Ser Pro His Val Leu Arg Asn Arg Ala Gln Ser
    1730            1735            1740

Gly Ser Val Pro Gln Phe Lys Lys Val Val Phe Gln Glu Phe Thr
    1745            1750            1755

Asp Gly Ser Phe Thr Gln Pro Leu Tyr Arg Gly Glu Leu Asn Glu
    1760            1765            1770

His Leu Gly Leu Leu Gly Pro Tyr Ile Arg Ala Glu Val Glu Asp
    1775            1780            1785

Asn Ile Met Val Thr Phe Arg Asn Gln Ala Ser Arg Pro Tyr Ser
    1790            1795            1800

Phe Tyr Ser Ser Leu Ile Ser Tyr Glu Glu Asp Gln Arg Gln Gly
    1805            1810            1815

Ala Glu Pro Arg Lys Asn Phe Val Lys Pro Asn Glu Thr Lys Thr
    1820            1825            1830

Tyr Phe Trp Lys Val Gln His His Met Ala Pro Thr Lys Asp Glu
    1835            1840            1845

Phe Asp Cys Lys Ala Trp Ala Tyr Phe Ser Asp Val Asp Leu Glu
    1850            1855            1860

Lys Asp Val His Ser Gly Leu Ile Gly Pro Leu Leu Val Cys His
    1865            1870            1875

Thr Asn Thr Leu Asn Pro Ala His Gly Arg Gln Val Thr Val Gln
    1880            1885            1890

Glu Phe Ala Leu Phe Phe Thr Ile Phe Asp Glu Thr Lys Ser Trp
    1895            1900            1905

Tyr Phe Thr Glu Asn Met Glu Arg Asn Cys Arg Ala Pro Cys Asn
    1910            1915            1920

Ile Gln Met Glu Asp Pro Thr Phe Lys Glu Asn Tyr Arg Phe His
    1925            1930            1935

Ala Ile Asn Gly Tyr Ile Met Asp Thr Leu Pro Gly Leu Val Met
    1940            1945            1950

Ala Gln Asp Gln Arg Ile Arg Trp Tyr Leu Leu Ser Met Gly Ser
    1955            1960            1965

Asn Glu Asn Ile His Ser Ile His Phe Ser Gly His Val Phe Thr
    1970            1975            1980

Val Arg Lys Lys Glu Glu Tyr Lys Met Ala Leu Tyr Asn Leu Tyr
    1985            1990            1995

Pro Gly Val Phe Glu Thr Val Glu Met Leu Pro Ser Lys Ala Gly
    2000            2005            2010

Ile Trp Arg Val Glu Cys Leu Ile Gly Glu His Leu His Ala Gly
    2015            2020            2025

Met Ser Thr Leu Phe Leu Val Tyr Ser Asn Lys Cys Gln Thr Pro
    2030            2035            2040

Leu Gly Met Ala Ser Gly His Ile Arg Asp Phe Gln Ile Thr Ala
    2045            2050            2055

Ser Gly Gln Tyr Gly Gln Trp Ala Pro Lys Leu Ala Arg Leu His
    2060            2065            2070

Tyr Ser Gly Ser Ile Asn Ala Trp Ser Thr Lys Glu Pro Phe Ser
    2075            2080            2085

Trp Ile Lys Val Asp Leu Leu Ala Pro Met Ile Ile His Gly Ile
    2090            2095            2100
```

```
Lys Thr Gln Gly Ala Arg Gln  Lys Phe Ser Ser Leu  Tyr Ile Ser
2105                 2110                 2115

Gln Phe Ile Ile Met Tyr Ser  Leu Asp Gly Lys Lys  Trp Gln Thr
2120                 2125                 2130

Tyr Arg Gly Asn Ser Thr Gly  Thr Leu Met Val Phe  Phe Gly Asn
2135                 2140                 2145

Val Asp Ser Ser Gly Ile Lys  His Asn Ile Phe Asn  Pro Pro Ile
2150                 2155                 2160

Ile Ala Arg Tyr Ile Arg Leu  His Pro Thr His Tyr  Ser Ile Arg
2165                 2170                 2175

Ser Thr Leu Arg Met Glu Leu  Met Gly Cys Asp Leu  Asn Ser Cys
2180                 2185                 2190

Ser Met Pro Leu Gly Met Glu  Ser Lys Ala Ile Ser  Asp Ala Gln
2195                 2200                 2205

Ile Thr Ala Ser Ser Tyr Phe  Thr Asn Met Phe Ala  Thr Trp Ser
2210                 2215                 2220

Pro Ser Lys Ala Arg Leu His  Leu Gln Gly Arg Ser  Asn Ala Trp
2225                 2230                 2235

Arg Pro Gln Val Asn Asn Pro  Lys Glu Trp Leu Gln  Val Asp Phe
2240                 2245                 2250

Gln Lys Thr Met Lys Val Thr  Gly Val Thr Thr Gln  Gly Val Lys
2255                 2260                 2265

Ser Leu Leu Thr Ser Met Tyr  Val Lys Glu Phe Leu  Ile Ser Ser
2270                 2275                 2280

Ser Gln Asp Gly His Gln Trp  Thr Leu Phe Phe Gln  Asn Gly Lys
2285                 2290                 2295

Val Lys Val Phe Gln Gly Asn  Gln Asp Ser Phe Thr  Pro Val Val
2300                 2305                 2310

Asn Ser Leu Asp Pro Pro Leu  Leu Thr Arg Tyr Leu  Arg Ile His
2315                 2320                 2325

Pro Gln Ser Trp Val His Gln  Ile Ala Leu Arg Met  Glu Val Leu
2330                 2335                 2340

Gly Cys Glu Ala Gln Asp Leu  Tyr Asp Lys Thr His  Thr Cys Pro
2345                 2350                 2355

Pro Cys Pro Ala Pro Glu Leu  Leu Gly Gly Pro Ser  Val Phe Leu
2360                 2365                 2370

Phe Pro Pro Lys Pro Lys Asp  Thr Leu Met Ile Ser  Arg Thr Pro
2375                 2380                 2385

Glu Val Thr Cys Val Val Val  Asp Val Ser His Glu  Asp Pro Glu
2390                 2395                 2400

Val Lys Phe Asn Trp Tyr Val  Asp Gly Val Glu Val  His Asn Ala
2405                 2410                 2415

Lys Thr Lys Pro Arg Glu Glu  Gln Tyr Asn Ser Thr  Tyr Arg Val
2420                 2425                 2430

Val Ser Val Leu Thr Val Leu  His Gln Asp Trp Leu  Asn Gly Lys
2435                 2440                 2445

Glu Tyr Lys Cys Lys Val Ser  Asn Lys Ala Leu Pro  Ala Pro Ile
2450                 2455                 2460

Glu Lys Thr Ile Ser Lys Ala  Lys Gly Gln Pro Arg  Glu Pro Gln
2465                 2470                 2475

Val Tyr Thr Leu Pro Pro Ser  Arg Asp Glu Leu Thr  Lys Asn Gln
2480                 2485                 2490
```

-continued

| | | | | | | | | | | | |
|---|---|---|---|---|---|---|---|---|---|---|---|
| Val | Ser 2495 | Leu | Thr | Cys | Leu | Val 2500 | Lys | Gly | Phe | Tyr | Pro 2505 | Ser | Asp | Ile |
| Ala | Val 2510 | Glu | Trp | Glu | Ser | Asn 2515 | Gly | Gln | Pro | Glu | Asn 2520 | Asn | Tyr | Lys |
| Thr | Thr 2525 | Pro | Pro | Val | Leu | Asp 2530 | Ser | Asp | Gly | Ser | Phe 2535 | Phe | Leu | Tyr |
| Ser | Lys 2540 | Leu | Thr | Val | Asp | Lys 2545 | Ser | Arg | Trp | Gln | Gln 2550 | Gly | Asn | Val |
| Phe | Ser 2555 | Cys | Ser | Val | Met | His 2560 | Glu | Ala | Leu | His | Asn 2565 | His | Tyr | Thr |
| Gln | Lys 2570 | Ser | Leu | Ser | Leu | Ser 2575 | Pro | Gly | Lys | | | | | |

METHODS OF REDUCING IMMUNOGENICITY AGAINST FACTOR VIII IN INDIVIDUALS UNDERGOING FACTOR VIII THERAPY

RELATED APPLICATIONS

This application is a continuation of U.S. patent application Ser. No. 14/371,931, filed Jul. 11, 2014, which is a 35 U.S.C. § 371 filing of International Patent Application No. PCT/US2013/021332, filed Jan. 12, 2013, which claims priority to U.S. Provisional Patent Application Ser. No. 61/668,961, filed Jul. 6, 2012, and 61/586,103, filed Jan. 12, 2012, the entire disclosures of which are hereby incorporated herein by reference.

FIELD OF THE DISCLOSURE

The present disclosure relates generally to the field of therapeutics for hemostatic disorders.

BACKGROUND ART

Hemophilia A is an X-linked bleeding disorder caused by mutations and/or deletions in the Factor VIII (FVIII) gene resulting in a deficiency of FVIII activity (Peyvandi, F. et al. *Haemophilia* 12:82-89 (2006). The disease is characterized by spontaneous hemorrhage and excessive bleeding after trauma. Over time, the repeated bleeding into muscles and joints, which often begins in early childhood, results in hemophilic arthropathy and irreversible joint damage. This damage is progressive and can lead to severely limited mobility of joints, muscle atrophy and chronic pain (Rodriguez-Merchan, E. C., *Semin. Thromb. Hemost.* 29:87-96 (2003), which is herein incorporated by reference in its entirety).

The A2 domain is necessary for the procoagulant activity of the FVIII molecule. Studies show that porcine FVIII has six-fold greater procoagulant activity than human FVIII (Lollar & Parker, *J. Biol. Chem.* 266:12481-12486 (1991)), and that the difference in coagulant activity between human and porcine FVIII appears to be based on a difference in amino acid sequence between one or more residues in the human and porcine A2 domains (Lollar, P., et al., *J. Biol. Chem.* 267:23652-23657 (1992)), incorporated herein by reference in its entirety.

Treatment of hemophilia A is by replacement therapy targeting restoration of FVIII activity to 1 to 5% of normal levels to prevent spontaneous bleeding (Mannucci, P. M., et al., *N. Engl. J. Med.* 344:1773-1779 (2001), which is herein incorporated by reference in its entirety). e.g.

Plasma-derived FVIII (pdFVIII) and recombinant human FVIII (rFVIII) products are utilized for treatment (on-demand therapy) and prevention (prophylaxis therapy) of bleeding episodes. rFVIII was developed to reduce the risk of blood-borne pathogen transmission following the widespread contamination of plasma products with HIV and hepatitis viruses, and to secure an adequate supply of FVIII product. However, hemostatic protection with current FVIII products is temporally limited due to a short half-life ($t_{1/2}$) of approximately 8-12 hours, requiring prophylactic injections three times per week or every other day for most patients in order to maintain FVIII levels above 1%, a level that has been established as protective against most spontaneous bleeding episodes. Manco-Johnson et al., *New Engl J Med.* 357(6):535-44 (2007).

Many studies have shown that, even at high doses, on-demand therapy is not effective in preventing arthropathy. Aledort L. et al., *J Intern Med.* 236:391-399 (1994); Petrini P. et al., *Am J Pediatr Hematol Oncol.* 13:280-287 (1991). The benefits of prophylactic therapy have been demonstrated in numerous clinical studies. Aznar J. et al., *Haemophilia* 6(3):170-176 (2000), Feldman B. et al., *J Thromb Haemost.* 4:1228-1236 (2006), Kreuz W. et al., *Haemophilia* 4:413-417 (1998), Liesner R. et al., *B J Haem.* 92:973-978 (1996), Ljung R., *Haemophilia.* 4(4):409-412 (1998), Lofquist T, et al., *J Intern Med* 241:395-400 (1997), Nilsson I, et al., *B. J Int Med* 232:25-32 (1992), Risebrough N. et al., *Haemophilia.* 14:743-752 (2008), Van Den Berg H. et al., *Haemophilia* 9 (Suppl. 1):27-31 (2003), Van Den Berg H. et al., *Haematologica* 89(6):645-650 (2004) and Manco-Johnson et al., supra, established that children started on primary prophylaxis after their first joint bleed had significantly fewer bleeds and less joint damage than children treated on-demand.

Compared to on-demand treatment, prophylactic therapy also decreases disability, hospitalization rate, and time lost from school or work; Aznar J. et al., *Haenzophilia* 6(3):170-176 (2000), Molho P. et al., *Haenzophilia* 6(1):23-32 (2000) and improves quality of life for patients and their families. Coppola A. et al., *Blood Transfus.* 6(2): 4-11 (2008). However, prophylactic therapy often requires use of central venous access devices in children, and their attendant risks of infection, sepsis, and thrombosis. In addition, despite the benefits, acceptance of and compliance with prophylaxis decreases with age, in part because of inconvenience and invasiveness. Geraghty S. et al., *Haemophilia* 12:75-81 (2006), Hacker M. et al., *Haemophilia* 7(4):392-396 (2001). Thus, an rFVIII product with a prolonged plasma $t_{1/2}$ would potentially be of benefit. Lillicrap D., *Current Opinion in Hematology* 17:393-397 (2010).

Reduced mortality, prevention of joint damage, and improved quality of life have been important achievements due to the development of pdFVIII and rFVIII. Prolonged protection from bleeding would represent another key advancement in the treatment of hemophilia A patients. However, to date, no products that allow for prolonged hemostatic protection have been developed. Therefore, there remains a need for improved methods of treating hemophilia due to FVIII deficiency that are more tolerable, longer lasting, and more effective than current therapies.

In addition, 15-30% of previously untreated patients develop neutralizing anti-FVIII antibodies (inhibitors) after transfusion with FVIII products. Various techniques for avoiding such immune responses have been considered. These techniques include high-dose tolerance protocols, use of peptide decoys mimicking the anti-FVIII antibody, bypassing immune recognition with human/porcine FVIII hybrid molecules, neutralizing FVIII-reactive CD4 T-cells with anticlonotypic antibodies, using universal CD4 epitopes, and blocking costimulation of CTLA-4-Ig or anti-CD40L. See, e.g., Lei et al., *Transfusion Medicine* 105:4865-4870 (2005). Presentation of FVIII by immune cells in order to induce tolerance has also been studied. For example, Lei et al. found that presentation of FVIII domains on an Ig backbone in B cells prevented or decreased antibodies. Id. In addition, Qadura et al. found that tolerogenic presentation of FVIII using immature dendritic cells may reduce immunogenicity. *Journal of Thrombosis and Haemostatis* 6: 2095-2104 (2008). However, such methods are costly, complicated (e.g., by requiring co-administration of other therapeutics in combination with FVIII or administration of whole cells instead of relatively simple proteins), likely to result in unwanted side-effects, and/or inefficient. Accordingly, there remains a need for simple methods of treating hemophilia due to FVIII deficiency that are effective in patients that develop inhibitory responses.

BRIEF SUMMARY

The present disclosure provides methods of administering Factor VIII (FVIII) that improve immune tolerance. The methods comprise administering a chimeric polypeptide comprising a FVIII portion and an Fc portion (rFVIIIFc) to a subject at risk of developing an inhibitory FVIII immune response. In some embodiments, the subject would develop an inhibitory immune response if administered an equivalent dose of a polypeptide consisting of the F VIII portion. In some embodiments, the subject has developed an inhibitory immune response or an inhibitory FVIII immune response. The administration of a chimeric polypeptide comprising a FVIII portion and an Fc portion can be sufficient to treat a bleeding condition and to induce immune tolerance to FVIII. The administration can be prophylactic. In some embodiments, the administration decreases the incidence of spontaneous bleeding or prevents bleeding.

The immune response can comprise inhibitory anti-FVIII antibodies. The antibody titer is at least 0.6 Bethesda Units (BU), at least 1.0 BU, or at least 5.0 BU. The immune response can also comprise a cell-mediated immune response, for example, the release of a cytokine. The cytokine can be IL-12, IL-4, or TNF-α, for example. The immune response can also result in clinical symptoms such as increased bleeding tendency, high FVIII consumption, lack of response to FVIII therapy, decreased efficacy of FVIII therapy, and/or shortened half-life of F VIII.

Subjects at risk of developing an inhibitory immune response include those with a mutation, deletion, or rearrangement in a FVIII gene. In some embodiments, the subject does not produce a FVIII protein. In some embodiments, the subject has severe hemophilia. In some embodiments, the subject has a relative (e.g., a parent, cousin, aunt, uncle, grandparent, child, or grandchild) that has developed an inhibitory immune response to FVIII or another therapeutic protein. In some embodiments, the subject is concurrently or was previously receiving a therapy that increases immune function when the FVIII is administered. In some embodiments the subject is receiving interferon therapy or anti-viral therapy in combination with FVIII. In some embodiments, the subject at risk of developing an inhibitory immune response has a genetic polymorphism associated with an increased cytokine level, such as increased TNF-α or increased IL10. In some embodiments, the subject at risk of developing an inhibitory immune response has a TNF-α-308G>A polymorphism or allele 134 of the IL10G microsatellite.

In some embodiments, the subject at risk for developing an inhibitory FVIII immune response has not been previously exposed to FVIII. In some embodiments, the subject at risk for developing an inhibitory FVIII immune response has been exposed to FVIII. In some embodiments, the subject at risk for developing an inhibitory FVIII immune response has had less than 150, less than 50, or less than 20 FVIII exposure days.

In some embodiments, the subject at risk for developing an inhibitory FVIII immune response has not previously developed an immune response to FVIII or another therapeutic protein. In some embodiments, the subject at risk for developing an inhibitory FVIII immune response has previously developed an immune response to FVIII (pdFVIII or rFVIII) or another therapeutic protein. In some embodiments, the subject at risk for developing an inhibitory FVIII immune response has previously developed an immune response to a FVIII product such as ADVATE®, RECOMBINATE®, KOGENATE FS®, HELIXATE FS®, XYNTHA®/REFACTO AB®, HEMOFIL-M®, MONARC-M®, MONOCLATE-P®, HUMATE-P®, ALPHANATE®, KOATE-DVI®, or HYATE:C®. In some embodiments, the FVIII products is a full length FVIII, a mature FVIII, or a B-domain deleted FVIII.

The methods of administering FVIII provided herein can induce immune tolerance. In some embodiments, the administration reduces the number of anti-FVIII antibodies in the subject, the titer of anti-FVIII antibodies in the subject and/or the level of a cytokine (e.g., IL-12, IL-4, or TNF) in the subject compared to the number, titer, or level prior to administration. In some embodiments, the administration reduces the number of anti-FVIII antibodies in the subject, the titer of anti-FVIII antibodies in the subject and/or the level of a cytokine (e.g., IL-12, IL-4, or a TNF) in the subject compared to the number, titer, or level that resulted from a previous treatment with a polypeptide consisting of a FVIII polypeptide. In some embodiments, the administration reduces the number of anti-FVIII antibodies in the subject, the titer of anti-FVIII antibodies in the subject and/or the level of a cytokine (e.g., IL-12, IL-4, or TNF) in the subject compared to the number, titer, or level that would result from administration of polypeptide consisting of a FVIII polypeptide to the subject.

The methods comprise administration of a chimeric polypeptide comprising a FVIII portion and an Fc portion. The FVIII portion can be human FVIII, full-length FVIII, or FVIII containing a full or partial deletion of the B domain. The FVIII portion can be a biologically active polypeptide, e.g., a FVIII polypeptide with coagulation activity. The FVIII portion can be at least 90% identical, 95% identical, or identical to a FVIII amino acid sequence shown in TABLE 2 without a signal sequence (amino acids 20 to 1457 of SEQ ID NO:2; amino acids 20 to 2351 of SEQ ID NO:6). The FVIII portion can also be at least 90% identical, 95% identical, or identical to a FVIII amino acid sequence shown in TABLE 2 with a signal sequence (amino acids 1 to 1457 of SEQ ID NO:2 or amino acids 1 to 2351 of SEQ ID NO:6). The Fc portion can be identical to the Fc amino acid sequence shown in TABLE 2 (amino acids 1458 to 1684 of SEQ ID NO:2 or amino acids 2352 to 2578 of SEQ ID NO:6).

The chimeric polypeptide can be in a form of a hybrid comprising a second polypeptide in association with the chimeric polypeptide. The second polypeptide can consist essentially of or consist of an Fc.

In some embodiments, the methods comprise administration of a chimeric polypeptide at a particular dose. The dose can be, for example, a dose of 10-100 IU/kg, a dose of 10-20, 20-30, 30-40, 40-50, 50-60, 60-70, 70-80, 80-90, or 90-100 IU/kg, or a dose of 10, 15, 20, 25, 30, 35, 40, 45, 50, 55, 60, 65, 70, 75, 80, 85, 90, 95, or 100 IU/kg.

In some embodiments, the chimeric polypeptide is administered to a subject with a bleeding condition. The bleeding condition can be, for example, a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. In some embodiments, the bleeding coagulation disorder is hemophilia A.

The present disclosure also provides a method of administering a clotting factor to a subject at risk of developing an inhibitory immune response to the clotting factor comprising administering to the subject a chimeric polypeptide comprising a clotting factor portion and an Fc portion. Also provided is a method of inducing immune tolerance to a clotting factor in a subject, wherein the subject is a fetus, the method comprising administering to the mother of the fetus a polypeptide comprising a chimeric polypeptide comprising a clotting factor portion and an Fc portion. In some embodiments, the clotting factor is FVII zymogen, activated FVII, activatable FVII, or FIX.

In some embodiments, the administration of the chimeric polypeptide decreases the incidence of spontaneous bleeding or prevents bleeding.

The present disclosure also provides a method of inducing immune tolerance to FVIII in a subject in need thereof, comprising administering to the subject a chimeric polypeptide comprising a FVIII portion and an Fc portion. In some embodiments, the subject is at risk of developing an inhibitory FVIII immune response. In other embodiments, the subject has developed an inhibitory Factor VIII immune response.

Also provided is method of preventing or inhibiting development of an inhibitor to FVIII, the method comprising administering to a subject in need of immune tolerance a chimeric polypeptide comprising FVIII portion and an Fc portion.

The present disclosure also provides a method of inducing immune tolerance to a clotting factor in a subject in need thereof, comprising administering to the subject a chimeric polypeptide comprising a clotting factor portion and an Fc portion. In some embodiments, the subject is at risk of developing an inhibitory clotting factor immune response. In other embodiments, the subject has developed an inhibitory clotting factor immune response. In some embodiments, the clotting factor portion comprises Factor VII, Factor IX or Von Willebrand factor.

Also provided is method of preventing or inhibiting development of an inhibitor to a clotting factor comprising administering to a subject in need thereof a chimeric polypeptide comprising a clotting factor portion and an Fc portion. In some embodiments, the clotting factor portion is Factor VII, Factor IX or Von Willebrand factor.

In some embodiments, the subject is a human and the method of administering FVIII is a method for treating a bleeding condition in said subject. In some embodiments, the bleeding condition is caused by a blood coagulation disorder. In some embodiments, the blood coagulation disorder is hemophilia or von Willebrand disease. In some embodiments, the blood coagulation disorder is hemophilia A. In some embodiments, the subject has a condition requiring prophylactic or on-demand treatment, such as a bleeding episode. In some embodiments, the subject is a patient who is suffering from a bleeding disorder or is expected to be in need of such treatment.

The present disclosure also provides a kit comprising: (a) a pharmaceutical composition comprising a chimeric polypeptide which comprises a clotting factor portion and an Fc portion or an FcRn binding partner portion and a pharmaceutically acceptable carrier, and (b) instructions to administer the composition to a subject in need of immune tolerance to the clotting factor. In some embodiments, the chimeric polypeptide comprises a FVIII portion, a FVII portion, or a FIX portion. In some embodiments, the chimeric polypeptide is a FVIII monomer dimer hybrid, a FVII monomer dimer hybrid, or a FIX monomer dimer hybrid. In some embodiments, the instructions further include at least one step to identify a subject in need of immune tolerance to the clotting factor. In some embodiments, the step to identify the subjects in need of immune tolerance includes one or more from the group consisting of: (a) identifying a subject having a mutation or deletion in the clotting factor gene; (b) identifying a subject having a rearrangement in the clotting factor gene; (c) identifying a subject having a relative who has previously developed an inhibitory immune response against the clotting factor; (d) identifying a subject receiving interferon therapy; (e) identifying a subject receiving antiviral therapy; (f) identifying a subject having a genetic mutation in a gene other than the gene encoding the clotting factor which is linked with an increased risk of developing an inhibitory immune response; and (g) two or more combinations thereof. In some embodiments, the genetic mutation in a gene other than the gene encoding the clotting factor comprises one or more mutations selected from the group consisting of: (a) a genetic polymorphism associated with increased TNF-α; (b) a genetic polymorphism associated with increased IL10; (c) a genetic polymorphism associated with decreased CTLA-4; (d) a mutation in DR15 or DQB0602 MHC Class II molecules; and (e) has two or more combinations thereof.

In some embodiments, the methods of the present disclosure further comprise measuring the level of an inhibitory immune response after the administration. In some embodiments, the methods of the present disclosure further comprise comparing the level of the inhibitory immune response after the administration with the level of the inhibitory immune response before the administration. In some embodiments, the inhibitory immune response is development of antibodies against FVIII. In some embodiments, the inhibitory immune response is cytokine secretion.

BRIEF DESCRIPTION OF THE DRAWINGS/FIGURES

Figure 3:
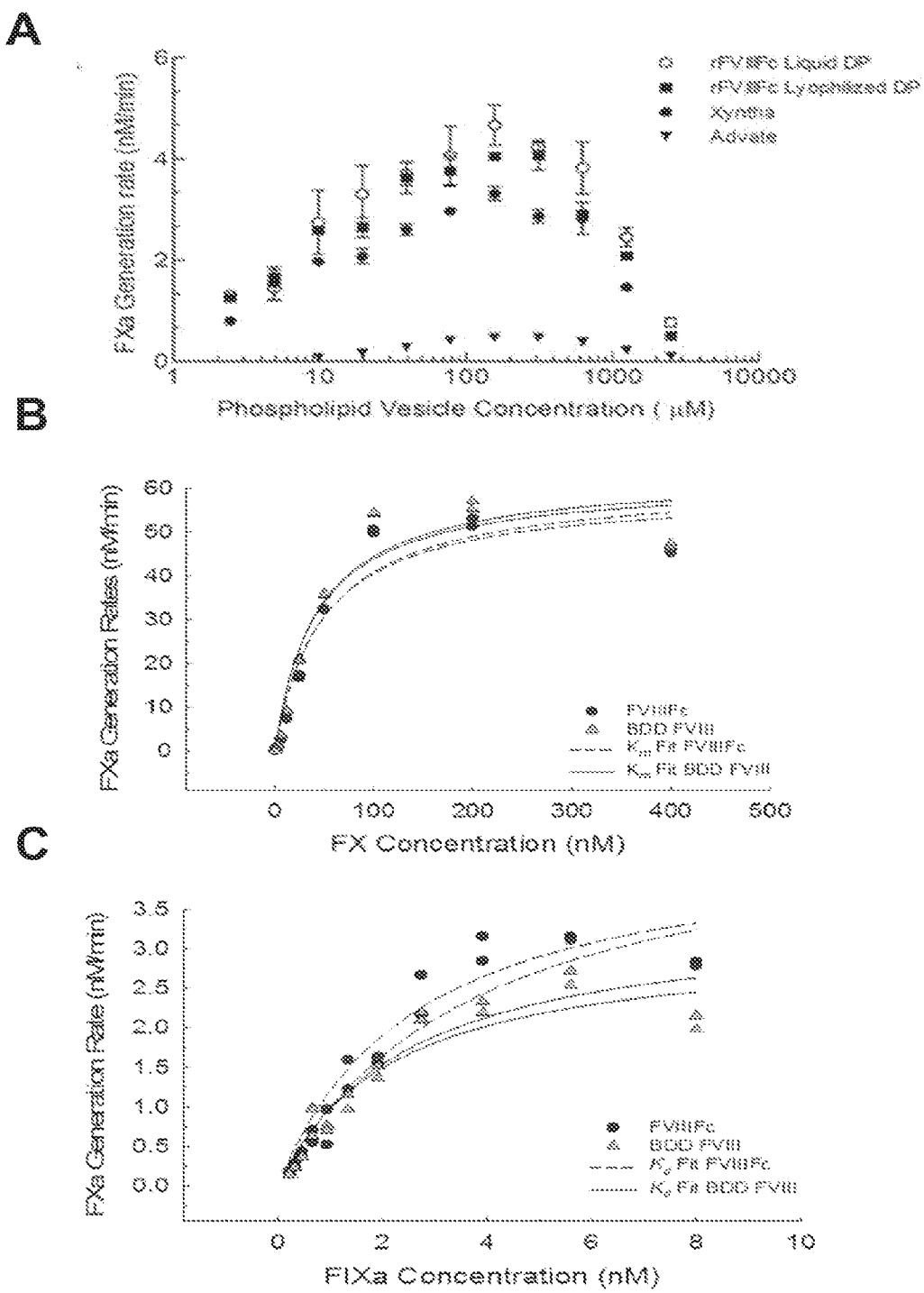

FIGS. 3A, 3B and 3C show the biochemical characterization of rFVIII-Fc. FIG. 3A shows the activation of Factor X (FX) as a function of phospholipid vesicle concentration. FIG. 3B shows the activation of FX as a function of FX concentration. FIG. 3C shows the activation of FX as a function of activated FIX (FIXa) concentration.

Figure 4:
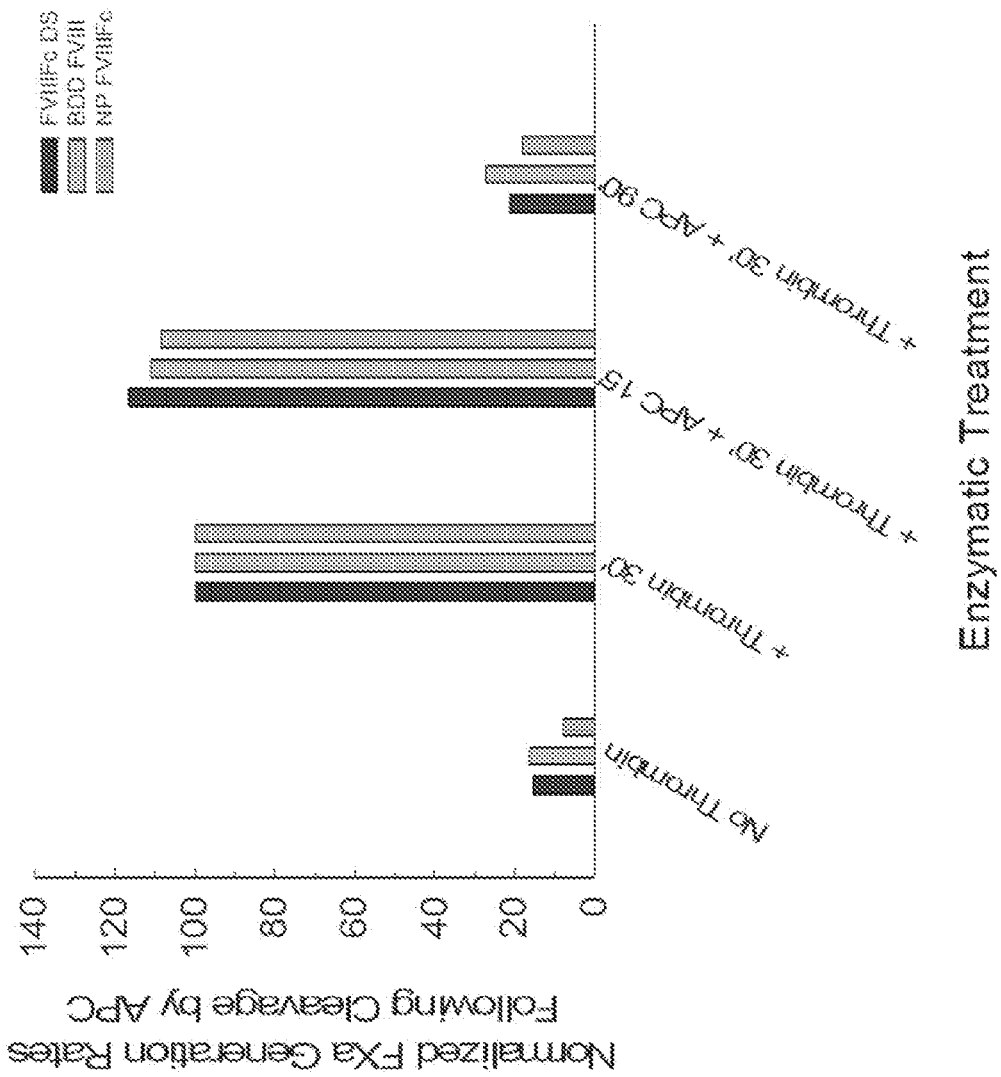

FIG. 4 shows the activation of FX following cleavage by activated Protein C.

FIGS. 5A, 5B, 5C and 5D show observed group mean FVIII activity (±SE) versus time profiles. Profiles are sorted by dose level, grouped by compound versus time. FIG. 5A corresponds to a one stage assay with a 25 IU/kg dose. FIG. 5B corresponds to a one stage assay with a 65 IU/kg dose. FIG. 5C corresponds to a chromogenic assay with a 25 IU/kg dose. FIG. 5D corresponds to a chromogenic assay with a 65 IU/kg dose.

Figure 6A:
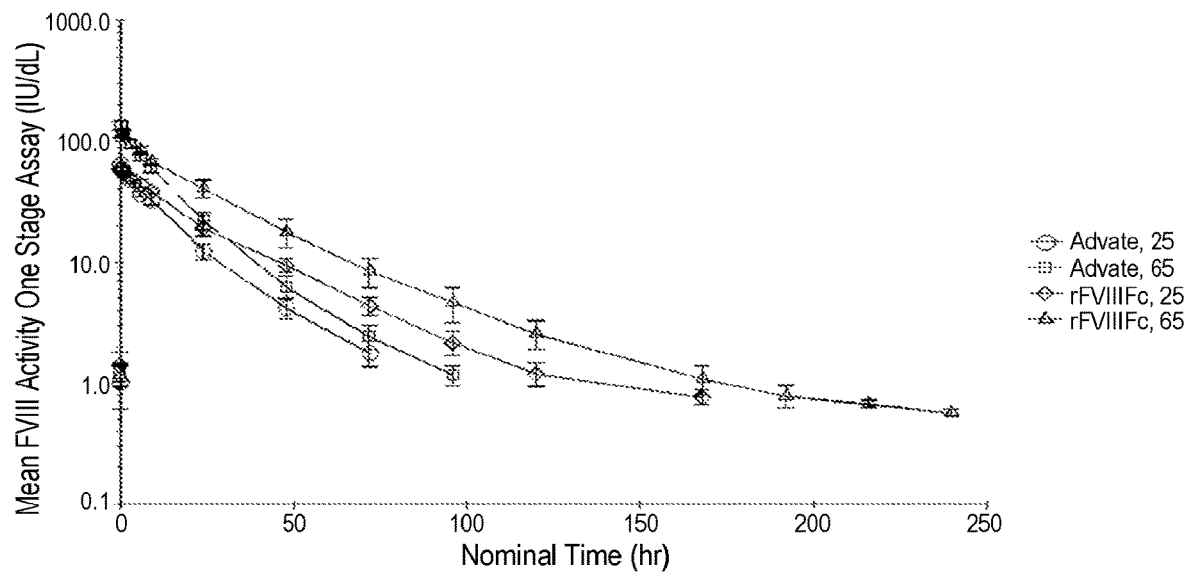
Figure 6B:
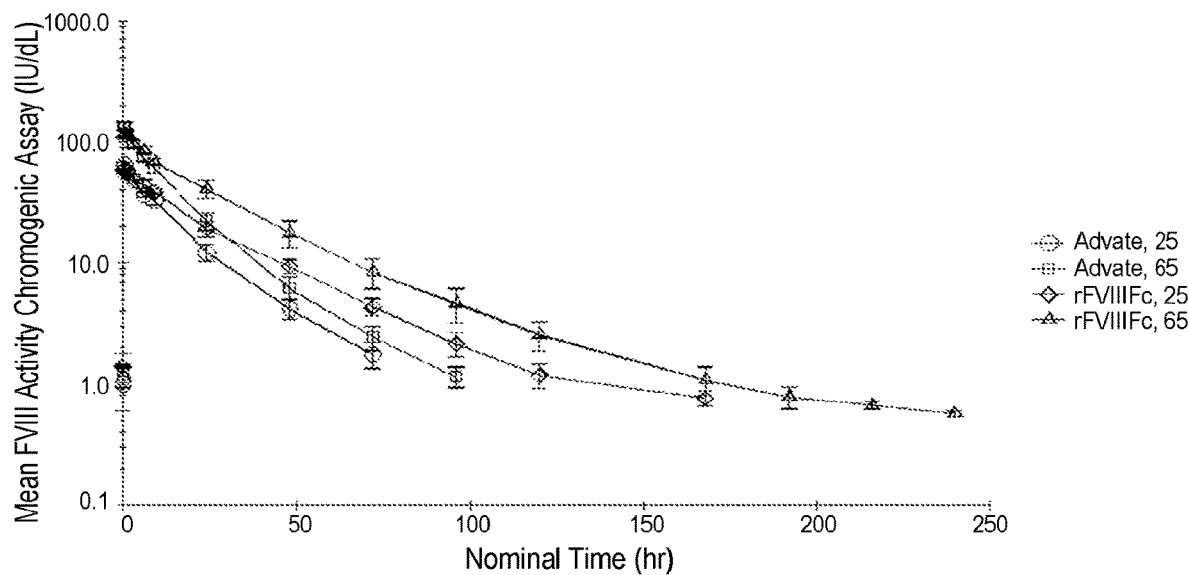

FIGS. 6A and 6B show observed group mean FVIII activity (±SE) versus time profiles, grouped by dose level and compound versus time. FIG. 6A corresponds to a one stage assay. FIG. 6B corresponds to a chromogenic assay.

FIGS. 7A, 7B and 7C show in vivo efficacy of single chain FVIIIFc (SC rFVIIIFc) in haemophilia A (HemA) mouse tail vein transection model. FIG. 7A shows the relationship between FVIII dose and protection. Single chain rFVIIIFc doses are shown as squares, and processed rFVIIIFc doses are shown as circles. FIG. 7B shows the percentage of survival following tail vein transection after administration of 4.6 µg/kg, 1.38 µg/kg, and 0.46 µg/kg of rFVIIIFc or SC rFVIIIFc. FIG. 7C shows the percentage of non-bleeders following tail vein transection, after administration of 4.6 µg/kg (black circle or inverted triangle), 1.38 µg/kg (triangle or diamond), and 0.46 µg/kg (square and gray circle) of rFVIIIFc or SC rFVIIIFc, respectively.

Figure 8:
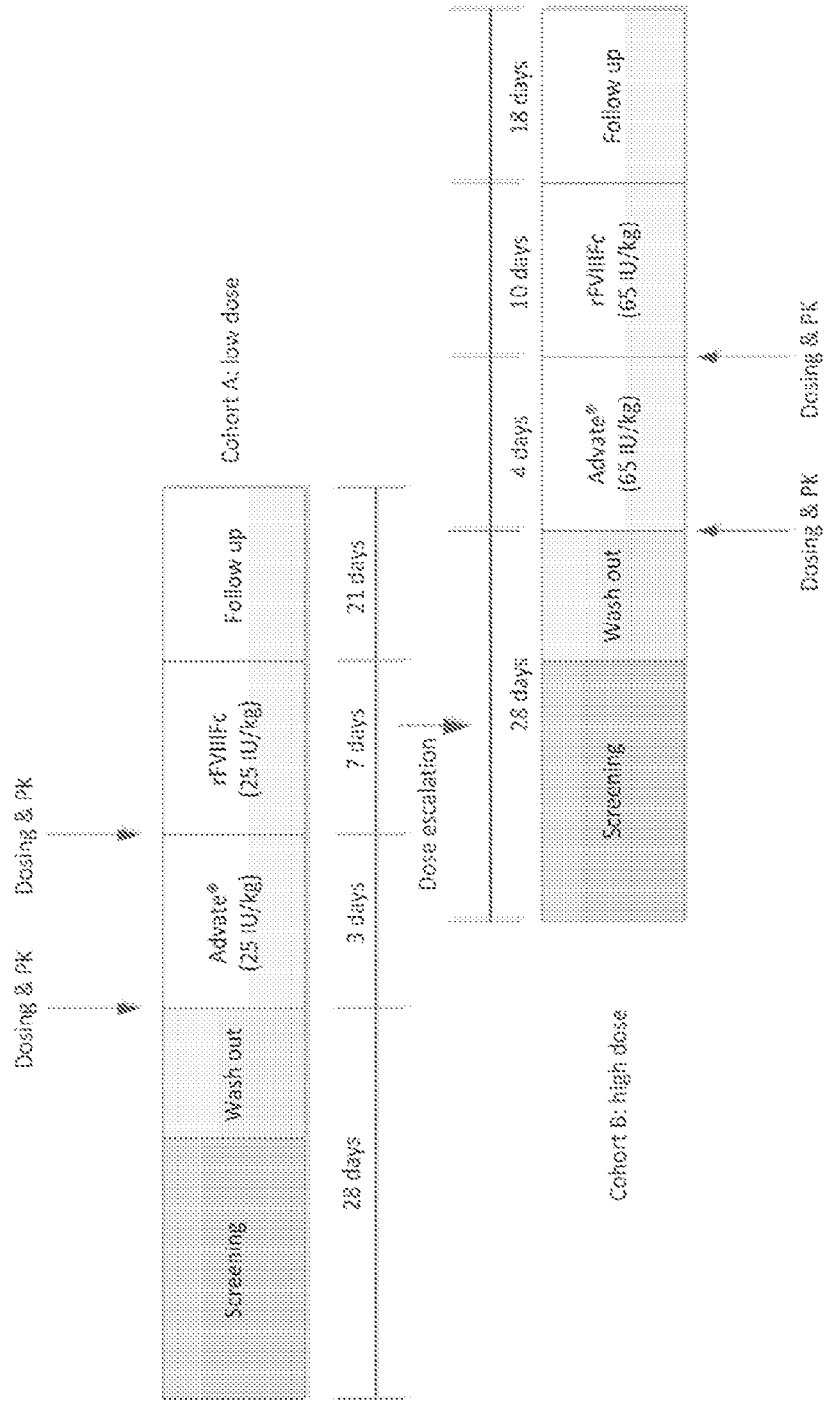

FIG. 8 depicts the study design of the phase 1/2a study, which was a dose-escalation, sequential design to evaluate the safety and PK of rFVIIIFc compared with ADVATE® after a single intravenous dose of either 25 IU/kg (low dose Cohort A) or 65 IU/kg (high dose Cohort B).

Figure 9:
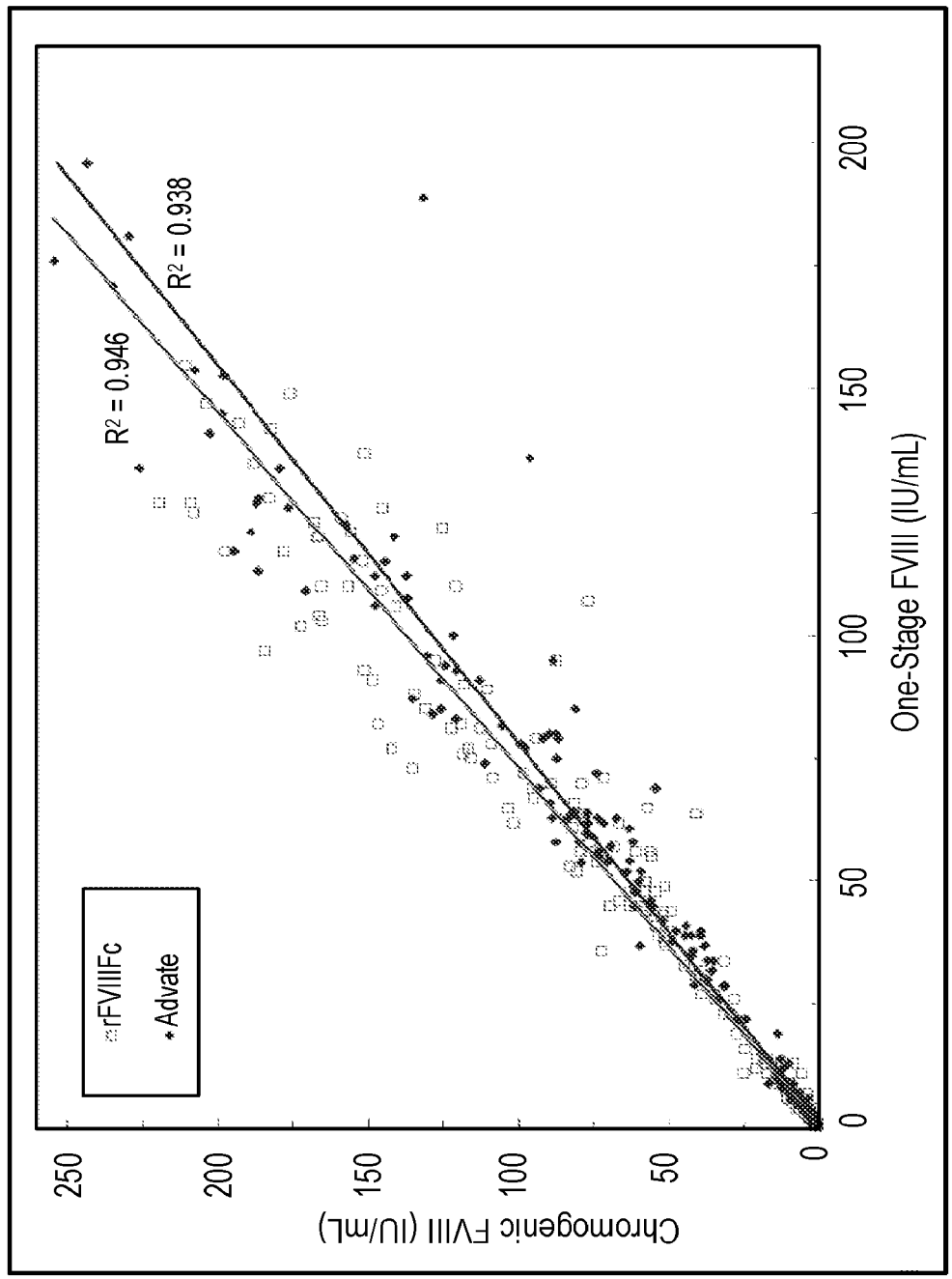

FIG. 9 shows the correlation of rFVIII Activity by one-stage (aPTT) and chromogenic assays. Results measure FVIII activity (IU/mL) following injection of ADVATE® (♦) and rFVIIIFc (□).

Figures 10A, 10B:
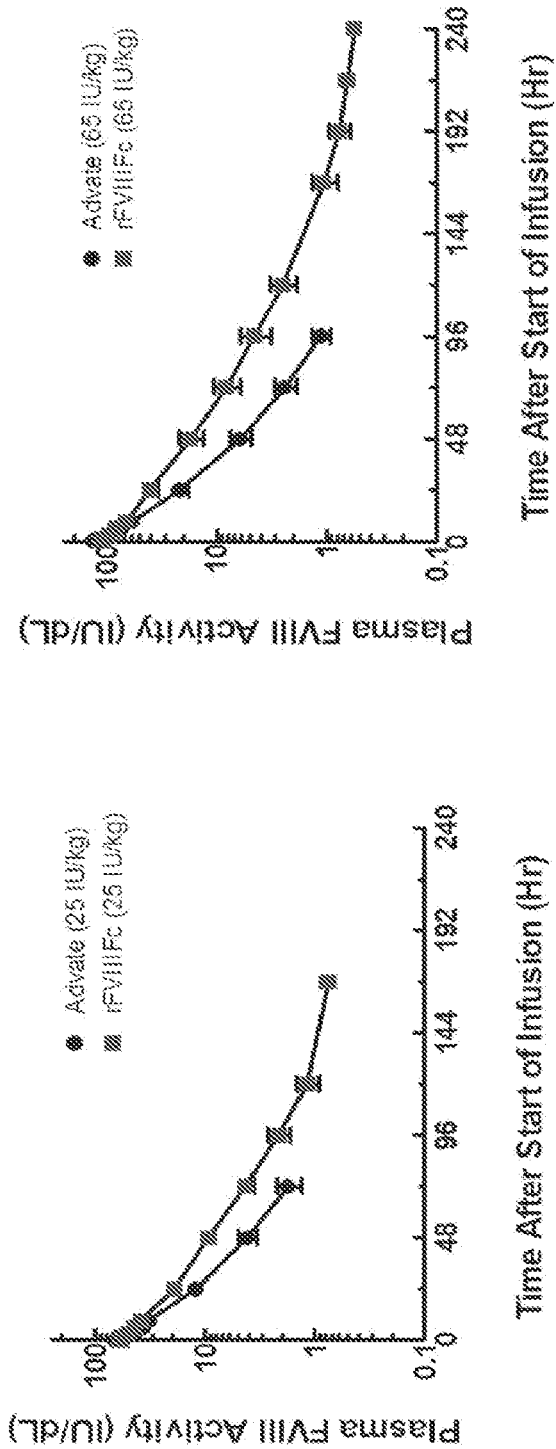

FIGS. 10A and 10B show group mean plasma FVIII activity pharmacokinetic profiles for low-dose and high-dose cohorts. The plasma FVIII activities (one stage aPTT assay) versus time curve after a single intravenous injection of rFVIIIFc or ADVATE® are shown for 25 IU/kg (low-dose cohort, n=6) (FIG. 10A); and 65 IU/kg (high dose cohort, n=10 [ADVATE®]; n=9 [rFVIIIFc]) (FIG. 10B). Results presented are group mean±standard error of mean (SEM).

Figure 11B:
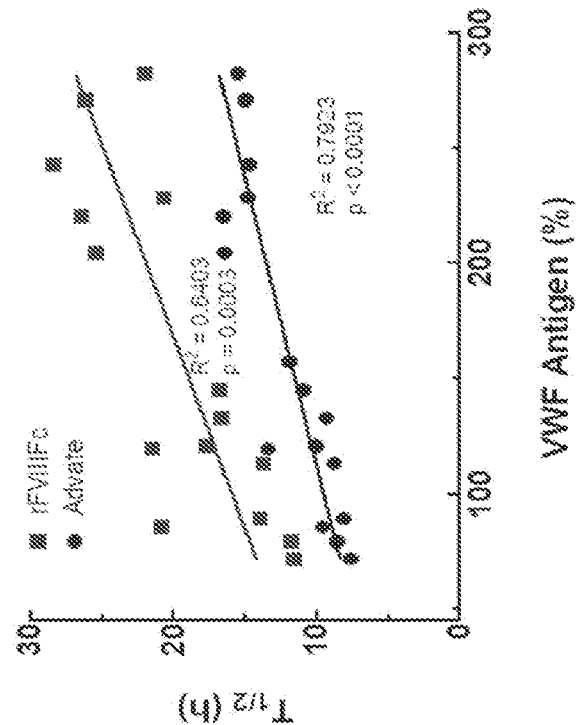
Figure 11A:
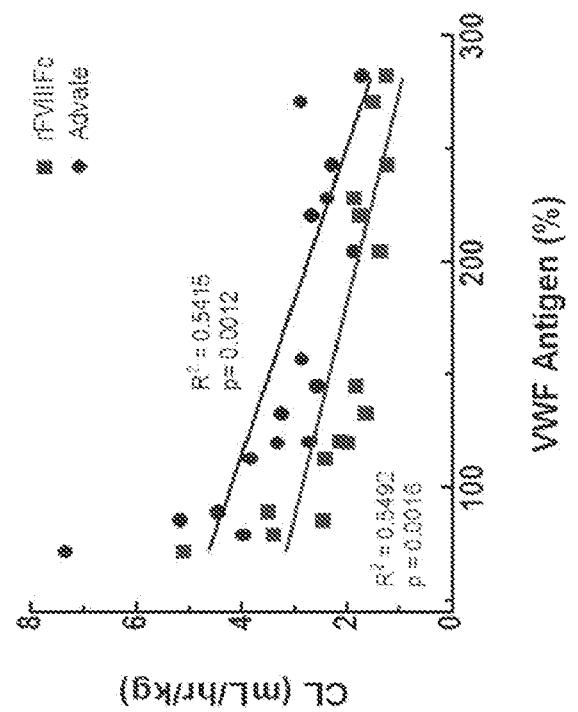

FIGS. 11A and 11B show the effect of VWF antigen levels on C1 and $t_{1/2}$ of FVIII activity after Injection of ADVATE® or rFVIIIFc. The correlation between VWF antigen levels and the weight-adjusted C1 of ADVATE® ($R^2$=0.5415 and p=0.0012) and rFVIIIFc ($R^2$=0.5492 and p=0.0016) (FIG. 11A); and the $t_{1/2}$ of ADVATE® ($R^2$=0.7923 and p<0.0001) and rFVIIIFc ($R^2$=0.6403 and p=0.0003) (FIG. 11B) are shown. Each dot represents an individual subject.

Figures 12A, 12B:
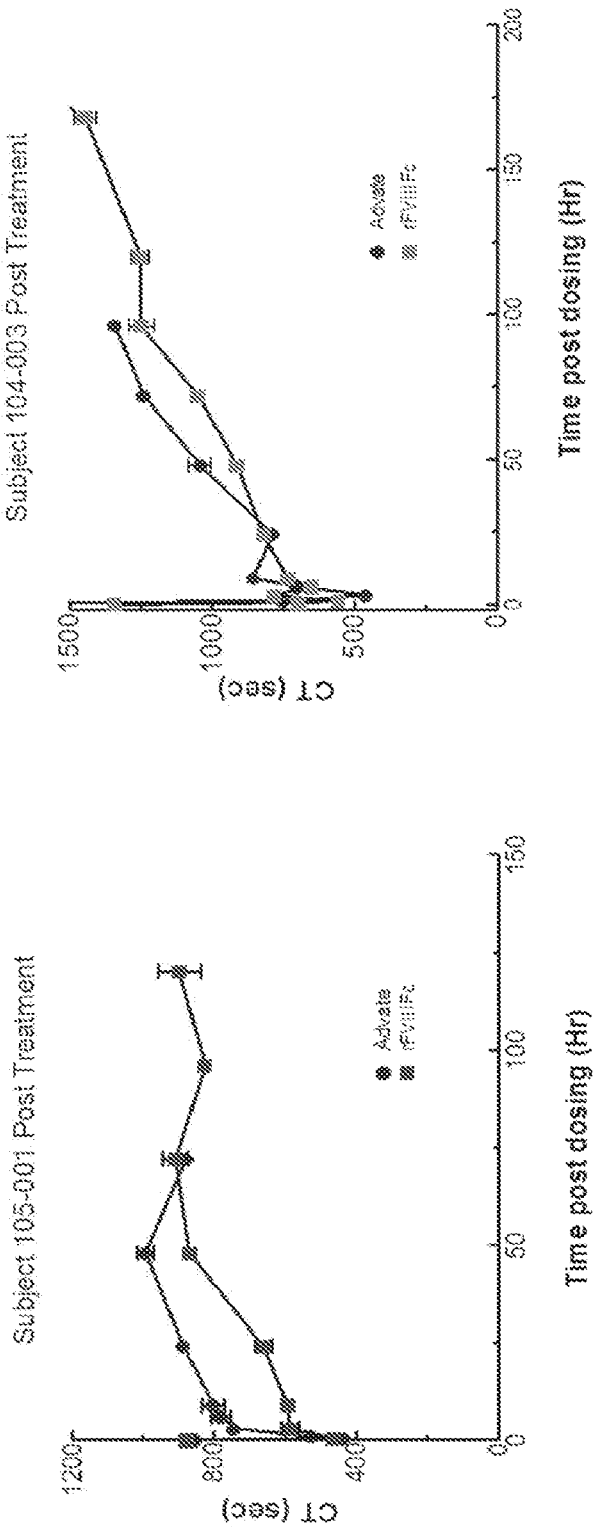
Figure 15:
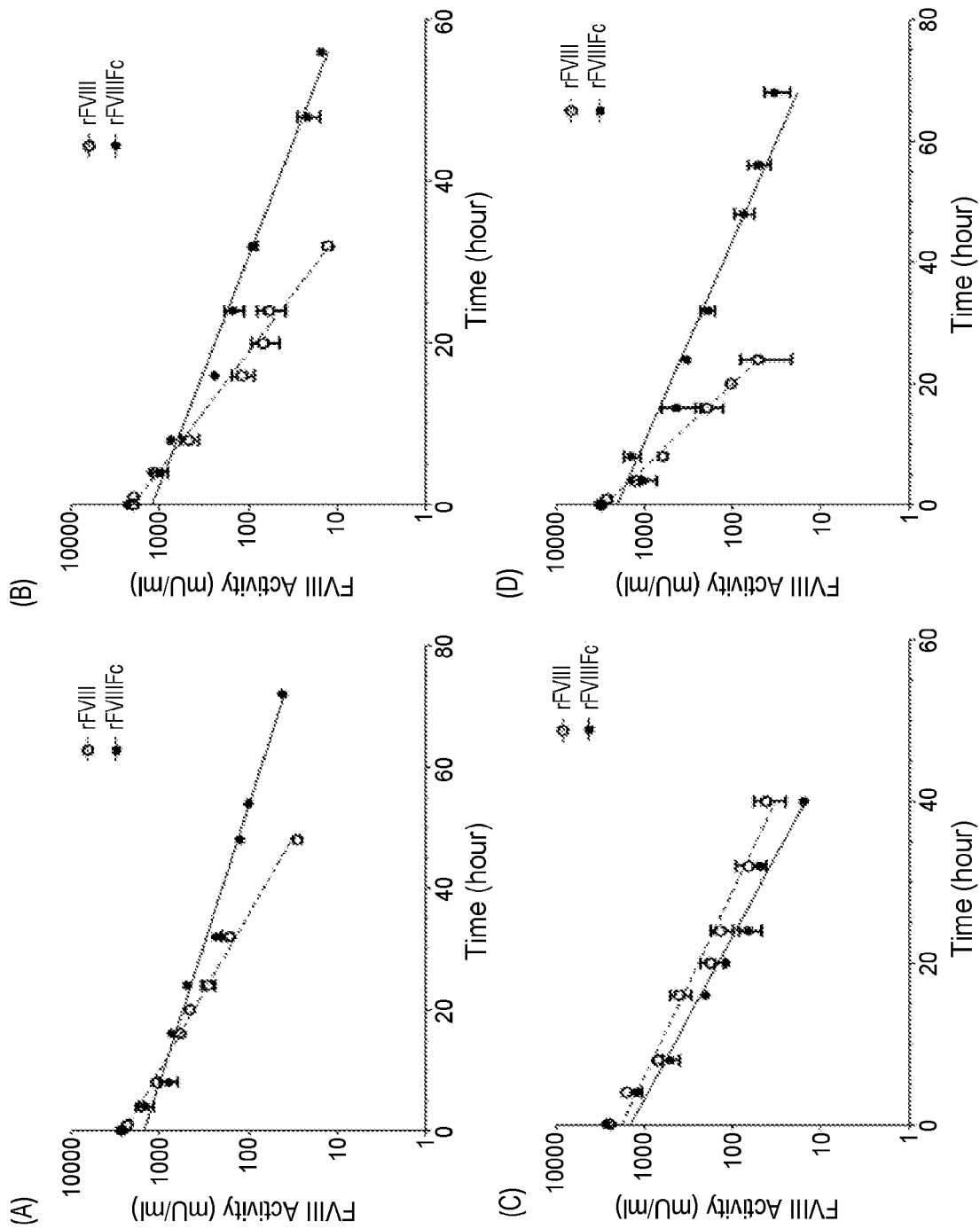

FIGS. 12A and 12B show ex vivo whole blood ROTEM® results for individual subjects after injection of ADVATE® or rFVIIIFc. Blood was sampled from subjects prior to and after treatment at doses of 25 IU/kg ADVATE® and rFVIIIFc (FIG. 12A); and 65 IU/kg ADVATE® and rFVIIIFc at specified time points (FIG. 12B). Clotting time was determined by NATEM initiated with Ca on a ROTEM® instrument. Results presented are mean±standard error of mean (SEM) from triplicate channel readings for each individual sample.

FIGS. 13A and 13B compare the activity of rFVIIIFc and SC rFVIIIFc in a thrombin generation assay (TGA). FIG. 13A compared endogenous thrombin potential (ETP) for rFVIIIFc, SC rFVIIIFc, fully processed rFVIIIFc and WHO standard FVIII. FIG. 13B compares peak thrombin for rFVIIIFc, SC rFVIIIFc, fully processed rFVIIIFc and WHO standard FVIII.

FIG. 14 shows a schematic representation of rFVIIIFc monomer. rFVIIIFc is a recombinant fusion of human B-domain deleted FVIII with Fc from human IgG1, with no intervening linker sequence.

FIGS. 15A, 15B, 15C and 15D show pharmacokinetic (PK) profiles comparing rFVIIIFc and rFVIII in HemA mice (FIG. 15A), C57BL/6 mice (FIG. 15B), FcRn KO mice (FIG. 15C), and human FcRn transgenic Tg32B mice (FIG. 15D) following a tail vein injection of 125 IU/kg. Results shown are Mean±SD from 4 mice per treatment at each time point. The PK parameter estimates are summarized in TABLE 12.

Figure 16:
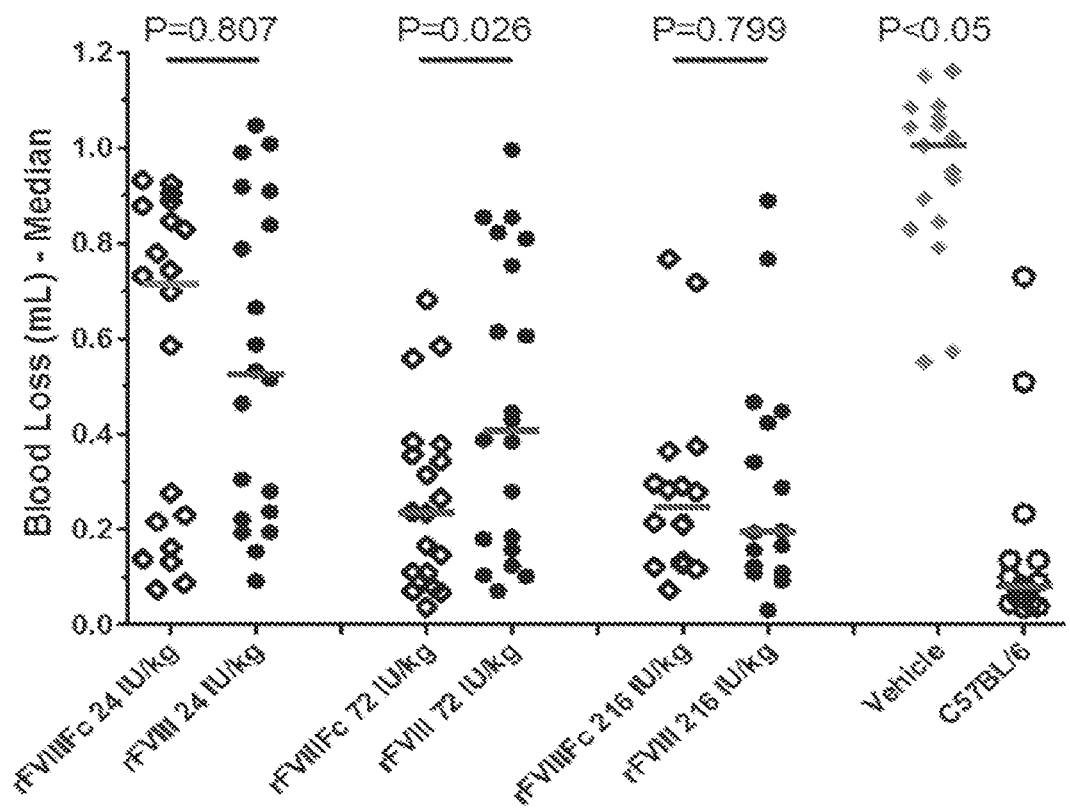

FIG. 16 compares the acute activity of rFVIIIFc and rFVIII in a HemA mice tail clip bleeding model. Male HemA mice received a tail vein injection of 24 IU/kg, 72 IU/kg, or 216 IU/kg of rFVIIIFc or rFVIII followed by a 10 mm tail clip 5 minutes post dosing. Results presented are individual and median blood loss over 30 minutes following the tail clip from 20 mice in each treatment group. P<0.05 for Vehicle vs. all other treatments, and P>0.05 for C57Bl/6 mice vs. HemA mice treated with 72 or 216 IU/kg of rFVIIIFc, or 216 IU/kg of rFVIII.

Figure 17:
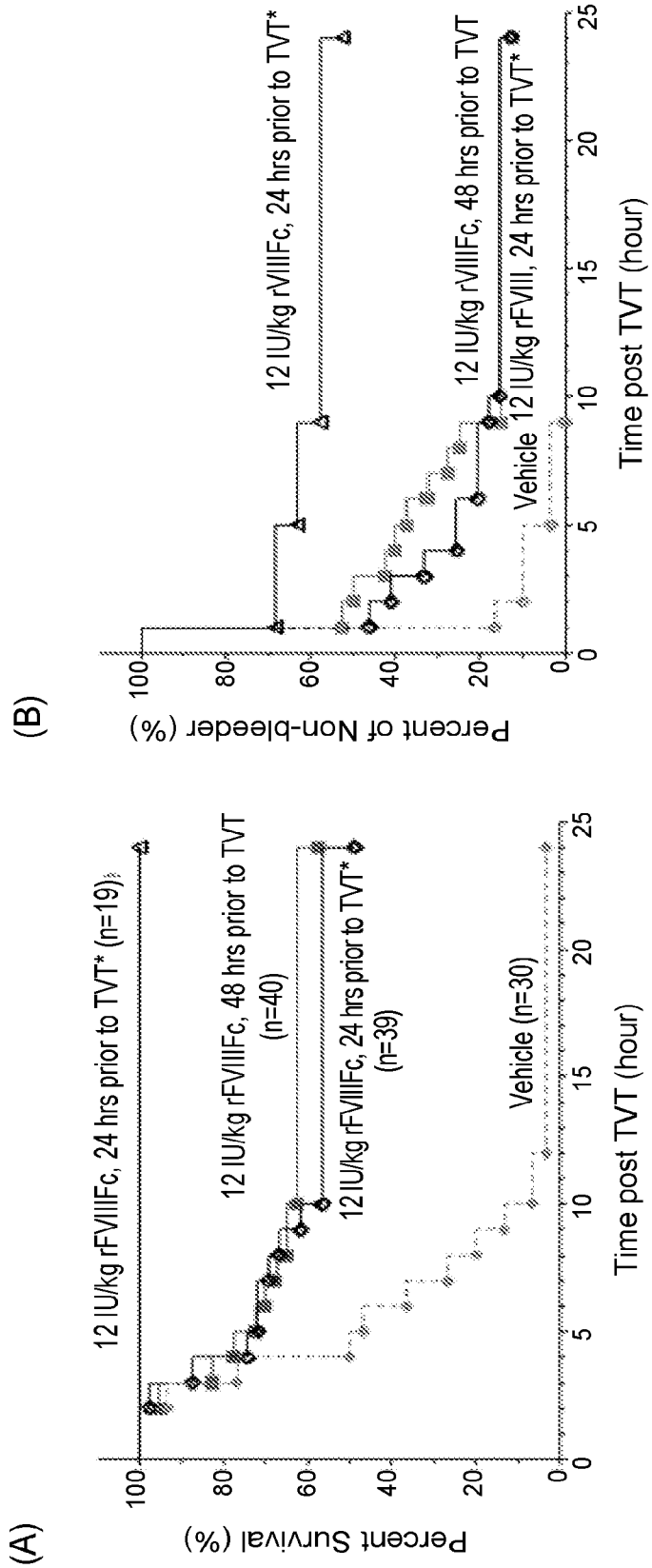

FIGS. 17A and 17B shows the prophylactic efficacy of rFVIIIFc relative to rFVIII in the tail vein transection (TVT) bleeding model. Male HemA mice were injured by TVT either 24 hours following vehicle, rFVIII, or rFVIIIFc treatment, or 48 hours following rFVIIIFc treatment. FIG. 17A shows survival following TVT. P<0.001 by Log-Rank test of the survival curves from animals that received 12 IU/kg rFVIIIFc vs. rFVIII 24 hours prior to TVT. FIG. 17B shows rebleed within 24 hours following TVT. P=0.002 by Log-Rank test of the non-rebleed curves from animals that received 12 IU/kg rFVIIIFc vs. rFVIII 24 hours prior to TVT.

FIGS. 18A and 18B show whole blood clotting time (WBCT) of rFVIIIFc and rFVIII in hemophilia A dogs. Normal WBCT range in dogs is shown by the large dashed lines. The area above the small dashed lines (20 minutes) indicates the point at which the plasma FVIII activity is expected to be below 1% of normal. FIG. 18A shows WBCT after administration of rFVIIIFc.

FIG. 18B shows WBCT after administration of rFVIII followed by administration of rFVIIIFc in a crossover study.

FIGS. 19A and 19B present pharmacokinetics (PK) data for rFVIIIFc compared to rFVIII in Hemophilia A dogs after an i.v. dose. FIG. 19A shows plasma antigen concentration measured by ELISA. FIG. 19B shows plasma FVIII activity was measured by chromogenic assay. N=4 for rFVIIIFc and N=2 for rFVIII.

FIG. 20 shows the design of a study to evaluate FVIII Immunogenicity in HemA mice. Intravenous (i.v.) dosing with rFVIIIFc; chimeric human FVIII-murine Fc; BDD-FVIII (XYNTHA®); full-length rFVIII (ADVATE®); and vehicle control took place at day 0, day 7, day 14, day 21 and day 35. Blood samples were collected a day 14, day 21, day 28, day 35 and day 42.

FIGS. 21A, 21B and 21C show anti-FVIII total antibody counts in immunogenicity experiments conducted in HemA mice according to the design study shown in FIG. 20. FIG. 21A corresponds to total anti-FVIII antibody measurements after repeated i.v. dosing with 50 IU/kg rFVIIIFc; chimeric human FVIII-murine Fc; BDD-FVIII)(XYNTHA®); or full-length rFVIII) (ADVATE®. FIG. 21B corresponds to total anti-FVIII antibody measurements after repeated i.v. dosing with 100 IU/kg rFVIIIFc; chimeric human FVIII-murine Fc; BDD-FVIII)(XYNTHA®; full-length rFVIII)(ADVATE®. FIG. 21C corresponds to total anti-FVIII antibody measurements after repeated i.v. dosing with 250 IU/kg rFVIIIFc; chimeric human FVIII-murine Fc; BDD-FVIII)(XYNTHA®; full-length rFVIII)(ADVATE®.

FIGS. 22A, 22B, 22C, and 22D shows anti-FVIII antibody measurements at different times after administration of 50 IU/kg, 100 IU/kg, and 250 IU/kg doses of rFVIIIFc; chimeric human FVIII-murine Fc; BDD-FVIII (XYNTHA®); full-length rFVIII (ADVATE®). FIG. 22A shows data corresponding to samples collected at day 14. FIG. 22B shows data corresponding to samples collected on day 21.

FIG. 22C shows data corresponding to samples collected on day 28. FIG. 22D shows data corresponding to samples collected on day 42.

FIG. 23 shows the correlation between total and neutralizing antibodies to FVIII.

Figure 24:
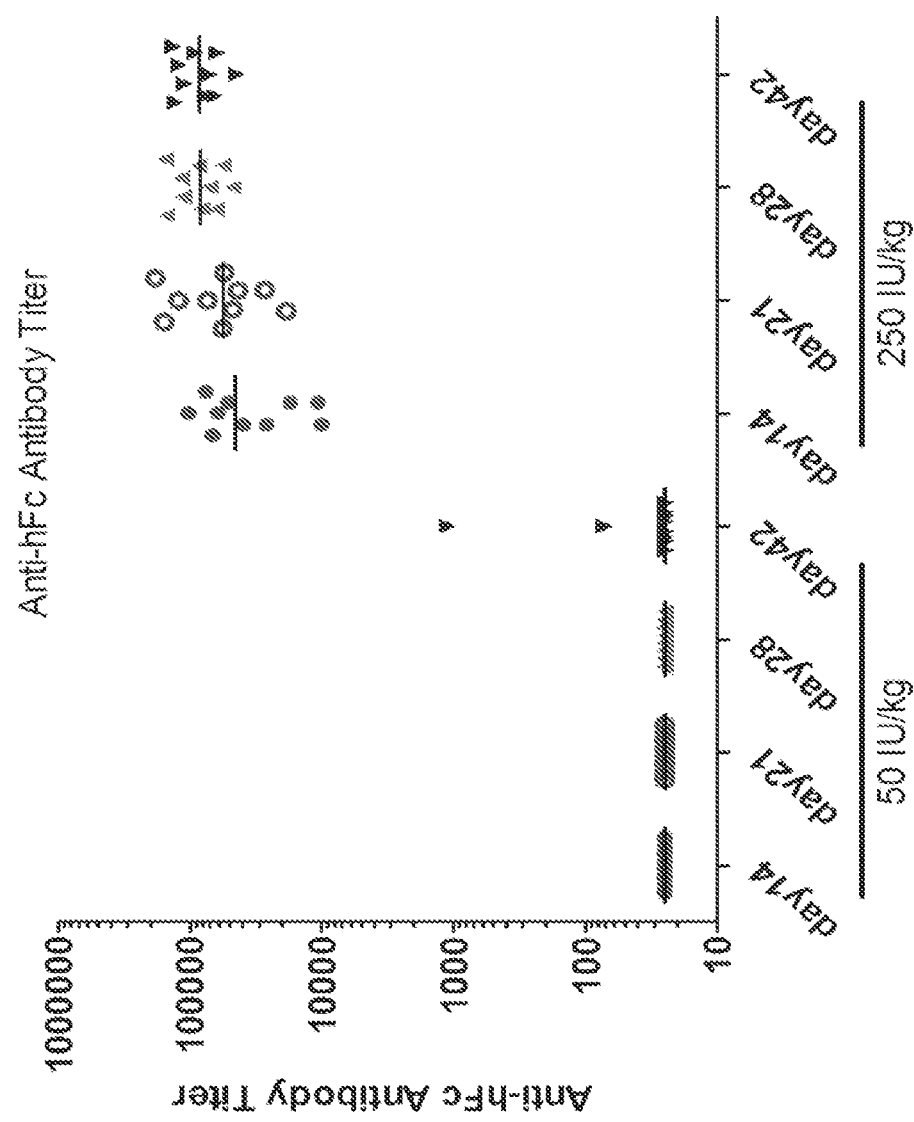

FIG. 24 shows anti-hFc antibody development after treatment with 50 IU/kg and 250 IU/kg doses of rFVIIIFc (rFVIII with human Fc).

Figure 25:
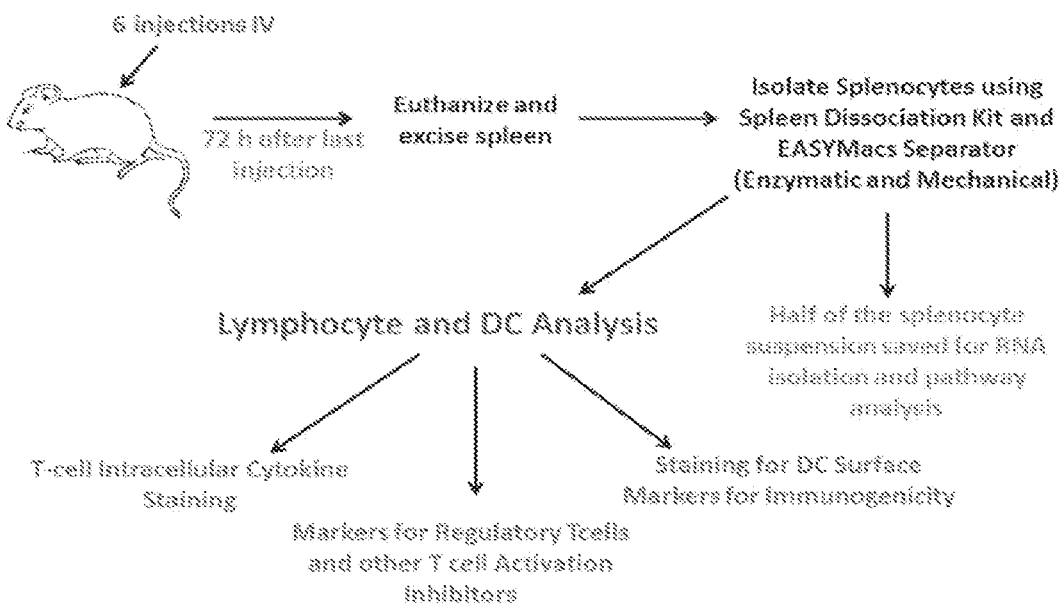

FIG. 25 is a diagram showing the experimental procedures for the isolation and analysis of splenocytes from HemA mice in a study to measure the splenic lymphocyte response to rFVIIIFc compared with commercially available FVIII.

Figure 26:
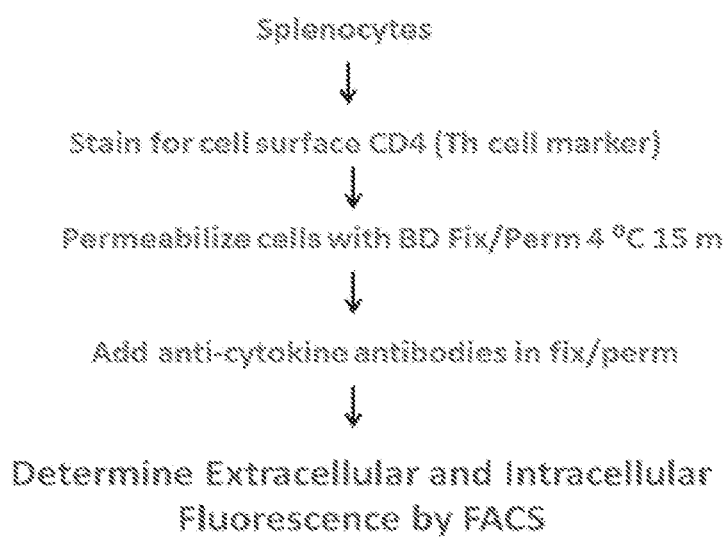

FIG. 26 is a diagram showing the procedure for intracellular cytokine staining using FACS (fluorescence-activated cell sorting). The procedure uses five colors, one for the CD4 lymphocyte marker, and another four colors for the IL2, IL-4, IL-10, and TNF-α cytokines.

Figure 27B:
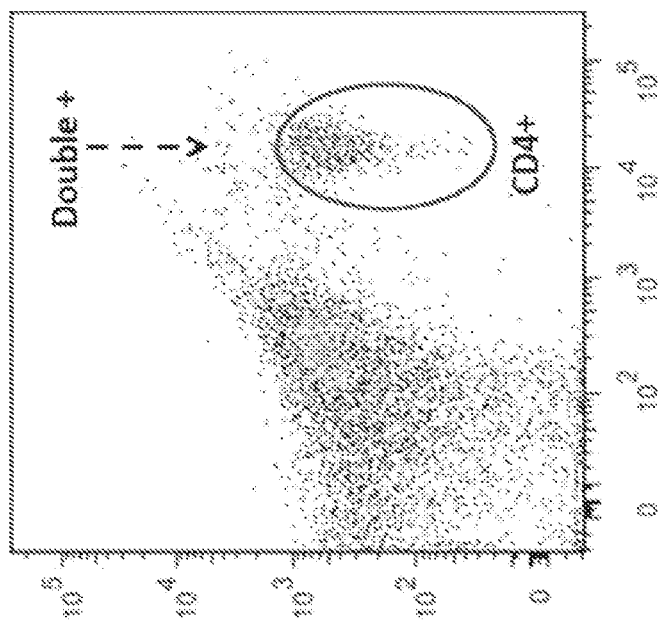
Figure 27A:
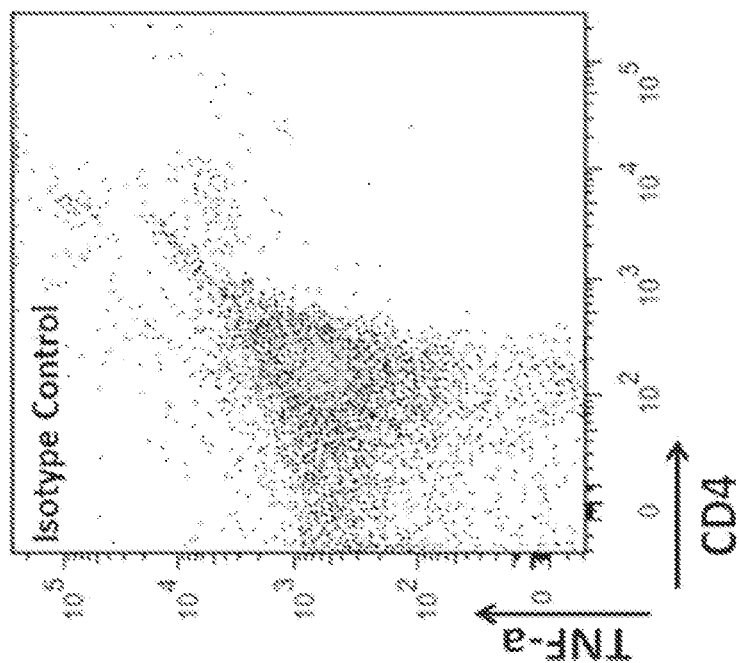

FIGS. 27A and 27B show representative FACS dot plot. FIG. 27A corresponds to the intracellular cytokine staining of the isotype control. FIG. 27 corresponds to the intracellular cytokine staining of double positive cell containing the CD4 and TNF-α markers.

Figure 28:
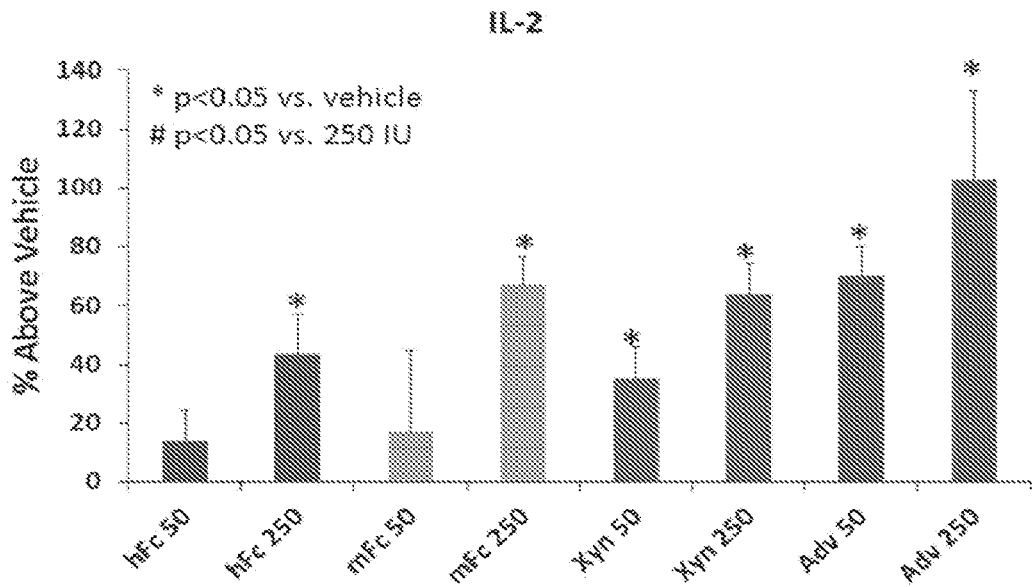

FIG. 28 shows intracellular cytokine staining above control (vehicle) for CD4 and interleukin-2 (IL-2). Percentages of double positive cells were determined from FACS dot plots from all the FVIII treatments and vehicle. Percent of double positive cells in FVIII treated mice was obtained by comparing with vehicle treated group. The samples correspond to rFVIIIFc with a human Fc (hFc), or mouse Fc (mFc), XYNTHA® (Xyn), and ADVATE® (Adv). FVIII treatments were administered at 50 IU/kg and 250 IU/kg doses.

Figure 29:
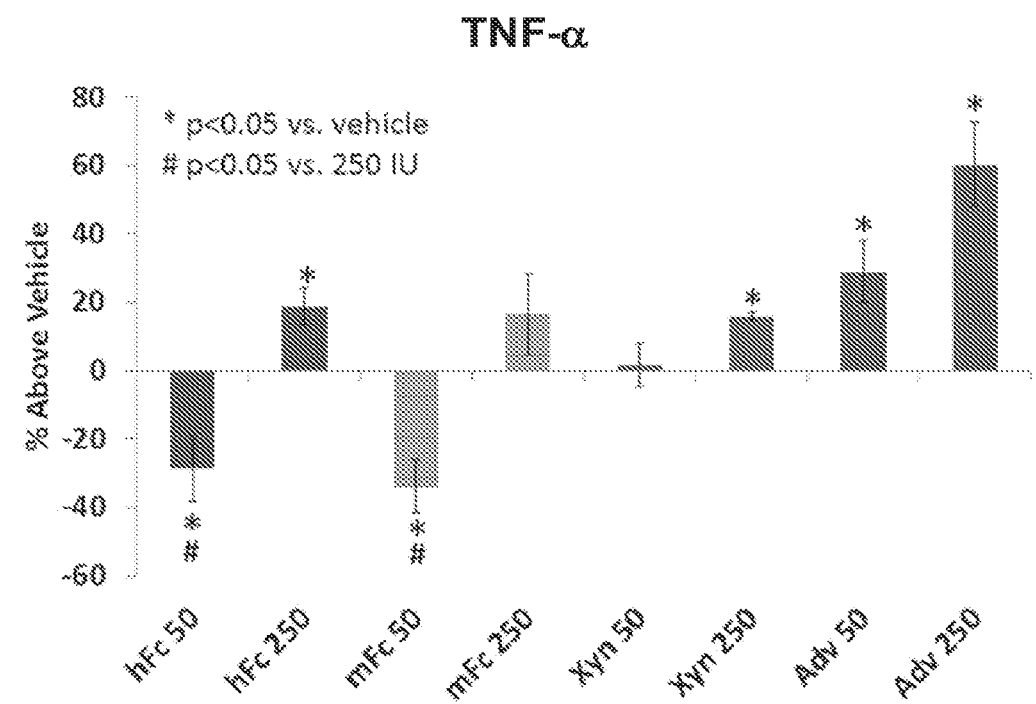

FIG. 29 shows intracellular cytokine staining above control (vehicle) for CD4 and TNF-α. Percentages of double positive cells were determined from FACS dot plots from all the FVIII treatments and vehicle. Percent of double positive cells in FVIII treated mice was obtained by comparing with vehicle treated group. The samples correspond to rFVIIIFc with a human Fc (hFc), or mouse Fc (mFc), XYNTHA® (Xyn), and ADVATE® (Adv). FVIII treatments were administered at 50 IU/kg and 250 IU/kg doses.

Figure 30:
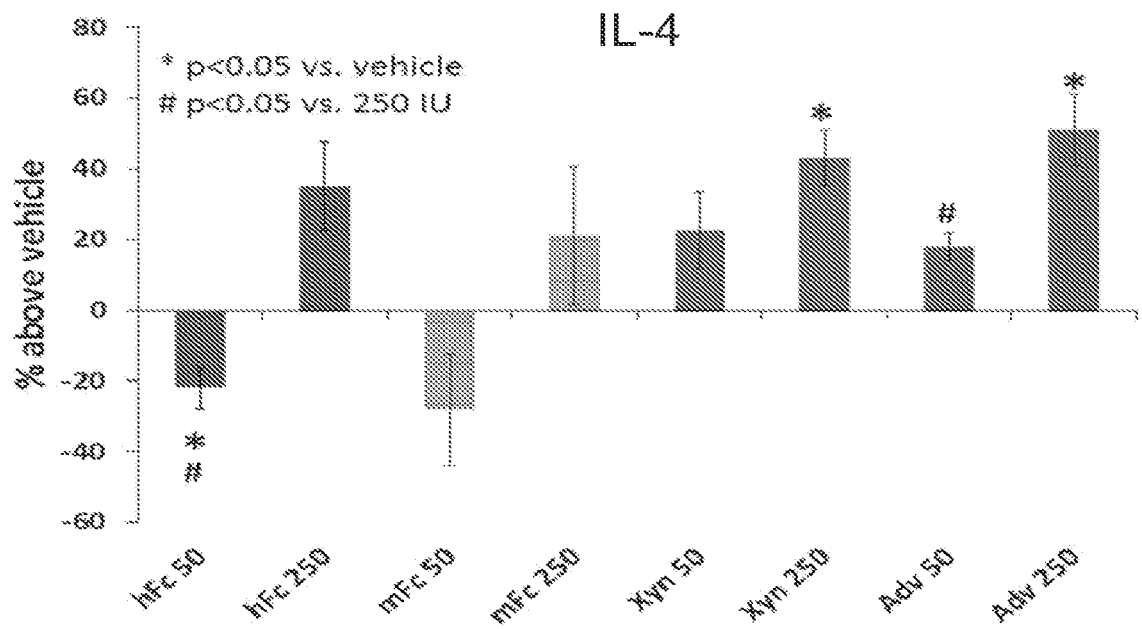

FIG. 30 shows intracellular cytokine staining above control (vehicle) for CD4 and interleukin-4 (IL-4). Percentages of double positive cells were determined from FACS dot plots from all the FVIII treatments and vehicle. Percent of double positive cells in FVIII treated mice was obtained by comparing with vehicle treated group. The samples correspond to rFVIIIFc with a human Fc (hFc), or mouse Fc (mFc), XYNTHA® (Xyn), and ADVATE® (Adv). FVIII treatments were administered at 50 IU/kg and 250 IU/kg doses.

Figure 31:
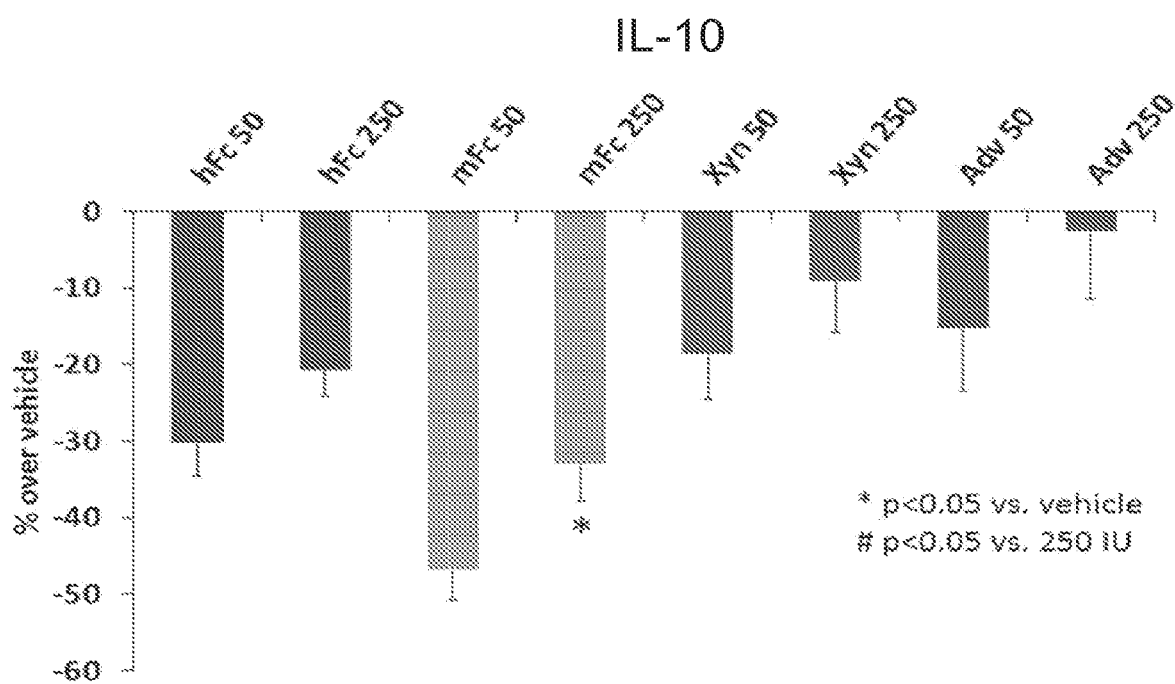

FIG. 31 shows intracellular cytokine staining above control (vehicle) for CD4 and interleukin-10 (IL-10). Percentages of double positive cells were determined from FACS dot plots from all the FVIII treatments and vehicle. Percent of double positive cells in FVIII treated mice was obtained by comparing with vehicle treated group. The samples correspond to rFVIIIFc with a human Fc (hFc), or mouse Fc (mFc), XYNTHA® (Xyn), and ADVATE® (Adv). FVIII treatments were administered at 50 IU/kg and 250 IU/kg doses.

Figure 32:
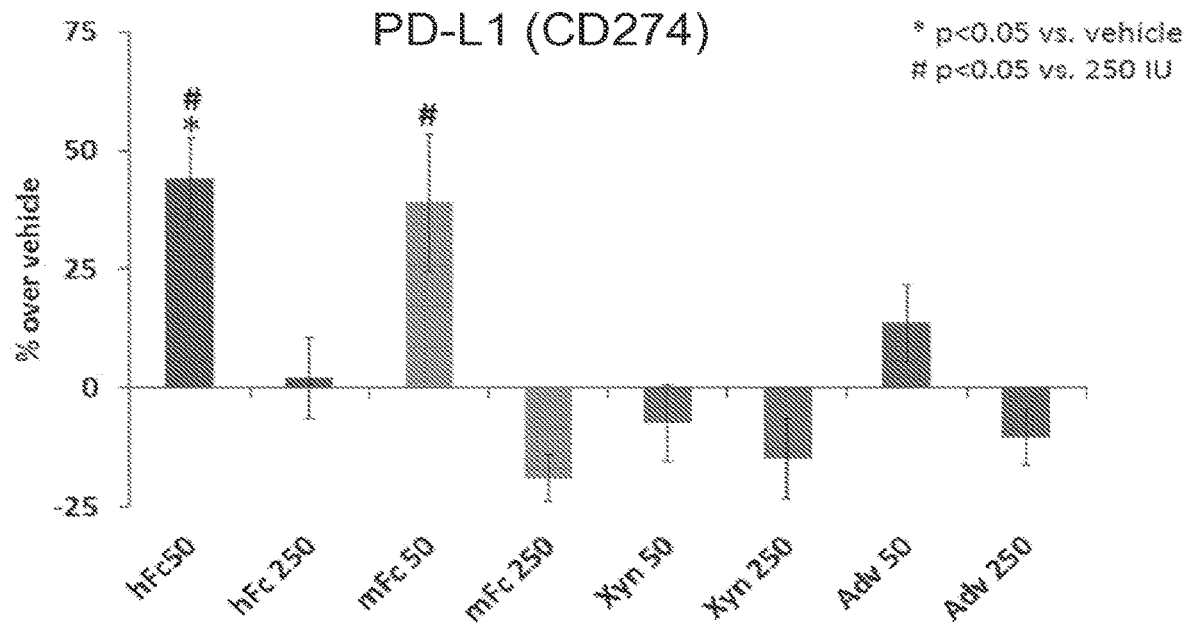

FIG. 32 shows intracellular cytokine staining above control (vehicle) for CD4 and dendritic cell marker PD-L1 (CD274). Percentages of double positive cells were determined from FACS dot plots from all the FVIII treatments and vehicle. Percent of double positive cells in FVIII treated mice was obtained by comparing with vehicle treated group. The samples correspond to rFVIIIFc with a human Fc (hFc), or mouse Fc (mFc), XYNTHA® (Xyn), and ADVATE® (Adv). FVIII treatments were administered at 50 IU/kg and 250 IU/kg doses.

Figure 33:
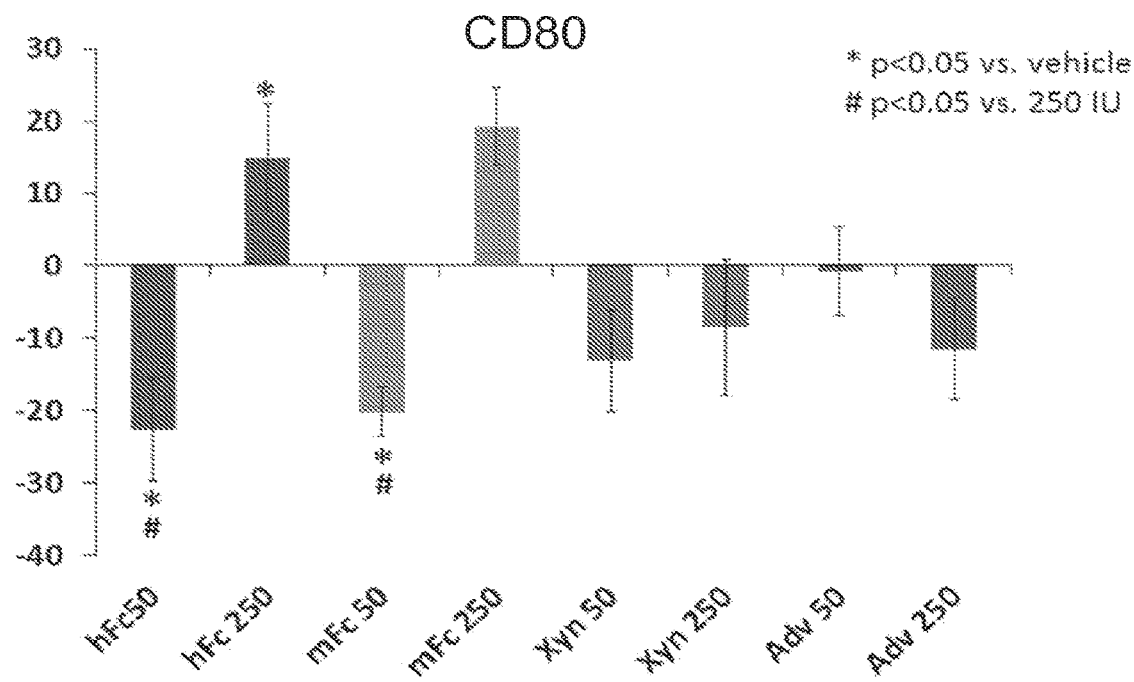

FIG. 33 shows intracellular cytokine staining above control (vehicle) for CD4 and dendritic cell marker CD80. Percentages of double positive cells were determined from FACS dot plots from all the FVIII treatments and vehicle. Percent of double positive cells in FVIII treated mice was obtained by comparing with vehicle treated group. The samples correspond to rFVIIIFc with a human Fc (hFc), or mouse Fc (mFc), XYNTHA® (Xyn), and ADVATE® (Adv). FVIII treatments were administered at 50 IU/kg and 250 IU/kg doses.

Figure 34:
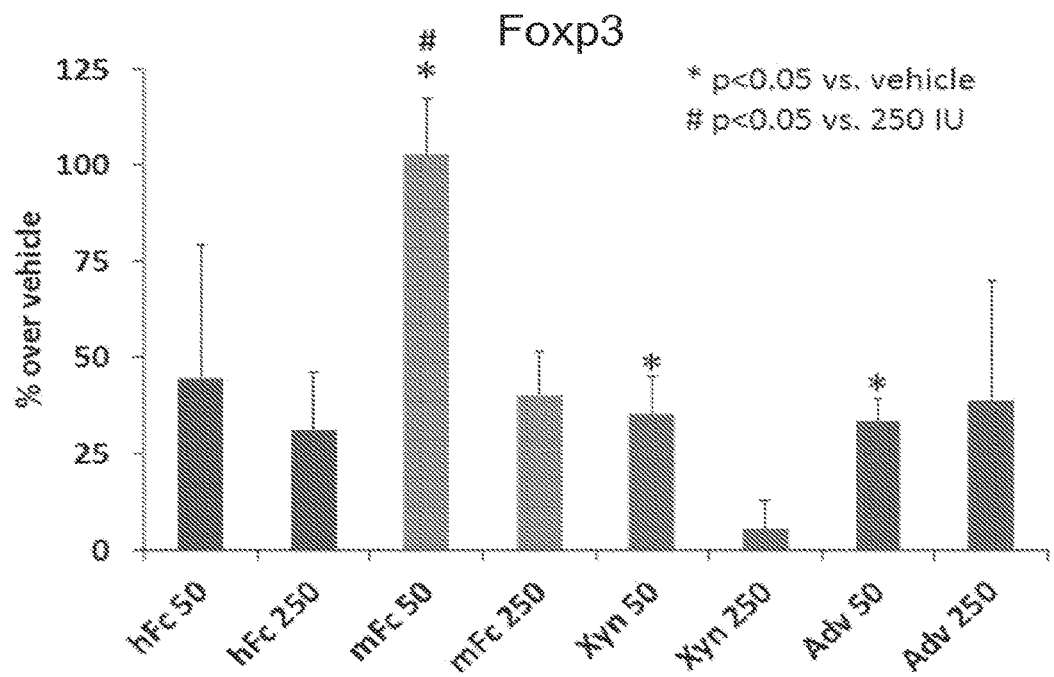

FIG. 34 shows intracellular cytokine staining above control (vehicle) for CD4 and Treg marker Foxp3. Percentages of double positive cells were determined from FACS dot plots from all the FVIII treatments and vehicle. Percent of double positive cells in FVIII treated mice was obtained by comparing with vehicle treated group. The samples correspond to rFVIIIFc with a human Fc (hFc), or mouse Fc (mFc), XYNTHA® (Xyn), and ADVATE® (Adv). FVIII treatments were administered at 50 IU/kg and 250 IU/kg doses.

Figure 35:
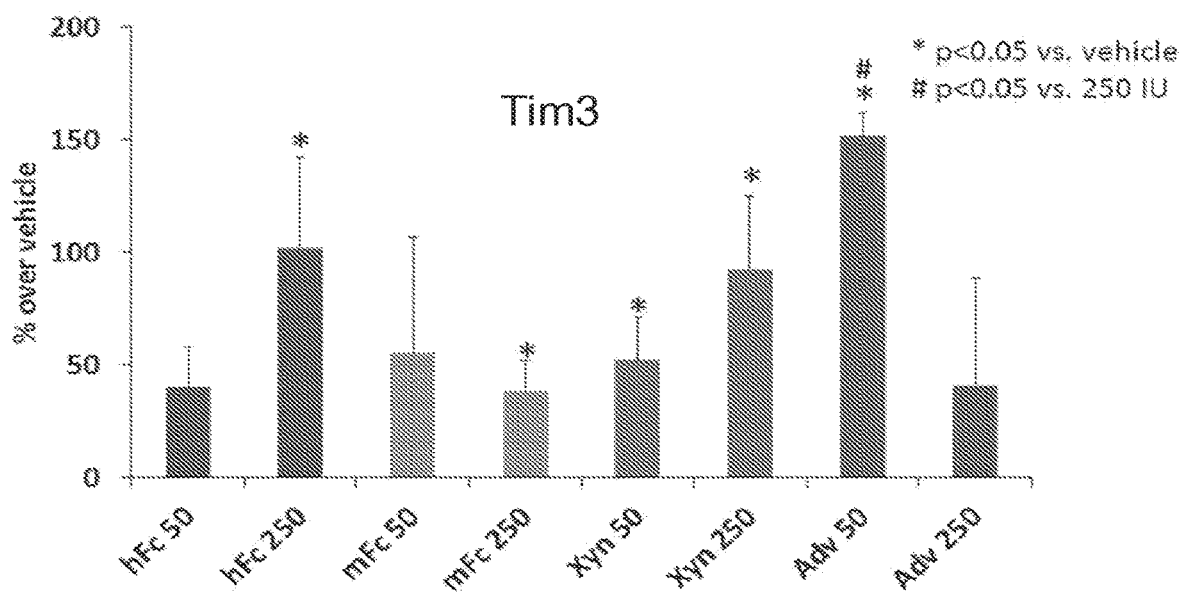

FIG. 35 shows intracellular cytokine staining above control (vehicle) for CD4 and the Th inhibitory molecule Tim3. Percentages of double positive cells were determined from FACS dot plots from all the FVIII treatments and vehicle. Percent of double positive cells in FVIII treated mice was obtained by comparing with vehicle treated group. The samples correspond to rFVIIIFc with a human Fc (hFc), or mouse Fc (mFc), XYNTHA® (Xyn), and ADVATE® (Adv). FVIII treatments were administered at 50 IU/kg and 250 IU/kg doses.

Figure 36:
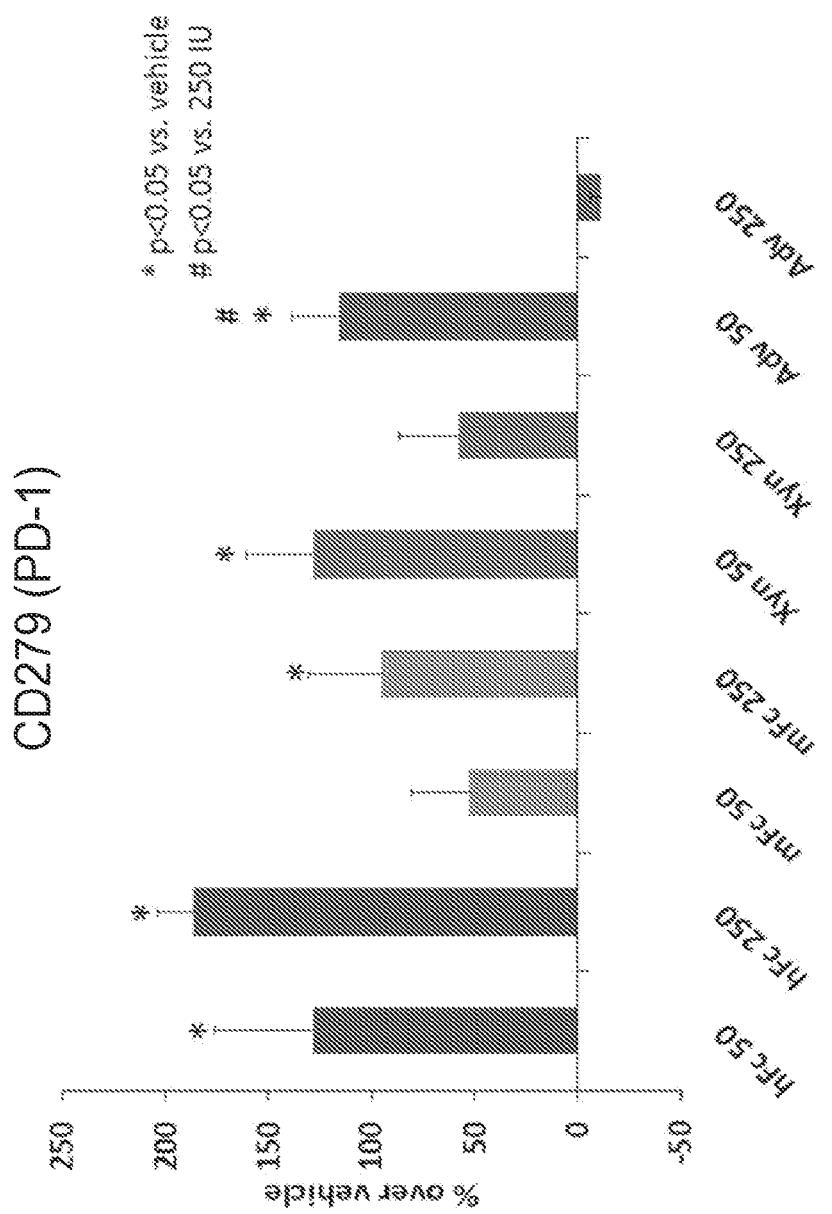

FIG. 36 shows intracellular cytokine staining above control (vehicle) for CD4 and the Th inhibitory molecule CD279 (PD-1). Percentages of double positive cells were determined from FACS dot plots from all the FVIII treatments and vehicle. Percent of double positive cells in FVIII treated mice was obtained by comparing with vehicle treated group. The samples correspond to rFVIIIFc with a human Fc (hFc), or mouse Fc (mFc), XYNTHA® (Xyn), and ADVATE® (Adv). FVIII treatments were administered at 50 IU/kg and 250 IU/kg doses.

Figure 37:
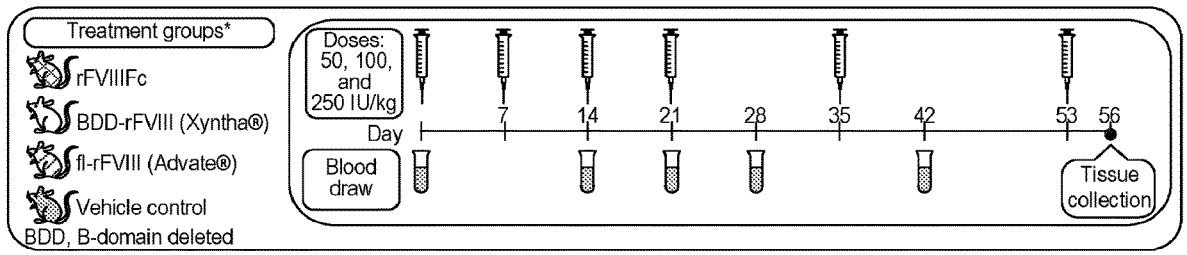

FIG. 37 is a diagram showing the design of the immunogenicity study presented in Example 13. FVIII (rFVIIIFc, XYNTHA®, ADVATE®) and vehicle control were administered to HemA mice on day 0, day 7, day 14, day 21, day 35 and day 53. Blood was drawn on day 0, day 14, day 21, day 28, and day 42. Spleens were collected on day 56. FVIII was administered in 50 IU/kg, 100 IU/kg, and 250 IU/kg doses.

Figure 38:
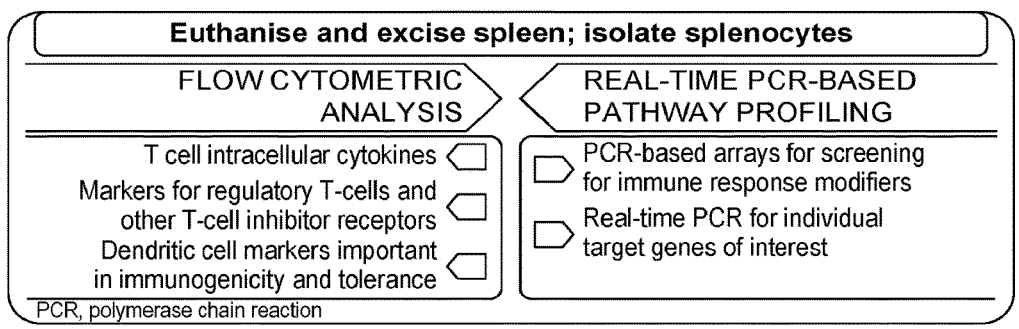

FIG. 38 shows the methodology used for analysis of mouse splenocytes and T-cell response profiling in Example 13.

Figure 39:
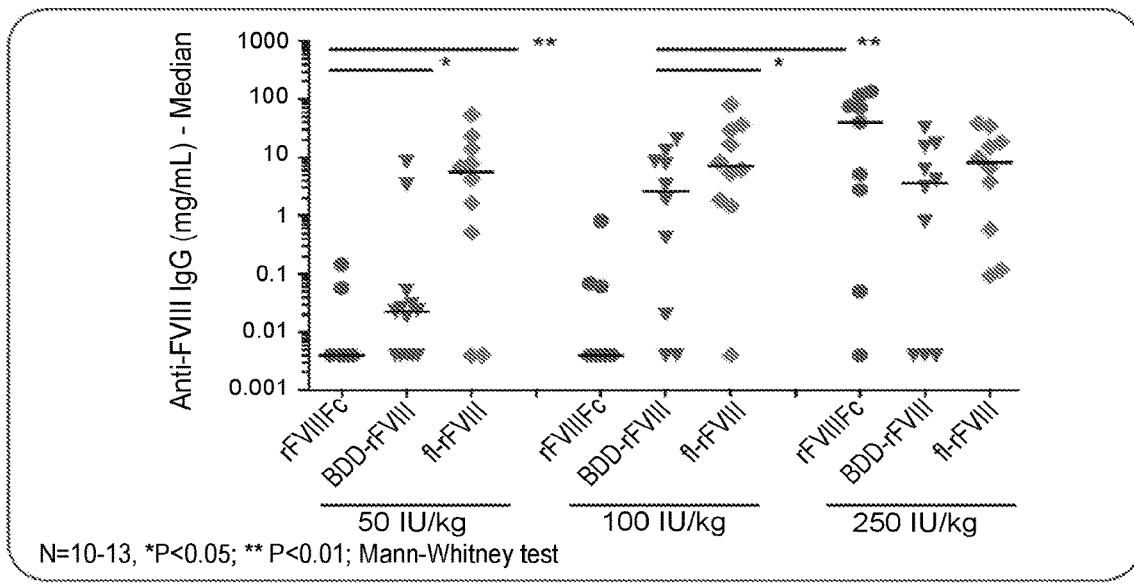

FIG. 39 shows total anti-FVIII antibody levels in blood samples collected on day 42. rFVIIIFc, BDD-rFVIII (XYNTHA®) and fl-rFVIII (ADVATE®) were administered in 50 IU/kg, 100 IU/kg, and 250 IU/kg doses.

Figure 40:
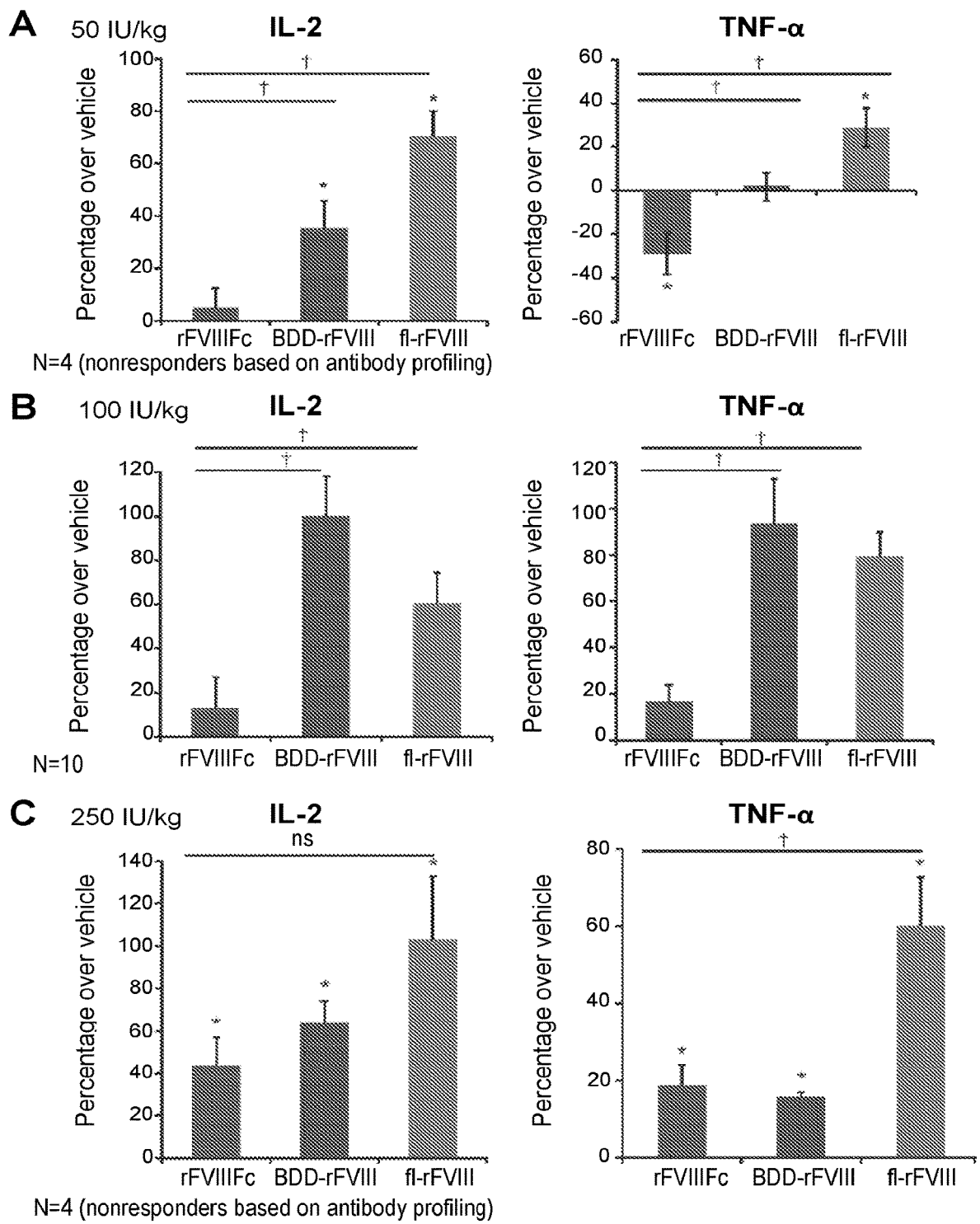

FIGS. 40A, 40B and 40C show intracellular cytokine staining of splenic CD4+ T-cells from HemA mice treated with different doses of FVIII (rFVIIIFc, BDD-rFVIII (XYNTHA®) or fl-rFVIII (ADVATE®)). Each figure shows results for IL-2 (left panel) and for TNF-α (right panel). FIG. 4A corresponds to HemA mice (N=4) injected with 50 IU/kg doses of FVIII. FIG. 4B corresponds to HemA mice (N=10)

injected with 100 IU/kg doses of FVIII. FIG. 4C corresponds to HemA mice (N=4) injected with 250 IU/kg doses of FVIII.

FIG. 4I shows intracellular cytokine staining for CD4/CD25/Foxp3 triple positive splenocytes isolated from HemA mice treated with 100 IU/kg doses of rFVIIIFc, BDD-rFVIII (XYNTHA®) or fl-rFVIII (ADVATE®).

Figure 42:
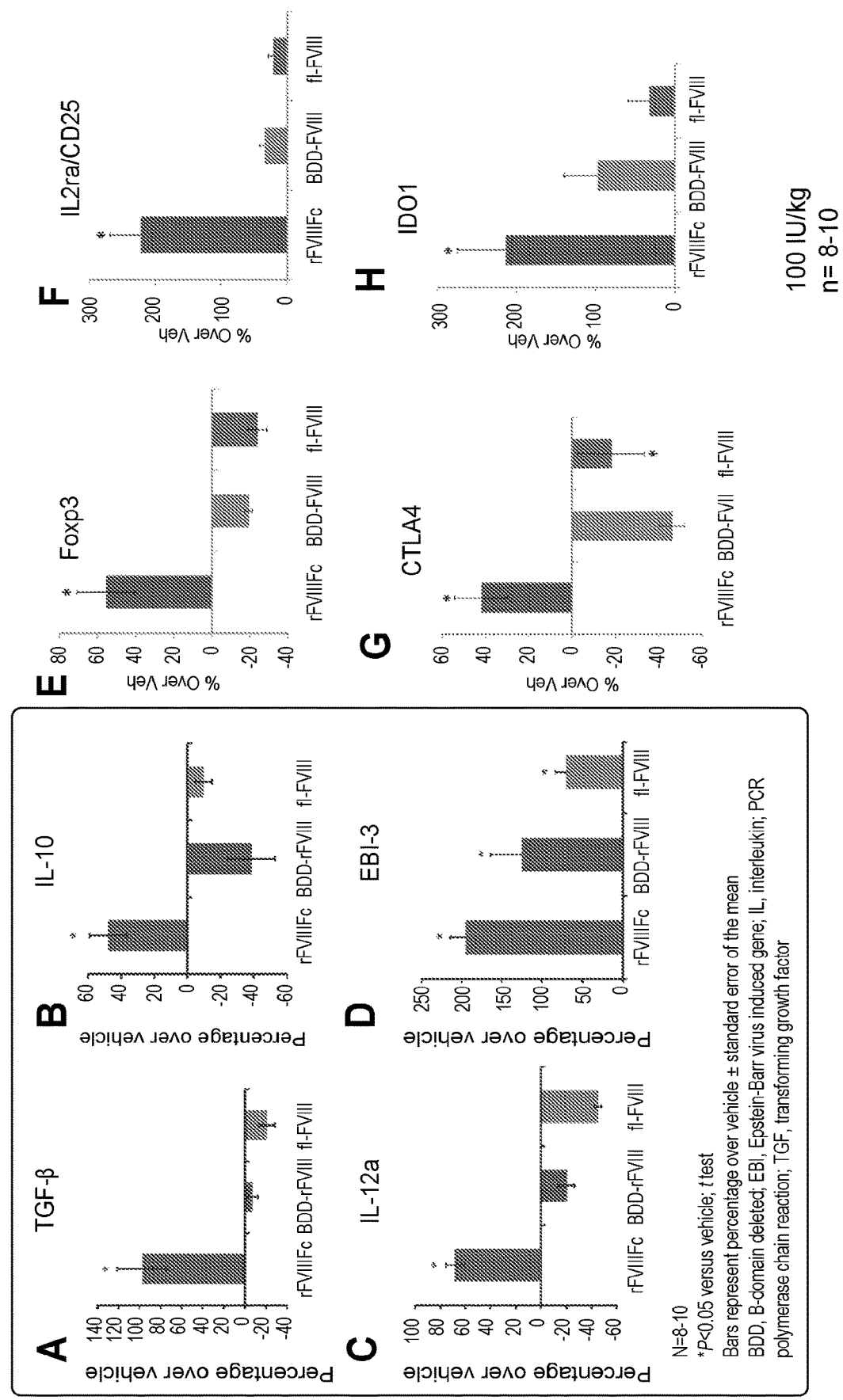

FIGS. 42A-H show real time PCR for immune tolerance related cytokines in 100 IU/kg-treated HemA mice. FIG. 42A shows results for TGF-β, FIG. 42B shows results for interleukin-10, FIG. 42C shows results for the IL-12a subunit of IL-35, and FIG. 42D shows results for the EBI-3 subunit of IL-35. FIG. 42E shows results for Foxp3. FIG. 42F shows results for IL2ra/CD25. FIG. 42G shows results for CTLA4. FIG. 42H shows results for IDO-1.

Figures 43A, 43B:
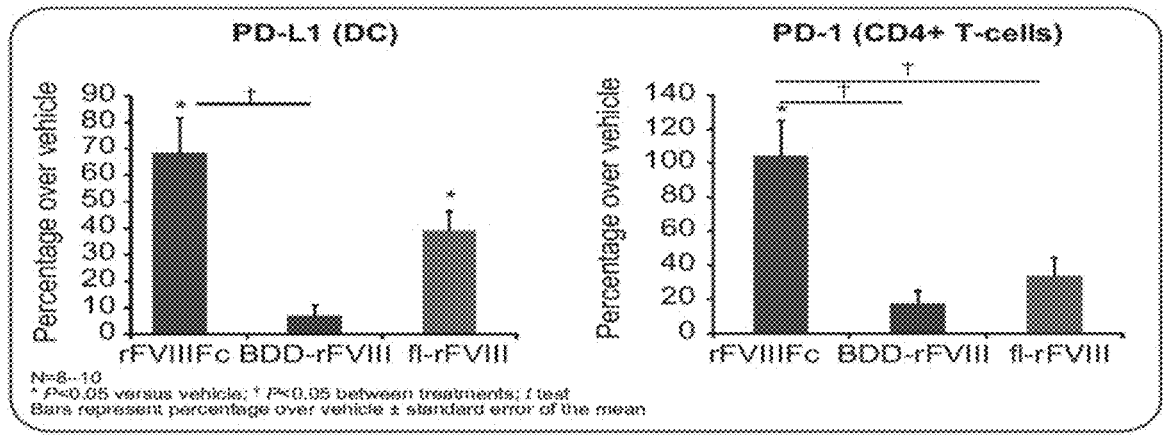

FIG. 43A-B shows FACS analysis of cells involved in the PD-L1-PD-1 pathway in 100 IU/kg treated mice. Splenocytes were stained for either surface CD11c and PD-L1 (FIG. 43A), or CD4 and PD-1 (FIG. 43B). Bars represent percent over vehicle (*p<0.05 vs. vehicle; +p<0.05 between treatments; T-test)

Figure 44:
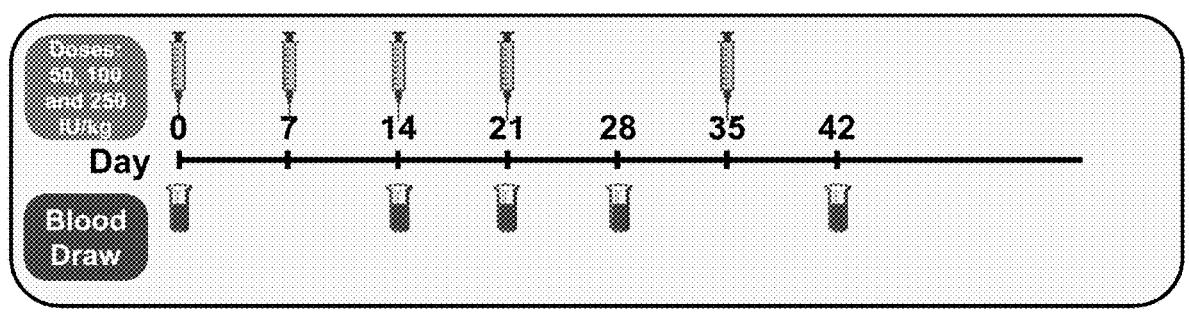

FIG. 44 is a diagram showing the design of an immunogenicity comparison study for rFVIIIFc, XYNTHA® and ADVATE® in HemA Mice. FVIII doses were administered to HemA mice on day 0, day 7, day 14, day 21, and day 35. Blood was drawn on day 0, day 14, day 21, day 28, and day 42. FVIII was administered in 50 IU/kg, 100 IU/kg, and 250 IU/kg doses.

Figure 45:
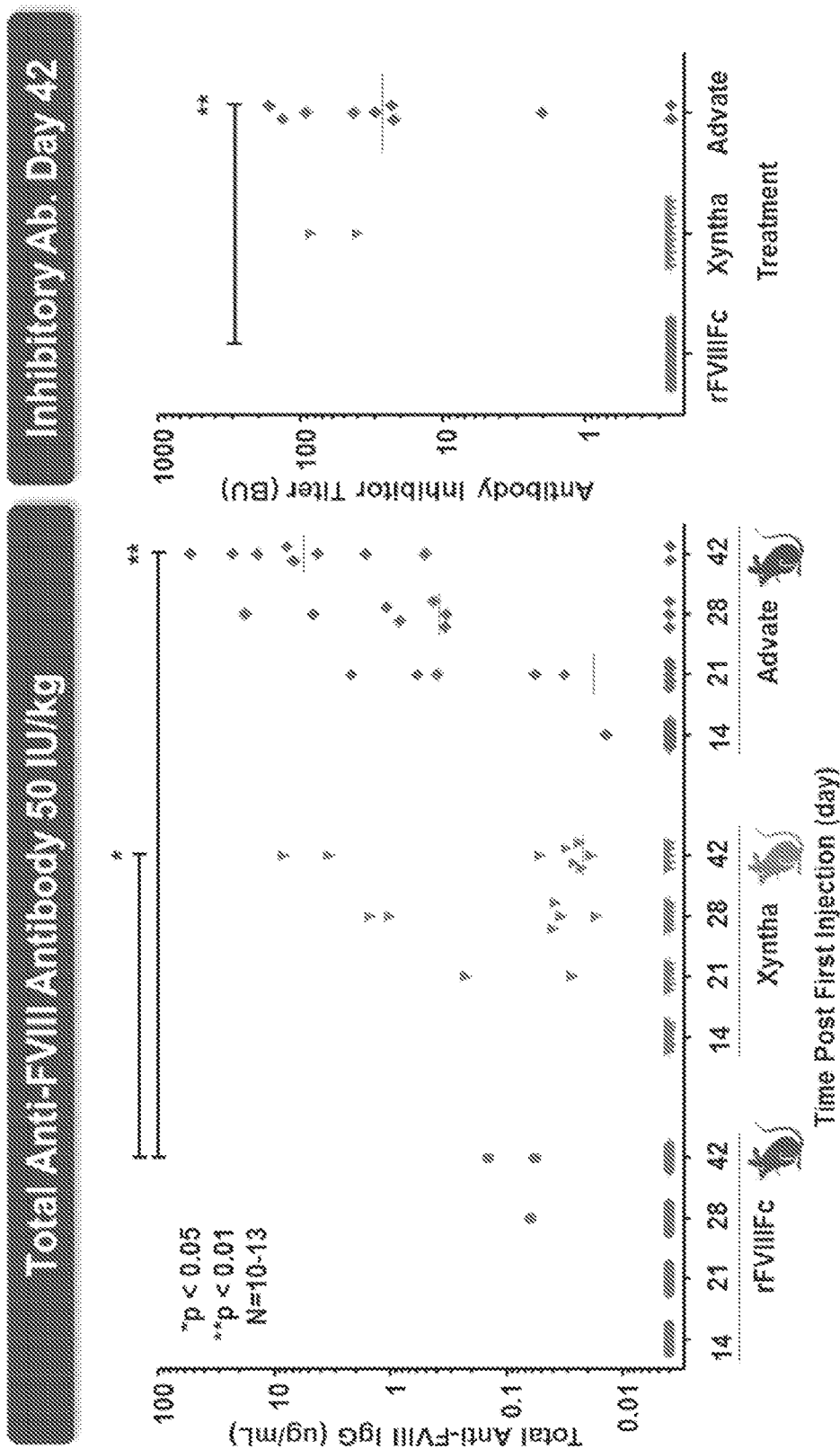

FIG. 45 shows anti-FVIII antibody measurements at 14, 21, 28 and 42 days after administration of 50 IU/kg doses of rFVIIIFc; BDD-FVIII (XYNTHA®); full-length rFVIII (ADVATE®), as well as levels of inhibitory antibodies at day 42.

Figure 46:
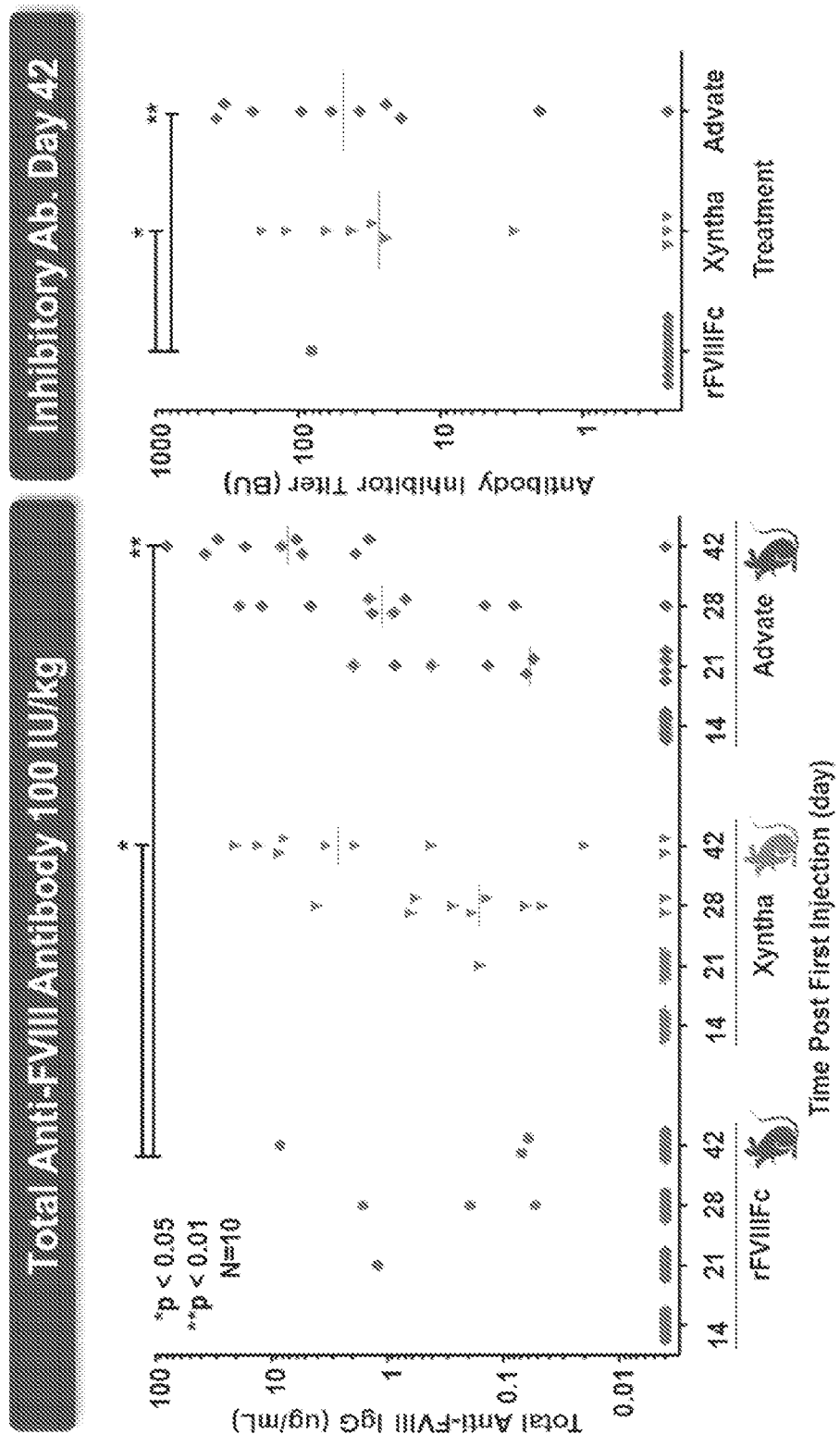

FIG. 46. shows anti-FVIII antibody measurements at 14, 21, 28 and 42 days after administration of 100 IU/kg doses of rFVIIIFc; BDD-FVIII)(XYNTHA®; full-length rFVIII) (ADVATE®, as well as levels of inhibitory antibodies at day 42.

Figure 47:
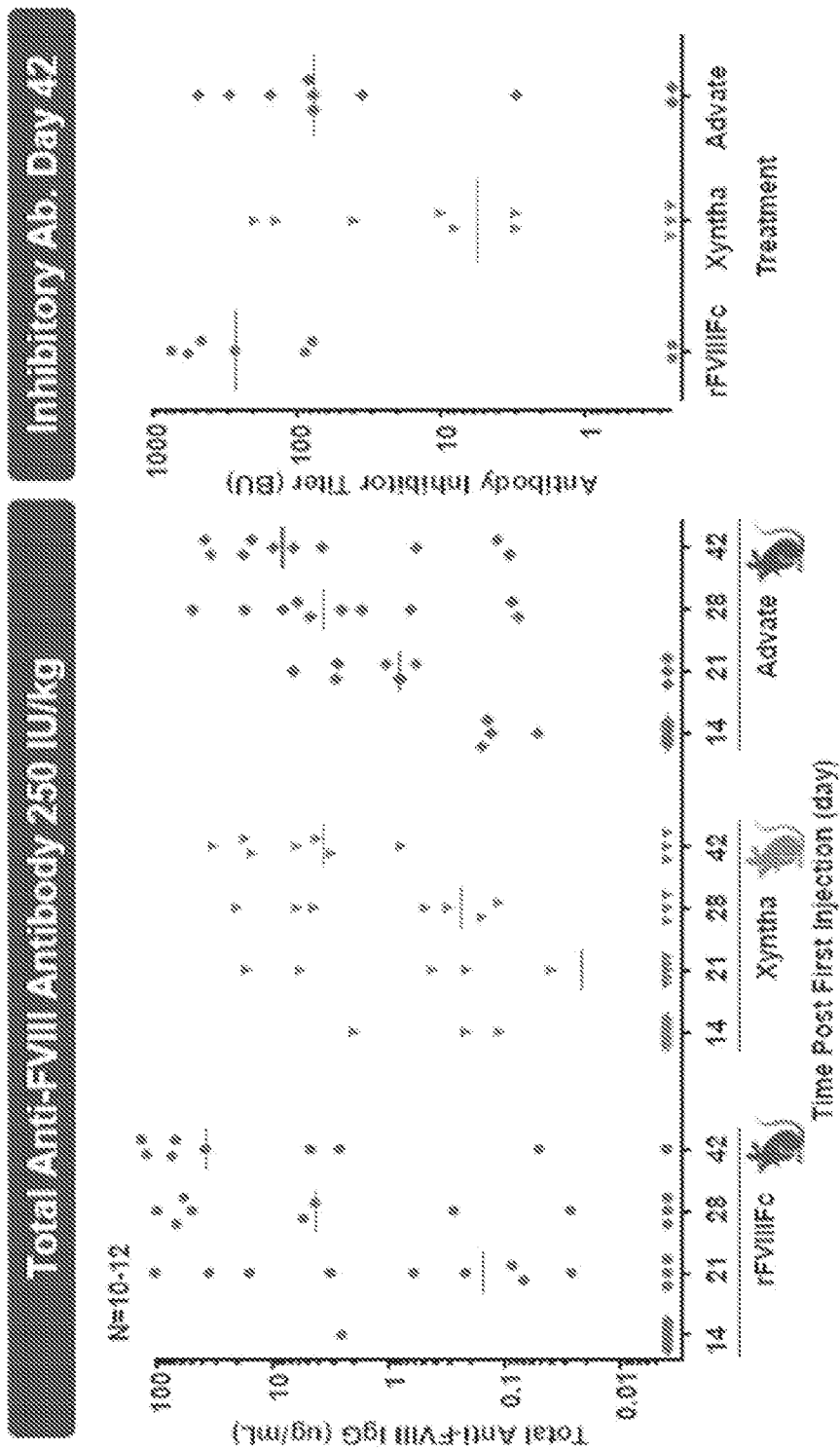

FIG. 47 shows anti-FVIII antibody measurements at 14, 21, 28 and 42 days after administration of 250 IU/kg doses of rFVIIIFc; BDD-FVIII)(XYNTHA®; full-length rFVIII) (ADVATE®, as well as levels of inhibitory antibodies at day 42.

Figure 48:
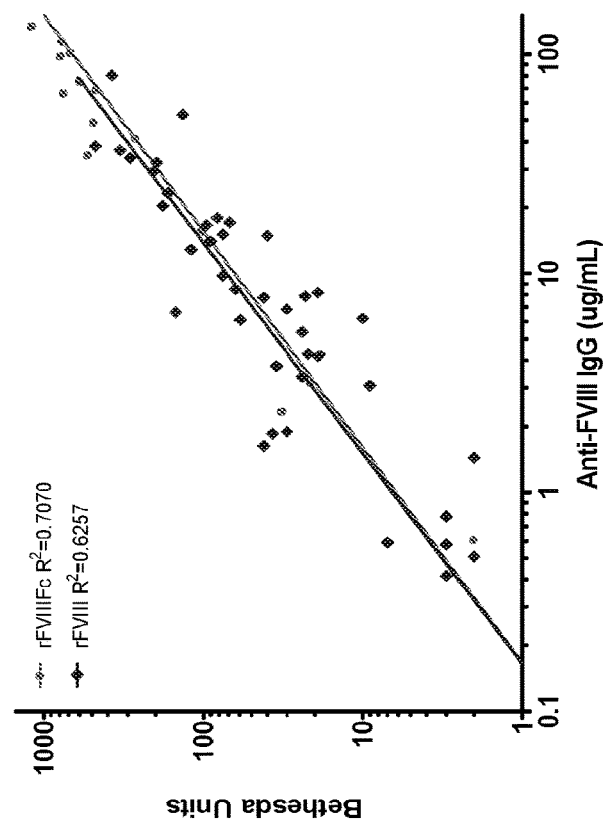

FIG. 48 shows the correlation between FVIII neutralizing antibody titers and total binding antibody levels after administration of rFVIII and rFVIIIFc.

Figure 49:
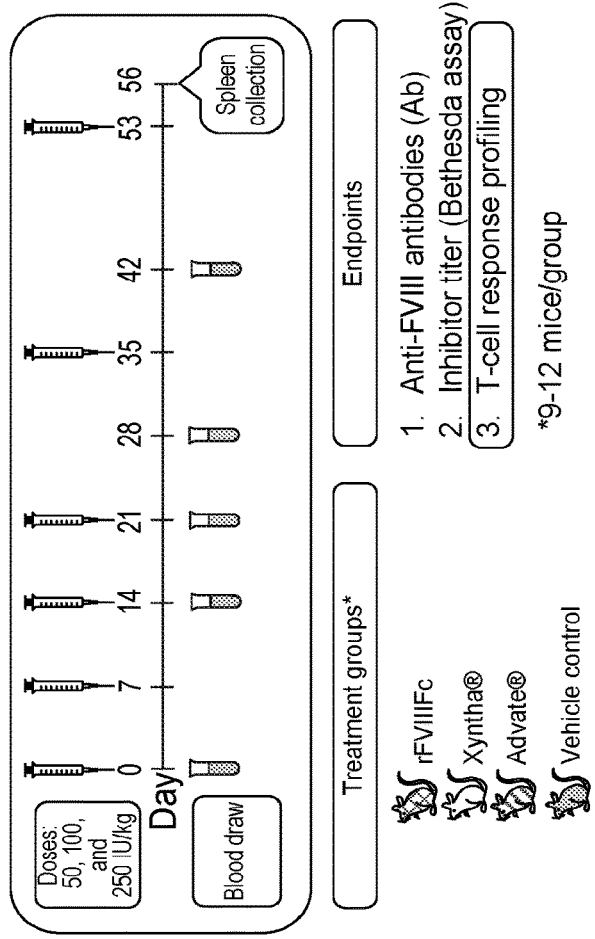

FIG. 49 is a diagram showing the T-cell response profiling component of the immunogenicity comparison study for rFVIIIFc, XYNTHA® and ADVATE® in HemA mice shown in FIG. 44. Additional FVIII doses were administered to HemA mice on day 53, and spleen were collected on day 56.

Figure 50:
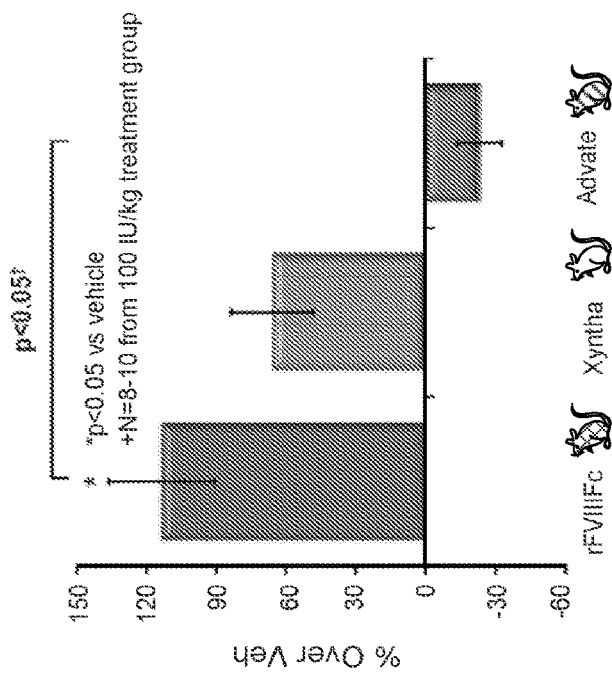

FIG. 50 (right panel) shows intracellular cytokine staining for CD4/CD25/Foxp3 triple positive splenocytes isolated from HemA mice treated with 100 IU/kg doses of rFVIIIFc, BDD-rFVIII (XYNTHA®) or fl-rFVIII)(ADVATE®). FIG. 50 (left panel) is a diagram showing the mechanism of action of regulatory T-cells.

Figure 51:
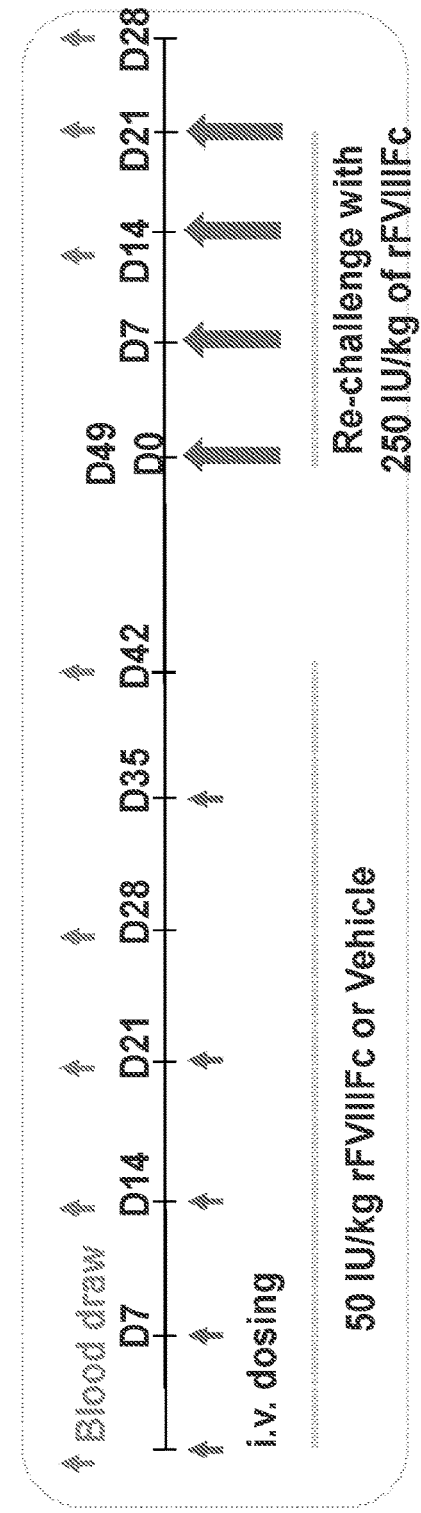

FIG. 51 is a diagram showing the design of an rFVIIIFc immune tolerization study. 50 IU/kg doses of rFVIIIFc were administered i.v. to HemA mice on day 0, day 7, day, day 21, and day 35. Blood was drawn on day 0, day 14, day 21, day 28, and day 42, followed by a 1 week rest period. Mice were then rechallenged with 250 IU/kg doses of rFVIIIFc on day 49 (day 0 of rechallenge), day 56 (day 7 of rechallenge), day 63 (day 14 of rechallenge), and day 70 (day 21 of rechallenge). Blood was collected during the rechallenge on day 63 (day 14 of rechallenge), day 70 (day 21 of rechallenge), and day 77 (day 28 of rechallenge).

Figure 52:
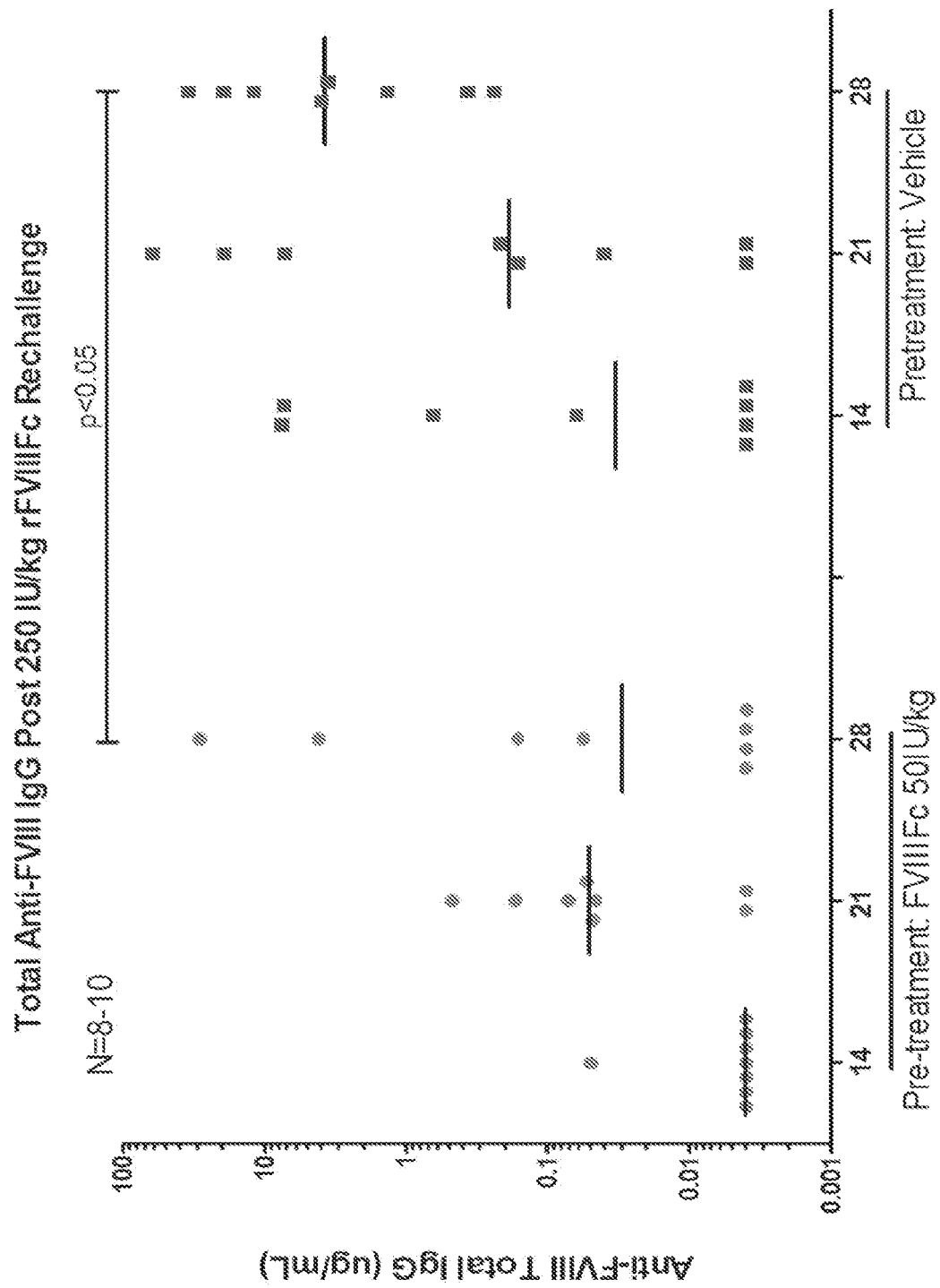

FIG. 52 shows total anti-FVIII antibody measurements at day 14, 21, and 28 post rechallenge with 250 IU/kg doses of rFVIIIFc. HemA mice were pretreated with 50 IU/kg rFVIIIFc or vehicle control. The results indicate that rFVIIIFc induces immune tolerance in HemA mice.

Figure 53:
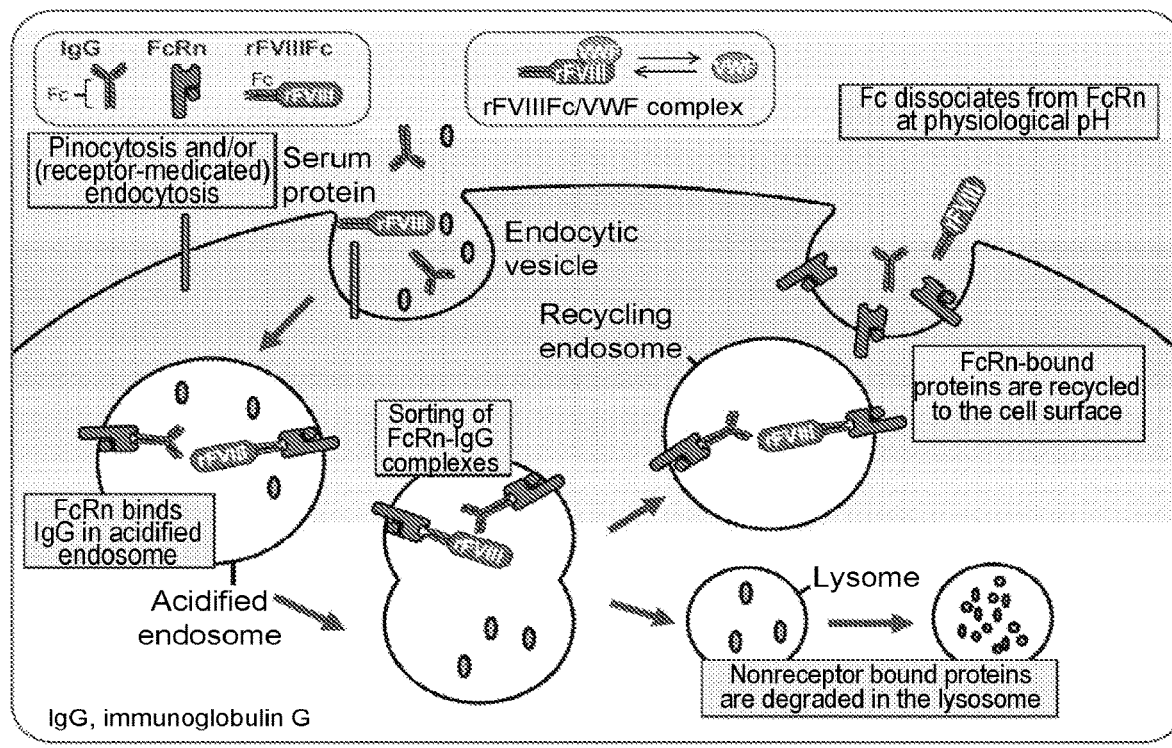

FIG. 53 is a diagram showing the recycling of IgG and rFVIIIFc by FcRn.

Figure 54:
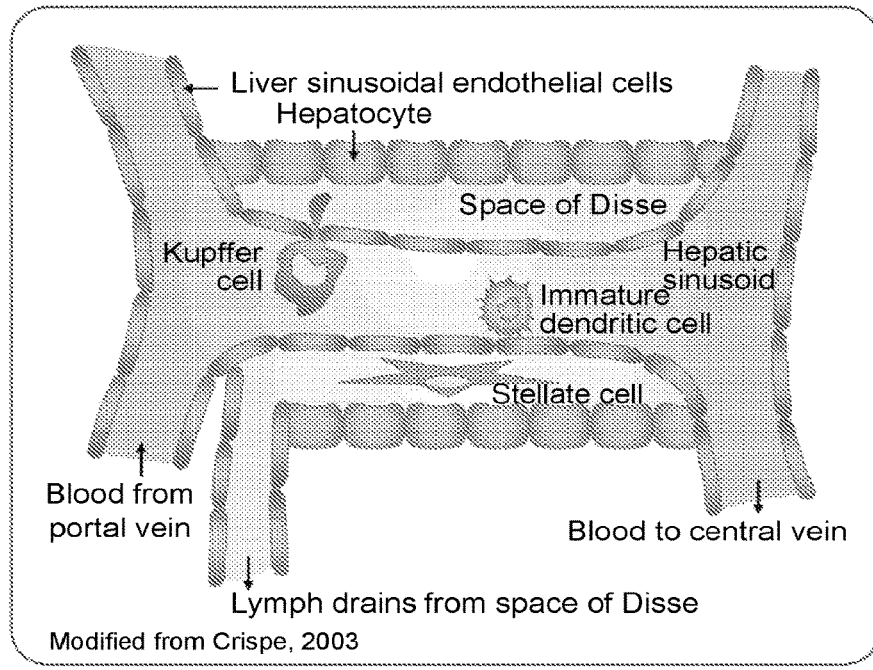

FIG. 54 is a diagram depicting cell types and cellular architecture surrounding a liver sinusoid.

Figure 55:
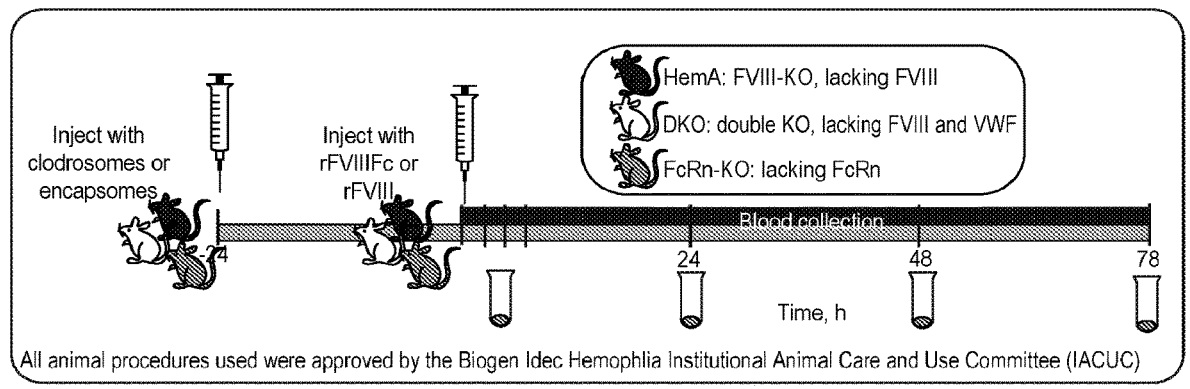

FIG. 55 is a diagram showing the design of a clearance assay in which macrophage and Kupffer are depleted with CLODROSOME® (ENCAPSOME® administered as control) prior to i.v. injection of FVIII or rFVIIIFc. Three knock-out mouse models were used: HemA, DKO, and FcRn-KO. Blood samples were collected at the specified time point (4 samples per time point).

Figure 56:
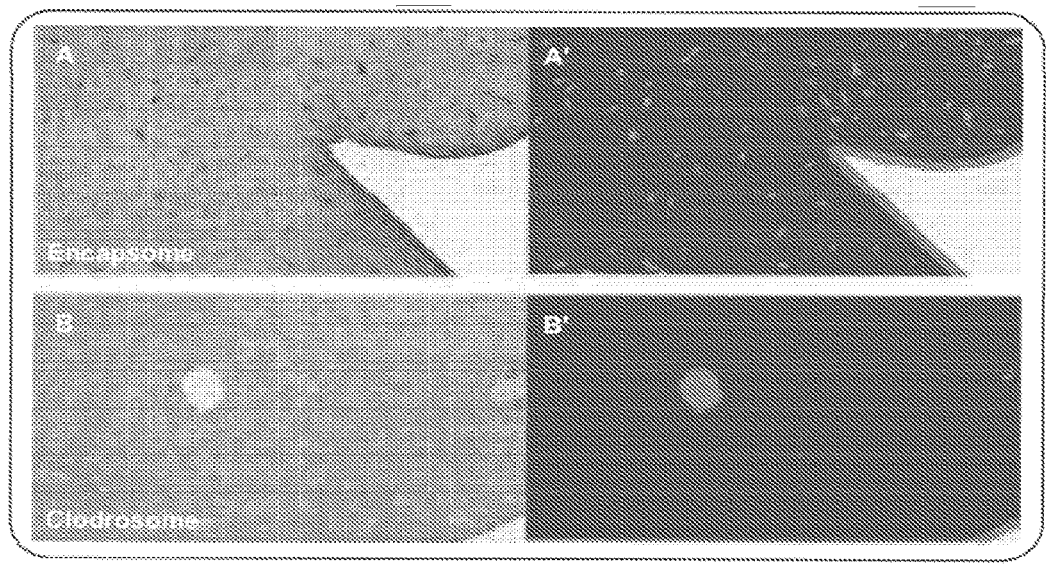

FIG. 56 shows a representative staining of HemA mouse liver section with an antibody to Iba-1, a specific macrophage marker. Panels A and A' show control ENCAPSOME® treatment of HemA mice. Panels B and B' show CLODROSOME® treatment of HemA mice. Panels A' and B' show the quantification masks highlighting the stained Kupffer cells, total tissue area, and empty areas.

Figure 57:
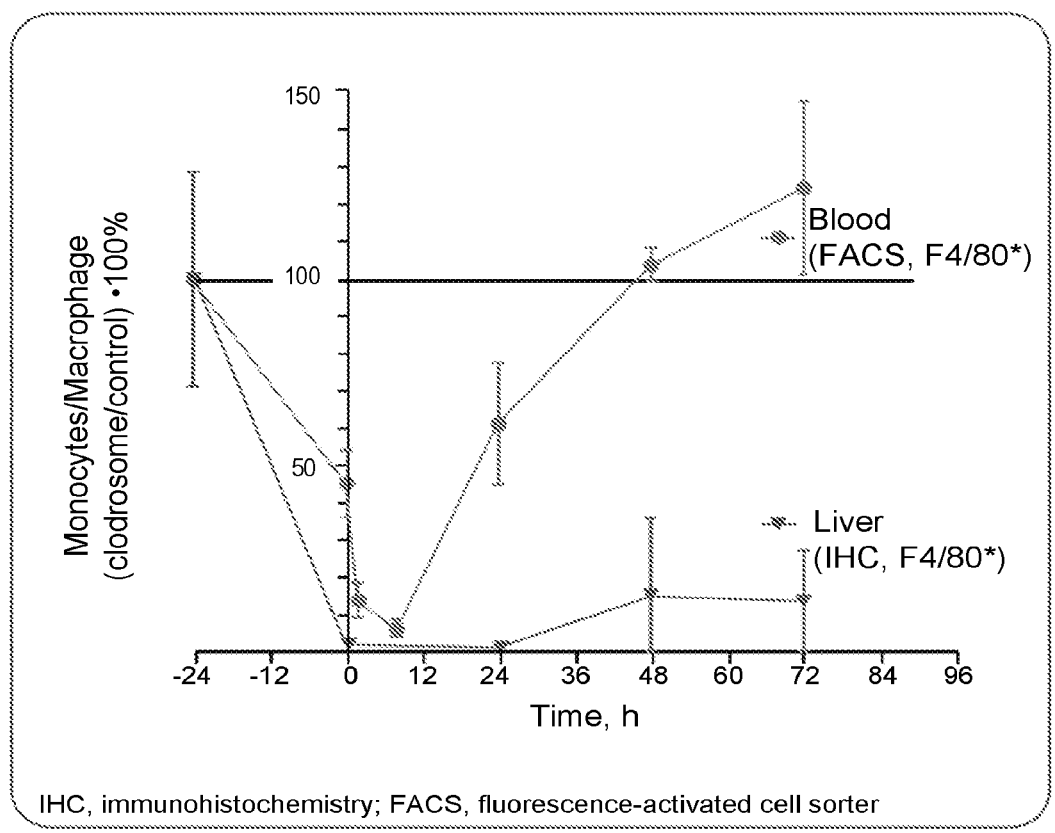

FIG. 57 shows an immunohistochemical (IHC) quantitative analysis of areas positively stained with a labeled antibody to F4/80 after treatment with CLODROSOME® or ENCAPSOME®, and a fluorescence-activated cell sorter (FACS) analysis identifying circulating monocytic cells in blood cells stained with the same labeled antibody to F4/80.

Figure 58:
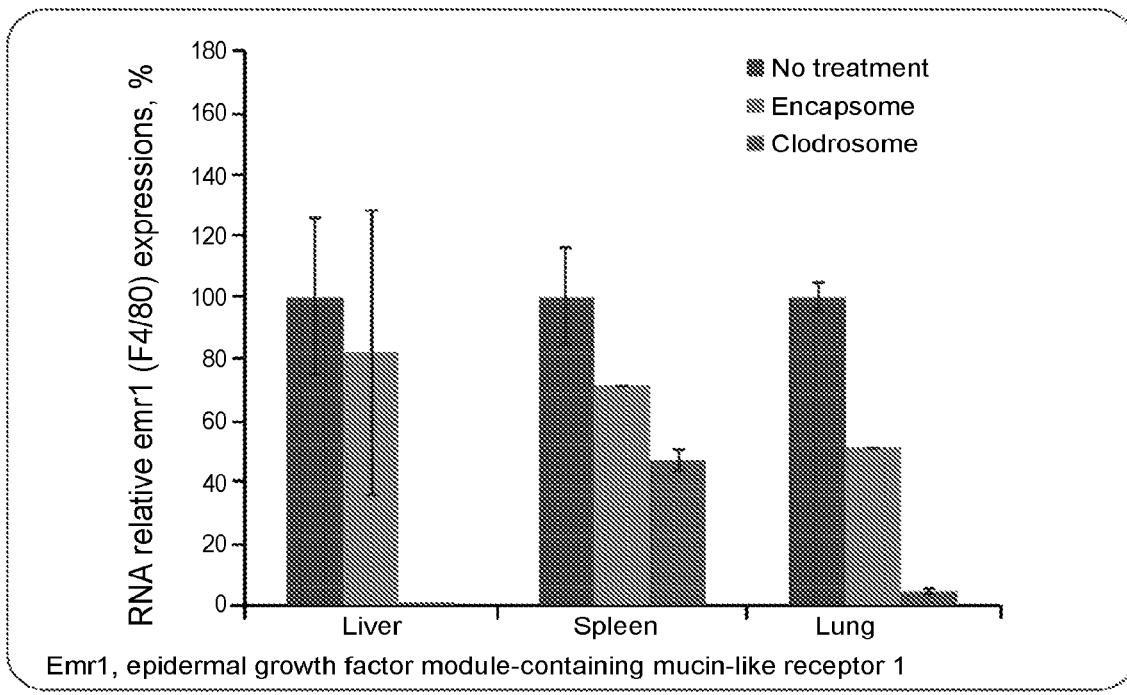

FIG. 58 shows RT-PCR analysis of the expression of the macrophage marker epidermal growth factor module-containing mucin-like receptor 1 (Emr1) (F4/80) in the liver, spleen, and lung of HemA mice treated with ENCAPSOME® or CLODROSOME®.

Figure 59:
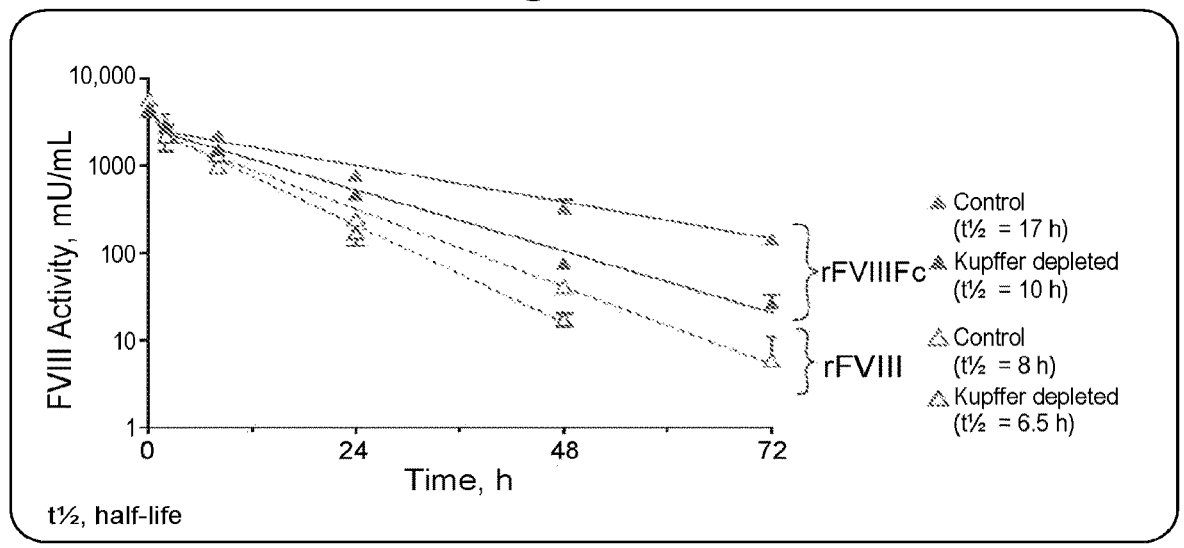

FIG. 59 shows clearance of rFVIII and rFVIIIFc in control HemA mice and macrophage/Kupffer cell depleted HemA mice.

Figure 60:
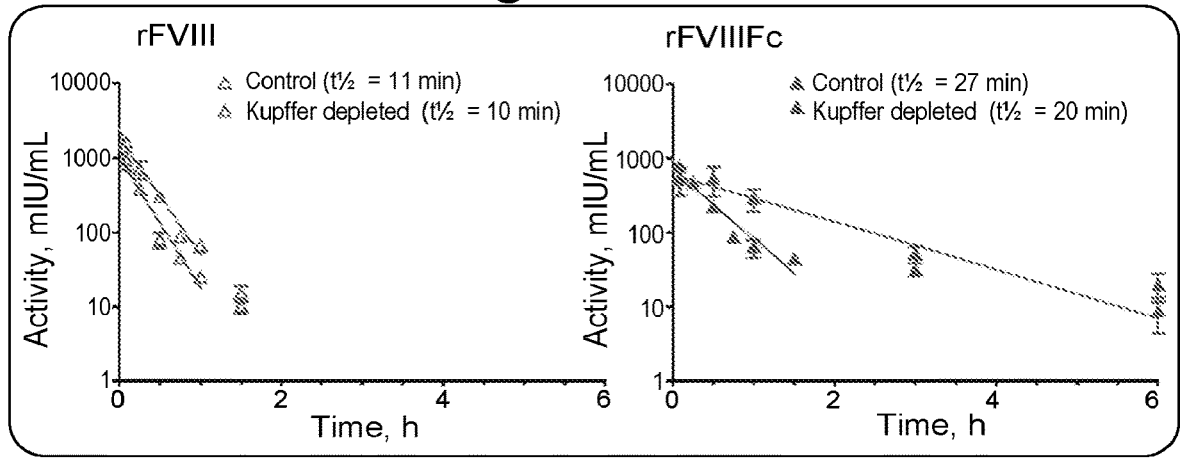

FIG. 60 shows clearance of rFVIII and rFVIIIFc in control DKO mice (mice lacking FVIII and VWF) and macrophage/Kupffer cell depleted DKO mice.

Figure 61:
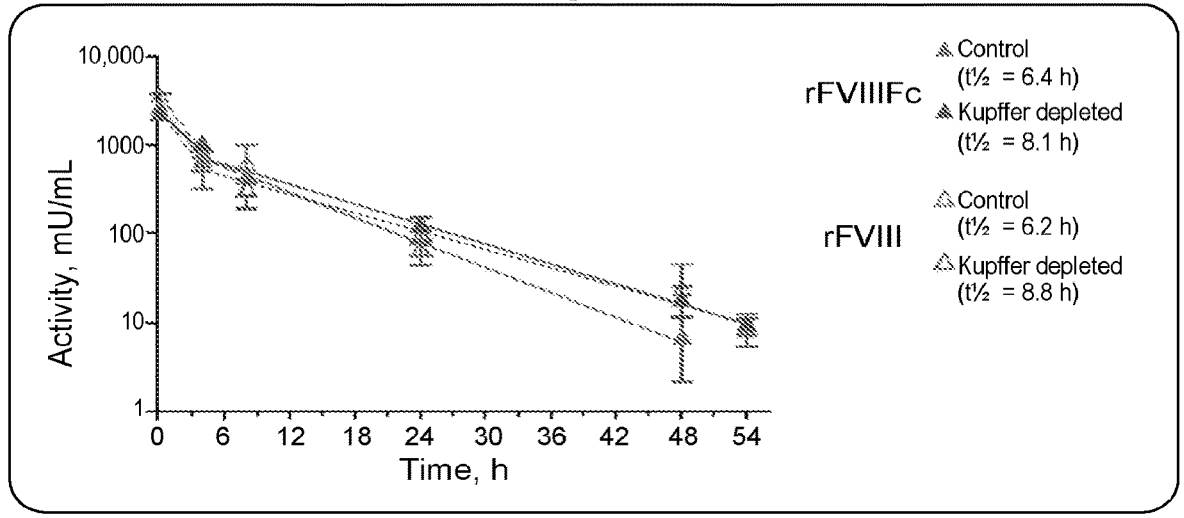
Figure 62:
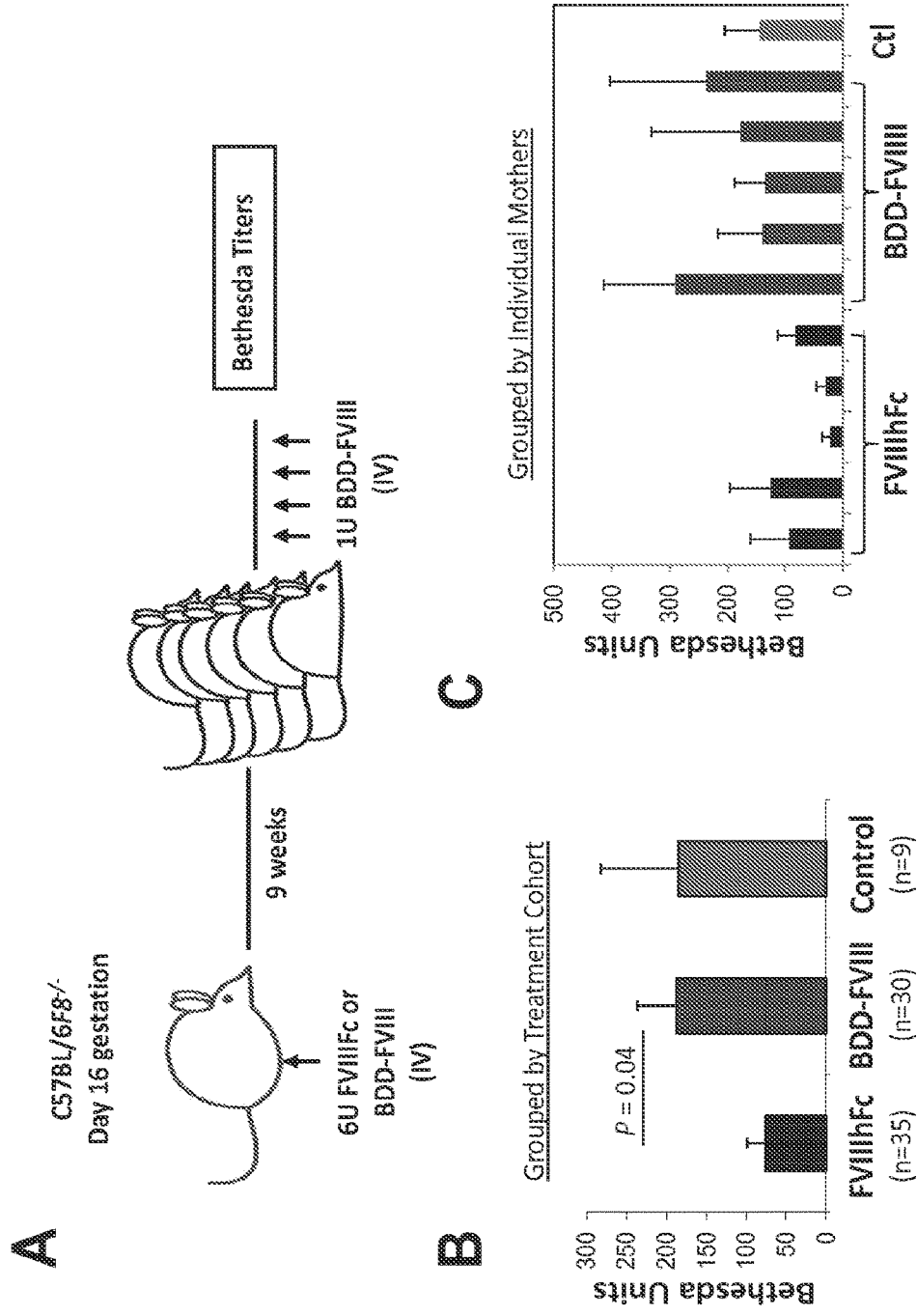

FIG. 61 shows clearance of rFVIII and rFVIIIFc in control FcRn-KO mice (mice lacking the FcRn recycling receptor) and macrophage/Kupffer cell depleted FcRn-KO mice FIG. 62 shows Bethesda titers of mice born out of mothers immunized on gestation day 16 with the indicated FVIII drug substance or Control (untreated). Panel A shows the experimental design, depicting the timings of treatment and dose of rFVIIIFc or XYNTHA® (BDD-FVIII) to pregnant mice and pups born out of them. Panels B and C show Bethesda titers for rFVIIIFc from pups born out of rFVIIIFc-treated, XYNTHA®-treated, or Control (untreated) mice, grouped according to treatment cohort (Panel B) or grouped by individual mothers (Panel C).

FIG. 63 shows Bethesda titers of mice born out of mothers immunized on gestation day 15-17 with the indicated FVIII drug substance or control (untreated). Panel A shows the experimental design, depicting the timings of treatment and dose of rFVIIIFc or XYNTHA® (BDD-FVIII) to pregnant mice and pups born out of them. Panels B and C show Bethesda titers for rFVIIIFc from pups born out of rFVIIIFc-treated, XYNTHA®-treated, or Control (untreated) mice, grouped according to treatment cohort (Panel B) or grouped by individual mothers (Panel C).

Figure 64:
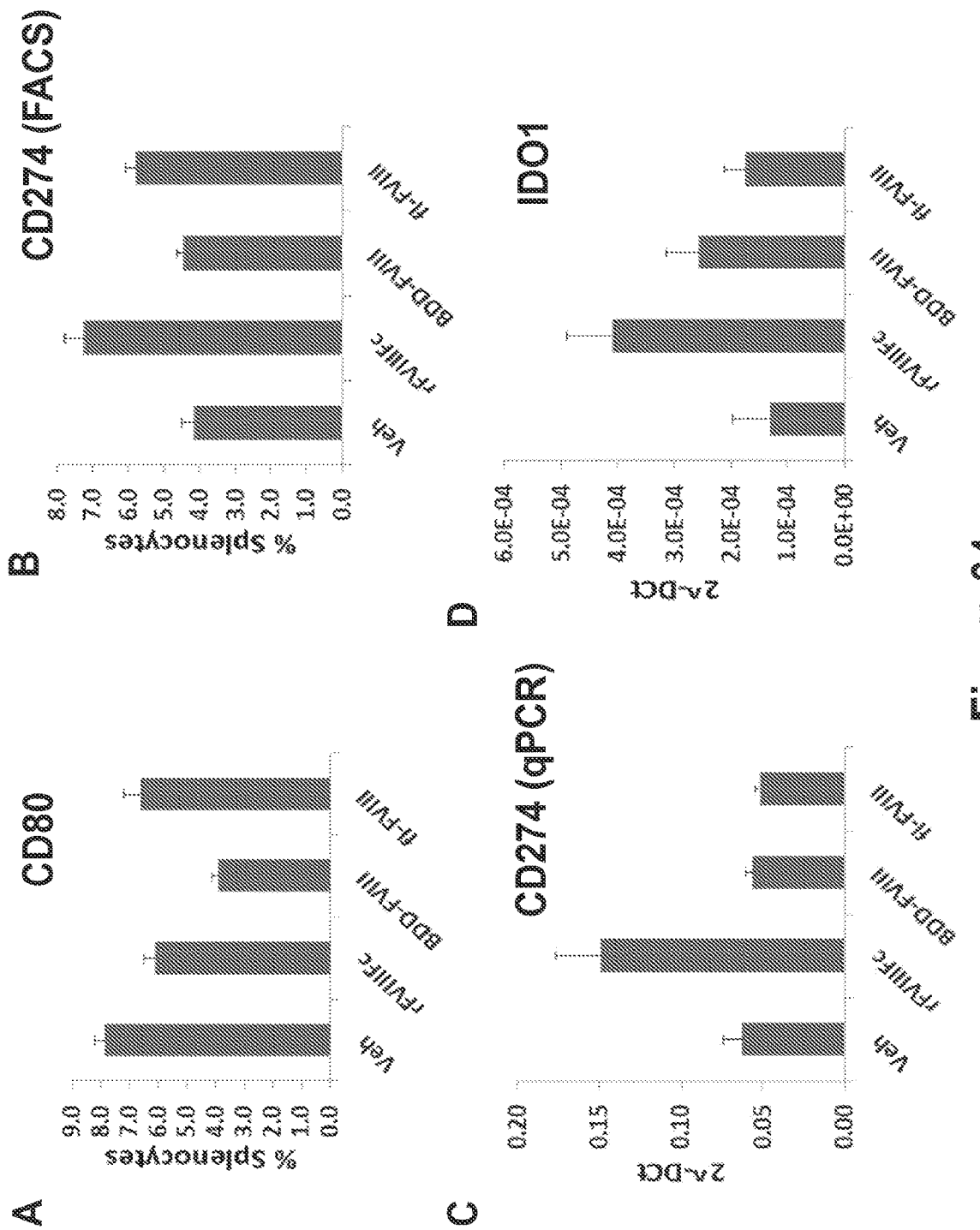

FIGS. 64A and 64B show dendritic cell surface expression of CD80 and CD274, respectively, determined by staining splenocytes from mice treated with 100 IU/kg rFVIIIFc, B-domain deleted FVIII (BDD-FVIII; XYNTHA®) or full length FVIII (fl-FVIII; ADVATE®) for these two antigens along with CD11c and MHC Class II. The results show percent splenocytes±SEM (n=7-9; *p<0.05 vs. vehicle; †p<0.05 vs. rFVIIIFc; T-test). FIGS. 64C and 64D show mRNA expression levels of CD274 and IDOL, respectively, determined by real time PCR from splenocytes normalized to GAPDH levels. Bars represent relative expression levels ($2^{-\Delta Ct}$)±SEM (n=4-9; *p<0.05 vs. vehicle; †p<0.05 vs. rFVIIIFc; T-test).

Figure 65:
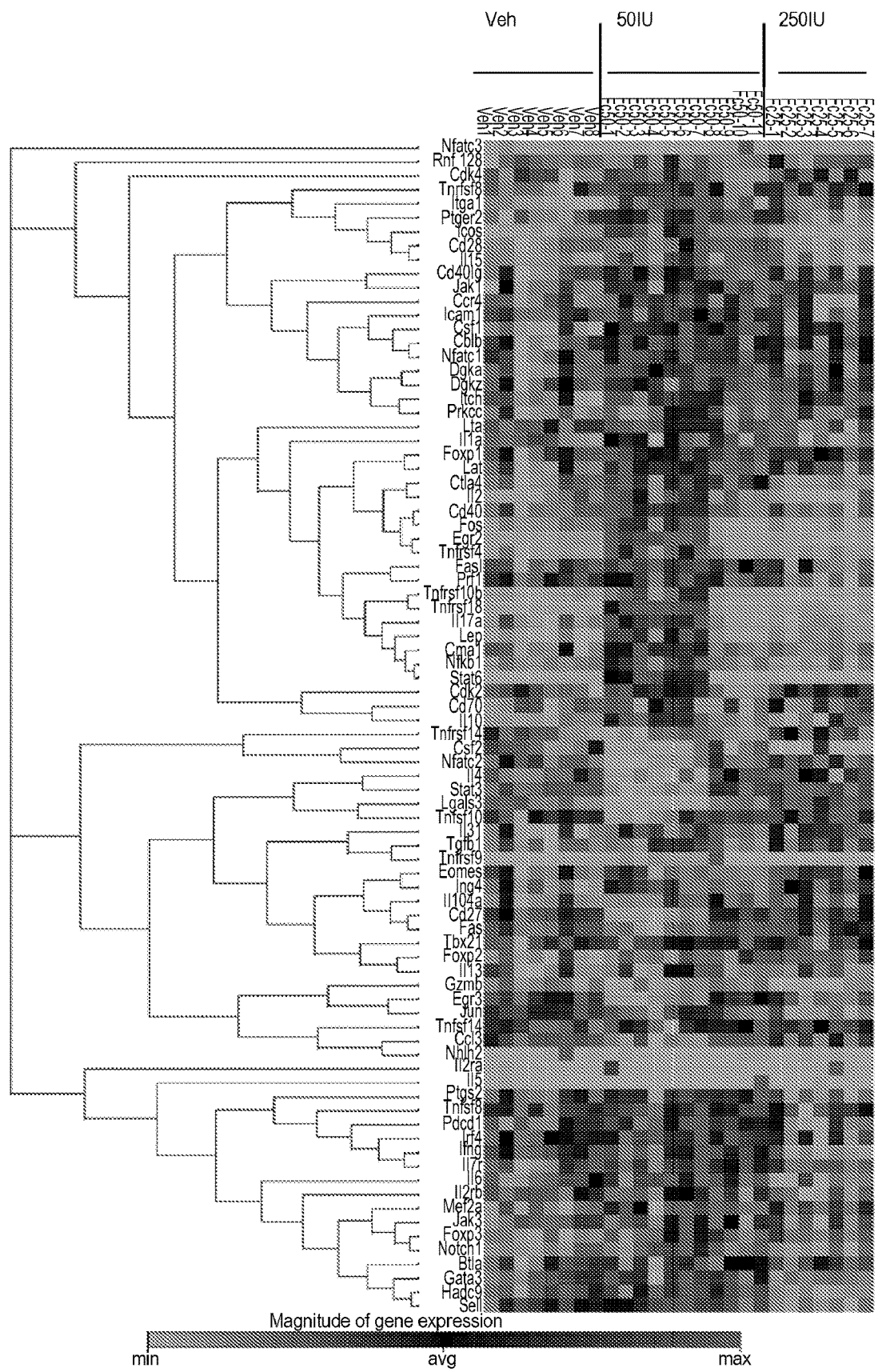

FIG. 65 shows a heat map depicting the expression profiles of all the genes in a real time PCR array among the three tested groups, i.e., splenocytes of vehicle, 50 IU/kg and 250 IU/kg rFVIIIFc treated HemA mice. cDNA from each of the samples was used to monitor the expression of individual genes using a real time PCR array consisting of genes focused on tolerance and anergy associated molecules.

Figure 66:
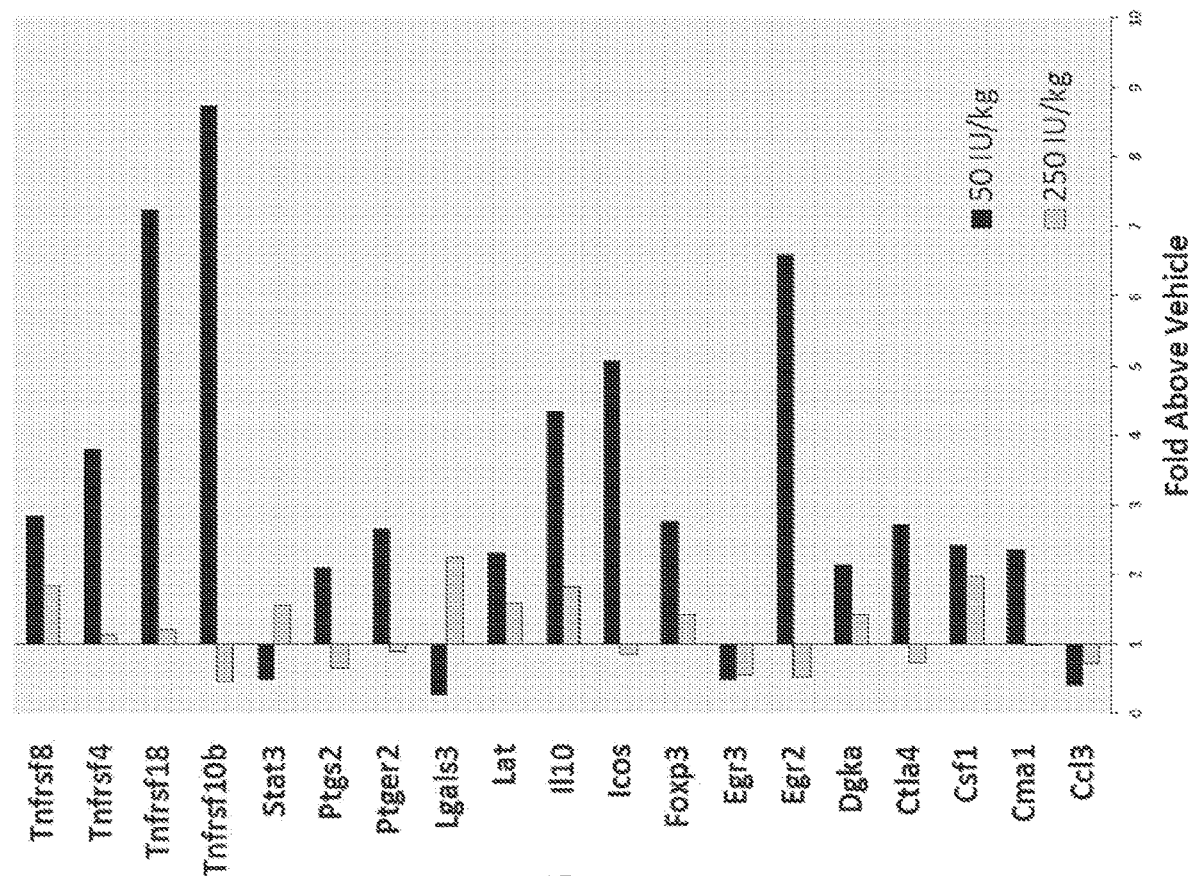

FIG. 66 shows an expression profile of candidate genes that were identified as being up- or down-regulated by the splenocytes of 50 IU/kg rFVIIIFc treated HemA mice and comparison with the 250 IU/kg rFVIIIFc treated group. Results illustrate the change in expression of genes above the vehicle group. The cut-off for fold change in regulation was taken as 2, i.e., fold change above 2 was considered upregulation and below 0.5 as downregulation. All the candidate genes belonging to the 50 IU/kg group shown here were significantly regulated (p<0.05 vs. vehicle as well as the 250 IU/kg group; n=8-11).

Figure 67:
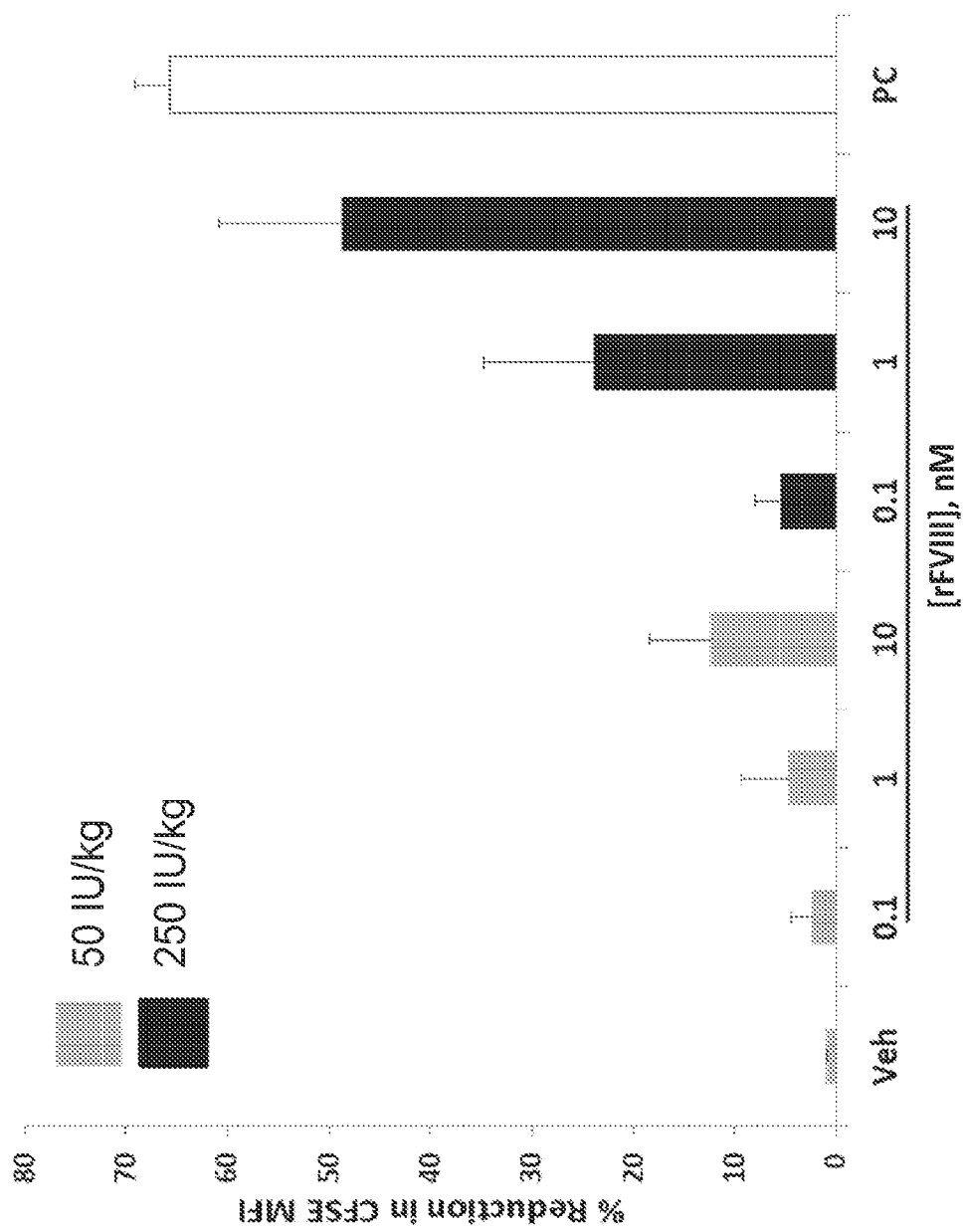

FIG. 67 shows a T-cell proliferation profile comparison between HemA mice receiving two weekly injections of either 50 IU/kg or 250 IU/kg of rFVIIIFc. Bars represent decrease in MFI of CFSE relative to control in T-cells±SEM (*p<0.05, T-test, n=3-5) from the 250 IU/kg and 50 IU/kg groups.

Figure 68:
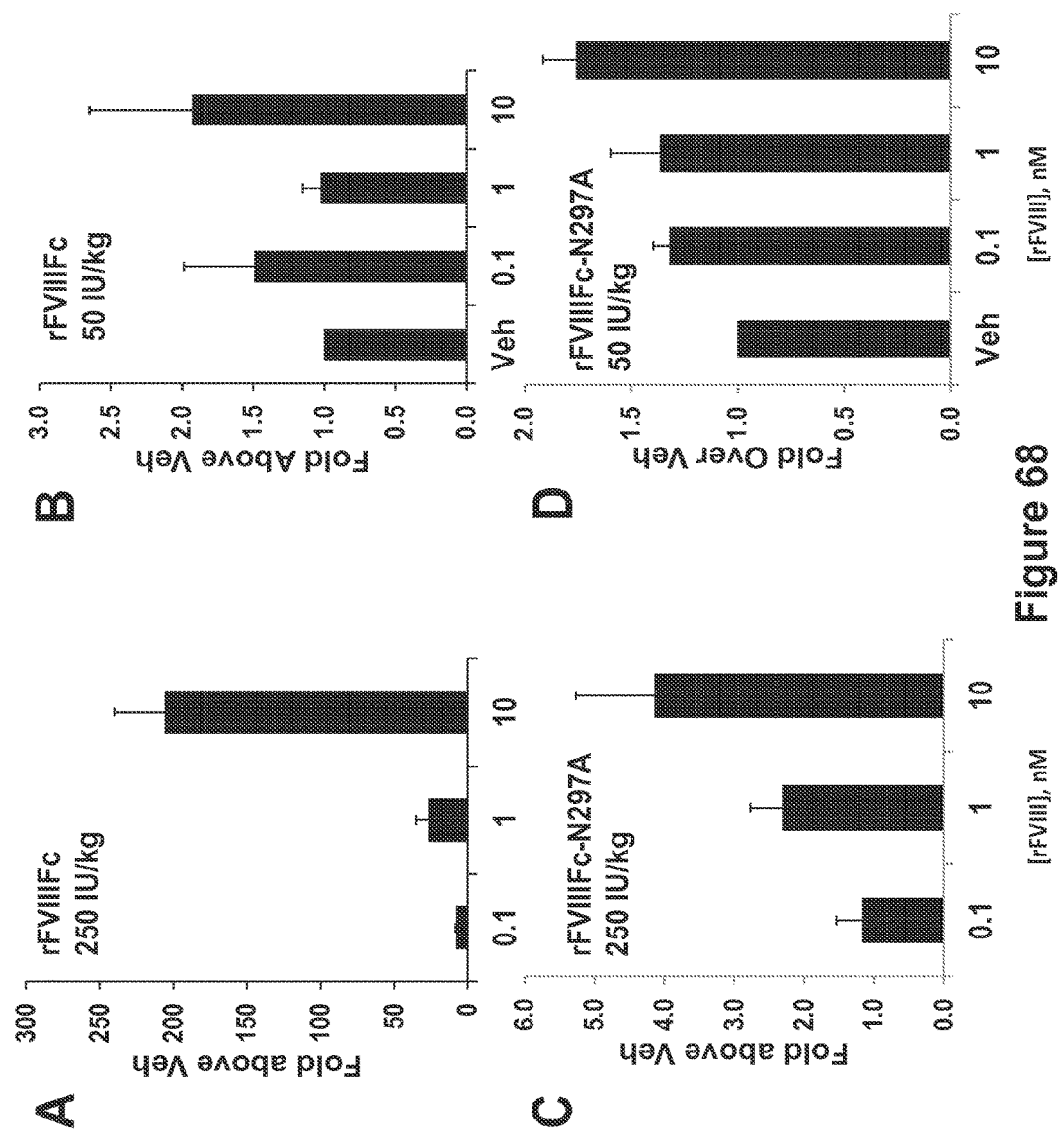

FIG. 68A-D shows IFNγ secretion profiles of T-cells from HemA mice receiving two weekly injections of either 250 IU/kg of rFVIIIFc (FIG. 68A), 50 IU/kg of rFVIIIFc (FIG. 68B), 250 IU/kg of rFVIIIFc-N297A (FIG. 68C), or 50 IU/kg rFVIIIFc-N297A (FIG. 68D). Bars represent fold above vehicle of IFNγ secretion±SEM (*p<0.05, T-test; n=3-5).

DETAILED DESCRIPTION

The present disclosure provides a method of treating Hemophilia A with Factor VIII (FVIII) (processed, single chain, or a combination thereof) using a longer dosing interval and/or greater AUC than is possible with currently known FVIII products. The present disclosure also provides methods of inducing immune tolerance to FVIII. The present disclosure also provides improved FVIII chimeric polypeptides and methods of production.

The methods of inducing immune tolerance and production of improved chimeric polypeptides disclosed herein are also generally applicable to one or more clotting factors, e.g., FVII and FIX. Accordingly, the present disclosures regarding FVIII chimeric polypeptides (e.g., FVIIIFc) and their uses, are equally applicable to other chimeric polypeptides comprising a clotting factor portion and an Fc portion. In some specific examples, the clotting factor portion of the chimeric polypeptide is FVII or FIX. In this respect, the present disclosure provides in general a method of inducing immune tolerance to a clotting factor in a subject in need thereof comprising administering to the subject a chimeric polypeptide comprises a clotting factor portion and an Fc portion. Also provided is a method of preventing or inhibiting development of an inhibitor to a clotting factor comprising administering to a subject in need of immune tolerance to the clotting factor a chimeric polypeptide, wherein the chimeric polypeptide comprises a clotting factor portion and an Fc portion.

Treatment of hemophilia A is by replacement therapy targeting restoration of FVIII activity to 1 to 5% of normal levels to prevent spontaneous bleeding (Mannucci, P. M. et al., *N. Engl. J. Med.* 344:1773-9 (2001), herein incorporated by reference in its entirety). There are plasma-derived and recombinant FVIII products available to treat bleeding episodes on-demand or to prevent bleeding episodes from occurring by treating prophylactically. Based on the short half-life of these products (8-12 hours) (White G. C., et al., *Thromb. Haemost.* 77:660-7 (1997); Morfini, M., Haemophilia 9 (suppl 1):94-99; discussion 100 (2003)), treatment regimens require frequent intravenous administration, commonly two to three times weekly for prophylaxis and one to three times daily for on-demand treatment (Manco-Johnson, M. J., et al., *N. Engl. J. Med.* 357:535-544 (2007)), each of which is incorporated herein by reference in its entirety. Such frequent administration is painful and inconvenient. Another major challenge associated with currently available FVIII products is the development of neutralizing anti-FVIII antibodies in patients receiving FVIII therapies. Inhibitory FVIII immune responses can comprise anti-Factor VIII antibodies and/or cell-mediated immune responses.

The present disclosure provides a method of administering FVIII to a human subject in need thereof (e.g., human patient) that is at risk of developing an inhibitory FVIII immune response. The method comprises administration of a chimeric polypeptide comprising a FVIII portion and an Fc portion.

In some embodiments, the administration of the chimeric polypeptide reduces the number of antibodies to FVIII in the subject compared to the number prior to administration. In some embodiments, the chimeric polypeptide is administered to a subject with an inhibitory FVIII immune response, and the administration can reduce the inhibitory immune response. The inhibitory FVIII immune response can be an inhibitory antibody immune response and/or a cell-mediated immune response. Administration of a chimeric polypeptide according to the methods provided herein can decrease or neutralize the inhibitory immune response. Thus, in some embodiments, anti-FVIII antibodies are decreased or eliminated in a subject after administration of a chimeric polypeptide comprising a FVIII portion and an Fc portion. The decrease can be, for example, a 10%, 20%, 30%, 40%, 50%, 60%, 70%, 80% or 90% reduction.

In some embodiments, the administration of the chimeric polypeptide reduces the titer of antibodies to FVIII in the subject compared to the titer prior to administration. In some embodiments, the titer of anti-FVIII antibodies is decreased in a subject after administration of a chimeric polypeptide comprising a FVIII portion and an Fc portion. Accordingly, administration of a chimeric polypeptide comprising a FVIII portion and an Fc portion can reduce inhibitors to less than 20, less than 10, less than 5, less than 4, less than 3, less than 2, less than 1, or less than 0.6 Bethesda Units (BU).

In some embodiments, the administration of the chimeric polypeptide reduces the level of a cytokine in the subject compared to the level prior to administration. In some embodiments, cytokine levels are decreased in a subject after administration of a chimeric polypeptide comprising a FVIII portion and an Fc portion. The cytokine can be, for example, Il-12, IL-4, and/or TNF-α. The decrease can be, for example, a 10%, 20%, 30%, 40%, 50%, 60%, 70%, 80% or 90% reduction.

In some embodiments, the chimeric polypeptide is administered to a subject that previously developed an inhibitory FVIII immune response. Administration of a chimeric polypeptide to such subjects, according to the methods provided herein, can result in a decreased immune response compared to the previous response. Thus, in some embodiments, fewer anti-FVIII antibodies are produced in a subject after administration of a chimeric polypeptide according to the present methods than were produced after administration of a polypeptide consisting of a FVIII polypeptide. In some embodiments, the administration of the chimeric polypeptide reduces the number of antibodies to FVIII in the subject compared to the number in the subject after a previous treatment with a polypeptide consisting of a FVIII polypeptide.

In some embodiments, the administration of the chimeric polypeptide reduces the titer of antibodies to FVIII in the subject compared to the titer in the subject after a previous treatment with a polypeptide consisting of a FVIII polypeptide. In some embodiments, the titer of anti-FVIII antibodies is lower in a subject after administration of a chimeric polypeptide comprising a FVIII portion and an Fc portion than was produced after administration of a polypeptide consisting of a FVIII polypeptide. In some embodiments, the administration of the chimeric polypeptide reduces the level of a cytokine in the subject compared to the level in the subject after a previous treatment with a polypeptide consisting of a FVIII polypeptide. In some embodiments, cytokine levels (e.g., IL-12, IL-4, and/or TNF-α) are lower in a subject after administration of a chimeric polypeptide comprising a FVIII portion and an Fc portion than the levels after administration of a polypeptide consisting of a FVIII polypeptide.

In some embodiments, the administration of the chimeric polypeptide reduces the number of anti-clotting factor antibodies in the subject compared to the number that would result from administration of a polypeptide consisting of the clotting factor portion or a polypeptide comprising the clotting factor portion, but not comprising the Fc portion to the subject. In some embodiments, the chimeric polypeptide is administered to a subject that has not previously developed an inhibitory FVIII immune response. Administration of a chimeric polypeptide to such subjects, according to the methods provided herein, can result in a lower immune response than would result from administration of a polypeptide consisting of a FVIII polypeptide. Thus, in some embodiments, fewer anti-FVIII antibodies are produced in a subject after administration of a chimeric polypeptide according to the present methods than would be produced by administration of a polypeptide consisting of a FVIII polypeptide.

In some embodiments, the administration of the chimeric polypeptide reduces the titer of anti-clotting factor antibodies in the subject compared to the titer that would result from administration of a polypeptide consisting of the clotting factor portion or a polypeptide comprising the clotting factor portion, but not comprising the Fc portion to the subject. In some embodiments, the titer of anti-FVIII antibodies is lower in a subject after administration of a chimeric polypeptide comprising a FVIII portion and an Fc portion than would be produced by administration of a polypeptide consisting of a FVIII polypeptide. In some embodiments, the administration of the chimeric polypeptide reduces the level of a cytokine (e.g., IL-12, IL-4, and/or TNF-α) in the subject compared to the level that would result from administration of a polypeptide consisting of the clotting factor portion or a polypeptide comprising the clotting factor portion, but not comprising the Fc portion to the subject. In some embodiments, cytokine levels (e.g., IL-12, IL-4, and/or TNF-α) are lower in a subject after administration of a chimeric polypeptide comprising a FVIII portion and an Fc portion than they would be after administration of a polypeptide consisting of a FVIII polypeptide.

The methods of the present disclosure can further comprise, prior to administration of the chimeric polypeptide, identifying that the subject has one or more characteristics selected from the group consisting of: (a) has a mutation or deletion in the gene encoding the clotting factor; (b) has a rearrangement in the gene encoding the clotting factor; (c) has a relative who has previously developed an inhibitory immune response against the clotting factor; (d) is receiving interferon therapy; (e) is receiving anti-viral therapy; (f) has a genetic mutation in a gene other than the gene encoding the clotting factor which is linked with an increased risk of developing an inhibitory immune response; and, (g) has two or more combinations thereof. In some embodiments, the subject has a genetic mutation in a gene other than the gene encoding the clotting factor comprises one or more mutation selected from the group consisting of: (i) a genetic polymorphism associated with increased TNF-α; (ii) a genetic polymorphism associated with increased IL10; (iii) a genetic polymorphism associated with decreased CTLA-4; (iv) a mutation in DR15 or DQB0602 MHC Class II molecules; and, (v) two or more combinations thereof. In some embodiments, the polymorphism is associated with increased TNF-α is 308G>A. In some embodiments, the polymorphism associated with increased IL10 is allele 134 of the IL10G microsatellite.

The present disclosure also provides a method of administering FVIII to a human subject in need thereof (e.g., human patient), comprising administering to the subject a therapeutic dose of a chimeric FVIII polypeptide, e.g., a chimeric FVIII-Fc polypeptide, or a hybrid of such a polypeptide at a dosing interval at least about one and one-half times longer than the dosing interval required for an equivalent dose of said FVIII without the non-FVIII portion (a polypeptide consisting of said FVIII portion), e.g., without the Fc portion. The present disclosure is also directed to a method of increasing dosing interval of FVIII administration in a human subject in need thereof comprising administering the chimeric FVIII polypeptide.

The dosing interval can be at least about one and one-half to six times longer, one and one-half to five times longer, one and one-half to four times longer, one and one-half to three times longer, or one and one-half to two times longer, than the dosing interval required for an equivalent dose of said FVIII without the non-FVIII portion (a polypeptide consisting of said FVIII portion), e.g., without the Fc portion. The dosing interval can be at least about one and one-half, two, two and one-half, three, three and one-half, four, four and one-half, five, five and one-half or six times longer than the dosing interval required for an equivalent dose of said FVIII without the non-FVIII portion (a polypeptide consisting of said FVIII portion), e.g., without the Fc portion. The dosing interval can be about every three, four, five, six, seven, eight, nine, ten, eleven, twelve, thirteen, or fourteen days or longer.

The dosing interval can be at least about one and one-half to 5, one and one-half, 2, 3, 4, or 5 days or longer.

The present disclosure also provides a method of administering FVIII to a human subject in need thereof, comprising administering to the subject a therapeutic dose of a chimeric FVIII polypeptide, e.g., a chimeric FVIII-Fc polypeptide, or a hybrid of such a polypeptide to obtain an area under the plasma concentration versus time curve (AUC) at least about one and one-quarter times greater than the AUC obtained by an equivalent dose of said FVIII without non-FVIII portion (a polypeptide consisting of said FVIII portion), e.g., without the Fc portion. The present disclosure thus includes a method of increasing or extending AUC of FVIII activity in a human patient in need thereof comprising administering the chimeric FVIII polypeptide.

The present disclosure also provides a method of administering FVIII to a subject in need thereof, comprising administering to the subject a therapeutic dose of a polypeptide comprising a FVIII and an Fc or a hybrid of such a polypeptide at a dosing interval of about every three, four, five, six, seven, eight, nine, ten, eleven, twelve, thirteen, or fourteen days or longer.

The methods disclosed herein can be practiced on a subject in need of prophylactic treatment or on-demand treatment.

"Administering," as used herein, means to give a pharmaceutically acceptable FVIII polypeptide disclosed herein to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. Chimeric polypeptides and hybrid proteins can be administered as part of a pharmaceutical composition comprising at least one excipient.

"Area under the plasma concentration versus time curve (AUC)," as used herein, is the same as the term of art in pharmacology, and is based upon the rate and extent of absorption of FVIII following administration. AUC is determined over a specified time period, such as 12, 18, 24, 36, 48, or 72 hours, or for infinity using extrapolation based on the slope of the curve. Unless otherwise specified herein, AUC is determined for infinity. The determination of AUC can be carried out in a single subject, or in a population of subjects for which the average is calculated.

A "B domain" of FVIII, as used herein, is the same as the B domain known in the art that is defined by internal amino acid sequence identity and sites of proteolytic cleavage by thrombin, e.g., residues Ser741-Arg1648 of full length human FVIII. The other human FVIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the FVIII light chain activation peptide. The locations of the boundaries for all of the domains, including the B domains, for porcine, mouse and canine FVIII are also known in the art. In one embodiment, the B domain of FVIII is deleted ("B domain deleted FVIII" or "BDD FVIII").

An example of a BDD FVIII is REFACTO® (recombinant BDD FVIII), which has the same sequence as the FVIII portion of the sequence in TABLE 2A(i) (amino acids 1 to 1457 or 20 to 1457 of SEQ ID NO:2). In another embodiment, the B domain deleted FVIII contains an intact intracellular processing site, which corresponds to Arginine at residue 754 of B domain deleted FVIII, which corresponds to Arginine residue 773 of SEQ ID NO: 2, or residue 1648 of full-length FVIII, which corresponds to Arginine residue 1667 of SEQ ID NO: 6. The sequence residue numbers used herein without referring to any SEQ ID Numbers correspond to the FVIII sequence without the signal peptide sequence (19 amino acids) unless otherwise indicated. For example, S743/Q1638 of full-length FVIII corresponds to S762/Q1657 of SEQ ID NO: 6 due to the 19 amino acid signal peptide sequence.

A "B domain deleted FVIII" can have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B domain deleted FVIII sequence comprises any one of the deletions disclosed at col. 4, line 4 to col. 5, line 28 and examples 1-5 of U.S. Pat. No. 6,316,226 (also in U.S. Pat. No. 6,346,513). In some embodiments, a B domain deleted FVIII has a deletion disclosed at col. 2, lines 26-51 and examples 5-8 of U.S. Pat. No. 5,789,203 (also U.S. Pat. Nos. 6,060,447, 5,595,886, and 6,228,620).

In some embodiments, a B domain deleted FVIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B domain deleted FVIII has a deletion of most of the B domain, but still contains amino-terminal sequences of the B domain that are essential for in vivo proteolytic processing of the primary translation product into two polypeptide chain (i.e., intracellular processing site), as disclosed in WO 91/09122, which is incorporated herein by reference in its entirety.

In some embodiments, a B domain deleted FVIII is constructed with a deletion of amino acids 747-1638, i.e., virtually a complete deletion of the B domain. Hoeben R. C., et al. *J. Biol. Chem.* 265 (13): 7318-7323 (1990), incorporated herein by reference in its entirety. A B domain deleted FVIII can also contain a deletion of amino acids 771-1666 or amino acids 868-1562 of FVIII. Meulien P., et al. *Protein Eng.* 2(4): 301-6 (1988), incorporated herein by reference in its entirety. Additional B domain deletions that are part of the instant disclosure include, e.g., deletion of amino acids 982 through 1562 or 760 through 1639 (Toole et al., *Proc. Natl. Acad. Sci. U.S.A.* 83:5939-5942 (1986)), 797 through 1562 (Eaton et al., *Biochemistry* 25:8343-8347 (1986)), 741 through 1646 (Kaufman (PCT published application No. WO 87/04187)), 747-1560 (Sarver et al., DNA 6:553-564 (1987)), 741 through 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety. Each of the foregoing deletions can be made in any FVIII sequence.

In one embodiment, the B domain deleted FVIII portion in the chimeric polypeptide is processed into two chains connected (or associated) by a metal bond, the first chain comprising a heavy chain (A1-A2-partial B) and a second chain comprising a light chain (A3-C1-C2). In another embodiment, the B domain deleted FVIII portion is a single chain FVIII. The single chain FVIII can comprise an intracellular processing site, which corresponds to Arginine at residue 754 of B domain deleted FVIII (residue 773 of SEQ ID NO: 2) or at residue 1648 of full-length FVIII (residue 1657 of SEQ ID NO: 6).

The metal bond between the heavy chain and the light chain can be any metal known in the art. For example, the metal can be a divalent metal ion. The metals that can be used to associate the heavy chain and light chain include, but not limited to, $Ca^{2+}$, $Mn^{2+}$, or $Cu^{2+}$. Fatouros et al., *Intern. J. Pharm.* 155(1): 121-131 (1997); Wakabayashi et al., *JBC.* 279(13): 12677-12684 (2004).

In some embodiments, the FVIII portion in the chimeric polypeptide comprises the A1 domain of FVIII. In some embodiments, the FVIII portion in the chimeric polypeptide comprises the A2 domain of FVIII. In some embodiments, the FVIII portion in the chimeric polypeptide comprises the A3 domain of FVIII. In some embodiments, the FVIII portion in the chimeric polypeptide comprises the C1 domain of FVIII. In some embodiments, the FVIII portion in the chimeric polypeptide comprises the C2 domain of FVIII.

"Chimeric polypeptide," as used herein, means a polypeptide that includes within it at least two polypeptides (or subsequences or peptides) from different sources. Chimeric polypeptides can include, e.g., two, three, four, five, six, seven, or more polypeptides from different sources, such as different genes, different cDNAs, or different animal or other species. Chimeric polypeptides can include, e.g., one or more linkers joining the different subsequences. Thus, the subsequences can be joined directly or they can be joined indirectly, via linkers, or both, within a single chimeric polypeptide. Chimeric polypeptides can include, e.g., additional peptides such as signal sequences and sequences such as 6His and FLAG that aid in protein purification or detection. In addition, chimeric polypeptides can have amino acid or peptide additions to the N- and/or C-termini.

In some embodiments, the chimeric polypeptide comprises a clotting factor portion (e.g., a FVIII portion) and a non-clotting factor portion (e.g., a non-FVIII portion). Exemplary non-clotting factor portions (e.g., non-FVIII portions) include, for example, Fc. Exemplary chimeric FVIII-Fc polypeptides include, e.g., SEQ ID NOs:2 or 6 (TABLE 2), with or without their signal sequences and the chimeric Fc polypeptide of SEQ ID NO:4 (TABLE 2).

As used herein, the term "portion" when applied to a chimeric polypeptide refers to one of the components or moieties of such chimeric polypeptide (e.g., "a chimeric polypeptide comprising a FVIII portion and an Fc portion," or "the FVIII portion of the chimeric polypeptide"). In other words, the term "portion" is used to indicate the source of different components in the chimeric polypeptide, but is not used to indicate a fragment of the FVIII protein or a fragment of an Fc region.

The chimeric polypeptide can comprise a sequence at least 90% or 95% identical to the FVIII and Fc amino acid sequence shown in TABLE 2A(i) without a signal sequence (amino acids 20 to 1684 of SEQ ID NO:2) or at least 90% or 95% identical to the FVIII and Fc amino acid sequence shown in TABLE 2A(i) with a signal sequence (amino acids 1 to 1684 of SEQ ID NO:2), wherein the sequence has FVIII activity. The FVIII activity can be measured by activated Partial Thromboplastin Time (aPPT) assay, chromogenic assay, or other known methods. The chimeric polypeptide can comprise a sequence identical to the FVIII and Fc amino acid sequence shown in TABLE 2A(i) without a signal sequence (amino acids 20 to 1684 of SEQ ID NO:2) or identical to the FVIII and Fc amino acid sequence shown in TABLE 2A(i) with a signal sequence (amino acids 1 to 1684 of SEQ ID NO:2).

In some embodiments, the FVIII portion comprises a FVIII A3 domain. In some embodiments, the FVIII portion comprises human FVIII. In some embodiments, the FVIII portion has a full or partial deletion of the B domain. In some embodiments, the FVIII portion is at least 90% or 95% identical to a FVIII amino acid sequence shown in TABLE 2 without a signal sequence (amino acids 20 to 1457 of SEQ ID NO:2; amino acids 20 to 2351 of SEQ ID NO:6). In some embodiments, the FVIII portion is identical to a FVIII amino acid sequence shown in TABLE 2 without a signal sequence (amino acids 20 to 1457 of SEQ ID NO:2 or amino acids 20 to 2351 of SEQ ID NO:6). The FVIII portion is at least 90% or 95% identical to a FVIII amino acid sequence shown in TABLE 2 with a signal sequence (amino acids 1 to 1457 of SEQ ID NO:2 or amino acids 1 to 2351 of SEQ ID NO:6). In some embodiments, the FVIII portion is identical to a FVIII amino acid sequence shown in TABLE 2 with a signal sequence (amino acids 1 to 1457 of SEQ ID NO:2 or amino acids 1 to 2351 of SEQ ID NO:6). In some embodiments, the FVIII portion has coagulation activity.

In some embodiments, the Fc portion is identical to the Fc amino acid sequence shown in TABLE 2 (amino acids 1458 to 1684 of SEQ ID NO:2 or amino acids 2352 to 2578 of SEQ TD NO:6). In some embodiments, the chimeric polypeptide is in the form of a hybrid comprising a second polypeptide in association with the chimeric polypeptide, wherein the second polypeptide consists essentially of or consists of the Fc portion or the FcRn binding partner.

In some embodiments, the clotting factor portion of the chimeric polypeptide comprises Factor IX. In some embodiments, the Factor IX portion of the chimeric polypeptide is at least 90%, 95%, or 100% identical to a FIX amino acid sequence shown in TABLE 2 without a signal sequence (amino acids 20 to 1457 of SEQ ID NO:2; amino acids 20 to 2351 of SEQ ID NO:6). In some embodiments, the chimeric polypeptide is a monomer dimer hybrid comprising a first chain comprising a FIX portion and the Fc portion and a second chain consisting essentially of or consisting of a Fc portion.

In some embodiments, the chimeric polypeptide comprises a Factor VII portion. In some embodiments, the chimeric polypeptide is a monomer dimer hybrid comprising a first chain comprising a FVII portion and the Fc portion and a second chain consisting essentially of or consisting of a Fc portion. In some embodiments, the FVII portion is inactive FVII, activated FVII, or activatable FVII.

In some embodiments, the chimeric polypeptide as disclosed herein comprises a clotting factor other than FVIII, e.g., FVII, FVIIa, or FIX. In one example, FVII is Factor VII zymogen (inactive form of FVII), activated FVII, or activatable FVII. In another example, FIX is FIX zymogen or activated FIX. A variety of non-clotting factor portions capable of increasing the half-life of a polypeptide are known in the art.

In some embodiments, a chimeric polypeptide comprising a FVIII portion has an increased half-life (t½) over a polypeptide consisting of the same FVIII portion without the non FVIII portion. A chimeric FVIII polypeptide with an increased $t_{1/2}$ can be referred to herein as a long-acting FVIII. Long-acting chimeric FVIII polypeptides include, e.g., FVIII fused to Fc (including, e.g., chimeric FVIII polypeptides in the form of a hybrid such as a FVIIIFc monomer dimer hybrid; see Example 1, FIG. 1, and Table 2A; and U.S. Pat. Nos. 7,404,956 and 7,348,004), and FVIII fused to albumin.

"Culture," "to culture" and "culturing," as used herein, means to incubate cells under in vitro conditions that allow for cell growth or division or to maintain cells in a living state. "Cultured cells," as used herein, means cells that are propagated in vitro.

"Factor VIII," abbreviated throughout the instant application as "FVIII," as used herein, means functional FVIII polypeptide in its normal role in coagulation, unless otherwise specified. Thus, the term FVIII includes variant polypeptides that are functional. FVIII proteins can be the human, porcine, canine, and murine FVIII proteins. As described in the Background Art section, the full length polypeptide and polynucleotide sequences are known, as are many functional fragments, mutants and modified versions. Examples of human FVIII sequences are shown as subsequences in SEQ ID NOs:2 or 6 (TABLE 2). FVIII polypeptides include, e.g., full-length FVIII, full-length FVIII minus Met at the N-terminus, mature FVIII (minus the signal sequence), mature FVIII with an additional Met at the N-terminus, and/or FVIII with a full or partial deletion of the B domain. FVIII variants include B domain deletions, whether partial or full deletions.

A great many functional FVIII variants are known, as is discussed above and below. In addition, hundreds of non-functional mutations in FVIII have been identified in hemophilia patients, and it has been determined that the effect of these mutations on FVIII function is due more to where they lie within the 3-dimensional structure of FVIII than on the nature of the substitution (Cutler et al., Hum. Mutat. 19:274-8 (2002)), incorporated herein by reference in its entirety. In addition, comparisons between FVIII from humans and other species have identified conserved residues that are likely to be required for function (Cameron et al., Thromb. Haemost. 79:317-22 (1998); U.S. Pat. No. 6,251,632), incorporated herein by reference in its entirety.

The human FVIII gene was isolated and expressed in mammalian cells (Toole, J. J., et al., Nature 312:342-347 (1984); Gitschier, J., et al., Nature 312:326-330 (1984); Wood, W. I., et al., Nature 312:330-337 (1984); Vehar, G. A., et al., Nature 312:337-342 (1984); WO 87/04187; WO 88/08035; WO 88/03558; U.S. Pat. No. 4,757,006), each of which is incorporated herein by reference in its entirety, and the amino acid sequence was deduced from cDNA. Capon et al., U.S. Pat. No. 4,965,199, incorporated herein by reference in its entirety, discloses a recombinant DNA method for producing FVIII in mammalian host cells and purification of human FVIII. Human FVIII expression in CHO (Chinese hamster ovary) cells and BHKC (baby hamster kidney cells) has been reported. Human FVIII has been modified to delete part or all of the B domain (U.S. Pat. Nos. 4,994,371 and 4,868,112, each of which is incorporated herein by reference in its entirety), and replacement of the human FVIII B domain with the human factor V B domain has been performed (U.S. Pat. No. 5,004,803, incorporated herein by reference in its entirety). The cDNA sequence encoding human FVIII and predicted amino acid sequence are shown in SEQ ID NOs:1 and 2, respectively, of U.S. Application Publ. No. 2005/0100990, incorporated herein by reference in its entirety.

U.S. Pat. No. 5,859,204, Lollar, J. S., incorporated herein by reference in its entirety, reports functional mutants of FVIII having reduced antigenicity and reduced immunoreactivity. U.S. Pat. No. 6,376,463, Lollar, J. S., incorporated herein by reference in its entirety, also reports mutants of FVIII having reduced immunoreactivity. U.S. Application Publ. No. 2005/0100990, Saenko et al., incorporated herein by reference in its entirety, reports functional mutations in the A2 domain of FVIII.

A number of functional FVIII molecules, including B-domain deletions, are disclosed in the following patents U.S. Pat. Nos. 6,316,226 and 6,346,513, both assigned to Baxter; U.S. Pat. No. 7,041,635 assigned to In2Gen; U.S. Pat. Nos. 5,789,203, 6,060,447, 5,595,886, and 6,228,620 assigned to Chiron; U.S. Pat. Nos. 5,972,885 and 6,048,720 assigned to Biovitrum, U.S. Pat. Nos. 5,543,502 and 5,610,278 assigned to Novo Nordisk; U.S. Pat. No. 5,171,844 assigned to Immuno Ag; U.S. Pat. No. 5,112,950 assigned to Transgene S. A.; U.S. Pat. No. 4,868,112 assigned to Genetics Institute, each of which is incorporated herein by reference in its entirety.

The porcine FVIII sequence is published, (Toole, J. J., et al., Proc. Natl. Acad. Sci. USA 83:5939-5942 (1986)), incorporated herein by reference in its entirety, and the complete porcine cDNA sequence obtained from PCR amplification of FVIII sequences from a pig spleen cDNA library has been reported (Healey, J. F. et al., Blood 88:4209-4214 (1996), incorporated herein by reference in its entirety). Hybrid human/porcine FVIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine FVIII and a chimeric FVIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. U.S. Pat. No. 6,458,563, incorporated herein by reference in its entirety assigned to Emory discloses a B-domain deleted porcine FVIII.

The FVIII (or FVIII portion of a chimeric polypeptide) can be at least 90% or 95% identical to a FVIII amino acid sequence shown in TABLE 2 without a signal sequence (amino acids 20 to 1457 of SEQ ID NO:2; and amino acids 20 to 2351 of SEQ ID NO:6), wherein said FVIII portion has FVIII activity. The FVIII (or FVIII portion of a chimeric polypeptide) can be identical to a FVIII amino acid sequence shown in TABLE 2 without a signal sequence (amino acids 20 to 1457 of SEQ ID NO:2; and amino acids 20 to 2351 of SEQ ID NO:6).

The FVIII (or FVIII portion of a chimeric polypeptide) can be at least 90% or 95% identical to a FVIII amino acid sequence shown in TABLE 2 with a signal sequence (amino acids 1 to 1457 of SEQ ID NO:2 and amino acids 1 to 2351 of SEQ ID NO:6), wherein said FVIII portion has FVIII activity. The FVIII (or FVIII portion of a chimeric polypeptide) can be identical to a FVIII amino acid sequence shown in TABLE 2 with a signal sequence (amino acids 1 to 1457 of SEQ ID NO:2 and amino acids 1 to 2351 of SEQ ID NO:6).

In some embodiments, the clotting factor is a mature form of Factor VII zymogen, activated FVII (FVIIa), or activatable FVII, or a variant thereof. Factor VII (FVII, F7; also referred to as Factor 7, coagulation factor VII, serum factor VII, serum prothrombin conversion accelerator, SPCA, proconvertin and eptacog alpha) is a serine protease that is part of the coagulation cascade. FVII includes a Gla domain, two EGF domains (EGF-1 and EGF-2), and a serine protease domain (or peptidase S1 domain) that is highly conserved among all members of the peptidase S1 family of serine proteases, such as for example with chymotrypsin. FVII occurs as a single chain zymogen, an activated zymogen-like two-chain polypeptide and a fully activated two-chain form. As used herein, a "zymogen-like" protein or polypeptide refers to a protein that has been activated by proteolytic cleavage, but still exhibits properties that are associated with a zymogen, such as, for example, low or no activity, or a conformation that resembles the conformation of the zymogen form of the protein. For example, when it is not bound to tissue factor, the two-chain activated form of FVII is a zymogen-like protein; it retains a conformation similar to the uncleaved FVII zymogen, and, thus, exhibits very low activity. Upon binding to tissue factor, the two-chain activated form of FVII undergoes conformational change and acquires its full activity as a coagulation factor. Exemplary FVII variants include those with increased specific activity, e.g., mutations that increase the activity of FVII by increasing its enzymatic activity (Kcat or Km). Such variants have been described in the art and include, e.g., mutant forms of the molecule as described for example in Persson et al. 2001. PNAS 98:13583; Petrovan and Ruf. 2001. J. Biol. Chem. 276:6616; Persson et al. 2001 J. Biol. Chem. 276:29195; Soejima et al. 2001. J. Biol. Chem. 276:17229; Soejima et al. 2002. J. Biol. Chem. 247:49027. In one embodiment, a variant form of FVII includes the mutations. Exemplary mutations include V158D-E296V-M298Q. In another embodiment, a variant form of FVII includes a replacement of amino acids 608-619 (LQQSRKVGDSPN, corresponding to the 170-loop) from the FVII mature sequence with amino acids EASYPGK from the 170-loop of trypsin. High specific activity variants of FIX are also known in the art. For example, Simioni et al. (2009 N. E. Journal of Medicine 361:1671) describe an R338L mutation. Chang et al. (1988 JBC 273:12089) and Pierri et al. (2009 Human Gene Therapy 20:479) describe an R338A mutation. Other mutations are known in the art and include those described, e.g., in Zogg and Brandstetter. 2009 Structure 17:1669; Sichler etl al. 2003. J. Biol. Chem. 278:4121; and Sturzebecher et al. 1997. FEBS Lett 412:295. The contents of these references are incorporated herein by reference. Full activation, which occurs upon conformational change from a zymogen-like form, occurs upon binding to is co-factor tissue factor. Also, mutations can be introduced that result in the conformation change in the absence of tissue factor. Hence, reference to FVIIa includes a zymogen-like form, a fully activated two-chain form, or an activatable form. An "activatable Factor VII" is Factor VII in an inactive form (e.g., in its zymogen form) that is capable of being converted to an active form.

In some embodiments, the clotting factor is a mature form of Factor IX or a variant thereof. Factor IX circulates as a 415 amino acid, single chain plasma zymogen (A. Vysotchin et al., J. Biol. Chem. 268, 8436 (1993)). The zymogen of FIX is activated by FXIa or by the tissue factor/FVIIa complex. Specific cleavages between arginine-alanine 145-146 and arginine-valine 180-181 result in a light chain and a heavy chain linked by a single disulfide bond between cysteine 132 and cysteine 289 (S. Bajaj et al., Biochemistry 22, 4047 (1983)).

The structural organization of FIX is similar to that of the vitamin K-dependent blood clotting proteins FVII, FX and protein C (B. Furie and B. Furie, supra). The approximately 45 amino acids of the amino terminus comprise the gamma-carboxyglutamic acid, or Gla, domain. This is followed by two epidermal growth factor homology domains (EGF), an activation peptide and the catalytic "heavy chain" which is a member of the serine protease family (A. Vysotchin et al., J. Biol. Chem. 268, 8436 (1993); S. Spitzer et al., Biochemical Journal 265, 219 (1990); H. Brandstetter et al., Proc. Natl. Acad Sci. USA 92, 9796 (1995)).

"Equivalent dose," as used herein, means the same dose of FVIII activity as expressed in International Units, which is independent of molecular weight of the polypeptide in question. One International Unit (IU) of FVIII activity corresponds approximately to the quantity of FVIII in one milliliter of normal human plasma. Several assays are available for measuring FVIII activity, including the European Pharmacopoeia chromogenic substrate assay and a one stage clotting assay.

"Fc," as used herein, means functional neonatal Fc receptor (FcRn) binding partners, unless otherwise specified. An FcRn binding partner is any molecule that can be specifically bound by the FcRn receptor with consequent active transport by the FcRn receptor of the FcRn binding partner. Thus, the term Fc includes any variants of IgG Fc that are functional. The region of the Fc portion of IgG that binds to the FcRn receptor has been described based on X-ray crystallography (Burmeister et al., Nature 372:379 (1994), incorporated herein by reference in its entirety). The major contact area of the Fc with the FcRn is near the junction of the CH2 and CH3 domains. Fc-FcRn contacts are all within a single Ig heavy chain. The FcRn binding partners include, e.g., whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain.

References made to amino acid numbering of immunoglobulins or immunoglobulin fragments, or regions, are all based on Kabat et al. 1991, Sequences of Proteins of Immunological Interest, U. S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al., J. Exp. Med. 180: 2377 (1994), incorporated herein by reference in its entirety.) An Fc can comprise the CH2 and CH3 domains of an immunoglobulin with or without the hinge region of the immunoglobulin. Exemplary Fc variants are provided in WO 2004/101740 and WO 2006/074199, incorporated herein by reference in its entirety.

An Fc (or Fc portion of a chimeric polypeptide) can contain one or more mutations, and combinations of mutations. E.g., an Fc (or Fc portion of a chimeric polypeptide) can contain mutations conferring increased half-life such as M252Y, S254T, T256E, and combinations thereof, as disclosed in Oganesyan et al., Mol. Immunol. 46:1750 (2009), which is incorporated herein by reference in its entirety; H433K, N434F, and combinations thereof, as disclosed in Vaccaro et al., Nat. Biotechnol. 23:1283 (2005), which is incorporated herein by reference in its entirety; the mutants disclosed at pages 1-2, paragraph [0012], and Examples 9 and 10 of U.S. Application Publ. No. 2009/0264627 A1, which is incorporated herein by reference in its entirety; and the mutants disclosed at page 2, paragraphs [0014] to [0021] of U.S. Application Publ. No. 20090163699 A1, which is incorporated herein by reference in its entirety.

Fc (or Fc portion of a chimeric polypeptide) can also include, e.g., the following mutations: The Fc region of IgG can be modified according to well recognized procedures such as site directed mutagenesis and the like to yield modified IgG or Fc fragments or portions thereof that will be bound by FcRn. Such modifications include, e.g., modifications remote from the FcRn contact sites as well as modifications within the contact sites that preserve or even enhance binding to the FcRn. For example the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. In addition to alanine other amino acids can be substituted for the wildtype amino acids at the positions specified above.

Mutations can be introduced singly into Fc giving rise to more than one hundred FcRn binding partners distinct from native Fc. Additionally, combinations of two, three, or more of these individual mutations can be introduced together, giving rise to hundreds more FcRn binding partners. Certain of these mutations can confer new functionality upon the FcRn binding partner. For example, one embodiment incorporates N297A, removing a highly conserved N-glycosylation site. The effect of this mutation is to reduce immunogenicity, thereby enhancing circulating half-life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847, which is incorporated herein by reference in its entirety; Friend et al. 1999, Transplantation 68:1632, which is incorporated herein by reference in its entirety; Shields et al. 1995, J. Biol. Chem. 276:6591, which is incorporated herein by reference in its entirety).

Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII which mediate various effector functions will not bind to IgG1 when such mutations have been introduced (Ward and Ghetie, Therapeutic Immunology 2:77 (1995), which is incorporated herein by reference in its entirety; and Armour et al., Eur. J. Immunol. 29:2613 (1999), which is incorporated herein by reference in its entirety). As a further example of new functionality arising from mutations described above affinity for FcRn can be increased beyond that of wild type in some instances. This increased affinity can reflect an increased "on" rate, a decreased "off" rate or both an increased "on" rate and a decreased "off" rate. Mutations believed to impart an increased affinity for FcRn include, e.g., T256A, T307A, E380A, and N434A (Shields et al., J. Biol. Chem. 276:6591 (2001), which is incorporated herein by reference in its entirety).

The Fc (or Fc portion of a chimeric polypeptide) can be at least 90% or 95% identical to the Fc amino acid sequence shown in TABLE 2 (amino acids 1458 to 1684 of SEQ ID NO:2 or amino acids 2352 to 2578 of SEQ ID NO:6). The Fc (or Fc portion of a chimeric polypeptide) can be identical to the Fc amino acid sequence shown in TABLE 2 (amino acids 1458 to 1684 of SEQ ID NO:2 and amino acids 2352 to 2578 of SEQ ID NO:6).

"Hybrid" polypeptides and proteins, as used herein, means a combination of a chimeric polypeptide with a second polypeptide. The chimeric polypeptide and the second polypeptide in a hybrid can be associated with each other via protein-protein interactions, such as charge-charge or hydrophobic interactions. The chimeric polypeptide and the second polypeptide in a hybrid can be associated with each other via disulfide or other covalent bond(s). Hybrids are described in WO 2004/101740 and WO 2006/074199, each of which is incorporated herein by reference in its entirety. See also U.S. Pat. Nos. 7,404,956 and 7,348,004, each of which is incorporated herein by reference in its entirety. The second polypeptide can be a second copy of the same chimeric polypeptide or it can be a non-identical chimeric polypeptide. See, e.g., FIG. 1, Example 1, and TABLE 2.

In one embodiment, the second polypeptide is a polypeptide comprising an Fc. In another embodiment, the chimeric polypeptide is a chimeric FVIII-Fc polypeptide and the second polypeptide consists essentially of Fc, e.g., the hybrid polypeptide of Example 1, which is a rFVIIIFc recombinant fusion protein consisting of a single molecule of recombinant B-domain deleted human FVIII (BDD-rFVIII) fused to the dimeric Fc domain of the human IgG1, with no intervening linker sequence. This hybrid polypeptide is referred to herein as FVIIIFc monomeric Fc fusion protein, FVIIIFc monomer hybrid, monomeric FVIIIFc hybrid, and FVIIIFc monomer-dimer. See Example 1, FIG. 1, and TABLE 2A. The Examples provide preclinical and clinical data for this hybrid polypeptide.

The second polypeptide in a hybrid can comprise or consist essentially of a sequence at least 90% or 95% identical to the amino acid sequence shown in TABLE 2A(ii) without a signal sequence (amino acids 21 to 247 of SEQ ID NO:4) or at least 90% or 95% identical to the amino acid sequence shown in TABLE 2A(ii) with a signal sequence (amino acids 1 to 247 of SEQ ID NO:4). The second polypeptide can comprise or consist essentially of a sequence identical to the amino acid sequence shown in TABLE 2A(ii) without a signal sequence (amino acids 21 to 247 of SEQ ID NO:4) or identical to the amino acid sequence shown in TABLE 2A(ii) with a signal sequence (amino acids 1 to 247 of SEQ ID NO:4).

Figure 1:
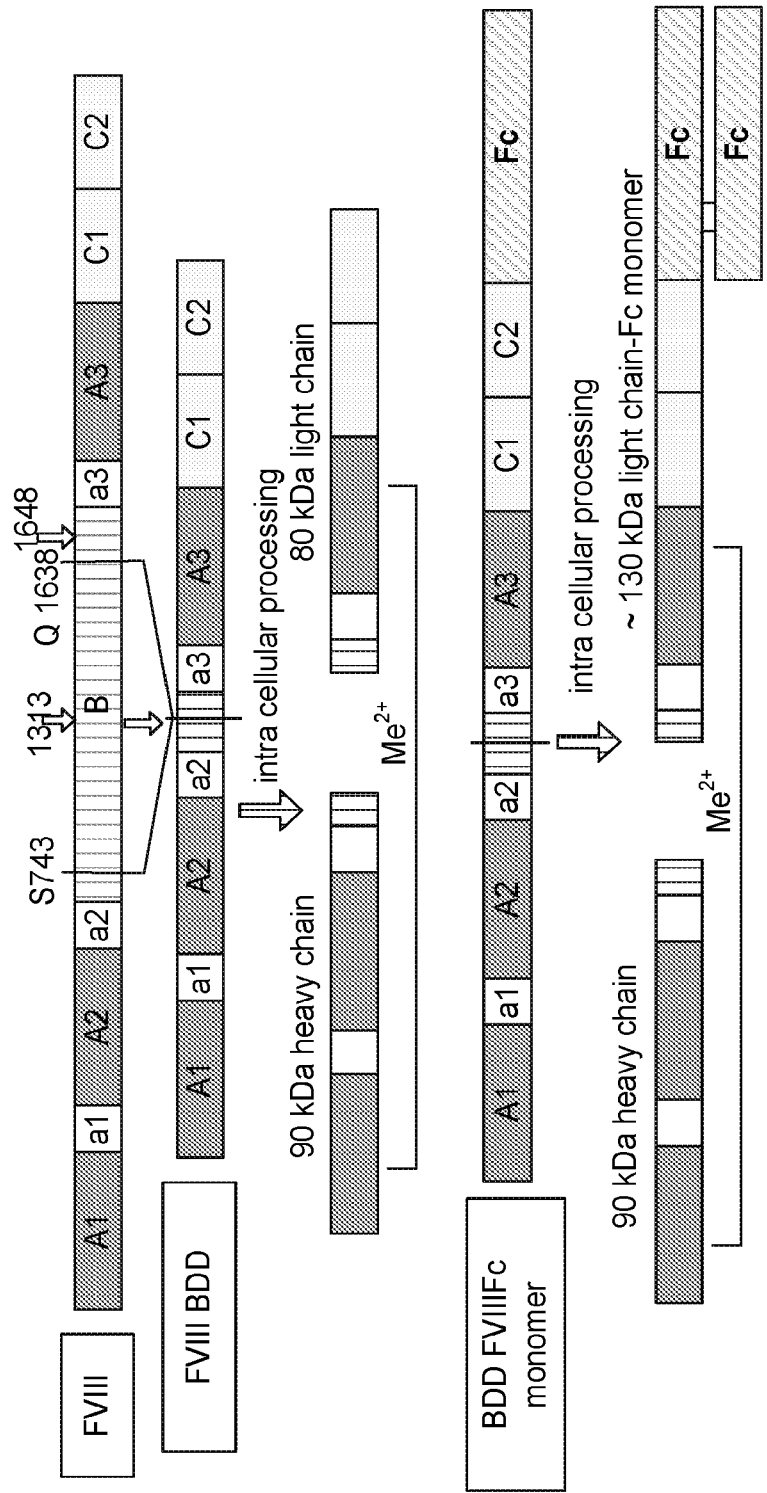
FIG. 1 shows a schematic representation of the rFVIIIFc monomer.

FIG. 1 is a schematic showing the structure of a B domain deleted FVIII-Fc chimeric polypeptide, and its association with a second polypeptide that is an Fc polypeptide. To obtain this hybrid, the coding sequence of human recombinant B-domain deleted FVIII was obtained by reverse transcription-polymerase chain reaction (RT-PCR) from human liver poly A RNA (Clontech) using FVIII-specific primers. The FVIII sequence includes the native signal sequence for FVIII. The B-domain deletion was from serine 743 (S743; 2287 bp) to glutamine 1638 (Q1638; 4969 bp) for a total deletion of 2682 bp. Then, the coding sequence for human recombinant Fc was obtained by RT-PCR from a human leukocyte cDNA library (Clontech) using Fc specific primers. Primers were designed such that the B-domain deleted FVIII sequence was fused directly to the N-terminus of the Fc sequence with no intervening linker. The FVIIIFc DNA sequence was cloned into the mammalian dual expression vector pBUDCE4.1 (Invitrogen) under control of the CMV promoter. A second identical Fc sequence including the mouse Igk signal sequence was obtained by RT-PCR and cloned downstream of the second promoter, EF1α, in the expression vector pBUDCE4.1.

The rFVIIIFc expression vector was transfected into human embryonic kidney 293 cells (HEK293H; Invitrogen)

using Lipofectamine 2000 transfection reagent (Invitrogen). Stable clonal cell lines were generated by selection with Zeocin (Invitrogen). One clonal cell line, 3C4-22 was used to generate FVIIIFc for characterization in vivo. Recombinant FVIIIFc was produced and purified (McCue et al. 2009) at Biogen Idec (Cambridge, Mass.). The transfection strategy described above was expected to yield three products, i.e., monomeric rFVIIIFc hybrids, dimeric rFVIIIFc hybrids and dimeric Fc. However, there was essentially no dimeric rFVIIIFc detected in the conditioned medium from these cells. Rather, the conditioned medium contained Fc and monomeric rFVIIIFc. It is possible that the size of dimeric rFVIIIFc was too great and prevented efficient secretion from the cell. This result was beneficial since it rendered the purification of the monomer less complicated than if all three proteins had been present. The material used in these studies had a specific activity of approximately 9000 IU/mg.

"Dosing interval," as used herein, means the dose of time that elapses between multiple doses being administered to a subject. The comparison of dosing interval can be carried out in a single subject or in a population of subjects and then the average obtained in the population can be calculated.

The dosing interval when administering a chimeric FVIII polypeptide, e.g., a chimeric FVIII-Fc polypeptide (a polypeptide comprising a FVIII or a hybrid) of the present disclosure can be at least about one and one-half times longer than the dosing interval required for an equivalent dose of said FVIII without the non-FVIII portion, e.g., without the Fc portion (a polypeptide consisting of said FVIII). The dosing interval can be at least about one and one-half to six times longer, one and one-half to five times longer, one and one-half to four times longer, one and one-half to three times longer, or one and one-half to two times longer, than the dosing interval required for an equivalent dose of said FVIII without the non-FVIII portion, e.g., without the Fc portion (a polypeptide consisting of said FVIII).

The dosing interval can be at least about one and one-half, two, two and one-half, three, three and one-half, four, four and one-half, five, five and one-half or six times longer than the dosing interval required for an equivalent dose of said FVIII without the non-FVIII portion, e.g., without the Fc portion (a polypeptide consisting of said FVIII). The dosing interval can be about every three, four, five, six, seven, eight, nine, ten, eleven, twelve, thirteen, or fourteen days or longer. The dosing interval can be at least about one and one-half to 5, one and one-half, 2, 3, 4, or 5 days or longer. For on-demand treatment, the dosing interval of said chimeric polypeptide or hybrid is about once every 24-36, 24-48, 24-72, 24-96, 24-120, 24-144, 24-168, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours or longer.

In one embodiment, the effective dose is 25-65 IU/kg (25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 62, 64, or 65 IU/kg) and the dosing interval is once every 3-5, 3-6, 3-7, 3, 4, 5, 6, 7, or 8 or more days, or three times per week, or no more than three times per week. In another embodiment, the effective dose is 65 IU/kg and the dosing interval is once weekly, or once every 6-7 days. The doses can be administered repeatedly as long as they are necessary (e.g., at least 10, 20, 28, 30, 40, 50, 52, or 57 weeks, at least 1, 2, 3, 4, 5, 6, 7, 8, 9, or 10 years).

In certain embodiments, the effective dose for on-demand treatment is 20-50 IU/Kg (20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 IU/kg). The on-demand treatment can be one time dosing or repeated dosing. For repeated dosing, the dosing interval can be every 12-24 hours, every 24-36 hours, every 24-48 hours, every 36-48 hours, or every 48-72 hours. Accordingly, the term "repeated dosing" refers to the administration of more than one dose over a period of time. Doses administered under a "repeated dosing" regimen are referred to as "repeated doses." In some embodiments, each of the repeated doses is separated from another by at least about 12 hours, at least about 24 hours, at least about two days, at least about three days, at least about four days, at least about five days, at least about six days, at least about seven days, at least about eight days, at least about nine days, at least about ten days, at least about 11 days, at least about 12 days, at least about 13 days, at least about 14 days, or at least about 15 days. In some embodiments, the repeated doses comprise at least about two doses, at least about five doses, at least about 10 doses, at least about 20 doses, at least about 25 doses, at least about 30 doses, at least about 35 doses, at least about 40 doses, at least about 45 doses, at least about 50 doses, at least about 55 doses, at least about 60 doses, at least about 65 doses, or at least about 70 doses. the repeated doses comprise from about two doses to about 100 doses, from about five doses to about 80 doses, from about 10 doses to about 70 doses, from about 10 doses to about 60 doses, from about 10 doses to about 50 doses, from about 15 doses to about 40 doses, from about 15 doses to about 30 doses, from about 20 doses to about 30 doses, or from about 20 doses to about 40 doses. the repeated doses comprise about two doses, about five doses, about 10 doses, about 15 doses, about 20 doses, about 25 doses, about 30 doses, about 35 doses, about 40 doses, about 45 doses, about 50 doses, about 55 doses, about 60 doses, about 65 does, about 70 doses, about 75 doses, about 80 doses, about 90 doses, or about 100 doses.

In some embodiments, the subject is further administered, after the repeated doses, a pharmaceutical composition comprising a clotting factor protein which comprises the clotting factor, but does not comprise an Fc portion. This clotting factor can be a full length or mature clotting factor. In some embodiments, such clotting factor can be ADVATE®, RECOMBINATE®, KOGENATE FS®, HELIXATE FS®, XYNTHA®/REFACTO AB®, HEMOFIL-M®, MONARC-M®, MONOCLATE-P®, HUMATE-P®, ALPHANATE®, KOATE-DVI®, AND HYATE:C®

The terms "long-acting" and "long-lasting" are used interchangeably herein. "Long-lasting clotting factors" or "long-acting clotting factors" (e.g., long-acting FVII, long-acting FVIII, and long-acting FIX) are clotting factors, e.g., FVII, FVIII, or FIX, having an increased half-life (also referred to herein as $t_{1/2}$, $t_{1/2}$ beta, elimination half-life and HL) over a reference clotting factor, e.g., FVII, FVIII or FIX. The "longer" FVIII activity can be measured by any known methods in the art, e.g., aPTT assay, chromogenic assay, ROTEM, TGA, and etc. In one embodiment, the "longer" FVIII activity can be shown by the $T_{1/2}$beta (activity). In another embodiment, the "longer" FVIII activity can be shown by the level of FVIII antigen present in plasma, e.g., by the $T_{1/2}$beta (antigen). In other embodiments, the long-acting or long-lasting FVIII polypeptide works longer in a coagulation cascade, e.g., is active for a longer period, compared to a wild-type FVIII polypeptide, REFACTO® or ADVATE®.

The increased half-life of a long-acting clotting factor, e.g., a long-acting FVIII, can be due to fusion to one or more non-clotting factor polypeptides such as, e.g., Fc. The increased half-life can be due to one or more modification, such as, e.g., pegylation. Exemplary long-acting clotting factor (e.g., long-acting FVIII polypeptides) include, e.g., chimeric clotting factors (e.g., chimeric FVIII polypeptides comprising Fc), and chimeric clotting factors comprising albumin (e.g., chimeric FVIII polypeptides comprising albumin). Additional exemplary long-acting clotting factors (e.g., long-acting FVIII polypeptides) include, e.g., pegylated clotting factors (e.g., pegylated FVIII).

The "reference" polypeptide, e.g., in the case of a long-acting chimeric clotting factor (e.g., a long-acting chimeric FVIII polypeptide), is a polypeptide consisting essentially of the clotting factor portion of the chimeric polypeptide. For example, in the case of a long-acting FVIII, the reference polypeptide is the FVIII portion of the chimeric polypeptide, e.g., the same FVIII portion without the Fc portion, or without the albumin portion. Likewise, the reference polypeptide in the case of a modified FVIII is the same FVIII without the modification, e.g., a FVIII without the pegylation.

In some embodiments, the long-acting FVIII has one or more of the following properties when administered to a subject:
  a mean residence time (MRT) (activity) in said subject of about 14-41.3 hours;
  a clearance (CL) (activity) in said subject of about 1.22-5.19 mL/hour/kg or less;
  a $t_{1/2}$beta (activity) in said subject of about 11-26.4 hours;
  an incremental recovery (K value) (activity; observed) in said subject of about 1.38-2.88 IU/dL per IU/kg;
  a $V_{ss}$ (activity) in said subject of about 37.7-79.4 mL/kg; and
  an AUC/dose in said subject of about 19.2-81.7 IU*h/dL per IU/kg.

In some embodiments, the long-acting FVIII has one or more of the following properties when administered to a patient population:
  a mean incremental recovery (K-Value) (activity; observed) greater that 1.38 IU/dL per IU/kg;
  a mean incremental recovery (K-Value) (activity; observed) of at least about 1.5, at least about 1.85, or at least about 2.46 IU/dL per IU/kg.
  a mean clearance (CL) (activity) in said patient population of about 2.33±1.08 mL/hour/kg or less;
  a mean clearance (CL) (activity) in said patient population of about 1.8-2.69 mL/hour/kg;
  a mean clearance (CL) (activity) in said patient population that is about 65% of the clearance of a polypeptide comprising said FVIII without modification;
  a mean residence time (MRT) (activity) in said patient population of at least about 26.3±8.33 hours;
  a mean MRT (activity) in said patient population of about 25.9-26.5 hours;
  a mean MRT (activity) in said patent population that is about 1.5 fold longer than the mean MRT of a polypeptide comprising said FVIII without modification;
  a mean $t_{1/2}$beta (activity) in said patient population of about 18.3±5.79 hours;
  a mean $t_{1/2}$beta (activity) in said patient population that is about 18-18.4 hours;
  a mean $t_{1/2}$beta (activity) in said patient population that is about 1.5 fold longer than the mean $t_{1/2}$beta of a polypeptide comprising said FVIII without modification;
  a mean incremental recovery (K value) (activity; observed) in said patient population of about 2.01±0.44 IU/dL per IU/kg;
  a mean incremental recovery (K value) (activity; observed) in said patient population of about 1.85-2.46 IU/dL per IU/kg;
  a mean incremental recovery (K value) (activity; observed) in said patient population that is about 90% of the mean incremental recovery of a polypeptide comprising said FVIII without modification;
  a mean $V_{ss}$ (activity) in said patient population of about 55.1±12.3 mL/kg;
  a mean $V_{ss}$ (activity) in said patient population of about 45.3-56.1 mL/kg;
  a mean AUC/dose (activity) in said patient population of about 49.9±18.2 IU*h/dL per IU/kg;
  a mean AUC/dose (activity) in said patient population of about 44.8-57.6 IU*h/dL per IU/kg.

In other embodiments, the long-acting FVIII has one or more of the following properties when administered to a patient population:
  a $C_{max}$_OBS in said subject administered with the chimeric polypeptide is comparable to the $C_{max}$_OBS in a subject administered with the same amount of a polypeptide consisting of the full-length, mature FVIII when measured by a one stage (aPTT) assay or a two stage (chromogenic) assay;
  a $C_{max}$_OBS in said subject of about 60.5 IU/dL, about 60.5±1 IU/dL, about 60.5±2 IU/dL, about 60.5±3 IU/dL, about 60.5±4 IU/dL, about 60.5±5 IU/dL, about 60.5±6 IU/dL, about 60.5±7 IU/dL, about 60.5±8 IU/dL, about 60.5±9 IU/dL, or about 60.5±10 IU/dL as measured by a one stage (aPTT) assay when about 25 IU/kg of the chimeric polypeptide is administered;
  a $C_{max}$_OBS in said subject of about 53.1-69 IU/dL as measured by a one stage (aPTT) assay when about 25 IU/kg of the chimeric polypeptide is administered;
  a $C_{max}$_OBS in said subject of about 119 IU/dL, about 119±1 IU/dL, about 119±2 IU/dL, about 119±3 IU/dL, about 119±4 IU/dL, about 119±5 IU/dL, about 119±6 IU/dL, about 119±7 IU/dL, about 119±8 IU/dL, about 119±9 IU/dL, about 119±10 IU/dL, about 119±11 IU/dL, about 119±12 IU/dL, about 119±13 IU/dL, about 119±14 IU/dL, about 119±15 IU/dL, about 119±16 IU/dL, about 119±17 IU/dL, or about 119±18 IU/dL, as measured by a one stage (aPTT) assay when about 65 IU/kg of the chimeric polypeptide is administered;
  a $C_{max}$ OBS in said subject of about 103-136 IU/dL as measured by a one stage (aPTT) assay when about 65 IU/kg of the chimeric polypeptide is administered;
  a C. OBS in said subject of about 76.5 IU/dL, about 76.5±1 IU/dL, about 76.5±2 IU/dL, about 76.5±3 IU/dL, about 76.5±4 IU/dL, about 76.5±5 IU/dL, about 76.5±6 IU/dL, about 76.5±7 IU/dL, about 76.5±8 IU/dL, about 76.5±9 IU/dL, about 76.5±10 IU/dL, about 76.5±11 IU/dL, about 76.5±12 IU/dL, about 76.5±13 IU/dL, about 76.5±14 IU/dL, or about 76.5±15 IU/dL, as measured by a two stage (chromogenic) assay when about 25 IU/kg of the chimeric polypeptide is administered;
  a $C_{max}$_OBS in said subject of about 64.9-90.1 IU/dL as measured by a two stage (chromogenic) assay when about 25 IU/kg of the chimeric polypeptide is administered;
  a $C_{max}$_OBS in said subject of about 182 IU/dL, about 182±2 IU/dL, about 182±4 IU/dL, about 182±6 IU/dL, about 182±8 IU/dL, about 182±10 IU/dL, about 182±12 IU/dL, about 182±14 IU/dL, about 182±16 IU/dL, about 182±18 IU/dL, or about 182±20 IU/dL as measured by a two stage (chromogenic) assay when about 65 IU/kg of the chimeric polypeptide is administered; or
  a $C_{max}$_OBS in said subject of about 146-227 IU/dL, about 146±5 IU/dL, about 146±10 IU/dL, about 227±5

IU/dL, or about 146±10 IU/dL as measured by a two stage (chromogenic) assay when about 65 IU/kg of the chimeric polypeptide is administered.

In certain embodiments, the long-acting FVIII has one or more of the following properties when administered to a patient population:

a $t_{1/2}$beta (activity) in said subject that is at least 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, or 1.90 times higher than the $t_{1/2}$beta (activity) in a subject administered with the same amount of a polypeptide consisting of the full-length, mature FVIII when measured by a one stage (aPTT) assay or a two stage (chromogenic) assay;

a $t_{1/2}$beta (activity) in said subject of about 18.8 hours, 18.8±1 hours, 18.8±1 hours, 18.8±2 hours, 18.8±3 hours, 18.8±4 hours, 18.8±5 hours, 18.8±6 hours, 18.8±7 hours, 18.8±8 hours, 18.8±9 hours, 18.8±10 hours, or 18.8±11 hours as measured by a one stage (aPTT) assay;

a $t_{1/2}$beta (activity) in said subject of about 14.3-24.5 hours as measured by a one stage (aPTT) assay;

a $t_{1/2}$beta (activity) in said subject of about 16.7 hours, 16.7±1 hours, 16.7±2 hours, 16.7±3 hours, 16.7±4 hours, 16.7±5 hours, 16.7±6 hours, 16.7±7 hours, 16.7±8 hours, 16.7±9 hours, 16.7±10 hours, or 16.7±11 hours as measured by a two stage (chromogenic) assay;

a $t_{1/2}$beta (activity) in said subject of about 13.8-20.1 hours as measured by a two stage (chromogenic) assay;

a $t_{1/2}$beta (activity) in said subject of about 19.8 hours, 19.8±1 hours, 19.8±2 hours, 19.8±3 hours, 19.8±4 hours, 19.8±5 hours, 19.8±6 hours, 19.8±7 hours, 19.8±8 hours, 19.8±9 hours, 19.8±10 hours, or 19.8±11 hours as measured by a two stage (chromogenic) assay; or a $t_{1/2}$beta (activity) in said subject of about 14.3-27.5 hours as measured by a two stage (chromogenic) assay.

In certain embodiments, the long-acting FVIII has one or more of the following properties when administered to a patient population:

a clearance (CL) (activity) in said subject is 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, or 0.70 times lower than the clearance in a subject administered with the same amount of a polypeptide consisting of the full-length, mature FVIII when measured by a one stage (aPTT) assay or a two stage (chromogenic) assay;

a clearance (CL) (activity) in said subject of about 1.68 mL/hour/kg, 1.68±0.1 mL/hour/kg, 1.68±0.2 mL/hour/kg, 1.68±0.3 mL/hour/kg, 1.68±0.4 mL/hour/kg, 1.68±0.5 mL/hour/kg, 1.68±0.6 mL/hour/kg, or 1.68±0.7 mL/hour/kg, as measured by a one stage (aPTT) assay when about 25 IU/kg of the chimeric polypeptide is administered;

a clearance (CL) (activity) in said subject of about 1.31-2.15 mL/hour/kg as measured by a one stage (aPTT) assay when about 25 IU/kg of the chimeric polypeptide is administered;

a clearance (CL) (activity) in said subject of about 2.32 mL/hour/kg, 2.32±0.1 mL/hour/kg, 2.32±0.2 mL/hour/kg, 2.32±0.3 mL/hour/kg, 2.32±0.4 mL/hour/kg, 2.32±0.5 mL/hour/kg, 2.32±0.6 mL/hour/kg, or 2.32±0.7 mL/hour/kg as measured by a one stage (aPTT) assay when about 65 IU/kg of the chimeric polypeptide is administered;

a clearance (CL) (activity) in said subject of about 1.64-3.29 mL/hour/kg as measured by a one stage (aPTT) assay when about 65 IU/kg of the chimeric polypeptide is administered;

a clearance (CL) (activity) in said subject of about 1.49 mL/hour/kg, 1.49±0.1 mL/hour/kg, 1.49±0.2 mL/hour/kg, 1.49±0.3 mL/hour/kg, 1.49±0.4 mL/hour/kg, 1.49±0.5 mL/hour/kg, 1.49±0.6 mL/hour/kg, or 1.49±0.7 mL/hour/kg as measured by a two stage (chromogenic) assay when about 25 IU/kg of the chimeric polypeptide is administered;

a clearance (CL) (activity) in said subject of about 1.16-1.92 mL/hour/kg as measured by a two stage (chromogenic) assay when about 25 IU/kg of the chimeric polypeptide is administered;

a clearance (CL) (activity) in said subject of about 1.52 mL/hour/kg, 1.52±0.1 mL/hour/kg, 1.52±0.2 mL/hour/kg, 1.52±0.3 mL/hour/kg, 1.52±0.4 mL/hour/kg, 1.52±0.5 mL/hour/kg, 1.52±0.6 mL/hour/kg, or 1.52±0.7 mL/hour/kg as measured by a two stage (chromogenic) assay when about 65 IU/kg of the chimeric polypeptide is administered; or a clearance (CL) (activity) in said subject of about 1.05-2.20 mL/hour/kg as measured by a two stage (chromogenic) assay when about 65 IU/kg of the chimeric polypeptide is administered.

In some embodiments, the long-acting FVIII has one or more of the following properties when administered to a patient population:

a MRT in said subject is at least 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90, 1.91, 1.92, or 1.93 times higher than the MRT in a subject administered with the same amount of a polypeptide consisting of the full-length, mature FVIII when measured by a one stage (aPTT) assay or a two stage (chromogenic) assay;

a MRT (activity) in said subject of about 27 hours, 27±1 hours, 27±2 hours, 27±3 hours, 27±4 hours, 27±5 hours, 27±6 hours, 27±7 hours, 27±8 hours, 27±9 hours, or 27±10 hours as measured by a one stage (aPTT) assay;

a MRT (activity) in said subject of about 20.6-35.3 hours as measured by a one stage (aPTT) assay;

a MRT (activity) in said subject of about 23.9-28.5 hours as measured by a two stage (chromogenic) assay;

a MRT (activity) in said subject of about 19.8-28.9 hours as measured by a two stage (chromogenic) assay; or a MRT (activity) in said subject of about 20.5-39.6 hours as measured by a two stage (chromogenic) assay.

In other embodiments, the long-acting FVIII has one or more of the following properties when administered to a patient population:

an incremental recovery in said subject that is comparable to the Incremental Recovery in a subject administered with the same amount of a polypeptide consisting of the full-length, mature FVIII when measured by a one stage (aPTT) assay or a two stage (chromogenic) assay;

an incremental recovery in said subject of about 2.44 IU/dL per IU/kg, 2.44±0.1 IU/dL per IU/kg, 2.44±0.2 IU/dL per IU/kg, 2.44±0.3 IU/dL per IU/kg, 2.44±0.4 IU/dL per IU/kg, 2.44±0.5 IU/dL per IU/kg, 2.44±0.6 IU/dL per IU/kg, 2.44±0.7 IU/dL per IU/kg, 2.44±0.8 IU/dL per IU/kg, 2.44±0.9 IU/dL per IU/kg, 2.44±1.0 IU/dL per IU/kg, 2.44±1.1 IU/dL per IU/kg, or 2.44±1.2 IU/dL per IU/kg as measured by a one stage (aPTT) assay when about 25 IU/kg of the chimeric polypeptide is administered;

an incremental recovery in said subject of about 2.12-2.81 IU/dL per IU/kg as measured by a one stage (aPTT) assay when about 25 IU/kg of the chimeric polypeptide is administered;

an incremental recovery in said subject of about 1.83 IU/dL per IU/kg, 1.83±0.1 IU/dL per IU/kg, 1.83±0.2 IU/dL per IU/kg, 1.83±0.3 IU/dL per IU/kg, 1.83±0.4 IU/dL per IU/kg, 1.83±0.5 IU/dL per IU/kg, 1.83±0.6 IU/dL per IU/kg, 1.83±0.7 IU/dL per IU/kg, 1.83±0.8 IU/dL per IU/kg, 1.83±0.9 IU/dL per IU/kg, 1.83±1.0 IU/dL per IU/kg, or 1.83±1.1 IU/dL per IU/kg as measured by a one stage (aPTT) assay when about 65 IU/kg of the chimeric polypeptide is administered;

an incremental recovery in said subject of about 1.59-2.10 IU/dL per IU/kg as measured by a one stage (aPTT) assay when about 65 IU/kg of the chimeric polypeptide is administered;

an incremental recovery in said subject of about 3.09 IU/dL per IU/kg, 3.09±0.1 IU/dL per IU/kg, 3.09±0.2 IU/dL per IU/kg, 3.09±0.3 IU/dL per IU/kg, 3.09±0.4 IU/dL per IU/kg, 3.09±0.5 IU/dL per IU/kg, 3.09±0.6 IU/dL per IU/kg, 3.09±0.7 IU/dL per IU/kg, 3.09±0.8 IU/dL per IU/kg, 3.09±0.9 IU/dL per IU/kg, 3.09±1.0 IU/dL per IU/kg, 3.09±1.1 IU/dL per IU/kg, 3.09±1.2 IU/dL per IU/kg, or 3.09±1.3 IU/dL per IU/kg, as measured by a two stage (chromogenic) assay when about 25 IU/kg of the chimeric polypeptide is administered;

an incremental recovery in said subject of about 2.80 IU/dL per IU/kg, 2.80±0.1 IU/dL per IU/kg, 2.80±0.2 IU/dL per IU/kg, 2.80±0.3 IU/dL per IU/kg, 2.80±0.4 IU/dL per IU/kg, 2.80±0.5 IU/dL per IU/kg, 2.80±0.6 IU/dL per IU/kg, 2.80±0.7 IU/dL per IU/kg, 2.80±0.8 IU/dL per IU/kg, 2.80±0.9 IU/dL per IU/kg, 2.80±1.0 IU/dL per IU/kg, 2.80±1.1 IU/dL per IU/kg, or 2.80±1.2 IU/dL per IU/kg, as measured by a two stage (chromogenic) assay when about 65 IU/kg of the chimeric polypeptide is administered;

an incremental recovery in said subject of about 2.61-3.66 IU/dL per IU/kg as measured by a two stage (chromogenic) assay when about 25 IU/kg of the chimeric polypeptide is administered; or an incremental recovery in said subject of about 2.24-3.50 IU/dL per IU/kg as measured by a two stage (chromogenic) assay when about 65 IU/kg of the chimeric polypeptide is administered.

In still other embodiments, the long-acting FVIII has one or more of the following properties when administered to a patient population:

a $V_{ss}$ (activity) in said subject that is comparable to the Vss (activity) in a subject administered with the same amount of a polypeptide consisting of the full-length, mature FVIII when measured by a one stage (aPTT) assay or a two stage (chromogenic) assay;

a $V_{ss}$ (activity) in said subject of about 45.5 mL/kg, 45.5±1 mL/kg, 45.5±2 mL/kg, 45.5±3 mL/kg, 45.5±4 mL/kg, 45.5±5 mL/kg, 45.5±6 mL/kg, 45.5±7 mL/kg, 45.5±8 mL/kg, 45.5±9 mL/kg, 45.5±10 mL/kg, or 45.5±11 mL/kg, as measured by a one stage (aPTT) assay when about 25 IU/kg of the chimeric polypeptide is administered;

a $V_{ss}$ (activity) in said subject of about 39.3-52.5 mL/kg as measured by a one stage (aPTT) assay when about 25 IU/kg of the chimeric polypeptide is administered;

a $V_{ss}$ (activity) in said subject of about 62.8 mL/kg, 62.8±1 mL/kg, 62.8±2 mL/kg, 62.8±3 mL/kg, 62.8±4 mL/kg, 62.8±5 mL/kg, 62.8±6 mL/kg, 62.8±7 mL/kg, 62.8±8 mL/kg, 62.8±9 mL/kg, 62.8±10 mL/kg, 62.8±11 mL/kg, 62.8±12 mL/kg, 62.8±13 mL/kg, 62.8±14 mL/kg, 62.8±15 mL/kg, or 62.8±16 mL/kg as measured by a one stage (aPTT) assay when about 65 IU/kg of the chimeric polypeptide is administered;

a $V_{ss}$ (activity) in said subject of about 55.2-71.5 mL/kg as measured by a one stage (aPTT) assay when about 65 IU/kg of the chimeric polypeptide is administered;

a $V_{ss}$ (activity) in said subject of about 35.9 mL/kg, 35.9±1 mL/kg, 35.9±2 mL/kg, 35.9±3 mL/kg, 35.9±4 mL/kg, 35.9±5 mL/kg, 35.9±6 mL/kg, 35.9±7 mL/kg, 35.9±8 mL/kg, 35.9±9 mL/kg, 35.9±10 mL/kg, 35.9±11 mL/kg, 35.9±12 mL/kg, or 35.9±13 mL/kg, as measured by a two stage (chromogenic) assay when about 25 IU/kg of the chimeric polypeptide is administered;

a $V_{ss}$ (activity) in said subject of about 30.4-42.3 mL/kg as measured by a two stage (chromogenic) assay when about 25 IU/kg of the chimeric polypeptide is administered;

a $V_{ss}$ (activity) in said subject of about 43.4 mL/kg, 43.4±1 mL/kg, 43.4±2 mL/kg, 43.4±3 mL/kg, 43.4±4 mL/kg, 43.4±5 mL/kg, 43.4±6 mL/kg, 43.4±7 mL/kg, 43.4±8 mL/kg, 43.4±9 mL/kg, 43.4±10 mL/kg, 43.4±11 mL/kg, 43.4±12 mL/kg, 43.4±13 mL/kg, 43.4±14 mL/kg, 43.4±15 mL/kg, or 43.4±16 mL/kg, as measured by a two stage (chromogenic) assay when about 65 IU/kg of the chimeric polypeptide is administered; or a $V_{ss}$ (activity) in said subject of about 38.2-49.2 mL/kg as measured by a two stage (chromogenic) assay when about 65 IU/kg of the chimeric polypeptide is administered.

In yet other embodiments, the long-acting FVIII has one or more of the following properties when administered to a patient population:

an $AUC_{INF}$ in said subject that is at least 1.45 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.77, 1.78, 1.79, 1.80, 1.81, 1.82, 1.83, 1.84, 1.85, 1.86, 1.87, 1.88, 1.89, 1.90 times higher than the $AUC_{INF}$ in a subject administered with the same amount of a polypeptide consisting of the full-length, mature FVIII when measured by a one stage (aPTT) assay or a two stage (chromogenic) assay;

an $AUC_{INF}$ in said subject of about 1440±316 hr*IU/dL per IU/kg as measured by a one stage (aPTT) assay when about 25 IU/kg of the chimeric polypeptide is administered;

an $AUC_{INF}$ in said subject of about 1160-1880 hr*IU/dL per IU/kg as measured by a one stage (aPTT) assay when about 25 IU/kg of the chimeric polypeptide is administered;

an $AUC_{INF}$ in said subject of about 1480 hr*IU/dL per IU/kg, 1480±100 hr*IU/dL per IU/kg, 1480±200 hr*IU/dL per IU/kg, 1480±300 hr*IU/dL per IU/kg, 1480±400 hr*IU/dL per IU/kg, 1480±500 hr*IU/dL per IU/kg, 1480±600 hr*IU/dL per IU/kg, 1480±700 hr*IU/dL per IU/kg, 1480±800 hr*IU/dL per IU/kg, 1480±900 hr*IU/dL per IU/kg, or 1480±1000 hr*IU/dL per IU/kg, as measured by a one stage (aPTT) assay when about 25 IU/kg of the chimeric polypeptide is administered;

an $AUC_{INF}$ in said subject of about 2910±1320 hr*IU/dL per IU/kg as measured by a one stage (aPTT) assay when about 65 IU/kg of the chimeric polypeptide is administered;

an $AUC_{INF}$ in said subject of about 1980-3970 hr*IU/dL per IU/kg as measured by a one stage (aPTT) assay when about 65 IU/kg of the chimeric polypeptide is administered;

an $AUC_{INF}$ in said subject of about 2800 hr*IU/dL per IU/kg, 2800±100 hr*IU/dL per IU/kg, 2800±200 hr*IU/dL per IU/kg, 2800±300 hr*IU/dL per IU/kg, 2800±400 hr*IU/dL per IU/kg, 2800±500 hr*IU/dL per IU/kg, 2800±600 hr*IU/dL per IU/kg, 2800±700 hr*IU/dL per IU/kg, 2800±800 hr*IU/dL per IU/kg, 2800±900 hr*IU/dL per IU/kg, or 2800±1000 hr*IU/dL per IU/kg as measured by a one stage (aPTT) assay when about 65 IU/kg of the chimeric polypeptide is administered;

an $AUC_{INF}$ in said subject of about 1660 hr*IU/dL per IU/kg, 1660±100 hr*IU/dL per IU/kg, 1660±200 hr*IU/dL per IU/kg, 1660±300 hr*IU/dL per IU/kg, 1660±400 hr*IU/dL per IU/kg, 1660±500 hr*IU/dL per IU/kg, 1660±600 hr*IU/dL per IU/kg, 1660±700 hr*IU/dL per IU/kg, 1660±800 hr*IU/dL per IU/kg, 1660±900 hr*IU/dL per IU/kg, or 1660±1000 hr*IU/dL per IU/kg as measured by a two stage (chromogenic) assay when about 25 IU/kg of the chimeric polypeptide is administered;

an $AUC_{INF}$ in said subject of about 1300-2120 hr*IU/dL per IU/kg as measured by a two stage (chromogenic) assay when about 25 IU/kg of the chimeric polypeptide is administered;

an $AUC_{INF}$ in said subject of about 4280 hr*IU/dL per IU/kg, 4280±100 hr*IU/dL per IU/kg, 4280±200 hr*IU/dL per IU/kg, 4280±300 hr*IU/dL per IU/kg, 4280±400 hr*IU/dL per IU/kg, 4280±500 hr*IU/dL per IU/kg, 4280±600 hr*IU/dL per IU/kg, 4280±700 hr*IU/dL per IU/kg, 4280±800 hr*IU/dL per IU/kg, 4280±900 hr*IU/dL per IU/kg, 4280±1000 hr*IU/dL per IU/kg, 4280±1100 hr*IU/dL per IU/kg, 4280±1200 hr*IU/dL per IU/kg, 4280±1300 hr*IU/dL per IU/kg, 4280±1400 hr*IU/dL per IU/kg, 4280±1500 hr*IU/dL per IU/kg, or 4280±1600 hr*IU/dL per IU/kg as measured by a two stage (chromogenic) assay when about 65 IU/kg of the chimeric polypeptide is administered; or an $AUC_{INF}$ in said subject of about 2960-6190 hr*TU/dL per IU/kg as measured by a two stage (chromogenic) assay when about 65 IU/kg of the chimeric polypeptide is administered.

"On-demand treatment," as used herein, means treatment that is intended to take place over a short course of time and is in response to an existing condition, such as a bleeding episode, or a perceived need such as planned surgery. The terms "on-demand treatment" and "episodic treatment" are used interchangeably. Conditions that can require on-demand (episodic) treatment include, e.g., a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject can be in need of surgical prophylaxis, peri-operative management, or treatment for surgery. Such surgeries include, e.g., minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

In one embodiment, on-demand (episodic) treatment resolves greater than 80% (greater than 80%, greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, greater than 99%, or 100%) or 80-100%, 80-90%, 85-90%, 90-100%, 90-95%, or 95-100% of bleeds (e.g., spontaneous bleeds) in a single dose. In another embodiment, greater than 80% (greater than 81%, greater than 82%, greater than 83%, greater than 84%, greater than 85%, greater than 86%, greater than 87%, greater than 88%, greater than 89%, greater than 90%, greater than 91%, greater than 92%, greater than 93%, greater than 94%, greater than 95%, greater than 96%, greater than 97%, greater than 98%, or 100%) or 80-100%, 80-90%, 85-90%, 90-100%, 90-95%, or 95-100% of bleeding episodes are rated excellent or good by physicians after on-demand (episodic) treatment. In other embodiments, greater than 5%, (greater than 6%, greater than 7%, greater than 8%, greater than 9%, greater than 10%, greater than 11%, greater than 12%, greater than 13%, greater than 14%, greater than 15%, greater than 16%, greater than 17%, greater than 18%, greater than 19%, greater than 20%), or 5-20%, 5-15%, 5-10%, 10-20%, or 10-15% of bleeding episodes are rated as fair by physicians after on-demand (episodic) treatment.

"Polypeptide," "peptide" and "protein" are used interchangeably and refer to a polymeric compound comprised of covalently linked amino acid residues.

"Polynucleotide" and "nucleic acid" are used interchangeably and refer to a polymeric compound comprised of covalently linked nucleotide residues. Polynucleotides can be DNA, cDNA, RNA, single stranded, or double stranded, vectors, plasmids, phage, or viruses. Polynucleotides include, e.g., those in TABLE 1, which encode the polypeptides of TABLE 2 (see TABLE 1). Polynucleotides also include, e.g., fragments of the polynucleotides of TABLE 1, e.g., those that encode fragments of the polypeptides of TABLE 2, such as the FVIII, Fc, signal sequence, 6His and other fragments of the polypeptides of TABLE 2.

"Prophylactic treatment," as used herein, means administering a FVIII polypeptide in multiple doses to a subject over a course of time to increase the level of FVIII activity in a subject's plasma. The increased level can be sufficient to decrease the incidence of spontaneous bleeding or to prevent bleeding, e.g., in the event of an unforeseen injury. During prophylactic treatment, the plasma protein level in the subject can not fall below the baseline level for that subject, or below the level of FVIII that characterizes severe hemophilia (<1 IU/dl [1%]).

In one embodiment, the prophylaxis regimen is "tailored" to the individual patient, for example, by determining PK data for each patient and administering FVIII of the present disclosure at a dosing interval that maintains a trough level of 1-3% FVIII activity. Adjustments can be made when a subject experiences unacceptable bleeding episodes defined as ≥2 spontaneous bleeding episodes over a rolling two-month period. In this case, adjustment will target trough levels of 3-5%. In another embodiment, prophylactic treatment results in prevention and control of bleeding, sustained control of bleeding, sustained protection from bleeding, and/or sustained benefit. Prophylaxis, e.g., sustained protection can be demonstrated by an increased AUC to last measured time point (AUC-LAST) and reduced clearance, resulting in increased terminal t½ compared to short acting FVIII. Prophylaxis can be demonstrated by better $C_{max}$, better $T_{max}$, and/or greater mean residence time versus short-acting FVIII. In some embodiments, prophylaxis results in no spontaneous bleeding episodes within about 24, 36, 48, 72, or 96 hours (e.g., 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, 90, 91, 92, 93, 94, 95, or 96 hours), after injection (e.g., the last injection). In certain embodiments, prophylaxis results in greater than 30% (e.g., greater than 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 96, 87, 88, 89, or 90%, for example, greater than 50%), mean reduction in annualized bleeding episodes with once weekly dosing (e.g., at 65 IU/kg).

"Subject," as used herein means a human individual. Subject can be a patient who is currently suffering from a bleeding disorder or is expected to be in need of such a treatment. In some embodiments, the subject has never been previously treated with the clotting factor (i.e., the subject is a previously untreated subject or previously untreated patient). In some embodiments, the subject is a fetus and the methods comprises administering the chimeric polypeptide to the mother of the fetus and the administration to the subject occurs from the mother across the placenta. In some embodiments, the subject is a child or an adult. In some embodiments, the subject is a child less than one-year-old, less than two-year-old, less than three-year-old, less than four-year-old, less than five-year-old, less than six-year-old, less than seven-year-old, less than eight-year-old, less than nine-year-old, less than ten-year-old, less than eleven-year-old, or less than twelve-year-old. In some embodiments, the child is less than one-year old. In some embodiments, the child or adult subject develops a bleeding disorder, wherein the onset of the symptoms of the bleeding disorder is after the one-year-old age. In some embodiments, the administration of the chimeric polypeptide to the subject is sufficient to prevent, inhibit, or reduce development of an immune response selected from a humoral immune response, a cell-mediated immune response, or both a humoral immune response and a cell-mediated immune response against the clotting factor.

In some embodiments described herein, the subject is at risk of developing an inhibitory FVIII immune response. A subject can be at risk of developing an inhibitory FVIII immune response because, for example, the subject previously developed an inhibitory FVIII immune response or currently has an inhibitory FVIII immune response. In some embodiments, the subject developed an inhibitory FVIII immune response after treatment with a plasma-derived FVIII product. In some embodiments, the subject developed an inhibitory FVIII immune response after treatment with a recombinant FVIII product. In some embodiments, the subject developed an inhibitory FVIII immune response after treatment with a full-length FVIII protein. In some embodiments, the subject developed an inhibitory FVIII immune response after treatment with FVIII protein containing a deletion, e.g., a full or partial deletion of the B domain.

In some embodiments, the subject developed an inhibitory FVIII immune response after treatment with a FVIII product selected from the group consisting of ADVATE®, RECOMBINATE®, KOGENATE FS®, HELIXATE FS®, XYNTHA®/REFACTO AB®, HEMOFIL-M®, MONARC-M®, MONOCLATE-P®, HUMATE-P®, ALPHANATE®, KOATE-DVI®, AND HYATE:C®.

In some embodiments, the immune response after treatment with a clotting factor, e.g., FVIII, comprises production of inhibitory antibodies to the clotting factor. In some embodiments, the inhibitory antibody concentration is at least 0.6 Bethesda Units (BU). In some embodiments, the inhibitory antibody concentration is at least 5 BU. In some embodiments, the inhibitory antibody concentration is at least 0.5, at least 0.6, at least 0.7, at least 0.8, at least 0.9, at least 1.0, at least 1.5, at least 2.0, at least 3.0, at least 4.0, at least 5.0, at least 6.0, at least 7.0, at least 8.0, at least 9.0, or at least 10.0 BU.

In some embodiments, the immune response after treatment with a clotting factor, e.g., FVIII, comprises a cell-mediated immune response. In some embodiments, the immune response comprises a cell-mediated immune response. The cell-mediated immune response can comprise that release of a cytokine selected from the group consisting of IL-12, IL-4 and TNF-α.

In some embodiments, the immune response after treatment with a clotting factor, e.g., FVIII, comprises a clinical symptom selected from the group consisting of: increased bleeding tendency, high clotting factor consumption, lack of response to clotting factor therapy, decrease efficacy of clotting factor therapy, and shortened half-life of clotting factor. In some embodiments, the subject has a mutation or deletion in the clotting factor gene. In some embodiments, the subject has a rearrangement in the clotting factor gene. In some embodiments, the subject has severe hemophilia. In some embodiments, the subject has a relative who has previously developed an inhibitory immune response against the clotting factor. In some embodiments, the subject is receiving interferon therapy. In some embodiments, the subject is receiving antiviral therapy.

In some embodiments, the subject at risk has previously developed an inhibitory immune response to a therapeutic protein other than FVIII.

In addition, the subject can also be at risk of developing an inhibitory FVIII immune response as a result of a number of environmental or genetic factors that increase the likelihood the subject will develop an inhibitory immune response. Factors that increase the likelihood that a subject will develop an inhibitory immune response are known. See e.g., Kasper, C. "Diagnosis and Management of Inhibitors to Factors VIII and IX—An Introductory Discussion for Physicians," *Treatment of Hemophilia* 34 (2004), which is herein incorporated by reference in its entirety. For example, inhibitors arise more commonly in severe hemophilia (e.g., FVIII baseline level of less than 1%) than in mild or moderate hemophilia. See *Report of Expert Meeting on FVIII Products and Inhibitor Development*, European Medicines Agency (Feb. 28, 2006-Mar. 2, 2006), which is herein incorporated by reference in its entirety.

As a result of the fact that genetic factors can increase the likelihood that a subject will develop an inhibitory immune response, a subject with at least one family member (e.g., a sibling, parent, child, grandparent, aunt, uncle, or cousin) who has developed an inhibitory immune response to FVIII or another therapeutic protein can be at risk of developing an inhibitory FVIII immune response.

Inhibitors are common in patients with genetic mutations that prevent expression of FVIII such as large genetic deletions, nonsense mutations causing premature stop codons, and large inversions in the FVIII gene. Thus, in some embodiments, a subject at risk of developing an inhibitory FVIII immune response comprises a mutation, deletion, or rearrangement in a FVIII gene. In some embodiments, a subject at risk of developing an inhibitory FVIII immune response comprises a mutation in FVIII that prevents FVIII from binding to T cells. An association of inhibitors with large rearrangements of FVIII genes has been observed. See Astermark et al., *Blood* 107:3167-3172 (2006), which is herein incorporated by reference in its entirety. Thus, in some embodiments, a FVIII-Fc fusion protein is administered to a subject with a large rearrangement in a FVIII gene, for example, an intron 22 inversion or an intron 1 inversion. In some embodiments, FVIII-Fc is administered to a subject with two large rearrangements in FVIII. An association of inhibitors with null mutations has also been observed. Astermark et al., *Blood* 108:3739-3745 (2006). Thus, in some embodiments, a FVIII-Fc fusion protein is administered to a subject with a null mutation.

Inhibitors also arise more commonly after treatment with exogenous clotting factors on only a few occasions. Thus, in some embodiments, a subject at risk of developing an inhibitory immune response has had less than 200, 175, 150, 125, 100, 75, 50, 25, 20, 15, 10, or 5 exposure days. In some embodiments, a subject at risk of developing an inhibitory immune response has not been previously exposed to treatment with FVIII.

In some embodiments, the subject is a fetus. Immune tolerance can be induced in a fetus by administering a chimeric polypeptide comprising a FVIII portion and an Fc portion to the mother of the fetus.

Inhibitors also arise more commonly in black African descent. See e.g., Kasper, C. "Diagnosis and Management of Inhibitors to Factors VIII and IX—An Introductory Discussion for Physicians," *Treatment of Hemophilia* 34 (2004), which is herein incorporated by reference in its entirety. Thus, in some embodiments, a subject at risk of developing an inhibitory immune response is of black African descent.

Genetic mutations in genes other than FVIII have also been linked with an increased risk of developing an inhibitory immune response. For example, the TNF-α-308G>A polymorphism within Hap2, which is associated with increased constitutive and inducible transcription levels of TNF has been linked with an increased risk of developing an inhibitory immune response. See Astermark et al., Blood 108: 3739-3745 (2006), which is herein incorporated by reference in its entirety. Thus, in some embodiments, a subject at risk of developing an inhibitory immune response has a genetic polymorphism associated with increased TNF-α. In some embodiments, the polymorphism is the TNF-α-308G>A polymorphism. In some embodiments, a subject at risk of developing an inhibitory immune response has a polymorphism in an IL10 gene, e.g. a polymorphism associated with increased secretion of IL10. In some embodiments, FVIII-Fc is administered to a subject with the allele 134 of the IL10G microsatellite in the promote region of the IL10 gene. See Astermark et al. Hemostatis, Thrombosis, and Vascular Biology 108: 3739-3745 (2006), which is herein incorporated by reference in its entirety.

In some embodiments, a subject at risk of developing an inhibitory immune response has a genetic polymorphism associated with decreased CTLA-4 (Cytotoxic T-Lymphocyte Antigen 4) expression. In some embodiments, a subject at risk of developing an inhibitory immune response has a mutation in DR15 (HLA-DR15) or DQB0602 MHC (Major histocompatibility complex) Class II molecules. Other MHC Class II molecules associated with the development of an inhibitory immune response in subjects with hemophilia are A3, B7, C7, DQA0102, C2, DQA0103, DQB0603, and DR13 (see Inhibitors in Patients with Hemophilia, E. C. Rodriguez-Merchan & C. A. Lee, Eds., Blackwell Science, Ltd, 2002).

In some embodiments, the subject at risk for developing an inhibitory immune response has not been previously exposed to clotting factor, e.g., FVIII. In some embodiments, the subject at risk for developing an inhibitory immune response to a clotting factor, e.g., FVIII, has been exposed to FVIII. In some embodiments, the subject at risk for developing an inhibitory immune response to a clotting factor, e.g., FVIII, has had less than 150, less than 50, or less than 20 FVIII exposure days. In some embodiments, the subject has had at least 1, 2, 3, 4, 5, 6, 7, 8, 9, 10, 11, 12, 13, 14, 15, 16, 17, 18, 19 or 20 days of clotting factor exposure. In some embodiments, the subject has had at least 25, 30, 35, 40, 45, or 50 days of clotting factor exposure. In some embodiments, the subject has had at least 60, 70, 80, 90, 100, 110, 120, 130, 140 or 150 days of clotting factor exposure.

In some embodiments, the inhibitory immune response is an inhibitory FVIII immune response. In some embodiments, the inhibitory FVIII immune response developed in response to a FVIII product selected from the group consisting of: ADVATE®, RECOMBINATE®, KOGENATE FS®, HELIXATE FS®, XYNTHA®/REFACTO AB®, HEMOFIL-M®, MONARC-M®, MONOCLATE-P®, HUMATE-P®, ALPHANATE®, KOATE-DVI®, AND HYATE:C®. In some embodiments, the inhibitory immune response is an inhibitory FVIII immune response developed in response to a recombinant FVIII product.

In some embodiments, a subject at risk of developing an inhibitory immune response is receiving or has recently received an immunostimulatory therapy. For example, inhibitors have also been reported in HCV positive hemophilia A patients undergoing treatment with interferon as well as in HIV positive hemophilia A patients having an immune reconstitution inflammatory syndrome associated with anti-retroviral therapy. See Report of Expert Meeting on FVIII Products and Inhibitor Development, European Medicines Agency (Feb. 28, 2006-Mar. 2, 2006), which is herein incorporated by reference in its entirety. Thus, in some embodiments, a subject at risk of developing an inhibitory immune response is receiving interferon therapy. In some embodiments, a subject at risk of developing an inhibitory immune response is receiving an anti-retroviral therapy and having an immune reconstitution inflammatory syndrome.

An inhibitory FVIII immune response can be determined based on clinical responses to FVIII treatment. Clinical presentations of FVIII inhibitors are known and described, for example, in Kasper, C. "Diagnosis and Management of Inhibitors to Factors VIII and IX—An Introductory Discussion for Physicians," *Treatment of Hemophilia* 34 (2004), which is herein incorporated by reference in its entirety. For example, the presence of an inhibitor makes controlling hemorrhages for difficult, so immune responses to FVIII are signaled by an increased bleeding tendency, high FVIII consumption, lack of response to FVIII therapy, decreased efficacy of FVIII therapy, and/or shortened half-life of FVIII.

Inhibitory FVIIII immune responses can also be determined using laboratory tests such as the Bethesda test or the Nijmegan modification of the Bethesda test. A level of at least 0.6 Bethesda Units (BU) can indicate the presence of an inhibitory immune response. A level of at least 5 BU can indicate the presence of a high titer inhibitor. Measurements of the in vivo recovery and half-life of bolus FVIII infusion can also be used.

In some embodiments, a subject at risk of developing an inhibitory immune response has previously had an inhibitory immune response with a peak titer of at least 0.5, at least 0.6, at least 0.7, at least 0.8, at least 0.9, at least 1.0, at least 1.5, at least 2.0, at least 3.0, at least 4.0, at least 5.0, at least 6.0, at least 7.0, at least 8.0, at least 9.0, or at least 10.0 BU.

In some embodiments provided herein, the methods comprise determining if a subject is at risk of developing an inhibitory FVIII immune response and administering to the subject a chimeric polypeptide comprising a FVIII portion and an Fc portion if the subject is at risk. Thus, in some embodiments, the methods comprise determining if the subject has a mutation, deletion, or rearrangement in FVIII and administering a chimeric polypeptide if the subject does. In some embodiments, the methods comprise determining if the subject produces FVIII protein and administering a chimeric polypeptide if the subject does not. In some embodiments, the methods comprise determining if the subject has mild, moderate, or severe hemophilia, and administering a chimeric polypeptide if the subject has severe hemophilia. In some embodiments, the methods comprise determining if the subject has an inhibitory FVIII immune response, e.g., by assessing clinical manifestations of an immune response, measuring anti-FVIII antibody levels, titers, or activities, or measuring cell-mediated immune response (e.g., by measuring levels of cytokines) and administering a chimeric polypeptide if the subject has at least one of these indicators.

"Therapeutic dose," as used herein, means a dose that achieves a therapeutic goal, as described herein. The calculation of the required dosage of FVIII is based upon the empirical finding that, on average, 1 IU of FVIII per kg body weight raises the plasma FVIII activity by approximately 2 IU/dL. The required dosage is determined using the following formula:

Required units=body weight (kg)×desired FVIII rise (IU/dL or % of normal)×0.5 (IU/kg per IU/dL)

The therapeutic doses that can be used in the methods of the present disclosure are about 10-100 IU/kg, more specifically, 10-20, 20-30, 30-40, 40-50, 50-60, 60-70, 70-80, 80-90, or 90-100 IU/kg, and more specifically, 10, 15, 20, 25, 30, 35, 40, 45, 50, 55, 60, 65, 70, 75, 80, 85, 90, 95, or 100 IU/kg.

Additional therapeutic doses that can be used in the methods of the present disclosure are about 10 to about 150 IU/kg, more specifically, about 100-110, 110-120, 120-130, 130-140, 140-150 IU/kg, and more specifically, about 110, 115, 120, 125, 130, 135, 140, 145, or 150 IU/kg.

"Variant," as used herein, refers to a polynucleotide or polypeptide differing from the original polynucleotide or polypeptide, but retaining essential properties thereof, e.g., FVIII coagulant activity or Fc (FcRn binding) activity. Generally, variants are overall closely similar, and, in many regions, identical to the original polynucleotide or polypeptide. Variants include, e.g., polypeptide and polynucleotide fragments, deletions, insertions, and modified versions of original polypeptides.

Variant polynucleotides can comprise, or alternatively consist of, a nucleotide sequence which is at least 85%, 90%, 95%, 96%, 97%, 98% or 99% identical to, for example, the nucleotide coding sequence in SEQ ID NO:1, 3, or 5 (the FVIII portion, the Fc portion, individually or together) or the complementary strand thereto, the nucleotide coding sequence of known mutant and recombinant FVIII or Fc such as those disclosed in the publications and patents cited herein or the complementary strand thereto, a nucleotide sequence encoding the polypeptide of SEQ ID NO:2, 4, or 6 (the FVIII portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

Variant polypeptides can comprise, or alternatively consist of, an amino acid sequence which is at least 85%, 90%, 95%, 96%, 97%, 98%, 99% identical to, for example, the polypeptide sequence shown in SEQ ID NOS:2, 4, or 6 (the FVIII portion, the Fc portion, individually or together), and/or polypeptide fragments of any of these polypeptides (e.g., those fragments described herein).

By a nucleic acid having a nucleotide sequence at least, for example, 95% "identical" to a reference nucleotide sequence, it is intended that the nucleotide sequence of the nucleic acid is identical to the reference sequence except that the nucleotide sequence can include up to five point mutations per each 100 nucleotides of the reference nucleotide sequence. In other words, to obtain a nucleic acid having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. The query sequence can be, for example, the entire sequence shown in SEQ TD NO:1 or 3, the ORF (open reading frame), or any fragment specified as described herein.

As a practical matter, whether any particular nucleic acid molecule or polypeptide is at least 85%, 90%, 95%, 96%, 97%, 98% or 99% identical to a nucleotide sequence or polypeptide of the present disclosure can be determined conventionally using known computer programs. In one embodiment, a method for determining the best overall match between a query sequence (reference or original sequence) and a subject sequence, also referred to as a global sequence alignment, can be determined using the FASTDB computer program based on the algorithm of Brutlag et al., *Comp. App. Biosci.* 6:237-245 (1990), which is herein incorporated by reference in its entirety In a sequence alignment the query and subject sequences are both DNA sequences. An RNA sequence can be compared by converting U's to T's. The result of said global sequence alignment is in percent identity. In another embodiment, parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present disclosure. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of the present disclosure.

By a polypeptide having an amino acid sequence at least, for example, 95% "identical" to a query amino acid sequence of the present disclosure, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted, (indels) or substituted with another amino acid. These alterations of the reference sequence can occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 85%, 90%, 95%, 96%, 97%, 98% or 99% identical to, for instance, the amino acid sequences of SEQ ID NO:2 (the FVIII portion, the Fc portion, individually or together) or 4, or a known FVIII or Fc polypeptide sequence, can be determined conventionally using known computer programs. In one embodiment, a method for determining the best overall match between a query sequence (reference or original sequence) and a subject sequence, also referred to as a global sequence alignment, can be determined using the FASTDB computer program based on the algorithm of Brutlag et al., *Comp. App. Biosci.* 6:237-245(1990), incorporated herein by reference in its entirety. In a sequence alignment the query and subject sequences are either both nucleotide sequences or both amino acid sequences. The result of said global sequence alignment is in percent identity. In another embodiment, parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present disclosure. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of the present disclosure.

The polynucleotide variants can contain alterations in the coding regions, non-coding regions, or both. In one embodiment, the polynucleotide variants contain alterations which produce silent substitutions, additions, or deletions, but do not alter the properties or activities of the encoded polypeptide. In another embodiment, nucleotide variants are produced by silent substitutions due to the degeneracy of the genetic code. In other embodiments, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present disclosure. Alternatively, non-naturally occurring variants can be produced by mutagenesis techniques or by direct synthesis.

Using known methods of protein engineering and recombinant DNA technology, variants can be generated to improve or alter the characteristics of the polypeptides. For instance, one or more amino acids can be deleted from the N-terminus or C-terminus of the secreted protein without substantial loss of biological function. Ron et al., *J. Biol. Chem.* 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J. Biol. Chem* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild-type.

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some embodiments, FVIII is modified, e.g., pegylated, at any convenient location. In some embodiments, FVIII is pegylated at a surface exposed amino acid of FVIII, e.g., a surface exposed cysteine, which can be an engineered cysteine. Id. In some embodiments, modified FVIII, e.g., pegylated FVIII, is a long-acting FVIII.

"Volume of distribution at steady state (Vss)," as used herein, has the same meaning as the term used in pharmacology, which is the apparent space (volume) into which a drug distributes. Vss=the amount of drug in the body divided by the plasma concentration at steady state.

"About," as used herein for a range, modifies both ends of the range. Thus, "about 10-20" means "about 10 to about 20."

The chimeric polypeptide used herein can comprise processed FVIII or single chain FVIII or a combination thereof "Processed FVIII," as used herein means FVIII that has been cleaved at Arginine 1648 (for full-length FVIII) or Arginine 754 (for B-domain deleted FVIII), i.e., intracellular processing site. Due to the cleavage at the intracellular processing site, processed FVIII comprises two polypeptide chains, the first chain being a heavy chain and the second chain being a light chain. For example, the processed FVIII-Fc fusion protein (i.e., Heavy chain and Light chain fused to Fc) run at approximately 90 kDa and 130 kDa on a non-reducing SDS-PAGE, respectively, and 90 kDa and 105 kDa on a reducing SDS-PAGE, respectively. Therefore, in one embodiment, at least about 50%, about 60%, about 70%, about 75%, about 80%, about 85%, about 90%, about 95%, about 96%, about 97%, about 98%, about 99%, or about 100% of the FVIII portion in the chimeric polypeptide is processed FVIII.

In another embodiment, about 50%, about 60%, about 70%, about 75%, about 80%, about 85%, about 90%, about 95%, about 96%, about 97%, about 98%, about 99%, or about 100% of the FVIII portion in the chimeric polypeptide is processed FVIII. In a particular embodiment, the chimeric polypeptide comprising processed FVIII is purified (or isolated) from the chimeric polypeptide comprising single chain FVIII, and at least about 90%, about 95%, about 96%, about 97%, about 98%, about 99%, or about 100% of the FVIII portion in the chimeric polypeptide is processed FVIII.

The terms "Single chain FVIII" or "SC FVIII" as used herein mean FVIII that has not been cleaved at the Arginine site (residue 1648 for full-length FVIII (i.e., residue 1667 of SEQ ID NO: 6) or residue 754 for B-domain deleted FVIII (i.e., residue 773 of SEQ ID NO: 2). Therefore, single chain FVIII in the chimeric polypeptide used herein comprises a single chain. In one embodiment, the single chain FVIII contains an intact intracellular processing site. The single chain FVIII-Fc fusion protein can run at approximately 220 kDa on a non reducing SDS-PAGE and at approximately 195 kDa on a reducing SDS-PAGE.

In one embodiment, the chimeric polypeptide comprising single chain FVIII is purified (or isolated) from the chimeric polypeptide comprising processed FVIII, and at least about 30%, about 40%, about 50%, about 60%, about 70%, about 75%, about 80%, about 85%, about 90%, about 95%, about 99%, or about 100% of the FVIII portion of the chimeric polypeptide used herein is single chain FVIII. In another embodiment, at least about 1%, about 5%, about 10%, about 15%, about 20%, or about 25% of the FVIII portion of the chimeric polypeptide is single chain FVIII. In other embodiments, about 1%-about 10%, about 5%-about 15%, about 10%-about 20%, about 15%-about 25%, about 20%-about 30%, about 25%-about 35%, about 30%-about 40% of the FVIII portion of the chimeric polypeptide used herein is single chain FVIII.

In a particular embodiment, about 1%, about 5%, about 10%, about 15%, about 20% or about 25% of the FVIII portion of the chimeric polypeptide used herein is single chain FVIII. In other embodiments, about 30%, about 40%, about 50%, about 60%, about 70%, about 80%, about 90%, about 95%, about 96%, about 97%, about 98%, about 99%, or about 100% of the FVIII portion of the chimeric polypeptide used herein is single chain FVIII. In some embodiments, the ratio of the single chain FVIII to the processed FVIII of the chimeric polypeptide is (a) about 25% of single chain FVIII and about 75% of processed FVIII; (b) about 20% of single chain FVIII and about 80% of processed FVIII; (c) about 15% of single chain FVIII and about 85% of processed FVIII; (d) about 10% of single chain FVIII and about 90% of processed FVIII; (e) about 5% of single chain FVIII and about 95% of processed FVIII; (f) about 1% of single chain FVIII and about 99% of processed FVIII; or (g) about 100% of processed FVIII.

In other embodiments, the ratio of the single chain FVIII to the processed FVIII of the chimeric polypeptide is (a) about 30% of single chain FVIII and about 70% of processed FVIII; (b) about 40% of single chain FVIII and about 60% of processed FVIII; (c) about 50% of single chain FVIII and about 50% of processed FVIII; (d) about 60% of single chain FVIII and about 40% of processed FVIII; (c) about 70% of single chain FVIII and about 30% of processed FVIII; (f) about 80% of single chain FVIII and about 20% of processed FVIII; (g) about 90% of single chain FVIII and about 10% of processed FVIII; (h) about 95% of single chain FVIII and about 5% of processed FVIII; (i) about 99% of single chain FVIII and about 1% of processed FVIII; or (j) about 100% of single chain FVIII.

The FVIII portion in the chimeric polypeptide used herein has FVIII activity. FVIII activity can be measured by any known methods in the art. For example, one of those methods can be a chromogenic assay. The chromogenic assay mechanism is based on the principles of the blood coagulation cascade, where activated FVIII accelerates the conversion of Factor X into Factor Xa in the presence of activated Factor IX, phospholipids and calcium ions. The Factor Xa activity is assessed by hydrolysis of a p-nitroanilide (pNA) substrate specific to Factor Xa. The initial rate of release of p-nitroaniline measured at 405 nM is directly proportional to the Factor Xa activity and thus to the FVIII activity in the sample.

The chromogenic assay is recommended by the FVIII and Factor IX Subcommittee of the Scientific and Standardization Committee (SSC) of the International Society on Thrombosis and Hemostatsis (ISTH). Since 1994, the chromogenic assay has also been the reference method of the European Pharmacopoeia for the assignment of FVIII concentrate potency. Thus, in one embodiment, the chimeric polypeptide comprising single chain FVIII has FVIII activity comparable to a chimeric polypeptide comprising processed FVIII (e.g., a chimeric polypeptide consisting essentially of or consisting of two Fc portions and processed FVIII, wherein said processed FVIII is fused to one of the two Fc portions), when the FVIII activity is measured in vitro by a chromogenic assay.

In another embodiment, the chimeric polypeptide comprising single chain FVIII of this disclosure has a Factor Xa generation rate comparable to a chimeric polypeptide comprising processed FVIII (e.g., a chimeric polypeptide consisting essentially of or consisting of two Fc portions and processed FVIII, wherein the processed FVIII is fused to one Fc of the two Fc portions).

In order to activate Factor X to Factor Xa, activated Factor IX (Factor IXa) hydrolyzes one arginine-isoleucine bond in Factor X to form Factor Xa in the presence of $Ca^{2+}$, membrane phospholipids, and a FVIII cofactor. Therefore, the interaction of FVIII with Factor IX is critical in coagulation pathway. In certain embodiments, the chimeric polypeptide comprising single chain FVIII can interact with Factor IXa at a rate comparable to a chimeric polypeptide comprising processed FVIII (e.g., a chimeric polypeptide consisting essentially of or consisting of two Fc portions and processed FVIII, wherein the processed FVIII is fused to one Fc of the two Fc portions).

In addition, FVIII is bound to von Willebrand Factor while inactive in circulation. FVIII degrades rapidly when not bound to vWF and is released from vWF by the action of thrombin. In some embodiments, the chimeric polypeptide comprising single chain FVIII binds to von Willebrand Factor at a level comparable to a chimeric polypeptide comprising processed FVIII (e.g., a chimeric polypeptide consisting essentially of or consisting of two Fc portions and processed FVIII, wherein the processed FVIII is fused to one Fc of the two Fc portions).

FVIII can be inactivated by activated protein C in the presence of calcium and phospholipids. Activated protein C cleaves FVIII heavy chain after Arginine 336 in the A1 domain, which disrupts a Factor X substrate interaction site, and cleaves after Arginine 562 in the A2 domain, which enhances the dissociation of the A2 domain as well as disrupts an interaction site with the Factor IXa. This cleavage also bisects the A2 domain (43 kDa) and generates A2-N (18 kDa) and A2-C(25 kDa) domains. Thus, activated protein C can catalyze multiple cleavage sites in the heavy chain. In one embodiment, the chimeric polypeptide comprising single chain FVIII is inactivated by activated Protein C at a level comparable to a chimeric polypeptide comprising processed FVIII (e.g., a chimeric polypeptide consisting essentially of or consisting of two Fc portions and processed FVIII, wherein the processed FVIII is fused to one Fc of the two Fc portions).

In other embodiments, the chimeric polypeptide comprising single chain FVIII has FVIII activity in vivo comparable to a chimeric polypeptide comprising processed FVIII (e.g., a chimeric polypeptide consisting essentially of or consisting of two Fc portions and processed FVIII, wherein the processed FVIII is fused to one Fc of the two Fc portions).

In a particular embodiment, the chimeric polypeptide comprising single chain FVIII is capable of protecting a HemA mouse at a level comparable to a chimeric polypeptide comprising processed FVIII (e.g., a chimeric polypeptide consisting essentially of or consisting of two Fc portions and processed FVIII, wherein said processed FVIII is fused to one Fc of the two Fc portions) in a HemA mouse tail vein transection model.

The term "comparable" as used herein means a compared rate or level resulted from using the chimeric polypeptide is equal to, substantially equal to, or similar to the reference rate or level. The term "similar" as used herein means a compared rate or level has a difference of no more than 10% or no more than 15% from the reference rate or level (e.g., FXa generation rate by a chimeric polypeptide consisting essentially of or consisting of two Fc portions and processed FVIII, wherein said processed FVIII is fused to one Fc of the two Fc portions). The term "substantially equal" means a compared rate or level has a difference of no more than 0.01%, 0.5% or 1% from the reference rate or level.

The present disclosure further includes a composition comprising a chimeric polypeptide having FVIII activity, wherein at least about 30%, about 40%, about 50%, about 60%, about 70%, about 80%, about 85%, about 90%, about 95%, or about 99% of the chimeric polypeptide comprises a FVIII portion, which is single chain FVIII and a second portion. In another embodiment, about 30%, about 40%, about 50%, about 60%, about 70%, about 80%, about 85%, about 90%, about 95%, about 96%, about 97%, about 98%, or about 99% of the chimeric polypeptide in the composition is single chain FVIII. In other embodiments, the second portion is an Fc. In yet other embodiments, the chimeric polypeptide comprises another half-life extending moiety, e.g., albumin.

In still other embodiments, the composition of the present disclosure comprises a combination of a chimeric polypeptide comprising processed FVIII and a chimeric polypeptide comprising single chain FVIII, (a) wherein about 30% of the FVIII portion of the chimeric polypeptide is single chain FVIII, and about 70% of the FVIII portion of the chimeric polypeptide is processed FVIII; (b) wherein about 40% of the FVIII portion of the chimeric polypeptide is single chain FVIII, and about 60% of the FVIII portion of the chimeric polypeptide is processed FVIII; (c) wherein about 50% of the FVIII portion of the chimeric polypeptide is single chain FVIII, and about 50% of the FVIII portion of the chimeric polypeptide is processed FVIII; (d) wherein about 60% of the FVIII portion of the chimeric polypeptide is single chain FVIII and about 40% of the FVIII portion of the chimeric polypeptide being processed FVIII; (e) wherein about 70% of the FVIII portion of the chimeric polypeptide is single chain FVIII and about 30% of the FVIII portion of the chimeric polypeptide is processed FVIII; (f) wherein about 80% of the FVIII portion of the chimeric polypeptide is single chain FVIII and about 20% of the FVIII portion of the chimeric polypeptide is processed FVIII; (g) wherein about 90% of the FVIII portion of the chimeric polypeptide is single chain FVIII and about 10% of the FVIII portion of the chimeric polypeptide is processed FVIII; (h) wherein about 95% of the FVIII portion of the chimeric polypeptide is single chain FVIII and about 5% of the FVIII portion of the chimeric polypeptide is processed FVIII; (i) wherein about 99% of the FVIII portion of the chimeric polypeptide is single chain FVIII and about 1% of the FVIII portion of the chimeric polypeptide is processed FVIII; or (j) wherein about 100% of the FVIII portion of the chimeric polypeptide is single chain FVIII.

In certain embodiments, the composition of the present disclosure has FVIII activity comparable to the composition comprising processed FVIII (e.g., a composition comprising a chimeric polypeptide, which consists essentially of or consists of two Fc portions and processed FVIII, wherein said processed FVIII is fused to one of the two Fc portions), when the FVIII activity is measured in vitro by a chromogenic assay.

In other embodiments, the composition of the disclosure has a Factor Xa generation rate comparable to a composition comprising processed FVIII (e.g., a composition comprising a chimeric polypeptide, which consists essentially of or consists of two Fc portions and processed FVIII, wherein the processed FVIII is fused to one Fc of the two Fc portions). In still other embodiments, the composition comprising single chain FVIII can interact with Factor IXa at a rate comparable to a composition comprising processed FVIII (e.g., a composition comprising a chimeric polypeptide, which consists essentially of or consists of two Fc portions and processed FVIII, wherein the processed FVIII is fused to one Fc).

In further embodiments, the single chain F VIII in the chimeric polypeptide of the present composition is inactivated by activated Protein C at a level comparable to processed FVIII in a chimeric polypeptide of a composition (e.g., a composition comprising a chimeric polypeptide, which consists essentially of or consists of two Fc portions and processed FVIII, wherein the processed FVIII is fused to one Fc of the two Fc portions). In a particular embodiment, the composition comprising single chain FVIII has FVIII activity in vivo comparable to the composition comprising processed FVIII (e.g., a composition comprising a chimeric polypeptide, which consists essentially of or consists of two Fc portions and processed FVIII, wherein the processed FVIII is fused to one Fc of the two Fc portions). In some embodiments, the composition comprising single chain FVIII of the present disclosure is capable of protecting HemA mouse at a level comparable to the composition comprising processed FVIII (e.g., a composition comprising a chimeric polypeptide, which consists essentially of or consists of two Fc portions and processed FVIII, wherein said processed FVIII is fused to one Fc of the two Fc portions) in HemA mouse tail vein transection model.

The present disclosure further provides a method for treating a bleeding condition in a human subject using the compositions disclosed herein. An exemplary method comprises administering to the subject in need thereof a therapeutically effective amount of a pharmaceutical composition/formulation comprising a chimeric polypeptide having FVIII activity, wherein at least about 30%, about 40%, about 50%, about 60%, about 70%, about 80%, about 85%, about 90%, about 95%, or about 99% of the chimeric polypeptide comprises a FVIII portion, which is single chain FVIII, and a second portion.

The bleeding condition can be caused by a blood coagulation disorder. A blood coagulation disorder can also be referred to as a coagulopathy. In one example, the blood coagulation disorder, which can be treated with a pharmaceutical composition of the current disclosure, is hemophilia or von Willebrand disease (vWD). In another example, the blood coagulation disorder, which can be treated with a pharmaceutical composition of the present disclosure is hemophilia A.

In some embodiments, the type of bleeding associated with the bleeding condition is selected from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

In other embodiments, the subject suffering from bleeding condition is in need of treatment for surgery, including, e.g., surgical prophylaxis or peri-operative management. In one example, the surgery is selected from minor surgery and major surgery. Exemplary surgical procedures include tooth extraction, tonsillectomy, inguinal herniotomy, synovectomy, craniotomy, osteosynthesis, trauma surgery, intracranial surgery, intra-abdominal surgery, intrathoracic surgery, joint replacement surgery (e.g., total knee replacement, hip replacement, and the like), heart surgery, and caesarean section.

In another example, the subject is concomitantly treated with FIX. Because the compounds of the present disclosure are capable of activating FIXa, they could be used to pre-activate the FIXa polypeptide before administration of the FIXa to the subject.

The methods disclosed herein can be practiced on a subject in need of prophylactic treatment or on-demand treatment.

The pharmaceutical compositions comprising at least 30% of single chain FVIII can be formulated for any appropriate manner of administration, including, for example, topical (e.g., transdermal or ocular), oral, buccal, nasal, vaginal, rectal or parenteral administration.

The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. The composition can be also for example a suspension, emulsion, sustained release formulation, cream, gel or powder. The composition can be formulated as a suppository, with traditional binders and carriers such as triglycerides.

In one example, the pharmaceutical formulation is a liquid formulation, e.g., a buffered, isotonic, aqueous solution. In another example, the pharmaceutical composition has a pH that is physiologic, or close to physiologic. In other examples, the aqueous formulation has a physiologic or close to physiologic osmolarity and salinity. It can contain sodium chloride and/or sodium acetate. In some examples, the composition of the present disclosure is lyophilized. In some embodiments, the pharmaceutical composition does not comprise an immune cell. In some embodiments, the pharmaceutical composition does not comprise a cell.

The present disclosure also provides a kit comprising (a) a pharmaceutical composition comprising a chimeric polypeptide which comprises a clotting factor portion and an Fc portion and a pharmaceutically acceptable carrier, and (b) instructions to administer to the composition to a subject in need of immune tolerance to the clotting factor. In some embodiments, the chimeric polypeptide in the kit comprises a FVIII portion, a FVII portion, or a FIX portion. In other embodiments, the chimeric polypeptide in the kit is a FVIII monomer dimer hybrid, a FVII monomer dimer hybrid, or a FIX monomer dimer hybrid. In some embodiments, the instructions further include at least one step to identify a subject in need of immune tolerance to the clotting factor. In some embodiments, the step to identify the subjects in need of immune tolerance includes one or more from the group consisting of:
(i) identifying a subject having a mutation or deletion in the clotting factor gene;
(ii) identifying a subject having a rearrangement in the clotting factor gene;
(iii) identifying a subject having a relative who has previously developed an inhibitory immune response against the clotting factor;
(iv) identifying a subject receiving interferon therapy;
(v) identifying a subject receiving anti-viral therapy;
(vi) identifying a subject having a genetic mutation in a gene other than the gene encoding the clotting factor which is linked with an increased risk of developing an inhibitory immune response; and
(vii) two or more combinations thereof.

In some embodiments, the genetic mutation in a gene other than the gene encoding the clotting factor comprises one or more mutations selected from the group consisting of:
(i) a genetic polymorphism associated with increased TNF-α;
(ii) a genetic polymorphism associated with increased IL10;
(iii) a genetic polymorphism associated with decreased CTLA-4;
(iv) a mutation in DR15 or DQB0602 MHC Class II molecules; and
(v) has two or more combinations thereof.

Optionally associated with the kit's container(s) can be a notice in the form prescribed by a governmental agency regulating the manufacture, use or sale of pharmaceuticals or biological products, which notice reflects approval by the agency of manufacture, use or sale for human administration.

EMBODIMENTS

E1. A method of inducing immune tolerance to a clotting factor in a subject in need thereof comprising administering to the subject a chimeric polypeptide, wherein the chimeric polypeptide comprises a clotting factor portion and an Fc portion.

E2. A method of preventing or inhibiting development of an inhibitor to a clotting factor comprising administering to a subject in need of immune tolerance to the clotting factor a chimeric polypeptide, wherein the chimeric polypeptide comprises a clotting factor portion and an Fc portion.

E3. The method of embodiment E1 or E2, wherein the subject would develop an inhibitory immune response against the clotting factor if administered an equivalent dose of a polypeptide consisting of the clotting factor.

E4. The method of any one of embodiments E1 to E3, wherein the subject has developed an inhibitory immune response against the clotting factor.

E5. The method of any one of embodiments E1 to E4, wherein the subject has never been previously treated with the clotting factor.

E6. The method of any one of embodiments E1 to E5, wherein the clotting factor portion comprises Factor VIII, Factor IX, Factor VII, Von Willebrand Factor, or a fragment thereof.

E7. The method of any one of embodiments E1 to E5, where in the subject is a fetus and the method further comprises administering the chimeric polypeptide to the mother of the fetus and the administration to the subject occurs from the mother across the placenta.

E8. The method of embodiment E7, wherein the clotting factor moiety comprises Factor VIII, Factor IX, Factor VII, Von Willebrand Factor, or a fragment thereof.

E9. The method of any one of embodiments E1 to E6, wherein the subject is a child or an adult.

E10. The method of embodiment E9, wherein the subject is a child less than one-year-old, less than two-year-old, less than three-year-old, less than four-year-old, less than five-year-old, less than six-year-old, less than seven-year-old, less than eight-year-old, less than nine-year-old, less than ten-year-old, less than eleven-year-old, or less than twelve-year-old.

E11. The method of embodiment E10, wherein the child is less than one-year old.

E12. The method of embodiment E11, wherein the child or adult develops a bleeding disorder, wherein the onset of the symptoms of the bleeding disorder is after the one-year-old age.

E13. The method of any one of embodiments E1 to E12 wherein the administration is sufficient to prevent, inhibit, or reduce development of an immune response selected from a humoral immune response, a cell-mediated immune response, or both a humoral immune response and a cell-mediated immune response against the clotting factor.

E14. The method of any one of embodiments E1 to E13, wherein the composition is administered in repeated doses.

E15. The method of embodiment E14, wherein each of the repeated doses is separated from another by at least about 12 hours, at least about 24 hours, at least about two days, at least about three days, at least about four days, at least about five days, at least about six days, at least about seven days, at least about eight days, at least about nine days, at least about ten days, at least about 11 days, at least about 12 days, at least about 13 days, at least about 14 days, or at least about 15 days.

E16. The method of embodiment E14 or E15, wherein the repeated doses comprise at least about two doses, at least about five doses, at least about 10 doses, at least about 20 doses, at least about 25 doses, at least about 30 doses, at least about 35 doses, at least about 40 doses, at least about 45 doses, at least about 50 doses, at least about 55 doses, at least about 60 doses, at least about 65 doses, or at least about 70 doses.

E17. The method of embodiment E16, wherein the repeated doses comprise from about two doses to about 100 doses, from about five doses to about 80 doses, from about 10 doses to about 70 doses, from about 10 doses to about 60 doses, from about 10 doses to about 50 doses, from about 15 doses to about 40 doses, from about 15 doses to about 30 doses, from about 20 doses to about 30 doses, or from about 20 doses to about 40 doses.

E18. The method of embodiment E16 or E17, wherein the repeated doses comprise about two doses, about five doses, about 10 doses, about 15 doses, about 20 doses, about 25 doses, about 30 doses, about 35 doses, about 40 doses, about 45 doses, about 50 doses, about 55 doses, about 60 doses, about 65 does, about 70 doses, about 75 doses, about 80 doses, about 90 doses, or about 100 doses.

E19. The method of any one of embodiments E14 to E18, wherein the subject is further administered, after the repeated doses, a pharmaceutical composition comprising a clotting factor protein which comprises the clotting factor, but does not comprise an Fc portion.

E20. The method of embodiment E19, wherein the clotting factor protein is full length or mature clotting factor.

E21. The method of embodiment E19, wherein the clotting factor protein comprises one or more half-life extending moiety other than an Fc portion.

E22. The method of any one of embodiments E1 to E21, wherein the administration treats one or more bleeding episodes.

E23. The method of any one of embodiments E1 to E22, wherein the administration prevents one or more bleeding episodes.

E24. The method of any one of embodiments E1 to E23, wherein the administration is an episodic treatment of one or more bleeding episodes.

E25. The method of any one of embodiments E1 to E23, wherein the subject is in need of surgical prophylaxis, peri-operative management, or treatment for surgery.

E26. The method of embodiment E25, wherein the surgery is minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

E27. The method of any one of embodiments E13 to E26, wherein the immune response comprises production of inhibitory antibodies to the clotting factor.

E28. The method of embodiment E27, wherein the antibody concentration is at least 0.6 Bethesda Units (BU).

E29. The method of embodiment E28, wherein the antibody concentration is at least 5 BU.

E30. The method of any one of embodiments E13 to E26, wherein the immune response comprises a cell-mediated immune response.

E31. The method of embodiment E30, wherein the cell-mediated immune response comprises the release of a cytokine selected from the group consisting of IL-12, IL-4, and TNF-α.

E32. The method of any one of embodiments E13 to E31, wherein the immune response comprises a clinical symptom selected from the group consisting of: increased bleeding tendency, high clotting factor consumption, lack of response to clotting factor therapy, decreased efficacy of clotting factor therapy, and shortened half-life of clotting factor.

E33. The method of any one of embodiments E1 to E32, wherein the subject has a mutation or deletion in the clotting factor gene.

E34. The method of any one of embodiments E1 to E32, wherein the subject has a rearrangement in the clotting factor gene.

E35. The method of any one of embodiments E1 to E34, wherein the subject has severe hemophilia.

E36. The method of any one of embodiments E1 to E34, wherein the subject has a relative who has previously developed an inhibitory immune response against the clotting factor.

E37. The method of any one of embodiments E1 to E36, wherein the subject is receiving interferon therapy.

E38. The method of any one of embodiments E1 to E37, wherein the subject is receiving anti-viral therapy.

E39. The method of any one of embodiments E1 to E38, wherein the subject has a genetic polymorphism associated with increased TNF-α.

E40. The method of embodiment E39, wherein the polymorphism is TNF-α 308G>A.

E41. The method of any one of embodiments E1 to E40, wherein the subject has a genetic polymorphism associated with increased IL10.

E42. The method of embodiment E41, wherein the polymorphism is allele 134 of the IL10G microsatellite.

E43. The method of any one of embodiments E1 to E42, wherein the subject has a genetic polymorphism associated with decreased CTLA-4 expression.

E44. The method of any one of embodiments E1 to E43, wherein the subject has a mutation in DR15 or DQB0602 MHC Class II molecules.

E45. The method of any one of embodiments E1 to E44, wherein the subject has had less than 150 clotting factor exposure days (ED).

E46. The method of embodiment E45, wherein the subject has had less than 50 ED.

E47. The method of embodiment E46, wherein the subject has had less than 20 ED.

E48. The method of any one of embodiment E3 to E47, wherein the inhibitory FVIII immune response developed in response to a full length or mature FVIII clotting factor.

E49. The method of embodiment E3-E48, wherein the inhibitory immune response is an inhibitory FVIII response developed in response to a recombinant FVIII product.

E50. The method of any one of embodiments E1 to E49, wherein the administration reduces the number of antibodies to FVIII in the subject compared to the number prior to administration.

E51. The method of any one of embodiments E1 to E50, wherein the administration reduces the titer of antibodies to FVIII in the subject compared to the titer prior to administration.

E52. The method of any one of embodiments E1 to E51, wherein the administration reduces the level of a cytokine in the subject compared to the level prior to administration.

E53. The method of any one of embodiments E1 to E52, wherein the administration reduces the number of antibodies to FVIII in the subject compared to the number in the subject after a previous treatment with a polypeptide consisting of a FVIII polypeptide.

E54. The method of any one of embodiments E1 to E53, wherein the administration reduces the titer of antibodies to FVIII in the subject compared to the titer in the subject after a previous treatment with a polypeptide consisting of a FVIII polypeptide.

E55. The method of any one of embodiments E1 to E54, wherein the administration reduces the level of a cytokine in the subject compared to the level in the subject after a previous treatment with a polypeptide consisting of a FVIII polypeptide.

E56. The method of any one of embodiments E1 to E55, wherein the administration reduces the number of anti-clotting factor antibodies in the subject compared to the number that would result from administration of polypeptide consisting of the clotting factor portion to the subject.

E57. The method of any one of embodiments E1 to E56, wherein the administration reduces the titer of anti-clotting factor antibodies in the subject compared to the titer that would result from administration of polypeptide consisting of the clotting factor portion to the subject.

E58. The method of any one of embodiments E1 to E57, wherein the administration reduces the level of a cytokine in the subject compared to the level that would result from administration of polypeptide consisting of the clotting factor portion to the subject.

E59. The method of embodiment E52, E55, or E58, wherein the cytokine is selected from the group consisting of IL-12, IL-4, and TNF-α.

E60. The method of any one of embodiments E1 to E59, which further comprises prior to administration of the chimeric polypeptide, identifying that the subject has one or more characteristics selected from the group consisting of:
(a) has a mutation or deletion in the gene encoding the clotting factor;
(b) has a rearrangement in the gene encoding the clotting factor;
(c) has a relative who has previously developed an inhibitory immune response against the clotting factor;
(d) is receiving interferon therapy;
(e) is receiving anti-viral therapy;
(f) has a genetic mutation in a gene other than the gene encoding the clotting factor which is linked with an increased risk of developing an inhibitory immune response; and
(g) two or more combinations thereof.

E61. The method of embodiment E60, wherein the genetic mutation in a gene other than the gene encoding the clotting factor comprises one or more mutations selected from the group consisting of:
(i) a genetic polymorphism associated with increased TNF-α;
(ii) a genetic polymorphism associated with increased IL10;
(iii) a genetic polymorphism associated with decreased CTLA-4;
(iv) a mutation in DR15 or DQB0602 MHC Class 11 molecules; and
(v) has two or more combinations thereof.

E62. The method of embodiment E61, wherein the polymorphism associated with increased TNF-α is 308G>A.

E63. The method of embodiment E61, wherein the polymorphism associated with increased IL10 is allele 134 of the IL10G microsatellite.

E64. The method of any one of embodiments E6, and E8 to E62, wherein the FVIII portion comprises the FVIII A3 domain.

E65. The method of any one of embodiments E6, and E8 to E63, wherein the FVIII portion comprises human FVIII.

E66. The method of any one of embodiments E6, and E8 to E64, wherein the FVIII portion has a full or partial deletion of the B domain.

E67. The method of any one of embodiments E6, and E8 to E66, wherein the FVIII portion is at least 90% or 95% identical to a FVIII amino acid sequence shown in TABLE 2 without a signal sequence (amino acids 20 to 1457 of SEQ ID NO:2; amino acids 20 to 2351 of SEQ ID NO:6).

E68. The method of any one of embodiments E6, and E8 to E66, wherein the FVIII portion is identical to a FVIII amino acid sequence shown in TABLE 2 without a signal sequence (amino acids 20 to 1457 of SEQ ID NO:2 or amino acids 20 to 2351 of SEQ ID NO:6).

E69. The method of any one of embodiments E6, and E8 to E66, wherein the FVIII portion is at least 90% or 95% identical to a FVIII amino acid sequence shown in TABLE 2 with a signal sequence (amino acids 1 to 1457 of SEQ ID NO:2 or amino acids 1 to 2351 of SEQ ID NO:6).

E70. The method of any one of embodiments E6, and E8 to E66, wherein the FVIII portion is identical to a FVIII amino acid sequence shown in TABLE 2 with a signal sequence (amino acids 1 to 1457 of SEQ ID NO:2 or amino acids 1 to 2351 of SEQ ID NO:6).

E71. The method of any one of embodiments E6, and E8 to E70, wherein the FVIII portion has coagulation activity.

E72. The method of any one of embodiments E1 to E71, wherein the Fc portion is identical to the Fc amino acid sequence shown in TABLE 2 (amino acids 1458 to 1684 of SEQ ID NO:2 or amino acids 2352 to 2578 of SEQ ID NO:6).

E73. The method of any one of embodiments E1 to E72, wherein the chimeric polypeptide is in the form of a hybrid comprising a second polypeptide in association with the chimeric polypeptide, wherein the second polypeptide consists essentially of or consists of the Fc portion or the FcRn binding partner.

E74. The method of any one of embodiments E1 to E73, wherein the chimeric polypeptide is administered at each dose of 10-100 IU/kg.

E75. The method of embodiment E74, wherein the dose is 10-20, 20-30, 30-40, 40-50, 50-60, 60-70, 70-80, 80-90, or 90-100 IU/kg.

E76. The method of embodiment E75, wherein the dose is 10, 15, 20, 25, 30, 35, 40, 45, 50, 55, 60, 65, 70, 75, 80, 85, 90, 95, or 100 IU/kg.

E77. The method of any one of embodiments E1 to E76, wherein the subject has a bleeding condition selected from the group consisting of a bleeding coagulation disorder, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

E78. The method of embodiment E77, wherein the bleeding coagulation disorder is hemophilia A.

E79. The method of any one of embodiments E6, and E8 to E63, wherein the clotting factor portion comprises Factor IX.

E80. The method of embodiment E79, wherein the Factor IX portion is at least 90%, 95%, or 100% identical to a FIX amino acid sequence shown in TABLE 2 without a signal sequence (amino acids 20 to 1457 of SEQ ID NO:2; amino acids 20 to 2351 of SEQ ID NO:6).

E81. The method of any one of embodiments E6, and E8 to E63, wherein the chimeric polypeptide is a monomer dimer hybrid comprising a first chain comprising a FIX portion and the Fc portion or the FcRn binding partner and a second chain consisting essentially of or consisting of a Fc portion.

E82. The method of any one of embodiments E6, and E8 to E63, wherein the chimeric polypeptide comprises a Factor VII portion.

E83. The method of embodiment E82, wherein the chimeric polypeptide is a monomer dimer hybrid comprising a first chain comprising a FVII portion and the Fc portion and a second chain consisting essentially of or consisting of a Fc portion.

E84. The method of embodiment E82 or E83, wherein the FVII portion is inactive FVII, activated FVII, or activatable FVII.

E85. A kit comprising (a) a pharmaceutical composition comprising a chimeric polypeptide which comprises a clotting factor portion and an Fc portion or an FcRn binding partner portion and a pharmaceutically acceptable carrier, and (b) instructions to administer to the composition to a subject in need of immune tolerance to the clotting factor.

E86. The kit of embodiment E85, wherein the chimeric polypeptide comprises a FVIII portion, a FVII portion, or a FIX portion.

E87. The kit of embodiment E86, wherein the chimeric polypeptide is a FVIII monomer dimer hybrid, a FVII monomer dimer hybrid, or a FIX monomer dimer hybrid.

E88. The kit of any one of embodiments E85 to E87, wherein the instructions further include at least one step to identify a subject in need of immune tolerance to the clotting factor.

E89. The kit of embodiment E88, wherein the step to identify the subjects in need of immune tolerance includes one or more from the group consisting of:
(a) identifying a subject having a mutation or deletion in the clotting factor gene;
(b) identifying a subject having a rearrangement in the clotting factor gene;
(c) identifying a subject having a relative who has previously developed an inhibitory immune response against the clotting factor;
(d) identifying a subject receiving interferon therapy;
(e) identifying a subject receiving anti-viral therapy;
(f) identifying a subject having a genetic mutation in a gene other than the gene encoding the clotting factor which is linked with an increased risk of developing an inhibitory immune response; and
(g) two or more combinations thereof.

E90. The kit of claim E89, wherein the genetic mutation in a gene other than the gene encoding the clotting factor comprises one or more mutations selected from the group consisting of:
(i) a genetic polymorphism associated with increased TNF-α;
(ii) a genetic polymorphism associated with increased IL10;
(iii) a genetic polymorphism associated with decreased CTLA-4;
(iv) a mutation in DR15 or DQB0602 MHC Class II molecules; and
(v) has two or more combinations thereof.

E91. The method of any one of embodiments E1 to E84, further comprising measuring the level of an inhibitory immune response after the administration.

E92. The method of embodiment E91, wherein further comparing the level of the inhibitory immune response after the administration with the level of the inhibitory immune response before the administration.

E93. The method of embodiments E91 or E92, wherein the inhibitory immune response is development of antibodies against FVIII.

E94. The method of E91 or E92, wherein the inhibitory immune response is cytokine secretion.

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLES

Example 1

Cloning, Expression and Purification of rFVIIIFc

All molecular biology procedures were performed following standard techniques. The coding sequence of human FVIII (Genbank accession number NM_000132), including its native signal sequence, was obtained by reverse transcription-polymerase chain reactions (RT-PCR) from human liver polyA RNA. Due to the large size of FVIII, the coding sequence was obtained in several sections from separate RT-PCR reactions, and assembled through a series of PCR reactions, restriction digests and ligations into an intermediate cloning vector containing a B domain deleted (BDD) FVIII coding region with a fusion of serine 743 (S743) to glutamine 1638 (Q1638), eliminating 2682 bp from the B domain of full length FVIII. The human IgG1 Fc sequence (e.g., GenBank accession number Y14735) was obtained by PCR from a leukocyte cDNA library, and the final expression cassette was made in such a way that the BDD FVIII sequence was fused directly to the N-terminus of the Fc sequence (hinge, CH2 and CH3 domains, beginning at D221 of the IgG1 sequence, EU numbering) with no intervening linker. For expression of the Fc chain alone, the mouse Igκ (kappa) light chain signal sequence was created with synthetic oligonucleotides and added to the Fc coding sequence using PCR to enable secretion of this protein product. The FVIIIFc and Fc chain coding sequences were cloned into a dual expression vector, pBudCE4.1 (Invitrogen, Carlsbad, Calif.).

HEK 293H cells (Invitrogen, Carlsbad, Calif.) were transfected with the pSYN-FVIII-013 plasmid using Lipofectamine transfection reagent (Invitrogen, Carlsbad, Calif.)), and a stable cell line was selected with zeocin. Cells were grown in serum free suspension culture, and rFVIIIFc protein purified from clarified harvest media using a four column purification process, including a FVIII-specific affinity purification step (McCue J. et al., *J. Chromatogr. A.,* 1216(45): 7824-30 (2009)), followed by a combination of anion exchange columns and a hydrophobic interaction column.

Example 2

Characterization of rFVIIIFc (a) Biochemical Characterization

Figure 2A:
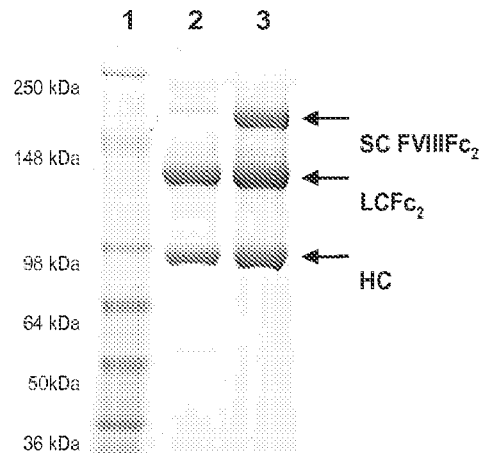
FIGS. 2A and 2B show non-reducing and reducing SDS-PAGE analysis of rFVIIIFc (processed or single chain).
Figure 2B:
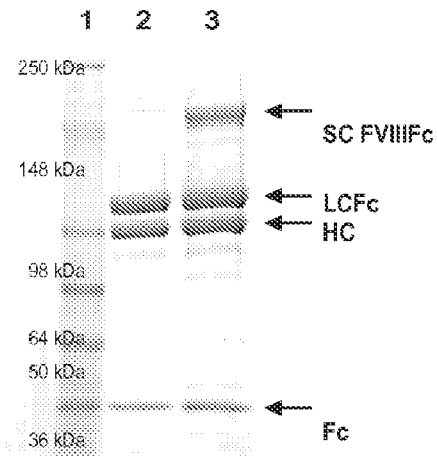
Figure 2C:
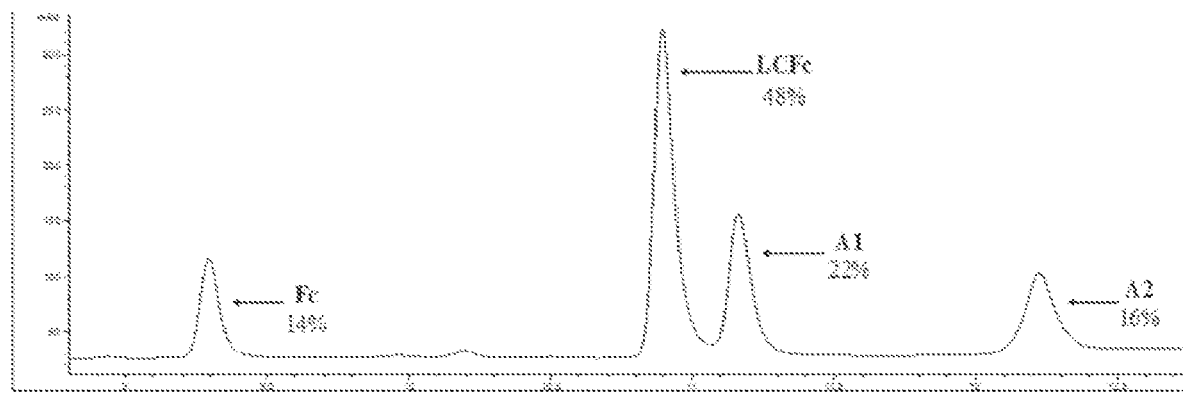
FIG. 2C shows the rFVIIIFc structure analyzed by LC/UV and LC/MS.

Processed recombinant FVIII-Fc (rFVIIIFc) was synthesized as two polypeptide chains, one chain consisting of BDD-FVIII (S743-Q1638 fusion, 1438 amino acids) fused to the Fc domain (hinge, CH2 and CH3 domains) of IgG1 (226 amino acids, extending from D221 to G456, EU numbering), for a total chain length of 1664 amino acids, the other chain consisting of the same Fc region alone (226 amino acids). Though cells transfected with the FVIIIFc/Fc dual expression plasmid were expected to secrete three products (FVIIIFc dimer, FVIIIFc monomer, and Fc dimer), only the FVIIIFc monomer and Fc dimer were detected in conditioned media. Purified FVIIIFc was analyzed by non-reducing and reducing SDS-PAGE analysis (FIGS. 2A and 2B). For the nonreduced SDS-PAGE, bands were found migrating at approximately 90 kDa and 130 kDa, consistent with the predicted molecular weights of the FVIIIFc heavy chain (HC) and light chain-dimeric Fc fusion (LCFc2) (FIG. 2A, lane 3). A third band was also detected at approximately 220 kDa, consistent with the predicted molecular weight for single chain FVIIIFc (SC FVIIIFc; HC+LCFc2), in which the arginine residue at position 754 (1648 with respect to the full length sequence) is not cleaved during secretion. For the reduced SDS-PAGE analysis, major bands were seen migrating at approximately 25 kDa, 90 kDa, 105 kDa, and 195 kDa, consistent with the predicted molecular weights for the single chain Fc, HC, LCFc, and SC FVIIIFc (FIG. 2B, lane 3). Cotransfection with human PC5, a member of the proprotein convertase subtlisin/kexin (PCSK) type proteases, resulted in full processing of the rFVIIIFc product (FIG. 2A, 2B, lane 2).

Densitometry analysis of several batches of rFVIIIFc after SDS-PAGE indicated greater than 98% purity of the expected bands. Size exclusion chromatography (SEC) was also used to assess the degree of aggregation present, and all batches were found to have aggregate levels at 0.5% or less.

rFVIIIFc structure was further analyzed by thrombin cleavage, reduction, and analysis by LC/UV and LC/MS. The four FVIII fragments generated by thrombin (by cleavages at three arginine residues, at positions 372, 740 and 795 (795 corresponds to 1689 with respect to the full length FVIII sequence), can be detected by UV absorbance (FIG. 2C), corresponding to the following segments of the protein: Fc (peak 1), light-chain-Fc (peak 2); the A1 domain from the heavy chain (peak 3) and the A2 domain from the heavy chain (peak 4). The 14 amino acid B domain linker and ~6 kDa a3-related peptides are not detected by UV absorbance due to their small size.

The rFVIIIFc polypeptide produced without cotransfected processing enzymes exhibited 15-25% single chain FVIIIFc (SC FVIIIFc), which differs from processed rFVIIIFc by a single peptide bond between R754 and E755 (R1648/E1649 with respect to the full length FVIII). This isoform was purified and characterized in all of the biochemical assays described above, and found to be comparable to rFVIIIFc as shown below. The activity of purified single chain FVIIIFc was found to be similar to rFVIIIFc in a chromogenic assay as well as by the various functional assays described below.

(b) Measurement of FVIII Activity by Chromogenic and One-Stage aPTT Assays

FVIII activity was measured by a FVIII chromogenic assay. The average specific activity from four separate batches of rFVIIIFc was found to be 9762±449 IU/mg by the chromogenic assay, corresponding to 2148±99 IU/nmol. FVIII activity of single chain FVIII:Fc was also measured by the chromogenic assay and compared to the completely processed rFVIIIFc or rFVIIIFc DS (containing about 25% single chain rFVIIIFc). As TABLE 3A shows, single chain rFVIIIFc showed no significant difference in FVIII activity compared to the FVIII activity of completely processed FVIIIFc or rFVIIIFc DS by the chromogenic assay, both in the presence and the absence of von Willebrand Factor (VWF). TABLE 3B shows that full activity of SCrFVIIIFc, as measured by one-stage activated partial thromboplastin time (aPTT) assay, was observed in the absence of VWF.

TABLE 3A

FVIII Activity by Chromogenic Assay

| Matrix | Sample | Chromogenic Specific Activity (IU/mg) | % CV* |
|---|---|---|---|
| FVIII depleted plasma | rFVIIIFcDS (25% NP) (RECD-19189-09-013) | 9066 | 2.49 |
| | Single chain rFVIIIFc (purified from RECD 19189-09-013) | 8194 | 2.72 |
| | Completely Processed rFVIIIFc (purified from an engineered cell line) | 9577 | 8.34 |
| FVIII and vWF depleted plasma | rFVIIIFcDS (25% NP) (RECD-19189-09-013) | 10801 | 8.92 |
| | Single chain rFVIIIFc (purified from RECD 19189-09-013) | 9498 | 4.70 |
| | Completely Processed rFVIIIFc (purified from an engineered cell line) | 9569 | 4.54 |

*CV = coefficient of variation

TABLE 3B

FVIII Activity by aPTT assay

| Matrix | Sample | Coagulation (aPTT) Specific Activity (IU/mg) | % CV |
|---|---|---|---|
| FVIII-depleted plasma | rFVIIIFcDS (25% NP) (RECD-19189-09-013) | 8210 | 5.88 |
| | Single chain rFVIIIFc (purified from RECD 19189-09-013) | 3108 | 6.57 |
| | Completely Processed rFVIIIFc (purified from an engineered cell line) | 8683 | 3.57 |
| FVIII and vWF depleted plasma | rFVIIIFcDS (25% NP) (RECD-19189-09-013) | 15621 | 6.47 |
| | Single chain rFVIIIFc (purified from RECD 19189-09-013) | 13572 | 2.41 |
| | Completely Processed rFVIIIFc (purified from an engineered cell line) | 15170 | 10.42 |

(c) Activity in Xase Complex

FVIII activity was also measured in the context of the Xase complex, by incubating activated FIX and thrombin-activated REFACTO® or rFVIIIFc protein on a phospholipid surface in the presence of calcium, and monitoring the conversion of FX to FXa as measured by cleavage of a chromogenic or fluorogenic substrate, from which FXa generation rates were determined. This assay was then modified by varying one component of the assay while keeping the others constant in order to examine the interactions with each individual component.

The FXa generation rate was determined as a function of varying phospholipid concentrations for rFVIIIFc DS, rBDD FVIII, and single chain rFVIIIFc (FIG. 3A), using synthetic phospholipid vesicles (25% phosphotadyl serine/75% phosphotadyl choline). Both proteins were found to have a similar activity profile, with peak activity at approximately 156 µM phospholipids.

The FXa generation rate was then determined as a function of varying FX concentrations, and $K_m$ and $V_{max}$ values calculated (FIG. 3B). The activity profiles for rFVIIIFc DS, rBDD FVIII, and single chain rFVIIIFc were found to be similar, with similar $K_m$ and $V_{max}$ (TABLE 4). Finally, the FXa generation rate was determined as a function of varying FIX concentrations (FIG. 3C). The activity profiles appeared similar, with similar $K_d$ and $V_{max}$ (TABLE 5). Similar results were obtained using platelets as a phospholipid source (unpublished data, June 2009).

TABLE 4

FXa Generation Parameters for FVIII Proteins on Phospholipids

| Lipid Source | Molecule | Km (nM) | Vmax (nM/min) |
|---|---|---|---|
| 25% PS-75% PC | rFVIIIFc DS | 55.0 ± 5.9 | 65.6 ± 8.6 |
| | rBDD FVIII | 51.0 ± 8.7 | 73.5 ± 10.1 |
| | NP rFVIIIFc | 53.2 ± 7.5 | 56.0 ± 13.8 |

TABLE 5

FIXa Interactions with FVIII Proteins

| Lipid Source | Molecule | Km (nM) | Vmax (nM/min) |
|---|---|---|---|
| 25% PS-75% PC | rFVIIIFc DS | 2.8 ± 0.4 | 4.5 ± 0.3 |
| | rBDD FVIII | 2.5 ± 0.3 | 4.0 ± 1.0 |
| | NP rFVIIIFc | 2.3 ± 0.2 | 3.8 ± 0.4 |

(d) Inactivation by APC

Once active, FVIII is inactivated by cleavage by activated protein C (APC), as well as by dissociation of the A2 domain. rFVIIIFc and rBDD FVIII were both activated by thrombin, then incubated with APC for different times and activity determined in a FXa generation assay (FIG. 4). In the absence of thrombin activation, little FXa generation was detected, and this was increased significantly with thrombin digestion. Treatment with APC for 90 minute led to a significant decrease in FXa generation rates, similar to non-activated samples, and these results were similar for rFVIIIFc DS, rBDD FVIII, and single chain rFVIIIFc.

(e) Affinity for vWF

FVIII interactions with von Willebrand factor (vWF) were measured by real-time biomolecular interaction analysis (BIAcore), based on surface Plasmon resonance (SPR) technology, to determine the kinetics of binding of rFVIIIFc and rBDD FVIII towards vWF (TABLE 6). Kinetic rate parameters of $K_a$ (on-rate) and $K_d$ (off-rate), and the affinity $K_D$ ($K_d/K_a$), were determined for each FVIII interaction under identical conditions. Both rFVIIIFc and rBDD FVIII were found to have a low nM binding affinity ($K_D$) for vWF, of 1.64±0.37 and 0.846±0.181 nM, respectively. The proteins had similar off-rates, with a two fold difference in on-rate resulting in a two fold difference in the affinity.

TABLE 6

Biocore Binding Analysis of FVIII Proteins to vWF

| | | | Kinetic rate parameters | | Off-rate/On-rate |
|---|---|---|---|---|---|
| Analyte | Ligand | N | On-rate (M−1s−1) | Off-rate (s−1) | KD(M) |
| rFVIIIFc DS | hvWf | 5 | 7.92 ± 1.51 × 10$^5$ | 1.25 ± 1.12 × 10$^{-3}$ | 1.64 ± 0.37 × 10$^{-9}$ |
| NP rFVIIIFc | hvWf | 5 | 8.66 ± 1.10 × 10$^5$ | 1.09 ± 0.09 × 10$^{-3}$ | 1.28 ± 0.22 × 10$^{-9}$ |
| rBDD FVIII | hvWf | 5 | 13.7 ± 1.50 × 10$^5$ | 1.14 ± 0.12 × 10$^{-3}$ | 0.846 ± 0.181 × 10$^{-9}$ |

As shown in TABLE 6, the affinity of rFVIIIFc DS or single chain rFVIIIFc with vWF was found to be in the low nM range, approximately two fold greater than that of BDD FVIII alone. At physiological concentrations, this would result in a slight decrease in the percentage of rFVIIIFc (processed or single chain) complexed with vWF as compared to free FVIII, however in vivo studies have indicated that the half-life of rFVIIIFc is significantly prolonged over full length or BDD FVIII despite this slightly lower affinity, and therefore this does not appear to compromise the half-life of the molecule. The free rFVIIIFc may be more efficiently recycled through the FcRn pathway and therefore contribute to a greater prolongation of half-life.

Example 3 rFVIIIFc Phase I/IIa Clinical Trial

A Phase I/IIa, open-label, crossover, dose-escalation, multi-center, and first-in-human study was designed to evaluate the safety, tolerability, and pharmacokinetics of a single dose of rFVIIIFc in subjects with severe (defined as <1 IU/dL [1%] endogenous FVIII hemophilia A. A total of approximately 12 previously treated patients were enrolled and dosed with rFVIIIFc at 25 or 65 IU/kg. After the screening (scheduled within 28 days prior to the first dose of the ADVATE® [rFVIII], the reference comparator agent) and a minimum of 4-days (96 hours) elapsing with no FVIII treatment prior to the first injection, approximately 6 subjects received a single 25 IU/kg dose of ADVATE® followed by a 3-day (72 hours) pharmacokinetic (PK) profile then crossover and receive a 25 IU/kg single, open-label dose of rFVIIIFc for a 7-day (168 hours) PK profiling. The first 3 subjects were dosed sequentially. For the first three (3) subjects dosed with 25 IU/kg of rFVIIIFc, each subject underwent an inhibitor assessment at 14-days (336 hours) post-injection of rFVIIIFc. Dosing of the next subject (for the first three subjects only) occurred once the inhibitor testing is completed. After the 3rd subject completed the 14 day inhibitor assessment, the remaining three subjects at 25 IU/kg and the six subjects at 65 IU/kg began enrollment sequentially at least 1 day apart within each dose group.

One week after the last subject received the 25 IU/kg dose of the rFVIIIFc, approximately 6 unique subjects were recruited for the 65 IU/kg cohort. Each subject in the 65 IU/kg cohort received a single 65 IU/kg dose of ADVATE® followed by a 4-day (96 hours) PK profiling then crossover and receive a 65 IU/kg single, open-label dose of rFVIIIFc for a 10-day (240 hours) profiling. If a bleeding episode occurred before the first injection of rFVIIIFc in any cohort, subject's pre-study FVIII product was used for treatment and an interval of at least 4 days had to pass before receiving the first injection of rFVIIIFc for the PK profile.

All subjects were followed for a 14-day (336 hours) and 28 day safety evaluation period after administration of rFVIIIFc 25 IU/kg or 65 IU/kg for safety. All subjects underwent pharmacokinetic sampling pre- and post-dosing along with blood samples for analysis of FVIII activity at designated time points.

The pharmacokinetic data for the Phase I/IIa clinical trial demonstrated the following results for FVIIIFc. FVIIIFc had about a 50% increase in systemic exposure ($AUC_{INF}$), about 50% reduction in clearance (Cl), and about 50-70% increase in elimination half-life and MRT compared to ADVATE® (full length rFVIII). In addition, FVIIIFc showed increased C168, TBLP1, TBLP3, and TBLP5 values compared to ADVATE®.

The measured PK parameters were:

$AUC_{INF}$ Area under the concentration-time curve from zero to infinity

Beta HL Elimination phase half-life; also referred to as $t_{1/2\beta}$

C168 Estimated FVIIIFc activity above baseline at approximately 168 h after dose Cl Clearance MRT Mean residence time TBLP1 Model-predicted time after dose when FVIIIFc activity has declined to approximately 1 IU/dL above baseline TBLP3 Model-predicted time after dose when FVIIIFc activity has declined to approximately 3 IU/dL above baseline TBLP5 Model-predicted time after dose when FVIIIFc activity has declined to approximately 5 IU/dL above baseline Example 4

Pharmacokinetics (PK) of rFVIIIFc

A recombinant B-domain-deleted FVIII-Fc (rFVIIIFc) fusion protein has been created as an approach to extend the half-life of FVIII. The pharmacokinetics (PK) of rFVIIIFc were compared to rFVIII in hemophilia A mice. The terminal half-life was twice as long for rFVIIIFc compared to rFVIII. In order to confirm that the underlying mechanism for the extension of half-life was due to the protection of rFVIIIFc by FcRn, the PK were evaluated in FcRn knockout and human FcRn transgenic mice.

A single intravenous dose (125 IU/kg) was administered and the plasma concentration measured using a chromogenic activity assay. The $C_{max}$ was similar between rFVIIIFc and rFVIII (XYNTHA®) in both mouse strains. However, while the half-life for rFVIIIFc was comparable to that of rFVIII in the FcRn knockout mice, the half-life for rFVIIIFc was extended to approximately twice longer than that for rFVIII in the hFcRn transgenic mice. These results confirmed that FcRn mediated or was responsible for the prolonged half-life of rFVIIIFc compared to rFVIII. Since hemostasis in whole blood measured by rotation thromboelastometry (ROTEM®) has been shown to correlate with the efficacy of coagulation factors in bleeding models of hemophilia mice as well as in clinical applications, we sought to evaluate the ex vivo efficacy of rFVIIIFc in the hemophilia A mice using ROTEM®.

Hemophilia A mice were administered a single intravenous dose of 50 IU/kg rFVIIIFc, XYNTHA® (FVIII) or ADVATE® (FVIII). At 5 minutes post dose, clot formation was similar with respect to clotting time (CT), clot formation time (CFT) and α-angle. However, rFVIIIFc showed significantly improved CT at 72 and 96 hr post dose, and CFT and α-angle were also improved at 96 hours compared to both XYNTHA® (FVIII) and ADVATE® (FVIII), consistent with prolonged PK of rFVIIIFc. These results indicated that rFVIIIFC has a defined mechanism of action resulting in an increased half-life, and the potential to provide prolonged protection from bleeding.

Example 5 rFVIIIFc Phase I/IIa Clinical Trial Results

This Example presents final analysis results for FVIII activity from 16 patients treated with 25 and 65 IU/kg FVIII products. See Example 3. rFVIIIFc is a recombinant fusion protein comprised of a single molecule of recombinant B-domain deleted human FVIII (BDD-rFVIII) fused to the dimeric Fc domain of the human IgG1, with no intervening linker sequence. This protein construct is also referred to herein as rFVIIIFc heterodimeric hybrid protein, FVIIIFc monomeric Fc fusion protein, FVIIIFc monomer hybrid, monomeric FVIIIFc hybrid, and FVIIIFc monomer-dimer. See Example 1, FIG. 1, and TABLE 2A.

Preclinical studies with rFVIIIFc showed an approximately 2-fold prolongation of the half-life of rFVIII activity compared to commercially available rFVIII products. The rationale for this study was to evaluate the safety and tolerability of a single dose of rFVIIIFc in frozen liquid formulation and provide data on the PK in severe hemophilia A subjects. For this study, 16 evaluable subjects were available for PK evaluation. Single administration of two doses of both rFVIIIFc and ADVATE® at a nominal dose of 25 (n=6) and 65 IU/kg of body weight (n=10) were infused intravenously over approximately 10 minutes. Blood samples for plasma PK assessments were obtained before infusion, as well as up to 10 days after dosing. The PK of FVIII activity for both ADVATE® and rFVIIIFc were characterized in this study using a model-dependent method.

Objectives

The primary objective of this study was to assess the safety and tolerability of single administration of two doses of rFVIIIFc (25 and 65 IU/kg) in previously treated patients (PTPs) aged 12 and above with severe hemophilia A. The secondary objective was to determine the pharmacokinetics (PK) parameters determined by pharmacodynamic (PD) activity of FVIII over time after a single administration of 25 or 65 IU/kg of rFVIIIFc compared to ADVATE® in one-stage clotting and chromogenic assays.

Study Design (See Example 3)

Blood samples were collected for FVIII activity PK evaluations at the screening visit (within 28 days prior to dosing ADVATE®); on Day 0 (injection of ADVATE®) pre-injection and at 10 and 30 minutes and 1, 3, 6, and 9 hours post-injection; on Day 1 at 24 hours post-injection of ADVATE®; on Day 2 at 48 hours post-injection of ADVATE®; on Day 3 at 72 hours post-injection of ADVATE®; and on Day 4 at 96 hours post-injection of high dose of ADVATE® (Cohort B only).

Blood samples were collected for FVIII activity PK evaluations on the day of rFVIIIFc injection just prior to the administration of rFVIIIFc, at 10 and 30 minutes and 1, 3, 6, and 9 hours post-injection of rFVIIIFc; on Day 1 at 24 hours post-injection of rFVIIIFc; on Days 2 through 5 at 48, 72, 96, and 120 hours post-injection of rFVIIIFc; on Day 7 at 168 hours post-injection of rFVIIIFc; on Days 8, 9, and 10 at 192, 216, and 240 hours post-injection of high dose of rFVIIIFc (Cohort B only). FVIII activity was also measured at the final study visit (28 days post-injection of rFVIIIFc) at 672 hours post-injection of rFVIIIFc.

Pharmacokinetic Modeling

Abbreviations

TBLP1 Model-predicted time after dose when FVIII activity has declined to approximately 1 IU/dL above baseline.

TBLP3 Model-predicted time after dose when FVIII activity has declined to approximately 3 IU/dL above baseline Calculations $KV\_M = C_{max\_M}/\text{Actual Dose (IU/kg)}$ $KV\_OB = C_{max\_OB}/\text{Actual Dose (IU/kg)}$ $IVR\_M = 100 \times C_{max\_M} \times \text{Plasma Volume (dL)/Total Dose in IU; where plasma volume in mL} = (23.7 \times \text{Ht in cm}) + (9.0 \times \text{Wt in kg}) - 1709.$ $IVR\_OB = 100 \times C_{max\_OB} \times \text{Plasma Volume (dL)/Total Dose in IU; where plasma volume in mL} = (23.7 \times \text{Ht in cm}) + (9.0 \times \text{Wt in kg}) - 1709.$ Results (a) Single-Dose Pharmacokinetics (One-Stage Assay)

Observed FVIII activity increased sharply after the short IV infusion of either ADVATE® or rFVIIIFc, with mean (±SD) model-predicted $C_{max}$ values of 56.6±4.74 and 121±28.2 IU/dL for ADVATE® and 55.6±8.18 and 108±16.9 IU/dL for rFVIIIFc for the 25 and 65 IU/kg dose groups, respectively. All ADVATE®- and rFVIIIFc-treated patients had dose-related increases in FVIII activity. The observed increase in both $C_{max}$ and $AUC_{INF}$ was slightly less than proportional to dose over the dose range evaluated.

After the end of the infusion, the decline of the observed FVIII activity exhibited monoexponential decay characteristics until the baseline level was reached. The rate of decline in FVIII activity was slower for rFVIIIFc than for ADVATE® with mean (±SD) model-predicted elimination half-life values of 11.9±2.98 and 10.4±3.03 hr for ADVATE® and 18.0±3.88 and 18.4±6.99 hr for rFVIIIFc for the 25 and 65 IU/kg dose groups, respectively. Elimination half-life values appeared to be dose-independent over the dose range evaluated for both FVIII products.

Total systemic FVIII exposure (assessed by $AUC_{INF}$) was ~48% and 61% greater following rFVIIIFc administration than ADVATE® at 25 and 65 IU/kg dose levels, respectively. Mean (±SD) model-predicted $AUC_{INF}$ values were 974±259 and 1810±606 hr*IU/dL for ADVATE® and 1440±316 and 2910±1320 hr*IU/dL for rFVIIIFc for the 25 and 65 IU/kg dose groups, respectively.

Similar to elimination half-life, the MRT was prolonged for rFVIIIFc relative to ADVATE®. Mean (±SD) model-predicted MRT values were 17.1±4.29 and 14.9±4.38 hr for ADVATE® and 25.9±5.60 and 26.5±10.1 hr for rFVIIIFc for the 25 and 65 IU/kg dose groups, respectively. MRT values appeared to be dose-independent over the dose range evaluated for both FVIII products.

In addition, primary PK parameter values for CL and V were determined. CL values for rFVIIIFc only accounted for ~66% of those observed for ADVATE® at equivalent doses. Mean (±SD) model-predicted CL values were 2.70±0.729 and 4.08±1.69 mL/hr/kg for ADVATE® and 1.80±0.409 and 2.69±1.25 mL/hr/kg for rFVIIIFc for the 25 and 65 IU/kg dose groups, respectively. V values were comparable between ADVATE® and rFVIIIFc with mean (±SD) model-predicted V values of 43.9±4.27 and 56.1±13.4 mL/kg for ADVATE® and 45.3±7.23 and 61.6±10.6 mL/kg for rFVIIIFc for the 25 and 65 IU/kg dose groups, respectively. Slight increases in mean CL and V values were noted with increasing dose of ADVATE® and rFVIIIFc; however, the increase in standard deviations at the 65 IU/kg dose coupled with limited dose levels confounded an assessment of the dose-dependency of these parameters. For example, the CV % geometric mean CL value for the rFVIIIFc treatment group increased from 23.0% (25 IU/kg) to 48.6% (65 IU/kg).

In addition to the primary PK parameters, secondary PK parameters (e.g. K-values, IVR, etc.) were determined to evaluate FVIII duration of effect. Evidence of PK difference was also observed with rFVIIIFc demonstrating increased TBLP1 and TBLP3 values compared to ADVATE® at equivalent doses. IVR and K-values for ADVATE® and rFVIIIFc appeared to be comparable. A slight increase in TBLP1 and TBLP3 values were observed with increasing dose of ADVATE® and rFVIIIFc. In contrast, slight decreases in mean IVR and K-values were noted with increasing dose of ADVATE® and rFVIIIFc. As previously indicated, an assessment of the dose dependency of these parameters is confounded by limited dose levels.

Mean (±SD) observed TBLP1 were 2.88±0.733 and 2.93±0.848 IU/dL per IU/kg for ADVATE® and 4.28±0.873 and 5.16±2.02 IU/dL per IU/kg for rFVIIIFc for the 25 and 65 IU/kg dose groups, respectively. Mean (±SD) observed TBLP3 were 2.06±0.527 and 2.26±0.666 IU/dL per IU/kg for ADVATE® and 3.09±0.623 and 3.93±1.59 IU/dL per IU/kg for rFVIIIFc for the 25 and 65 IU/kg dose groups, respectively.

Mean IVR and K-values calculated using observed $C_{max}$ values (subtracted with baseline and residual drug within the model) were generally greater than values determined using model-predicted $C_{max}$ values; consistent with slight underestimation of the observed peak activity using the one-compartment model. Mean (±SD) observed K-values were 2.57±0.198 and 2.13±0.598 IU/dL per IU/kg for ADVATE® and 2.46±0.330 and 1.85±0.332 IU/dL per IU/kg for rFVIIIFc for the 25 and 65 IU/kg dose groups, respectively. Mean (±SD) observed IVR values were 94.1±15.6 and 85.8±16.5% for ADVATE® and 89.5±11.9 and 74.8±6.72% for rFVIIIFc for the 25 and 65 IU/kg dose groups, respectively.

(b) Single-Dose Pharmacokinetics (Chromogenic Assay)

Observed FVIII activity increased sharply after the short IV infusion of either ADVATE® or rFVIIIFc, with mean (±SD) model-predicted $C_{max}$ values of 70.2±9.60 and 157±38.6 IU/dL for ADVATE® and 70.3±10.0 and 158±34.7 IU/dL for rFVIIIFc for the 25 and 65 IU/kg dose groups, respectively.

All ADVATE®- and rFVIIIFc-treated patients had dose-related increases in FVIII activity. The observed increase in both $C_{max}$ and $AUC_{INF}$ was slightly less than proportional to dose over the dose range evaluated.

After the end of the infusion, the decline of the observed FVIII activity exhibited monoexponential decay characteristics until the baseline level was reached. The rate of decline in FVIII activity was slower for rFVIIIFc than for ADVATE® with mean (±SD) model-predicted elimination half-life values of 10.7±1.98 and 10.3±3.27 hr for ADVATE® and 16.2±2.92 and 19.0±7.94 hr for rFVIIIFc for the 25 and 65 IU/kg dose groups, respectively. Elimination half-life values appeared to be dose-independent over the dose range evaluated for both FVIII products.

Total systemic FVIII exposure (assessed by $AUC_{INF}$) was ~53% and 84% greater following rFVIIIFc administration than ADVATE® at 25 and 65 IU/kg dose levels, respectively. Mean (±SD) model-predicted $AUC_{INF}$ values were 1080±236 and 2320±784 hr*IU/dL for ADVATE® and 1650±408 and 4280±1860 hr*IU/dL for rFVIIIFc for the 25 and 65 IU/kg dose groups, respectively.

Similar to elimination half-life, the MRT was prolonged for rFVIIIFc relative to ADVATE®. Mean (±SD) model-predicted MRT values were 15.3±2.86 and 14.8±4.72 hr for ADVATE® and 23.4±4.22 and 27.3±11.4 hr for rFVIIIFc for the 25 and 65 IU/kg dose groups, respectively. MRT values appeared to be dose-independent over the dose range evaluated for both FVIII products.

In addition, primary PK parameter values for CL and V were determined. CL values for rFVIIIFc only accounted for ~58-66% of those observed for ADVATE® at equivalent doses. Mean (±SD) model-predicted CL values were 2.39±0.527 and 3.21±1.40 mL/hr/kg for ADVATE® and 1.57±0.349 and 1.86±0.970 mL/hr/kg for rFVIIIFc for the 25 and 65 IU/kg dose groups, respectively. V values were comparable between ADVATE® and rFVIIIFc with mean (±SD) model-predicted V values of 35.8±5.52 and 43.6±11.2 mL/kg for ADVATE® and 35.9±6.65 and 42.7±8.91 mL/kg for rFVIIIFc for the 25 and 65 IU/kg dose groups, respectively. Increases in mean CL and V values were noted with increasing dose of ADVATE® and rFVIIIFc; however, the increase in standard deviations at 65 IU/kg coupled with limited dose levels confounded an assessment of the dose-dependency of these parameters.

In addition to the primary PK parameters, secondary PK parameters (e.g. K-values, IVR, etc.) were determined to evaluate FVIII duration of effect. Evidence of PK difference was also observed with rFVIIIFc demonstrating increased TBLP1 and TBLP3 values compared to ADVATE® at equivalent doses. IVR and K-values for ADVATE® and rFVIIIFc appeared to be comparable.

A slight increase in TBLP1 and TBLP3 values were observed with increasing dose of ADVATE® and rFVIIIFc. In contrast, slight decreases in mean IVR and K-values were noted with increasing dose of ADVATE® and rFVIIIFc. As previously indicated, an assessment of the dose dependency of these parameters is confounded by limited dose levels.

Mean (±SD) observed TBLP1 were 2.70±0.511 and 3.09±0.978 IU/dL per IU/kg for ADVATE® and 4.06±0.798 and 5.66±2.38 IU/dL per IU/kg for rFVIIIFc for the 25 and 65 IU/kg dose groups, respectively. Mean (±SD) observed TBLP3 were 1.98±0.377 and 2.39±0.718 IU/dL per IU/kg for ADVATE® and 3.04±0.598 and 4.44±1.84 IU/dL per IU/kg for rFVIIIFc for the 25 and 65 IU/kg dose groups, respectively.

Mean IVR and K-values calculated using observed $C_{max}$ values (subtracted with baseline and residual drug within the model) were generally greater than values determined using model-predicted $C_{max}$ values; consistent with slight underestimation of the observed peak activity using the one-compartment model. Mean (±SD) observed K-values were 3.08±0.429 and 2.85±0.721 IU/dL per IU/kg for ADVATE® and 3.12±0.451 and 2.92±0.985 IU/dL per IU/kg for rFVIIIFc for the 25 and 65 IU/kg dose groups, respectively. Mean (±SD) observed IVR values were 112±14.5 and 116±26.9% for ADVATE® and 113±16.3 and 117±33.6% for rFVIIIFc for the 25 and 65 IU/kg dose groups, respectively.

Conclusions

All ADVATE®- and rFVIIIFc-treated patients had comparable dose-related increases in $C_{max}$ and $AUC_{INF}$ over the dose range evaluated. Peak plasma levels of ADVATE® and rFVIIIFc activity were generally observed within the first hour after the end of the infusion and remained detectable for several days after dosing. After the end of infusion, the decline in baseline corrected FVIII activity exhibited monoexponential decay until the baseline was reached for both products. Parameter values for elimination half-life and MRT appeared to be dose-independent over the dose range evaluated for both FVIII products. Slight increases in mean CL and V values were noted with increasing dose of ADVATE® and rFVIIIFc; however, increased intersubject variability at the 65 IU/kg coupled with limited dose levels confounded an assessment of the dose-dependency of these parameters.

Comparison of rFVIIIFc and ADVATE® activity PK revealed an approximate 48-61% (One-Stage Assay) or 53-84% (Chromogenic Assay) increase in systemic exposure, approximate 30-40% reduction in clearance, and an approximate 50-80% increase in both elimination half-life and MRT for rFVIIIFc relative to ADVATE® at comparable doses. Evidence of PK difference was also observed with rFVIIIFc demonstrating increased TBLP1 and TBLP3 values compared to ADVATE® at equivalent doses. IVR and K-values for ADVATE® and rFVIIIFc appeared to be comparable.

The PK parameters obtained from the Chromogenic Assay results generally agreed with those from the One-Stage Assay, except that the Chomogenic Assay yielded a higher estimation of exposure parameters (e.g., $C_{max}$, $AUC_{INF}$, etc.).

The observed improvements in PK, indicate that rFVIIIFc can provide prolonged protection from bleeding, allowing less frequent injections for individuals with Hemophilia A.

Example 6 rFVIIIFc A-LONG Phase 3 Clinical Study

On the basis of the interim PK analysis from the first in-human study of rFVIIIFc (see Example 3), the A-LONG study was designed. A-LONG was an open label, global, multi-center, Phase 3 evaluation of the safety, pharmacokinetics, and efficacy of recombinant FVIII Fc fusion (FVIII: Fc) in the prevention and treatment of bleeding in previously treated subjects with severe hemophilia A (defined as <1 IU/dL [<1%] endogenous FVIII).

The primary objectives of the A-LONG study were (i) to evaluate safety and tolerability of rFVIIIFc administered as prophylaxis, weekly, on-demand, and surgical treatment regimens, and (ii) to evaluate the efficacy of rFVIIIFc administered as tailored prophylaxis, on-demand, and surgical treatment regimens. The secondary objective of the A-LONG study were (i) to characterize the PK profile of rFVIIIFc and compare the PK of rFVIIIFc with the currently marketed product, ADVATE®, (ii) to evaluate individual responses with rFVIIIFc, (iii) to characterize the range of dose and schedules required to adequately prevent bleeding in a prophylaxis regimen, maintain homeostasis in a surgical setting, or to treat bleeding episodes in an on-demand, weekly treatment, or prophylaxis setting, and (iv) to evaluate rFVIIIFc consumption (e.g., total annualized rFVIIIFc consumption per subject).

165 subjects were enrolled into one of three regimens: a tailored prophylaxis regimen (Arm 1), a weekly dosing regimen (Arm 2), and an on-demand regimen (Arm 3). In addition, rFVIIIFc was evaluated in a perioperative management subgroup.

Key inclusion criteria: (i) male, (ii) ≥12 years of age and at least 40 kg, (iii) diagnosis of severe hemophilia A defined as <1% (<1 IU/dL) endogenous FVIII activity, and (iv) history of ≥150 prior documented exposure days with any currently marketed FVIII product.

Arm 1: Tailored Prophylaxis Regimen

Arm 1 included an overall group and a PK subgroup. The initial regimen was twice weekly at 25 IU/kg on the first day, followed by 50 IU/kg on the fourth day of the week (Day 4). Subjects were administered rFVIIIFc on this weekly prophylaxis regimen until PK results for rFVIIIFc were available. Based on these results, a tailored prophylaxis regimen was established for each individual, in which the dose and interval was determined to maintain a trough level of 1-3% FVIII activity. Each subject was then administered his individually tailored prophylaxis regimen throughout the study.

Subjects were monitored throughout the study and ongoing dose and interval adjustments were made. Adjustments were only made when a subject experienced unacceptable bleeding episodes defined as ≥2 spontaneous bleeding episodes over a rolling two-month period. In this case, adjustment targeted trough levels of 3-5%.

Arm 2: Weekly Dosing Regimen

Subjects underwent abbreviated rFVIIIFc PK profiling as follows: Washout of at least 96 hours; a single dose of rFVIIIFc 65 IU/kg; Abbreviated sampling beginning on rFVIIIFc Day 0, including pre-injection and 10 (±2) minutes, 3 hours (±15 minutes), 72 (±2) hours [Day 3], and 96 (±2) hours [Day 4] from the start of injection. Following the abbreviated PK profiling, subjects were then administer a fixed dose of 65 IU/kg rFVIIIFc every 7 days at least for 28 weeks and up to 52 weeks.

Arm 3: Episodic (On-Demand) Treatment

Subjects received rFVIIIFc episodic treatment as needed for bleeding. Subjects were enrolled and randomized and underwent abbreviated rFVIIIFc PK profiling as follows:
  (i) Washout: At least 96 hours.
  (ii) Dosing at rFVIIIFc Day 0: A single dose of rFVIIIFc 50 IU/kg administered under medical supervision.
  (iii) Abbreviated sampling beginning at rFVIIIFc Day 0: Preinjection and 30 (±3) minutes, 3 hours (±15 minutes), 72 (±2) hours [Day 3], and 96 (±2) hours [Day 4] from the start of the injection.

At the selection sites, sampling for TGA was done coincident with all PL profiling time points. For the subset of subjects undergoing sampling for ROTEM/TEG, collections were done at the following time points: Preinjection and 3 hours (±15 minutes), 72 (±2) hours [Day 3], and 96 (±2) hours [Day 4] from the start of the injection.

Between scheduled visits, the subjects treated bleeding episodes at rFVIIIFc doses between 10 and 50 IU/kg, depending on the severity of the bleeding.

Perioperative Management Subgroup rFVIIIFc was administered prior to a following surgery in the subset of patients requiring a major surgical procedure during the study. Major surgery is defined as any surgical procedure (elective or emergent) that involves general anesthesia and/or respiratory assistance in which a major body cavity is penetrated and exposed, or for which a substantial impairment of physical or physiological functions is produced (e.g., laparotomy, thoracotomy, craniotomy, joint replacement, and limb amputation).

For prophylaxis during surgery, subjects were treated with 20 to 50 IU/kg rFVIIIFc every 12 to 24 hours. Prior to surgery, the physician reviewed the subject's rFVIIIFc PK profile and assessed the dose regimen of FVIII replacement generally required for the type of planned surgery and the clinical status of the subject. Recommendation for the appropriate dosing of rFVIIIFc in the surgical treatment period, including any rehabilitation time, took these factors into consideration.

Pharmacokinetic (PK) Assessment:

All subjects in all arms had an initial PK assessment after their first dose of rFVIIIFc. A subset of subjects from Arm 1 were assigned to a protocol-specified sequential PK subgroup to compare the PK of rFVIIIFc with recombinant factor VIII (rFVIII, ADVATE® [anti-hemophilic factor (recombinant) plasma/albumin-free method]) as follows:
  (i) Prior to treatment in Arm 1, PK was assessed after a single dose of ADVATE® 50 IU/kg. PK was then assessed in these same subjects after a single dose of rFVIIIFc 50 IU/kg.
  (ii) PK of rFVIIIFc was repeated at 12 to 24 weeks.

Key Efficacy Outcome Measures (Included in Initial Readout):
  (i) Annualized bleeding rate (ABR) in Arm 1 versus Arm 3 (individualized prophylaxis arm compared with episodic treatment arm), (ii) number of injections required to resolve a bleeding episode, (iii) treating physicians' assessments of subjects' response to surgery with rFVIIIFc using a 4-point scale.

PK Outcome Measures:
  PK of rFVIIIFc and ADVATE®.

Key Safety Outcome Measures:
  (i) Incidence of inhibitor development; and, (ii) incidence of adverse events (AEs) occurring outside of the perioperative management period.

Results:

Subjects:

A total of 165 subjects were enrolled in the study. Arm 1 (individualized prophylaxis), n=118; Arm 2 (weekly prophylaxis), n=24; Arm 3 (episodic treatment), n=23; Perioperative management subgroup, n=9, 9 surgeries (8 subjects from Arm 1, and 1 from Arm 2). 92.7% of subjects completed the study.

Efficacy:

Median ABR (individualized prophylaxis arm: 1.6; weekly prophylaxis arm: 3.6; episodic treatment arm: 33.6). In the individualized prophylaxis arm, the median dosing interval was 3.5 days during the last 3 months on study. 30 percent of patients in the individualized prophylaxis arm achieved a mean dosing interval of at least 5 days. 98% of bleeding episodes were controlled by one or two injections of rFVIIIFc. In perioperative management, treating physicians rated the hemostatic efficacy of rFVIIIFc as excellent or good in 100% of surgeries.

Pk:

The geometric mean terminal half-life of rFVIIIFc was approximately 19.0 hours, which is 1.53-fold longer than that of ADVATE® (approximately 12.4 hours).

Safety:

No inhibitors were detected to rFVIIIFc, and no cases of anaphylaxis were reported. rFVIIIFc was generally well tolerated. The most common AEs, regardless of causality, (incidence ≥5%) occurring outside of the perioperative management period were nasopharyngitis, arthralgia, headache, and upper respiratory tract infection. 12 subjects (7.3%) experienced at least one serious AE (SAE) outside of the perioperative management period. No SAEs were assessed to be related to drug by the investigator.

Summary

Individualized and weekly prophylactic regimens resulted in low single-digit median annualized bleeding rates. In the individualized prophylaxis arm, the median dosing interval was 3.5 days. During the last 3 months on study, 30 percent of patients in the individualized prophylaxis arm achieved a mean dosing interval of at least 5 days. 98% of bleeding episodes were controlled by one or two injections of rFVIIIFc. Hemostatic efficacy of rFVIIIFc during surgery was rated by treating physicians as excellent or good in 100% of surgeries. The half-life of rFVIIIFc was approximately 19.0 hours compared to 12.4 hours for ADVATE®. No subject developed an inhibitor or experienced an anaphylactic reaction to rFVIIIFc. Recombinant FVIIIFc was generally well tolerated.

Example 7

Clinical ROTEM® Assessment

In addition to the measurement of plasma FVIII activity by one-stage activated partial thromboplastin time (aPTT) assay, whole blood rotational thromboelastometry (ROTEM®) has also been explored to assess the improvement in global hemostasis by rFVIIIFc and ADVATE® in 2 subjects, specifically, 1 in the low dose cohort and 1 in the high dose cohort.

rFVIIIFc and ADVATE® appear to be comparably active in clot formation when spiked into subjects' blood prior to rFVIIIFc treatment. The clotting time (CT) was linear with respect to the dose of rFVIIIFc and ADVATE® in the range of approximately 1% of 100% of normal, and the dose response was comparable between rFVIIIFc and ADVATE® in the same subject.

Following dosing with ADVATE® and subsequently rFVIIIFc, citrated whole blood was sampled at various time points and the clot formation following recalcification was monitored by ROTEM®. Despite the variable baseline CT due to residue FVIII levels prior to ADVATE® or rFVIIIFc dosing, both products effectively corrected the CT to comparable levels 30 minutes post-injection. In addition, the improvement in CT was better sustained at and after 3 hours post-injection of 25 IU/kg of rFVIIIFc relative to ADVATE® in the subject dosed at this low dose. However, the differential improvement of rFVIIIFc versus ADVATE® was much less appreciable at the 65 IU/kg dose.

Example 8

In Vivo Efficacy of rFVIIIFc and Single Chain (SC) rFVIII in HemA Mice

Recombinant Factor VIIIFc (rFVIIIFc) is comprised of a B domain deleted (BDD) rFVIII protein genetically fused to the Fc domain of human immunoglobulin G1 (IgG1). Prior to secretion from HEK 293 cells, most of the rFVIIIFc is processed into a FVIII heavy chain (HC) and light chain (LC+Fc). In circulation, rFVIIIFc is complexed with von Willebrand factor (VWF) and released upon activation in a manner that is indistinguishable from native FVIII. Spontaneous dissociation of the HC and LC is thought to contribute to the loss of FVIII activity in plasma and during storage of FVIII drug products. Here we describe a single chain non-processed isoform of rFVIIIFc (SC rFVIIIFc), which can provide superior manufacturability and enhanced stability compared to native FVIII.

SC rFVIIIFc was purified from rFVIIIFc, which contains a fraction of the non-processed isoform. Compared to rFVIIIFc, SC rFVIIIFc showed equivalent chromogenic activity but approximately 60% reduced activity by the one stage (aPTT) assay, (TABLES 3A and 3B). Thrombin generation assay (TGA) was performed using calibrated automated thrombogram (from Thrombinoscope®). In a thrombin generation assay (TGA), SC rFVIIIFc also showed a reduced thrombin potential (FIG. 13A), and peak thrombin (FIG. 13B) compared to rFVIIIFc. However, as shown in TABLE 3B, full activity of SC rFVIIIFc by aPTT was observed in the absence of vWF, suggesting release from vWF can be delayed due to covalent linkage of the a3 acidic region to the HC after Arg 1680 cleavage in SC rFVIIIFc, in contrast to a3 release and dissociation from fully processed FVIII. Delayed dissociation from vWF can explain the reduced activity observed in the aPTT assay and TGA, while full activity was observed in the two-stage chromogenic assay. A reduced rate of activation in the presence of vWF was confirmed in a modified chromogenic substrate assay with limiting thrombin as FVIII activator.

In vivo function of SC rFVIIIFc was assessed in the HemA mouse tail vein transection (TVT) model. The mice were first anesthetized and then injected with 4.6 µg/kg, 1.38 µg/kg, or 0.46 µg/kg of either processed rFVIIIFc (Drug Substance, which contain about 75%-85% processed rFVIIIFc) and purified single chain (SC) rFVIIIFc 48 hours prior to TVT. The tail was cut from the tip and immediately placed into a tube to collect blood. Percentage of protection on survival was measured for rFVIIIFc processed (drug substance) and single chain (SC) FVIIIFc as shown in TABLE 7 and FIGS. 7A, 7B and 7C.

TABLE 7

In vivo Efficacy of rFVIIIFc DS and Single Chain (SC) rFVIIIFc

| Dose (µg/kg) | | 4.6 | 1.38 | 0.46 |
|---|---|---|---|---|
| % of Protection on Survival | FVIIIFc DS | 93 | 52 | 19 |
| | Single chain rFVIIIFc | 93 | 64 | 14 |

In vivo Tail re-bleeding and survival were monitored hourly up to 12 hours post TVT with final observation performed at 24-hour post TVT. SC rFVIIIFc and the rFVIIIFc demonstrated equivalent in vivo efficacy in this model, with an ED50 of 1.17 µg/kg and 1.23 µg/kg respectively when TVT was performed at 48 hours post infusion (FIG. 7A). Comparable 24 hour post TVT survival curves (p≥0.65) (FIG. 7B) and re-bleed rates (FIG. 7C) in HemA mice were observed for the SC rFVIIIFc and rFVIIIFc at each tested dose level, indicating that SC rFVIIIFc was equally effective as rFVIIIFc despite its lower apparent aPTT activity. The delayed in vitro activation of SC rFVIIIFc in the presence of vWF therefore appeared to have no significant impact on its in vivo efficacy. These observations indicated that SC rFVIIIFc represents a novel and efficacious isoform of rFVIIIFc with potential clinical applications.

Example 9

Phase 1/2a Study Clinical Trial rFVIIIFc is a recombinant fusion protein composed of a single molecule of FVIII covalently linked to the Fc domain of human $IgG_1$ to extend circulating rFVIII half-life. This first-in-human study in previously-treated male subjects with severe hemophilia A investigated safety and pharmacokinetics of rFVIIIFc. Sixteen subjects received a single dose of ADVATE® at 25 or 65 IU/kg followed by an equal dose of rFVIIIFc. Most adverse events were unrelated to study drug. None of the study subjects developed anti-FVIIIFc antibodies or inhibitors. Across dose levels, as compared with ADVATE®, rFVIIIFc showed 1.54 to 1.71-fold longer elimination $t_{1/2}$ and mean residence time, 1.49 to 1.56-fold lower clearance, and 1.48 to 1.56-fold higher total systemic exposure. ADVATE® and rFVIIIFc had comparable dose-dependent peak plasma concentrations and recoveries. Time to 1% FVIII activity above baseline was approximately 1.53 to 1.68-fold longer than ADVATE® across dose levels. Thus, rFVIIIFc can offer a viable therapeutic approach to achieve prolonged hemostatic protection and less frequent dosing in patients with hemophilia A.

rFVIIIFc is a recombinant fusion protein composed of a single molecule of B-domain deleted rFVIII covalently linked to the human $IgG_1$ Fc domain. Potential advantages of Fc-fusion proteins include better tolerability and prolonged hemostatic protection, and the Fc domain represents a natural molecule with no known inherent toxicity. Dumont J. A. et al., *BioDrugs* 20(3):151-60 (2006), Dumont J. A. et al., "Monomeric Fc fusion technology: an approach to create long-lasting clotting factors," in: Kontermann R., ed., *Therapeutic Proteins—Strategies to Modulate Half-Life*, Chapter 11, Wiley VCH publisher; prepublished online, DOI: 10.1002/9783527644827.ch10. Attachment to the IgG$_1$ Fc domain permits binding to the neonatal Fc receptor (FcRn), which is expressed in many cell types, including endothelial cells. FcRn expression remains stable throughout life and is responsible for protecting IgG$_1$ and Fc-fusion proteins from lysosomal degradation, thus prolonging the $t_{1/2}$ of the protein. Dumont J. A. et al., *BioDrugs* 20(3): 151-60 (2006), Roopenian D. C. et al., *Nat Rev Immunol.* 7(9):715-25 (Epub 2007 Aug. 17). Numerous proteins within the circulation are internalized into the cells lining the vasculature via nonspecific pinocytosis and are trafficked to endosomal and lysosomal degradation pathways.

Fc proteins interact with FcRn, resident within endosomes. Endosomes containing FcRn direct the Fc fusion proteins back to the plasma membrane, releasing them into circulation in a pH-dependent manner, Lencer W. I. and Blumberg R. S., *Trends Cell Biol.* 15(1):5-9 (2005) thereby avoiding lysosomal degradation. This recycling approach has been used successfully to extend the $t_{1/2}$ of therapeutic biologics; a number of Fc fusion-based drugs have been approved for clinical use (e.g., etanercept, romiplostim) and others are in development. Huang C., *Curr Opin Biotechnol.* 20(6):692-9. (Epub 2009 Nov. 4), Schmidt S. R., *Curr Opin Drug Discov Devel.* 12(2):284-295 (2009).

Preclinical data for rFVIIIFc indicate that FVIII can be rescued from degradation by a natural protective pathway mediated by FcRn, thus extending $t_{1/2}$. In Hemophilia A mice and dogs, terminal plasma $t_{1/2}$ for rFVIIIFc was approximately 2 times longer than with rFVIII. Dumont J. et al., *Blood.* 116(21) Abstract 545 (2009), Liu T. et al., *J Thromb Haemost.* 9(S2):561 (2011). Based on these data, we conducted a first-in-human clinical study to investigate the safety and PK of a long-lasting rFVIIIFc fusion protein in subjects with hemophilia A.

Study Design

This open-label, dose-escalation, multicenter Phase 1/2a study in previously treated patients with severe hemophilia A investigated the safety of rFVIIIFc and its pharmacokinetics (PK) compared with ADVATE® (antihemophilic factor [recombinant], plasma/albumin-free method, octocog alfa, Baxter Healthcare). This study was performed in accordance with the US CFR and ICH Guidelines on Good Clinical Practices. Prior to any testing, approval from participating Institutional Review Boards and written informed consents from all subjects were obtained. The study design was sequential; a single dose of ADVATE® was administered at 25 or 65 IU/kg followed by an equal dose of rFVIIIFc (FIG. 8). Both drugs were injected intravenously over approximately 10 minutes. The two dose levels were expected to bracket the typical therapeutic dose ranges. Subjects were followed for 28 days after receiving rFVIIIFc for safety analyses, including testing for anti-FVIII antibodies and inhibitors at 14 and 28 days post-injection. Plasma FVIII activity was measured in subjects before injection, 10 and 30 minutes, 1, 3, 6, 9, 24, 48, 72, 96, 120, and 168 hours (7 days) after rFVIIIFc injection, with additional samples at 192, 216, and 240 hours (10 days) for subjects dosed at 65 IU/kg of rFVIIIFc. Plasma FVIII activity was measured at the same time points after ADVATE® treatment, through 72 hours for the 25 IU/kg group and 96 hours for the 65 IU/kg group.

(a) Subjects

Male subjects were at least 12 years of age with severe hemophilia A (defined as FVIII activity level <1%) and had at least 100 documented prior exposure days to FVIII concentrates (pdFVIII or rFVIII). Subjects with known hypersensitivity to mouse or hamster protein, history of inhibitor or detectable inhibitor titer at screening, or who were taking any medications that could affect hemostasis or systemic immunosuppressive drugs, or who experienced an active bacterial or viral infection (other than hepatitis or HIV) within 30 days of screening were excluded. Subject's genotype was recorded at study entry, when known.

(b) Treatment Product

The human rFVIIIFc and Fc transgenes were stably transfected into HEK293 cells and the cell line was extensively tested for stability, sterility, and viral contamination to ensure safety. The purified drug product is composed of a monomeric B-domain-deleted FVIII covalently linked through its carboxy-terminus to the N-terminus of an Fc monomer, which forms a disulfide bond with a second Fc monomer during synthesis and secretion from the cells. rFVIIIFc was purified by chromatography and nanofiltration, and was fully active in one-stage and chromogenic clotting assays relative to commercially available rFVIII preparations. It was supplied as a frozen liquid containing 1000 IU per 2 mL of solution and formulated with L-histidine (pH 7), sodium chloride, calcium chloride, sucrose, mannitol, and Polysorbate 20. For injection, the product was diluted with saline solution (0.9% NaCl).

(c) Outcome Measures

The primary objective of the study was safety, evaluated through physical examination, reporting of treatment-emergent adverse events (AEs), development of antibodies, and laboratory monitoring over time. The secondary objectives included parameters derived from PK analyses. Laboratory assessments included prothrombin time, activated partial thromboplastin time (aPTT), international normalized ratio, levels of D-dimer, von Willebrand factor (vWF) antigen, standard hematology and blood chemistry tests, and urinalysis. FVIII activity was measured by the one-stage clotting (aPTT) assay on a Siemens BCS-XP analyzer using commercial reagents (Dade Actin FSL) with calibration against a normal reference plasma (Precision Biologics CRYOcheck™) traceable to the World Health Organization (WHO) 5$^{th}$ International Standard (IS) for human plasma. In addition to the aPTT assay, FVIII activity was measured by a chromogenic substrate assay Rosen S., *Scand J Haematol Suppl.* 33(Suppl 40):139-45 (1984) using a commercially available kit (Aniara BIOPHEN FVIII:C) that complies with European Pharmacopoeia recommendations. The chromogenic assay was calibrated against normal human reference plasma (Instrumentation Laboratories ORKE45), which also had a potency assigned against the WHO 5th IS human plasma standard.

The lower limit of quantification (LLOQ) for the one-stage and chromogenic assays was 0.5 IU/dL and 0.4 IU/dL, respectively. FVIII inhibitors were measured by the Nijmegen-modified Bethesda assay and less than 0.6 BU/mL was considered negative. Anti-rFVIIIFc antibodies were assessed using a specific bridging electrochemiluminescent immunoassay which uses biotin and sulfo-tagged rFVIIIFc. Assay sensitivity was determined to be 89 ng/mL using an anti-human FVIII monoclonal antibody as a surrogate control. Exploratory whole blood rotation thromboelastometry (ROTEM®) was performed in two subjects, one from each dose level, at various time points to assess the improvement in global hemostasis following injection with ADVATE® and rFVIIIFc.

(d) Pharmacokinetic Analyses

A user-defined one-compartment disposition model, which automatically estimates the endogenous FVIII level and subsequent residual decay, was utilized in WINNONLIN® for analysis of the individual subject plasma FVIII activity-versus-time data following a single administration of ADVATE® or rFVIIIFc. Actual sampling times, doses, and duration of injection were used for calculations of parameters including maximum activity ($C_{max}$), $t_{1/2}$, clearance (CL), volume of distribution at steady-state ($V_{ss}$), area under the curve (time zero extrapolated to infinity [$AUC_{INF}$]), mean residence time (MRT), and incremental recovery.

Monte Carlo Simulation of rFVIIIFc Activity-Versus-Time Profile:

To construct FVIII activity-time profiles following dosing regimens of 25 IU/kg or 65 IU/kg, a Monte Carlo simulation was conducted using the population PK model of ADVATE® and rFVIIIFc. The mean estimates of model parameters (CL, volume of distribution) in the tested population, the inter-individual variance, and the residual variability were estimated based on the one-stage (aPTT) clotting assay activity data of ADVATE® and rFVIIIFc from 16 subjects in this Phase1/2a study. Five hundred subjects were simulated with 15 sampling points for each subject for each dosing regimen. The percentage of the population with FVIII activity above or equal to 1% and 3% at different times following different dosing regimens of ADVATE® or rFVIIIFc was estimated.

Statistical Analyses:

Selected PK parameters for rFVIIIFc and ADVATE® were compared using an analysis of variance model. PK parameters were log-transformed for these analyses and estimated means, mean differences, and confidence intervals on the log-scale were transformed to obtain estimates for geometric means, geometric mean ratios (GMR), and confidence intervals, respectively, on the original scale. The GMR is the geometric mean of the intra-subject ratio of the rFVIIIFc PK parameter value to the ADVATE® PK parameter value.

Results

Subject Disposition:

Nineteen subjects were enrolled in the study; 16 underwent PK evaluation for both ADVATE® and rFVIIIFc. One subject self-administered his previous product prior to completing the wash-out period following the dose with ADVATE® and was thus excluded from the PK analysis, but was included in the safety analysis. Three subjects were discontinued from the study before receiving either study drug: one voluntarily withdrew; a second was withdrawn by the Investigator for non-compliance; and one was withdrawn at the Sponsor's request due to completion of study enrollment. Of the subjects dosed, six subjects received 25 IU/kg and 10 subjects received 65 IU/kg of both ADVATE® and rFVIIIFc. Mean age was 40.3 years (23 to 61 years). Genotypic identification was collected for seven subjects; inversion of intron 22 was reported in six subjects; and a frame-shift defect was reported in one subject. The genotype was unknown for nine subjects. Thirteen subjects had hepatitis C antibodies, four of whom were also positive for HIV.

Safety:

Forty-four treatment-emergent AEs were reported by 11 (69%) subjects during the treatment and follow-up periods. This included the day of dosing with ADVATE® or rFVIIIFc through a 28-day post-dosing observation period. The majority of events were considered mild and none led to withdrawal from the study. One event, dysgeusia, occurred transiently in one subject while receiving a 65 IU/kg dose of rFVIIIFc and was considered related to rFVIIIFc. One subject experienced an anxiety attack after receiving 65 IU/kg of rFVIIIFc which resulted in 21 AEs, 19 of which were graded as mild, and two of which (headache and photophobia) were rated as moderate. Neither was deemed related to rFVIIIFc by the Investigator. No serious bleeding episodes were reported. No evidence of allergic reactions to injection was detected. All plasma samples tested negative for FVIII inhibitors and anti-rFVIIIFc antibodies. No signs of injection site reactions were observed. No clinically meaningful changes in abnormal laboratory values were reported.

Pharmacokinetics:

Correlation Between aPTT and Chromogenic Activity for rFVIIIFc in Plasma:

ADVATE® and rFVIIIFc activities were determined in the same assays using commercially available reagents and calibration against normal human plasma standards. There was a strong correlation between the results obtained by the one-stage clotting assay and the chromogenic assay in samples that had an activity above the LLOQ. Correlation coefficients (Pearson $R^2$) of 0.94 and 0.95 were observed between the two assay results for 151 samples following ADVATE® dosing and 185 samples following rFVIIIFc dosing, respectively. Compared to the aPTT results, the chromogenic FVIII activities were, on average, 21% higher for ADVATE® and 32% higher for rFVIIIFc, not statistically significant (FIG. 9). This observation led to a slightly higher estimation of exposure parameters by the chromogenic assessment for both drugs. The apparent higher FVIII recoveries by the chromogenic assay are typical for recombinant FVIII products tested in clinical assays, and are in agreement with most other marketed FVIII products. Lee C. A. et al., *Thromb Haemost.* 82(6):1644-7 (December 1999), Mikaelsson M. and Oswaldsson U., *Semin Thromb Hemost.* 28(3):257-64 (June 2002), Stroobants A. K. et al., *J Thromb Haemost.* 9 (Suppl 2) (2011).

Improved Pharmacokinetics for rFVIIIFc:

The primary PK estimates were derived from one-stage (aPTT) clotting assay activity data. In subjects who received 25 or 65 IU/kg of ADVATE® followed by an equal dose of rFVIIIFc, the plasma FVIII activity rose sharply and reached $C_{max}$ within the first hour following dosing. The subsequent decline of the observed F VIII activity exhibited monoexponential decay characteristics until the baseline FVIII activity was reached (FIGS. 10A and 10B). The $C_{max}$ increased proportionally to the dose, but was comparable between equal doses of ADVATE® and rFVIIIFc (TABLE 8). The total exposure ($AUC_{INF}$) also increased proportionally to the dose. However, the $AUC_{INF}$ of rFVIIIFc was 1.48 and 1.56-fold greater than that of ADVATE® at 25 IU/kg (p=0.002) and 65 IU/kg (p<0.001), respectively (TABLE 8).

TABLE 8

PK Parameters by One-Stage (aPTT) Assay for rFVIIIFc and ADVATE ® Per Dose Group

| | Dose: 25 IU/kg (N = 6) | | | Dose: 65 IU/kg (N = 9) | | |
|---|---|---|---|---|---|---|
| Parameter | ADVATE ® Geom. Mean [95% CI] | rFVIIIFc Geom. Mean [95% CI] | Geom. Mean Ratio [95% CI] (p-value) | ADVATE ® Geom. Mean [95% CI] | rFVIIIFc Geom. Mean [95% CI] | Geom. Mean Ratio [95% CI] (p-value) |
| $C_{max\_OBS}$ (IU/dL) | 63.6 [59.1, 68.3] | 60.5 [53.1, 69.0] | 0.952 [0.819, 1.11] (p = 0.440) | 133 [105, 168] | 119 [103, 136] | 0.895 [0.795, 1.01] (p = 0.061) |
| $AUC_{INF}$ (hr * IU/dL) | 994 [723, 1370] | 1480 [1160, 1880] | 1.48 [1.26, 1.76] (p = 0.002) | 1800 [1350, 2400] | 2800 [1980, 3970] | 1.56 [1.33, 1.83] (p < 0.001) |
| $t_{1/2}$ (hr) | 12.2 [9.14, 16.3] | 18.8 [14.8, 23.8] | 1.54 [1.40, 1.69] (p < 0.001) | 11.0 [8.76, 13.9] | 18.8 [14.3, 24.5] | 1.70 [1.54, 1.89] (p < 0.001) |
| MRT (hr) | 17.5 [13.1, 23.4] | 27.0 [21.3, 34.2] | 1.54 [1.40, 1.69] (p < 0.001) | 15.8 [12.6, 19.9] | 27.0 [20.6, 35.3] | 1.71 [1.54, 1.89] (p < 0.001) |
| CL (mL/hour/kg) | 2.49 [1.80, 3.45] | 1.68 [1.31, 2.15] | 0.673 [0.569, 0.796] (p = 0.002) | 3.61 [2.71, 4.83] | 2.32 [1.64, 3.29] | 0.642 [0.547, 0.753] (p < 0.001) |
| $V_{ss}$ (mL/kg) | 43.9 [39.3, 49.0] | 45.4 [39.3, 52.5] | 1.04 [0.947, 1.13] (p = 0.357) | 57.4 [48.3, 68.3] | 62.8 [55.2, 71.5] | 1.09 [0.976, 1.22] (p = 0.107) |
| Incremental Recovery (IU/dL per IU/kg) | 2.56 [2.36, 2.78] | 2.44 [2.12, 2.81] | 0.952 [0.819, 1.11] (p = 0.444) | 2.04 [1.61, 2.59] | 1.83 [1.59, 2.10] | 0.894 [0.795, 1.01] (p = 0.060) |

CI = Confidence Interval;
Geom. Mean = Geometric Mean;
OBS = observed.
Estimated means, 95% CI for means, and mean differences were transformed to obtain estimated geometric means, 95% CI for geometric means, and geometric mean ratios, respectively.

The $t_{1/2}$, MRT, CL, and $V_{ss}$ appeared to be independent of dose (TABLE 8). The geometric mean $t_{1/2}$ of rFVIIIFc was 18.8 hours for both the 25 IU/kg and 65 IU/kg dose groups. This represents a 1.54 and 1.70-fold improvement over that of ADVATE® (12.2 hours and 11.0 hours) at equivalent doses (p<0.001), respectively (TABLE 8). The same intra-subject improvement was observed in the MRT of rFVIIIFc (27.0 hours for both dose groups) compared with ADVATE® (17.5 hours for the 25 IU/kg and 15.8 hours for the 65 IU/kg) (p<0.001). Consistent with improvement in the $t_{1/2}$ and MRT was a corresponding 1.49 and 1.56-fold reduction in intra-subject CL at doses of 25 IU/kg (p=0.002) and 65 IU/kg (p<0.001), respectively. There were no significant differences in $V_{ss}$ and incremental recovery between ADVATE® and rFVIIIFc. Therefore, within each subject, rFVIIIFc demonstrated an improved PK profile compared with ADVATE®.

The improved PK profile of rFVIIIFc resulted in increased time post-dosing to 1% FVIII activity which was 1.53 and 1.68-fold longer respectively, than with ADVATE® at 25 IU/kg (p<0.001) and 65 IU/kg (p<0.001) (data not shown), suggesting a potentially longer therapeutic duration for rFVIIIFc. The favorable PK profile of rFVIIIFc relative to ADVATE® was also demonstrated by FVIII activity measured in the chromogenic assay (TABLE 9), which was comparable to data derived from aPTT assays. The estimation of exposure, i.e., $C_{max}$ and $AUC_1$, was slightly higher, however, based on the chromogenic assay than on the one-stage (aPTT) clotting assay for both ADVATE® and rFVIIIFc.

TABLE 9

PK Parameters by Two-Stage (Chromogenic) Assay for rFVIIIFc and ADVATE ® Per Dose Group

| | Dose: 25 IU/kg (N = 6) | | | Dose: 65 IU/kg (N = 9) | | |
|---|---|---|---|---|---|---|
| Parameter | ADVATE ® Geom. Mean [95% CI] | rFVIIIFc Geom. Mean [95% CI] | Geom. Mean Ratio [95% CI] (p-value) | ADVATE ® Geom. Mean [95% CI] | rFVIIIFc Geom. Mean [95% CI] | Geom. Mean Ratio [95% CI] (p-value) |
| $C_{max\_OBS}$ (IU/dL) | 75.5 [65.5, 87.1] | 76.5 [64.9, 90.1] | 1.01 [0.940, 1.09] (p = 0.686) | 175 [143, 215] | 182 [146, 227] | 1.04 [0.900, 1.20] (p = 0.571) |

TABLE 9-continued

PK Parameters by Two-Stage (Chromogenic) Assay for rFVIIIFc and ADVATE ® Per Dose Group

| | Dose: 25 IU/kg (N = 6) | | | Dose: 65 IU/kg (N = 9) | | |
|---|---|---|---|---|---|---|
| Parameter | ADVATE ® Geom. Mean [95% CI] | rFVIIIFc Geom. Mean [95% CI] | Geom. Mean Ratio [95% CI] (p-value) | ADVATE ® Geom. Mean [95% CI] | rFVIIIFc Geom. Mean [95% CI] | Geom. Mean Ratio [95% CI] (p-value) |
| $AUC_{INF}$ (hr * IU/dL) | 1060 [822, 1360] | 1660 [1300, 2120] | 1.57 [1.38, 1.80] ($p < 0.001$) | 2270 [1670, 3070] | 4280 [2960, 6190] | 1.89 [1.61, 2.21] ($p < 0.001$) |
| $t_{1/2}$ (hr) | 10.5 [8.49, 12.9] | 16.7 [13.8, 20.1] | 1.59 [1.35, 1.87] ($p < 0.001$) | 10.8 [8.16, 14.2] | 19.8 [14.3, 27.5] | 1.84 [1.60, 2.12] ($p < 0.001$) |
| MRT (hr) | 15.0 [12.2, 18.6] | 23.9 [19.8, 28.9] | 1.59 [1.35, 1.87] ($p < 0.001$) | 15.4 [11.7, 20.4] | 28.5 [20.5, 39.6] | 1.85 [1.61, 2.12] ($p < 0.001$) |
| CL (mL/hour/kg) | 2.35 [1.80, 3.06] | 1.49 [1.16, 1.92] | 0.636 [0.557, 0.727] ($p < 0.001$) | 2.87 [2.12, 3.89] | 1.52 [1.05, 2.20] | 0.530 [0.453, 0.620] ($p < 0.001$) |
| Vss (mL/kg) | 35.5 [30.5, 41.3] | 35.9 [30.4, 42.3] | 1.01 [0.898, 1.14] ($p = 0.822$) | 44.5 [36.7, 54.1] | 43.4 [38.2, 49.4] | 0.975 [0.863, 1.10] ($p = 0.653$) |
| Incremental Recovery (IU/dL per IU/kg) | 3.05 [2.62, 3.54] | 3.09 [2.61, 3.66] | 1.01 [0.940, 1.09] ($p = 0.679$) | 2.70 [2.20, 3.31] | 2.80 [2.24, 3.50] | 1.04 [0.900, 1.20] ($p = 0.571$) |

CI = Confidence Interval;
Geom. Mean = Geometric Mean;
OBS = observed.
Estimated means, 95% CI for means, and mean differences were transformed to obtain estimated geometric means, 95% CI for geometric means, and geometric mean ratios, respectively.

Correlation Between Von Willebrand Factor and Disposition of rFVIIIFc:

Because the majority of FVIII in circulation is in complex with VWF, Lenting P. J. et al., *J Thromb Haemost.* 5: 1353-60 (2007) and because the genome-wide association study has identified that the genetic determinants of FVIII levels are primarily dependent on VWF levels, Smith N. L. et al., *Circulation* 121:1382-1392 (2010) we examined the association between VWF and rFVIIIFc. A strong correlation was observed between VWF levels and CL and $t_{1/2}$ for both rFVIIIFc and ADVATE®. As shown in FIGS. 11A and 11B, as the level of VWF increased, the CL of rFVIIIFc ($p=0.0016$) and of ADVATE® ($p=0.0012$) decreased.

The opposite relationship was observed between the level of VWF and $t_{1/2}$. As the level of VWF increased, the $t_{1/2}$ of rFVIIIFc ($p=0.0003$) and of ADVATE® ($p<0.0001$) increased. This correlation indicates that the Fc moiety of rFVIIIFc does not alter the role of VWF in protecting FVIII from clearance.

Effects of Prolonged PK of rFVIIIFc on Whole Blood ROTEM®:

Prior to administration of study drug, blood from one subject in each dose group was spiked with an equal dose of rFVIIIFc or ADVATE® and analyzed by whole blood ROTEM®. Clotting time (CT) was linear with respect to the dose in the range of approximately 1% to 100% of normal, and the dose response was comparable between rFVIIIFc and ADVATE® in the same subject (data not shown), indicating comparable potency of rFVIIIFc and ADVATE® in clot formation.

Despite the variable baseline CT due to residual FVIII levels prior to the administration of ADVATE® or rFVIIIFc, both products effectively corrected the CT to comparable levels 30 minutes post-dosing (see FIGS. 12A and 12B). The improvement in CT was better sustained by rFVIIIFc than ADVATE® after 3 hours following a dose of 25 IU/kg (FIG. 12A), and after 24 hours following a dose of 65 IU/kg (FIG. 12B).

rFVIIIFc was well tolerated by subjects at both doses. There were no clinically significant changes observed in hematology, blood chemistry, or urinalysis parameters. The majority of AEs were mild, unrelated to rFVIIIFc, and resolved without sequelae. No serious AEs or deaths occurred during the study, and no subjects at either dose developed neutralizing or binding antibodies to rFVIIIFc.

rFVIIIFc demonstrated a significantly improved FVIII activity PK profile relative to ADVATE®, with $t_{1/2}$ and MRT across dose levels being 1.54 to 1.71-fold longer, as measured by the one-stage (aPTT) clotting assay and 1.59 to 1.84-fold longer by the two-stage chromogenic assay. The prolonged activity of rFVIIIFc predicts possible prolonged efficacy, allowing for a less frequent dosing regimen in the prophylactic treatment of patients with Hemophilia A.

Adopting the PK parameters derived from this study, the Monte Carlo simulation predicted that a higher percentage of patients receiving rFVIIIFc will sustain FVIII levels above 1% or 3% as compared with patients receiving equal doses of ADVATE® (TABLE 10). For example, at a dose of 25 IU/kg, 12.2% of ADVATE® patients versus 71.2% of rFVIIIFc patients were predicted to have FVIII trough levels above 1% on Day 4; at a dose of 65 IU/kg, 11.0% of ADVATE® patients versus 66.4% of rFVIIIFc patients are predicted to have FVIII levels above 3% on Day 4. Clinical trials in larger numbers of patients are planned to confirm results from this Phase 1/2a study and from the Monte Carlo simulation predictions.

TABLE 10

Predicted Percentage of Subjects Achieving FVIII Trough
Levels Above 1% and 3% of Normal at a Specified Dose Regimen
of ADVATE ® or rFVIIIFc

| Timepoint following dosing | ADVATE ® | | rFVIIIFc | |
|---|---|---|---|---|
| (Day) | 25 IU/kg | 65 IU/kg | 25 IU/kg | 65 IU/kg |
| Percent of Subjects with FVIII Trough Levels above 1% | | | | |
| 3 | 40.0 | 67.8 | 92.6 | 99.0 |
| 4 | 12.2 | 31.0 | 71.2 | 90.0 |
| 5 | 4.20 | 13.6 | 39.4 | 71.6 |
| 7 | 0.200 | 1.40 | 7.80 | 26.4 |
| Percent of Subjects with FVIII Trough Levels above 3% | | | | |
| 3 | 10.6 | 34.6 | 62.2 | 91.0 |
| 4 | 1.60 | 11.0 | 25.4 | 66.4 |
| 5 | 0.200 | 3.20 | 7.00 | 36.2 |
| 7 | 0 | 0.200 | 0.400 | 6.60 |

In vitro coagulation assays demonstrate no loss of specific activity for rFVIIIFc, compared to B-domain deleted or native FVIII, by either clotting or chromogenic assays, using commercially available reagents and commonly used FVIII reference standards (Dumont et al., Blood (2012), prepublished online DOI:10.1182/blood-2011-08-367813). In addition, these results indicate that rFVIIIFc can be reliably assayed in a clinic setting by either the one-stage assay or the chromogenic method.

In summary, this Phase 1/2a clinical trial has demonstrated the safety and prolonged $t_{1/2}$ of rFVIIIFc in patients with severe hemophilia A. A pivotal Phase 3 study is ongoing with rFVIIIFc to establish effective prophylaxis dosing regimens for individuals with hemophilia A.

Example 10

Pharmacokinetics and Efficacy of rFVIIIFc in Mouse and Dog Models of Hemophilia A The pharmacokinetics and efficacy of rFVIIIFc compared to rFVIII was evaluated in mouse and dog models of hemophilia A, in support of human studies. rFVIIIFc is a heterodimeric protein comprising a single B-domain-deleted (BDD) FVIII linked recombinantly to the Fc domain of human immunoglobulin G1 (IgG1). Traditional dimeric Fc fusions, created through the fusion of the monomeric effector protein to a monomer of Fc and then coupled through a disulfide bond to create a dimer, were not effective for large coagulation proteins such as FVIII. Thus, we have developed methods to create novel Fc fusion protein constructs in which a single (monomeric) effector molecule is attached to Fc (Dumont J. A., et al., BioDrugs 20(3):151-60 (2006)), (Dumont J. A., et al., Journal of aerosol medicine. 18(3): 294-303 (2005)), (Bitonti, et al., Proc Natl Acad Sci U.S.A. 101(26):9763-9768 (2004)). We have applied this approach to a number of proteins, including human rFIX (Peters, R. T., et al., Blood. 115(10):2057-2064 (2010)), rFVIIa (Salas, J., et al., J Thromb Haemost. 9(s2):O-TU-026. doi: 10.11141538-7836.2011.04380_2.x (2011)), and BDD rFVIII.

Methods and Materials

Recombinant FVIII-Fc Fusion Protein (rFVIIIFc):

The rFVIIIFc expression plasmid pBUDCE4.1 (Invitrogen) contained two expression cassettes. One expressed, under the control of CMV promoter, native human FVIII signal sequence followed by BDD FVIII (S743 to Q1638 fusion) directly linked to the Fc region of human IgG1 (amino acids D221 to K457, EU numbering) with no intervening sequence. The other used the EF1α promoter to express the Fc region alone with a heterologous mouse IgκB signal sequence. Human embryonic kidney 293 cells (HEK293H, Invitrogen) were transfected with this plasmid, and a stable clonal suspension cell line was generated that expressed rFVIIIFc. Protein was purified from defined cell culture harvest media using a three column purification process, including a FVIII-specific affinity purification step (McCue J. et al., J. Chromatogr. A., 1216(45): 7824-30 (2009)) followed by a combination of anion exchange and hydrophobic interaction chromatographic steps.

Recombinant FVIII (rFVIII):

Recombinant BDD FVIII (REFACTO® and XYN-THA®), and full length FVIII (ADVATE®) were purchased from Novis Pharmaceuticals (Miami, Fla.) and reconstituted according to the manufacturer's instructions.

Animals:

The hemophilia A (HemA) mice bearing a FVIII exon 16 knockout on a 129×B6 background were obtained from Dr. H. Kazazian at the University of Pennsylvannia (Bi, L., et al., Nat Genet. 10(1):119-121 (1995)) and bred at Biogen Idec Hemophilia. Murine FcRn knockout (FcRn KO) and human FcRn transgenic (Tg32B) mice were derived from C57BL/6J mice and were obtained from Dr. Derry Roopenian of The Jackson Laboratory in Bar Harbor, Me. The genotypes for FcRn KO mice are mFcRn (−/−) and mβ2m (−/−), and for Tg32B are mFcRn (−/−), mβ2m (−/−), hFcRn (±/+), and hβ2m (±/+). C57BL/6 mice were purchased from The Jackson Laboratories (Bar Harbor, Me.). All animal activities were approved by the Institutional Animal Care Committees and performed in accordance with the "Guide to the Care and Use of Laboratory Animals."

Hemophilia A dogs were from the in-bred colony maintained at the Francis Owen Blood Research Laboratory at the University of North Carolina, Chapel Hill. These dogs have a severe hemophilic phenotype comparable to the severe form of the human disease (Graham, J. B. and Buckwalter, J. A., et al., The Journal of Exp. Med. 90(2): 97-111 (1949)), (Lozier, J. N., et al., Proc Natl Acad Sci U.S.A. 99(20):12991-12996 (2002)).

Pharmacokinetic (PK) Studies in Mice:

The PK of rFVIIIFc and rFVIII (XYNTHA®) was evaluated in HemA, C57BL/6, FcRn KO, and Tg32B mice after an intravenous dose of 125 IU/kg. Blood was collected from the vena cava in one-tenth volume of 4% sodium citrate at 5 minutes, and 4, 8, 16, 24, 32, 48, 54, and 72 hours post-dosing for rFVIIIFc and at 5 minutes, and 1, 4, 8, 16, 20, 24, 32, and 48 hours post-dosing for rFVIII (4 mice/time point/treatment). Plasma was snap frozen in an ethanol/dry ice bath and stored at −80° C. until analysis for FVIII activity using a human FVIII-specific chromogenic assay (FVIII Coatest SP kit from DiaPharma [West Chester, Ohio]). The pharmacokinetic parameters were estimated by non-compartmental modeling using WINNONLIN® version 5.2 (Pharsight, Mountain View, Calif.).

Efficacy Studies in HemA Mice:

All efficacy studies were performed blinded. Acute efficacy was studied in the tail clip bleeding model. Male HemA mice (8-12 weeks old) were anesthetized with a cocktail of 50 mg/kg of Ketamine and 0.5 mg/kg of Dexmedetomidine. The tail was then immersed in 37° C. saline for 10 minutes to dilate the lateral vein followed by tail vein injection of rFVIIIFc, rFVIII (ADVATE®), or vehicle. Five minutes later, the distal 1 cm of the tail was clipped and the shed blood was collected into 13 mL of warm saline for 30 minutes. The blood loss was quantified gravimetrically.

The prophylactic efficacy was studied in the tail vein transection (TVT) bleeding model as described previously (Pan, J. and Kim, J. Y., *Blood.* 114(13):2802-2811 (2009)) except that HemA mice received a single intravenous administration of 12 IU/kg of rFVIIIFc, rFVIII (ADVATE®), or vehicle at 24 or 48 hours prior to the transection of a lateral tail vein. The dose of 12 IU/kg was identified from a prior dose response experiment with rFVIII in which 12 IU/kg achieved 50% protection of HemA mice from a TVT injury inflicted 24 hours post dosing (data not shown).

Hemophilia a Dog Studies:

In a single dose PK/PD study of rFVIIIFc, two naïve hemophilia A dogs (M10 and M11) received an intravenous dose of 125 IU/kg. Blood samples were collected pre-dosing and post-dosing at 5 and 30 min, and 1, 2, 4, 8, 24, 32, 48, 72, 96, 144, and 168 hours for whole blood clotting time (WBCT). Blood collections for FVIII activity (aPTT and chromogenic assay), rFVIIIFc antigen (ELISA), hematology, and blood chemistry included the time points listed above for WBCT as well as 15 minute and 3, 6, and 12 hours post-dosing.

In the following sequential design study, rFVIII (REFACTO®) was administered intravenously at 114 IU/kg for dog M12 and 120 IU/kg for dog M38. WBCT was measured until clotting times were ≥20 minutes (the time consistent with FVIII:C≤1%), and samples were also collected at the specified time points for FVIII activity (aPTT and chromogenic assay), antigen (ELISA). and hematology tests. Then 125 IU/kg rFVIIIFc was administered intravenously to the same dogs and blood samples were collected for WBCT, aPTT, ELISA, hematology, and serum chemistry. Time points for WBCT included pre-dosing, and 5 and 30 minutes and 1, 2, 4, 8, 24, 32, 48, and 72 hours post-dosing of rFVIII and rFVIIIFc. Blood was also collected at 96, 120, 144, and 168 hours post-dosing with FVIIIFc. Blood collections for FVIII activity and antigens included the time points listed above for WBCT as well as 15 minutes and 3, 6, 12 hours after dosing. The WBCT and aPTT were performed as previously described (Herzog, et al., *Nat Med.* 5(1):56-63 (1999)).

FVIII Chromogenic Assays:

FVIII activity in hemophilia A dog plasma was tested by an automated chromogenic assay on a Sysmex CA1500 instrument (Sysmex, IL) with reagents from Siemens Healthcare Diagnostics (Dallas, Tex.). The standard curve was generated with the 7th International Standard FVIII Concentrate (NIBSC code 99/678) spiked into human FVIII-depleted plasma (Stago, USA) at concentrations ranging from 1.5-0.016 IU/mL.

FVIII activity in HemA mouse plasma was measured using the Coatest SP FVIII assay from Chromogenix (DiaPharma, Lexington, Mass.), following the manufacturer's instructions. The standard curve was generated using rFVIIIFc or rFVIII serially diluted from 100 mU/mL to 0.78 mU/mL in buffer containing naive HemA mouse plasma. To measure the human FVIII activity in C57BL/6, FcRn KO, and Tg32B mouse plasma, the infused rFVIIIFc or rFVIII in mouse plasma was first captured by human FVIII-specific mAb GMA8016 (Green Mountain Antibodies, VT) followed by the standard Coatest assay.

rFVIII- and rFVIIIFc-Specific ELISA:

rFVIII and rFVIIIFc antigen levels in hemophilia A dog plasma were measured by ELISA following the standard protocol. The FVIII A1 domain-specific mAb GMA-8002 (Green Mountain Antibodies, Burlington, Vt.) was used as the capture antibody. HRP-conjugated polyclonal anti-FVIII Ab F8C-EIA-D (Affinity Biologicals) was used to detect rFVIII. HRP-conjugated donkey anti-human (F(ab)'$_2$) 709-036-098 (Jackson Immunologicals) was used to detect rFVIIIFc.

SPR analysis of rFVIIIFc-FcRn interactions: Surface plasmon resonance (SPR) experiments were performed with a Biacore T100 instrument. Research-grade CM5 sensor chips, buffers, and immobilization reagents were purchased from Biacore (GE Healthcare, Piscataway, N.J.). Single-chain human, canine, and murine FcRn preparations were immobilized using standard amine coupling on adjacent flow cells of a single chip at a density of approximately 370 resonance units (RU), followed by blocking with ethanolamine. The steady-state association of Fc-containing analytes (FVIIIFc and IgG) with immobilized FcRn of different species was evaluated by sequential injection of analytes at 16 concentrations (0.0625-2000 nM) in pH 6.0 running buffer (50 mM MES [4-morpholineethanesulfonic acid], 250 mM sodium chloride, 2 mM calcium chloride, 0.01% Tween 20 [polyethylene glycol sorbitan monolaurate]). Each cycle was performed in duplicate and comprised a 45 minutes association phase and a 15 minutes dissociation phase, both at a flow rate of 5 μL/min, followed by regeneration with two 60 sec injections of 1M Tris-HCl at 25 μL/min. After double reference-subtraction (blank flow cell and running buffer alone), binding responses recorded near the end of the association phase were plotted as a function of analyte concentration, and $EC_{50}$ values (50% of $R_{max}$) were derived by non-linear regression analysis.

Statistical Analyses:

Unpaired t-test, one-way ANOVA, Mann-Whitney test, Kruskal-Wallis test with Dunn post-test, survival curves and associated log-rank test were performed in GraphPad Prism 5 (Graph-Pad Software Inc., La Jolla, Calif.). A 2-tailed P value less than 0.05 was considered statistically significant.

Results

Recombinant FVIII Fc Fusion Protein (rFVIIIFc):

rFVIIIFc is a recombinant fusion of human B-domain deleted FVIII with Fc from human IgG1, with no intervening linker sequence (FIG. 14), that was produced in well characterized HEK 293H cells. The rFVIIIFc is proteolytically cleaved intracellularly to yield an ~90 kDa heavy chain and ~130 kDa light chain-Fc that are bound together non-covalently through a metal bond interaction mediated by the A1 and A3 domains of FVIII.

The average specific activity of rFVIIIFc from fourteen separate batches was 8460±699 IU/mg by the one stage clotting (aPTT) assay, and 9348±1353 IU/mg by the chromogenic assay, corresponding to 1861±154 and 2057±298 IU/nmol, respectively. The specific activity of rFVIIIFc is comparable to that of wild type human FVIII in plasma (1429 IU/nmol) (Butenas, S. and Mann, K. G., *Biochemistry* (Mosc). 67(1):3-12 (2002)). Thus the FVIII activity of rFVIIIFc is not affected by fusion of the C-terminus of human FVIII to the N-terminus of human Fc, and the results obtained with the aPTT and chromogenic assays are within approximately 10% of one another.

Binding of rFVIIIFc to FcRn:

The affinity of rFVIIIFc for single-chain mouse, canine, and human FcRn was evaluated using surface plasmon resonance. The rates of association and dissociation for the complex between rFVIIIFc and mouse FcRn were much slower than those for canine and human FcRn. Half-maximal binding ($EC_{50}$) of rFVIIIFc to human FcRn was approximately 4-fold weaker than that to canine FcRn, and more than 20-fold weaker than that to mouse FcRn (TABLE 11). Similarly, human IgG1 also showed the highest affinity to murine FcRn, while binding affinity to canine FcRn was less compared to murine FcRn, but greater compared to human FcRn (TABLE 11).

TABLE 11

Surface Plasmon resonance analysis of murine, canine, and human FcRn with rFVIIIFc and human IgG1

| Fc Sample * | FcRn | FcRn Density (RU) | $EC_{50}$ (nM) † | Rmax (RU) |
|---|---|---|---|---|
| rFVIIIFc | murine | 370 | <1.5 ‡ | 581.4 |
| rFVIIIFc | canine | 367 | 8.6 | 499.3 |
| rFVIIIFc | human | 369 | 33.4 | 365.4 |
| Human IgG1 | murine | 378 | <22.4 ‡ | 320.0 |
| Human IgG1 | canine | 367 | 196.3 | 282.2 |
| Human IgG1 | human | 378 | 558.4 | 211.0 |

* rFVIIIFc or IgG1 were injected over a flow cell to which various FcRn molecules were chemically conjugated at approximately equal densities (~370 RU).
† $EC_{50}$ values (50% of $R_{max}$) were the average derived from non-linear regression analysis of the binding response curves fitted to 16 analyte concentrations (0.0625-2000 nM) repeated in duplicate.
‡ Due to the high affinities, the low binding curves at low analyte concentrations did not reach equilibrium under the normal operating conditions of the instrument.

FcRn-Dependent Improvement in Pharmacokinetics of rFVIIIFc in Mice:

Interaction of Fc with FcRn is considered the underlying mechanism for extending half-life for IgG and Fc-fusion proteins. To confirm that this mechanism of action is also responsible for extending half-life of rFVIIIFc, we compared pharmacokinetic (PK) profiles of rFVIIIFc with rFVIII in FVIII-deficient (HemA) mice (FIG. 15A), normal (C57BL/6) mice (FIG. 15B), FcRn-deficient (FcRn KO) mice (FIG. 15C), and human FcRn transgenic (Tg32B) mice (FIG. 15D) following a single intravenous administration of 125 IU/kg.

The PK parameters (TABLE 12) were determined by the chromogenic measurement of the human FVIII activity in mouse plasma. The $t_{1/2}$ of rFVIIIFc was 1.8-2.2 fold longer than rFVIII in HemA mice (13.7 vs 7.6 hours) and normal mice (9.6 vs 4.3 hours). The $t_{1/2}$ extension of rFVIIIFc relative to rFVIII was abolished in FcRn KO mice (6.4 vs 6.9 hours) and restored in human FcRn transgenic Tg32B mice (9.6 vs 4.1 hours). The results thus confirm that the interaction of rFVIIIFc with the FcRn receptor is responsible for its extended $t_{1/2}$. Furthermore, consistent with the improved $t_{1/2}$, rFVIIIFc also showed a 1.6-2.4 fold longer MRT and a 1.2-1.8 fold increased systemic exposure (AUC) compared to rFVIII in FcRn-expressing (HemA, C57Bl/6 and Tg32B) mice but not in FcRn KO mice.

TABLE 12

Summary of PK parameters for rFVIIIFc and rFVIII in different mouse strains

| | Mouse Strain | | | | | | | |
|---|---|---|---|---|---|---|---|---|
| | HemA† | | C57BL/6† | | FcRn KO† | | hFcRn Transgenic (Tg32B)† | |
| Mouse Strain | rFVIIIFc* | rFVIII* | rFVIIIFc* | rFVIII* | rFVIIIFc* | rFVIII* | rFVIIIFc* | rFVIII* |
| $C_{max}$ (mIU/mL) | 2613.6 | 2710.4 | 2356.2 | 2000.1 | 2734.9 | 2458.4 | 3135.3 | 3137.0 |
| Half-life (hr) | 13.7 | 7.6 | 9.6 | 4.3 | 6.4 | 6.9 | 9.6 | 4.1 |
| MRT (hr) | 17.6 | 11.0 | 9.8 | 5.4 | 6.3 | 8.5 | 12.8 | 5.4 |
| Vss (mL/kg) | 68.2 | 49.2 | 67.5 | 50.8 | 49.3 | 51.6 | 64.1 | 49.6 |
| CL (mL/hr/kg) | 3.9 | 4.5 | 6.9 | 9.3 | 7.8 | 6.1 | 4.1 | 7.3 |
| AUC (hr * mIU/mL) | 32332.4 | 28026.8 | 18089.1 | 13404.0 | 16087.2 | 20609.3 | 30534.5 | 17165.7 |

$C_{max}$: maximum plasma FVIII activity post infusion;
MRT: mean residence time;
Vss: volume of distribution at steady-state;
¹CL: clearance;
²AUC: area under the curve.
†PK parameters of rFVIII and rFVIIIFc were compared only within the same mouse strain not across strains, because the same molecule can display different $t_{1/2}$ in different mouse strains.
*The PK evaluation of each molecule used a cohort of 36 mice, sampled by terminal vena cava bleeding from 4 mice at each of the 9 time points. The group means at each time point were used for non-compartment modeling in WINNONLIN ® to derive PK parameter estimates.

rFVIIIFc is Fully Active in Treating Acute Bleeds in HemA Mice:

To evaluate the acute efficacy of rFVIIIFc in comparison to rFVIII, HemA mice (16-20 mice/group) were treated with escalating doses (24, 72, and 216 IU/kg) of rFVIIIFc or rFVIII and injured by tail clip 5 minutes post-dosing. In comparison to vehicle-treated mice (n=18) that had a median blood loss of 1 mL, both rFVIIIFc and rFVIII treatments resulted in significantly improved protection (P<0.05, Kruskal-Wallis test with Dunn post-test) (FIG. 16). The median blood loss progressively decreased with increasing doses, reaching maximum reduction to 0.23 mL at 72 IU/kg of rFVIIIFc, and 0.20 mL at 216 IU/kg of rFVIII. Overall, the blood loss was comparable in animals treated with equal doses of rFVIIIFc or rFVIII, indicating that both therapeutics are comparably active in resolving acute arterial bleeds.

Prolonged Prophylactic Efficacy of rFVIIIFc in HemA Mice:

To determine if prolonged PK lead to prolonged protection from injury, we compared the prophylactic efficacy of rFVIIIFc and rFVIII in HemA mice. Twenty-four hours after an intravenous dose of 12 IU/kg, one lateral tail vein in HemA mice was transected. Following injury, 49% of rFVIII-treated mice (n=39) survived, compared with 100% survival of rFVIIIFc-treated mice (n=19) (P<0.001, Log-Rank test) (FIG. 17A). To further demonstrate that rFVIIIFc sustains a longer duration of efficacy, HemA mice were injured 48 hours post-dosing with 12 IU/kg of rFVIIIFc. Nevertheless, 58% of rFVIIIFc-treated mice (n=40) survived, which is similar to that achieved in rFVIII-treated mice (49%) injured at 24 hours post dosing (FIG. 17A). Both rFVIIIFc and rFVIII treatments are significantly better than the HemA vehicle-control group (n=30) in which only 3% of mice survived the injury (P<0.0001) (FIG. 17A). The improved and prolonged prophylactic efficacy of rFVIIIFc is also evident by the measurement of rebleeding post injury (FIG. 17B). Whereas 100% of vehicle-treated HemA mice rebled within 10 hours following tail vein transection, 87% of rFVIII-treated and 47% of rFVIIIFc-treated mice rebled after the injury inflicted at 24 hours post dosing, respectively (P=0.002, rFVIIIFc vs rFVIII) (FIG. 17B). The rebleed profile for rFVIIIFc-treated mice injured at 48 hours is largely comparable to that for rFVIII-treated mice injured at 24 hours post dosing. In contrast, both the survival and rebleed profile for rFVIII-treated mice injured at 48 hours are indistinguishable from the profile for the vehicle-control group (data not shown). Therefore, the results indicate that rFVIIIFc protects HemA mice from tail vein injury twice as long as that achieved by the same dose of rFVIII.

Improved PK/PD of rFVIIIFc in Hemophilia a Dogs:

The PK and pharmacodynamics (PD) of rFVIIIFc were also studied in hemophilia A dogs. Following an intravenous dose of 125 IU/kg of rFVIIIFc, the WBCT was immediately corrected to normal, which is in the range of 8-12 minutes in normal dogs (FIGS. 18A and B). The WBCT remained below 20 min, indicating FVIII activity >1%, through approximately 4 days in 3 out of 4 rFVIIIFc-treated dogs and 3 days in the remaining dog (FIG. 18A). In dog M12 treated with 114 IU/kg of rFVIII and dog M38 with 120 IU/kg of rFVIII, the WBCT was also corrected to normal immediately after dosing. However, the WBCT remained below 20 minutes for 2 days in M12 and 3 days in M38, approximately 1.5-2-fold shorter than that achieved by rFVIIIFc (FIG. 18B). Furthermore, both rFVIIIFc and rFVIII treatment also improved aPTT clotting time similarly at 5 minutes post dosing.

The PK of rFVIIIFc antigen (FIG. 19A) was determined by measuring the concentration of rFVIIIFc in plasma with a rFVIIIFc-specific ELISA that detects both the FVIII and Fc portions of the molecule. The $t_{1/2}$ of rFVIIIFc antigen is 15.7±1.7 hr (FIG. 19A), similar to the $t_{1/2}$ of rFVIIIFc activity (FIG. 19B), as measured by the chromogenic assay: 15.4±0.3 hr (TABLE 13). There is a good correlation between the FVIII activity and the rFVIIIFc antigen data, thereby demonstrating that rFVIIIFc protein was fully active in vivo.

TABLE 13

Summary of PK parameters for rFVIIIFc and rFVIII in hemophilia A dogs

| PK by FVIII activity measurement | | | | | |
|---|---|---|---|---|---|
| Treatment | $C_{max}$ (IU/mL) | AUC (hr · IU/mL) | $T_{1/2}$ (hr) | CL (mL/hr/kg) | Vss (mL/kg) |
| rFVIIIFc* | 2.0 ± 0.54 | 25.9 ± 6.47 | 15.4 ± 0.3 | 5.1 ± 1.4 | 86.4 ± 14.0 |
| rFVIII† | 2.0 | 18.2 | 7.4 | 6.5 | 64.0 |

| PK by rFVIII and rFVIIIFc antigen measurement | | | | | |
|---|---|---|---|---|---|
| Treatment | $C_{max}$ (ng/mL) | AUC (hr · ng/mL) | $T_{1/2}$ (hr) | CL (mL/hr/kg) | Vss (mL/kg) |
| rFVIIIFc* | 210 ± 33 | 2481 ± 970 | 15.7 ± 1.7 | 6.2 ± 3.0 | 86.1 ± 19.2 |
| rFVIII† | 211 | 1545 | 6.9 | 8.7 | 80.7 |

*Results presented are Mean ± SD from 4 dogs.
†Results presented are Mean. SD not reported since two dogs were utilized.

In two of the dogs (M12 and M38) that also received a single dose of rFVIII 72 hours prior to dosing with rFVIIIFc, the $t_{1/2}$ of rFVIII antigen was determined to be 6.9 hours and rFVIII activity 7.4 hours. Therefore, the plasma half-life of rFVIIIFc was approximately twice as long compared to that for rFVIII by both antigen and activity measurements.

In addition, platelet count and fibrinogen were assessed to serve as preliminary tests for thrombogenicity. After dosing with either rFVIIIFc or rFVIII, platelet numbers and plasma fibrinogen concentration did not change from pre-dose values (data not shown).

Discussion

These studies have shown rFVIIIFc to be fully active in treating acute bleeds in HemA mice, in addition to retaining normal specific activity. Other studies, not reported here, have shown that rFVIIIFc is also fully functional in interacting with FIXa, FX, and phospholipids in forming the Xase complex (Peters et al., *J. Thromb Haemost.* DOI: 10.1111/jth.12076 (2012)). Furthermore, the binding affinity to von Willebrand Factor (VWF) was comparable between rFVIIIFc and rFVIII, with a Kd of approximately 1.4 and 0.8 nM for rFVIIIFc and rFVIII, respectively (Peters et al., *J. Thromb Haemost.* DOT: 10.1111/jth.12076 (2012)).

The activity of rFVIIIFc was not affected by fusion of the C-terminus of FVIII with the N-terminus of Fc since the C1 and C2 domains of FVIII were involved in phospholipid binding which is essential for the formation of prothrombinase complex on activated platelet surfaces (Foster, P. A., et al., *Blood.* 75(10:1999-2004 (1990)). However, this finding was consistent with the observation that residues thought to bind phospholipids, e.g., K2092/F2093 in C1, M2199/F2200 and L2251/L2252 in C2, all appear to form a surface that is distant from the C-terminal residues of FVIII (Shen, B. W., et al., *Blood.* (2007); Ngo, J. C., et al., *Structure.* 16(4):597-606 (2008)).

The half-life of rFVIIIFc was doubled only in mice expressing either endogenous murine or transgenic human FcRn, but not in FcRn KO mice (see FIG. 15 and TABLE 12), demonstrating that the mechanism of prolonging half-life of rFVIIIFc is mediated by FcRn. While it is known that both endothelial and hematopoietic cells contribute equally in recycling internalized IgG to the cell surface to facilitate the longevity of IgG and protection from degradation, (Borvak, J., et al., *Int Immunol.* 10(9):1289-1298 (1998)), (Akilesh, S., et al., *J Immunol.* 179(7):4580-4588 (2007)) it is not known specifically which FcRn-expressing cell type(s) are responsible for the uptake and recycling of rFVIIIFc. FcRn is broadly expressed in the vascular endothelium, epithelium of kidney, liver, spleen, as well as in bone marrow-derived APCs including macrophages (Borvak, J., et al., *Int Immunol.* 10(9):1289-1298 (1998)), (Akilesh, S., et al., *J Immunol.* 179(7):4580-4588 (2007)), (Yoshida, M., et al., *Immunity.* 20(6):769-783 (2004)). Since FVIII circulates largely (~98%) in complex with VWF (Lenting, P. J., et al., *J Thromb Haemost.* 5(7):1353-1360 (2007)), and both proteins were colocalized to the macrophages in liver and spleen when recombinant FVIII and VWF were co-injected into VWF-deficient mice (van Schooten, C. J., et al., *Blood.* 112(5):1704-1712 (2008)), macrophages can play a role in rescue of rFVIIIFc from degradation and prolongation of half-life. However, the results can also be indicative of a previously unrecognized pathway for FVIII catabolism, and rescue of the protein permitted by Fc fusion.

Approaches in development to extend the half-life of clotting factors include pegylation (Rostin, J., et al., *Bioconjug Chem.* 11(3):387-396 (2000)), (Mei, B., et al., *Blood.* 116(2):270-279 (2010)), glycopegylation (Moss, J., et al., *J Thromb Haemost.* 9(7):1368-1374 (2011)), (Negrier, C., et al., *Blood.* (2011)), and conjugation with albumin (Metzner, H. J., et al., *Thromb Haemost.* 102(4):634-644 (2009)), (Weimer, T., et al., *Thromb Haemost.* 99(4):659-667 (2008)). Regardless of the protein engineering utilized, the half-life of modified rFVIII variants appears to be maximally twice as long as wild-type FVIII in a variety of preclinical animal models (Liu, T., et al., *Blood.* 112:511 (2008)), (Karpf, D. M., et al., 16(Suppl. S4):40 (2010)). Consistent results have been demonstrated in humans, e.g., rFVIIIFc was reported to improve half-life approximately 1.7-fold compared to ADVATE® in hemophilia A patients (Powell, J. S., et al., *Blood.* (2012) prepublished online. DOI:10.1182/blood-2011-09-382846). This limitation of extending FVIII half-life appears to be related to VWF. In FVIII and VWF knockout mice, preliminary experiments observed a 5-fold increase in the half-life of rFVIIIFc compared to rFVIII (Liu, T et al., unpublished results). Similar findings were reported previously in VWF knockout mice utilizing Pegylated-FVIII (Mei, B., et al., *Blood.* 116(2):270-279 (2010)). Taken together, these results indicate that VWF can be a limiting factor for further extending FVIII half-life.

Beyond extending half-life, rFVIIIFc provides additional benefits. One major challenge with FVIII replacement therapy is the development of neutralizing anti-FVIII antibodies (inhibitors). This occurs in 15-30% of previously untreated patients. rFVIIIFc has the potential to induce immune tolerance and thus prevent the development of neutralizing antibodies. It has been reported that retroviral vector-transduced B-cells, presenting FVIII domains as Ig fusion proteins, specifically prevent or decrease existing FVIII antibodies in HemA mice (Lei, T. C. and Scott, D. W., *Blood.* 105(12):4865-4870 (2005)). It was also found that Fc contains regulatory T-cell epitopes capable of inducing Treg expansion and suppression of antigen-specific immune responses in vitro (De Groot, et al., *Blood.* 112(8):3303-3311 (2008)). In addition, the FcRn-mediated transfer of maternal IgG and Fe-fusion proteins across placenta to fetal circulation (Simister, N. E., Vaccine. 21(24):3365-3369 (2003)), Grubb, J. H., et al., *Proc Natl Acad Sci U.S.A.* 105(24):8375-8380 (2008)) could induce neonatal tolerance to rFVIIIFc while also providing needed protection in the newborn from bleeding during delivery.

In conclusion, we have demonstrated that rFVIIIFc, provides approximately 2-fold longer efficacy duration relative to rFVIII in protecting HemA mice from tail vein transection injury and improving WBCT in HemA dogs. The prolonged efficacy correlates well with a 2-fold extended $t_{1/2}$ of rFVIIIFc, a result of recycling of the Fc fusion protein via a specific and well established intracellular pathway.

Example 11

Immunogenicity of rFVIIIFc in Mice 130 male Hemophilia A mice, age 7-9 weeks old at the beginning of the study, were randomized into 13 treatment groups based on age and Body weight (n=10/group). Mice were treated with repeated intravenous dosing of either rFVIIIFc, rFVIII-mFc, XYNTHA® or ADVATE® at 50, 100 and 250 IU/kg, a mixture of the three formulation buffers for FVIIIFc, XYNTHA® and ADVATE® was used for the vehicle control group. The IV administration times were day 0, day 7, day 14, day 21, day 35 post the first IV injection and blood samples were collected via Retro-orbital blood collection at day (−1), day 14, day 21, day 28 and day 42 post the first treatment (FIG. 20).

Immediately after blood collection, plasma samples were isolated through centrifugation and inactivated by 30 minute heat treatment at 56° C. to insure the accurate measurement of anti-FVIII antibodies. The development of total anti-FVIII antibody (FIGS. 21A, 21B and 21C), anti-FVIII neutralizing antibody (FIG. 23) and total anti-Fc antibody (FIG. 24) were investigated using the plasma samples.

When treated with 50 IU/kg FVIII, 28 days post the first injection, only 1 out of 10 mice in the rFVIIIFc treatment group, 2 out of 10 mice in the rFVIII-mFc treatment group developed detectable anti-FVIII antibody compared to 5 out of 10 mice and 7 out of 10 mice for the XYNTHA® and ADVATE® treated mice (FIG. 22C). At 100 IU/kg, the numbers of mice that had detectable anti-FVIII antibody at day 28 were 2, 5, 8 and 9 in the rFVIIIFc, rFVIII-mFc, XYNTHA® and ADVATE® treatment group respectively (FIG. 22C). At 250 IU/kg, a supra-physiological dose, the numbers of mice that had detectable anti-FVIII antibody at day 28 were 10, 10, 7 and 7 in the rFVIIIFc, rFVIII-mFc, XYNTHA® and ADVATE® treatment group respectively (FIG. 22C). Data corresponding to day 14, day 21, and day 42 is shown in FIGS. 22A, 22B, and 22D, respectively.

In general, we observed a good correlation between the total and neutralizing antibodies to FVIII ($R^2$=0.7452), and the titers of both increased over time (FIG. 23). Within the therapeutic dose range (50 and 100 IU/kg), the number of mice that developed FVIII-specific antibodies as well as the antibody titers in rFVIIIFc treatment groups were significantly lower compared to ADVATE® ($p<0.05$), and marginally lower versus XYNTHA® (p=0.05). The results indicate a potentially low immunogenicity of rFVIIIFc.

Example 12

Splenic Lymphocyte Response to rFVIIIFc Compared with Commercially Available rFVIII The splenic lymphocyte response to recombinant Factor VIII (rFVIII) when linked to either human Fc (hFc, IgG1) or mouse Fc (mFc, IgG2a) was determined and compared with the splenic lymphocyte response to commercially available rFVIII [full-length FVIII (ADVATE®) and B-domain-deleted FVIII (XYNTHA®/REFACTO AF®)].

HemA mice were injected once weekly for six weeks with either 50 or 250 IU/kg of the tested molecules. On day 56, four mice from each group were euthanized and splenocytes were isolated (FIG. 25). One half of the splenocytes was used for determining the splenic immunogenicity profile by staining for intracellular cytokines, markers for regulatory T cells, and dendritic cells using flow cytometry (FACS) (FIG. 26). The other half of the cells were used for isolating RNA and carrying out pathway profiling using real time PCR based arrays. FIG. 27A shows a FACS dot plot profile of the isotype control. FIG. 27B shows a FACS dot plot profile of a sample containing splenocytes positive for both CD4 and TNF-α. Percentage of double positive cells were determined from dot plots from all the treatments and vehicle. Percent of double positive cells in FVIII treated mice was obtained by comparing with vehicle treated group.

Intracellular cytokine staining was performed by co-staining for the T-helper cell marker CD4 and cytokines such as IL-2 (FIG. 28), IL-4 (FIG. 30), and TNF-α (FIG. 29). IL-2 is a T-cell mitogen involved in T-cell proliferation, which is secreted by activated T-cells in response to FVIII in hemA mice. IL-4 has been identified as a cytokine secreted by activated T cells in response to FVIII in hemA mice. TNF-α is a pro-inflammatory cytokine responsible for higher antibody production in hemophilia patients. The fluorescence intensities of each of the staining were measured using flow cytometry.

Similarly, the proportion of tolerogenic and immunogenic dendritic cells was determined by surface staining and flow cytometry analysis of markers such as PD-L1 (CD274) (FIG. 32) and CD80 (FIG. 33). PD-L1 is an inhibitory ligand that engages the PD-1 receptor on activated T-cells thereby blocking T-cell Receptor (TCR) mediated production of IL-2 and proliferation. Higher DC expression of PD-L1 is a critical factor that can inhibit immunogenicity and promote tolerance. CD80 is a surface marker usually seen on dendritic cells upon phagocytosing antigen and during maturation to present antigen to T cells. CD80 belongs to a panel of co-receptors in activating T cells for proliferation. More CD80 surface staining indirectly indicates better maturation and antigen presentation by dendritic cells.

In addition, the percentage of regulatory cells (Treg) in the spleen was assessed by co-staining for CD4 and foxp3 (FIG. 34), a marker for these cells. Foxp3 is an intracellular marker of regulatory T cells. Foxp3+ T-cells are involved in the establishment, maintenance, and adoptive transfer of T-cell mediated peripheral tolerance.

The presence of cells expressing both CD4 and the Tim3 (FIG. 35) or CD279 (PD-1) (FIG. 36) makers was also assessed. Tim3 (T-cell immunoglobulin domain and mucin domain 3) as a negative regulator of T helper 1 (Th1)-cell responses. Tim3 is also expressed by innate immune cells and can promote a pro-inflammatory response. Tim3 inhibits Th1-mediated auto- and alloimmune responses and acts via its ligand, galectin-9, to induce cell death in Th1 but not Th2 cells. CD279 (PD-1) is a member of the extended CD28/CTLA-4 family of T cell regulators. PD-1 is expressed on the surface of activated T cells, B cells, and macrophages suggesting that compared to CTLA-4, PD-1 more broadly negatively regulates immune responses.

Among the tested cytokines that are responsible for immunogenicity and inhibitor formation, in mice injected with the 50 IU/kg of rFVIII-hFc or rFVIII-mFc, there was a significant inhibition in the levels of IL-4 and TNF-α and the levels of IL-2 did not change compared to vehicle injected group. Conversely, the levels of these cytokines were higher in groups receiving 250 IU/kg of these molecules. Mice injected with 50 IU/kg of either XYNTHA® or ADVATE® did not exhibit any inhibition, whereas the 250 IU/kg group showed an increase in intracellular content of IL-2, IL-4, and TNF-α. In addition, there was a higher percentage of foxp3 positive T cells in mice injected with 50 IU/kg of rFVIII-mFc compared to other treatments. Mice receiving 50 IU/kg of rFVIII-hFc and rFVIII-mFc had a higher percentage of splenic dendritic cells positive for PD-L1 (CD274), an inhibitory signal for T-cell activation and proliferation. These groups also had a higher percentage of immature dendritic cells as illustrated by a decrease in CD80 staining.

These results indicated that rFVIIIFc at 50 IU/kg in hemA mice exhibited lower immunogenicity than commercially available rFVIII [full-length FVIII (ADVATE®) and B-domain-deleted FVIII (XYNTHA®/REFACTO AF®)]. Accordingly, rFVIIIFc can promote lower antibody production and induce immune tolerance.

Example 13

Biodistribution and Clearance of rFVIIIFc in Mice

Recombinant fusion of a single FVIII molecule to the constant region of IgG1 Fc (rFVIIIFc) has been shown to decrease clearance compared to rFVIII in an FcRn dependent manner (Powell et al., 2012 Blood), using a natural pathway that recirculates antibodies into the blood stream. In addition, as disclosed above, a phase 1/2a clinical trial in hemophilia A subjects demonstrated that rFVIIIFc has a 1.5 to 1.7-fold longer half-life than recombinant full length FVIII (ADVATE®). Accordingly, a study was conducted (i) to identify the cell types and organs that contribute to the protection of rFVIIIFc and (ii) to assess the relative contributions of the FVIII and Fc domains to the biodistribution and clearance of rFVIIIFc in mice.

The clearance of rFVIIIFc to rFVIII was compared in genetically engineered KO mouse models deficient in either FVIII (HemA) or von Willebrand Factor (VWF). Intravenously dosed clodronate-containing lipid vesicles were used to deplete Kupffer cells and monocytes/macrophages in these mouse models. The effectiveness of depletion was quantitated by immunohistochemistry and FACS analysis. Pharmacokinetic analysis was performed with a FVIII-specific Coatest assay following intravenous injection of rFVIIIFc or rFVIII.

Kupffer cell depletion in HemA mice increased rFVIIIFc clearance. Furthermore, in the absence of VWF (HemA/VWF double knockout mice), the depletion of Kupffer cells and macrophages increased the clearance of rFVIIIFc to levels similar to that of rFVIII, indicating that these cells are responsible for the majority of the difference in clearance between rFVIII and rFVIIIFc in this model.

These studies suggest that Kupffer cells can contribute to the FcRn-mediated recycling of rFVIIIFc. Studies using bone marrow transplants with FcRn KO mice are in progress to verify this mechanism. These studies, combined with in vitro cellular uptake experiments will attempt to distinguish the contribution of Kupffer cells from other FcRn-expressing cell types, including endothelial cells.

Example 14

Cell-Mediated Immune Response to rFVIIIFc in Hemophilia A Mice

The objective of the present study was to identify cell-mediated immune responses to recombinant FVIII, which is of interest in designing better therapeutic management of hemophilia A. Thus, we investigated the splenic lymphocyte response to recombinant FVIII (rFVIII) when linked to human Fc (rFVIIIFc; IgG1) in comparison with commercially available full-length rFVIII (ADVATE®) and B-domain-deleted rFVIII (XYNTHA®/REFACTO AF®). HemA mice were injected with 4 weekly followed by 2 every other week doses of 50 100 or 250 IU/kg. At the end of 8 weeks, mice from each group were euthanized and their splenic leukocyte immunogenicity profile was determined by testing for intracellular cytokines, markers for regulatory T cells and dendritic cells using flow cytometry and RNA profiling. In mice injected with the 50 IU/kg of rFVIIIFc, there was a significant inhibition in the levels of IL-2, IL-4 and TNF-α (cytokines that promote immunogenicity). The levels of these cytokines were higher in mice receiving 250 IU/kg of this molecule. Mice injected with 50 IU/kg of either XYNTHA® or ADVATE® did not exhibit any inhibition, whereas the 250 IU/kg group showed an increase in intracellular content of IL-2, IL-4, and TNF-α. In addition, there was a higher percentage of foxp3 positive T cells in mice injected with 50 and 100 IU/kg of rFVIIIFc compared to other treatments. Mice receiving 50 and 100 IU/kg of rFVIIIFc had a higher percentage of splenic dendritic cells positive for PD-L1 (CD279), an inhibitory signal for T-cell activation and proliferation. These groups also had a higher percentage of immature dendritic cells as illustrated by a decrease in CD80 staining Thus, both the 50 and 100 IU/kg doses of rFVIIIFc showed lower immunogenicity and antibody production in this model.

Introduction

Development of inhibitors to FVIII is recognized as a serious complication in the management of hemophilia A. The incidence of inhibitor formation is estimated to range from 20% to 30% in all hemophilia A to 30-40% in severe disease. (Green, Haemophilia 17:831-838 (2011); Eckhardt et al. J. Thromb. Haemost. 9:1948-58 (2011)). Inhibitor positive disease is currently managed by immune tolerance induction involving the frequent high-dose administration of FVIII. Mechanisms of inhibitor formation in patients are largely unknown and depend on a multitude of risk factors and cells and molecules of the immune system.

Inhibitor development in hemophilia involves a complex interplay of multiple cell types, surface molecules and secreted proteins of the immune system including, T-lymphocytes, B-lymphocytes, antigen presenting cells (APC; dendritic cells and macrophages), cytokines, and regulatory components of these cell types. Antibody production by B-cells depends on optimal help from T-cells, which are activated by antigen presentation from APC.

Tolerance to injected therapeutic peptides and proteins including recombinant FVIII is mediated by a class of T-cells called regulatory T-cells (Treg) (Cao et al., J. Thromb. Haemost. 7(S1):88-91 (2009)). Several key molecules have been identified that correlate with inhibitor formation in hemophilia patients. These include the pro-inflammatory cytokine TNF-α, the anti-inflammatory cytokine interleukin (IL)-10, and the Treg marker CTLA4, to name a few (Astermark et al., J. Thromb. Haemost. 5:263-5 (2007); Pavlova et al. J. Thromb. Haemost. 7:2006-15 (2009)).

In this study, we investigated the splenic lymphocyte response to recombinant factor VIII Fc fusion protein (rFVIIIFc) compared with commercially available full-length rFVIII (fl-rFVIII; ADVATE®) and B-domain deleted rFVIII (BDD-rFVIII; XYNTHA®/REFACTO AF®).

Materials and Methods

Materials:

Factor FVIII-deficient mice (Bi et al. *Nat Genet.* 10:119-21 (1995)) were originally acquired from Dr. Kazazian (University of Pennsylvania, Philadelphia, Pa.) and maintained as breeding colonies either at Biogen Idec Hemophilia or Charles River Laboratory.

Antibodies used for staining and FACS analysis were obtained either from BD Biosciences (Franklin Lakes, N.J., USA) or eBioscience (San Diego, Calif., USA). Antibodies used were directed against murine surface markers such as CD4 (T-helper cells), CD11c and CD80 (dendritic cells), PD-1, PD-L1, CD25 (Treg cells), intracellular cytokines (IL-2, IL-4, TNF-α), and transcription factors (Foxp3).

Immunogenicity Study Design:

Three treatment groups received intravenous doses of 50, 100, or 250 IU/kg, which were administered on days (FIG. 37). Each treatment and dose level were administered to 10 mice. Animals were euthanised on day 56 by CO2 inhalation and spleens were dissected in sterile PBS.

Splenocytes were separated using the mouse spleen dissociation kit and a gentle MACS dissociator (Miltenyi Biotec, Cologne, Germany). Single cell suspensions of splenocytes were either fixed in 3% formalin for FACS staining or stored in dissociation buffer for RNA isolation (Roche).

Assessments:

Anti-FVIII antibodies were determined using an in-house developed ELISA. Briefly, FVIII was coated on 96-well plates and used to capture antibodies from mouse plasma collected at specific time points. FVIII-specific antibodies were detected using a secondary anti-mouse IgG antibody. T-cell response profiling was conducted on isolated mouse splenocytes (FIG. 38). Lymphocytes and dendritic cells in spleen were stained for surface and intracellular targets.

For surface staining, 1×10$^6$ total splenocytes were incubated with antibodies at appropriate concentrations. For intracellular staining, cells were permeabilised with BD Fix-Perm solution (BD Biosciences) followed by incubation with antibodies to cytokines in the same buffer. Foxp3 staining was carried out using antibody in Foxp3 staining buffer (BD Biosciences). Fluorescence intensity was recorded using a BD FACS Canto II and analysis performed using FLOWJO® software.

Lymphocytes were costained with CD4 and intracellular markers IL-2, TNF-α, and IL-4. Treg cells were stained for surface markers CD4 and CD25 followed by intracellular Foxp3. Splenocytes were stained for CD11c and PD-L1 (dendritic cells) or CD4 and PD-1 (CD4+ T-cells) to identify cells involved in the PD-L1-PD-1 pathway. Total RNA was isolated (Roche) and reverse transcribed to cDNA (Qiagen, Hilden, Germany). Primers for TGF-β, IL-10, IL-12a, and EBI-3 were purchased from IDT technologies. SYBR green-based real-time polymerase chain reaction (PCR) was carried out using Quantitect system (Qiagen) using an ABI 7900 Fast Block real-time PCR machine. Data were analysed using the 7500 software version 2.0.5.

Results

Total Anti-FVIII Antibody Levels on Day 42:

Total anti-FVIII IgG levels on day 42 were assayed from plasma of haemophilia A mice injected with 50, 100 or 250 IU/kg of rFVIIIFc, BDD-FVIII (XYNTHA®) or full length FVIII (fl-rFVIII) (ADVATE®) using ELISA. At both 50 and 100 IU/kg the rFVIIIFc group had significantly lower antibody levels compared to BDD-rFVIII and full length fl-FVIII, which indicated lower antigenicity to FVIII imparted by rFVIIIFc injections. At 250 IU/kg the groups were not significantly different from each other and had high antibody levels (FIG. 39).

Intracellular Cytokines (IL-2 and TNF-α) in CD4+ Cells:

Mice receiving 50 IU/kg in each treatment group were nonresponders based on antibody levels to FVIII, whereas the mice receiving 250 IU/kg in each treatment group were responders with the highest antibody levels (data not shown). rFVIIIFc at 50 and 100 IU/kg doses (FIG. 40A and FIG. 40B) lowered the percentage of IL-2 and TNF-α positive CD4+ cells, which indicated lower immunogenicity whereas BDD rFVIII and full-length rFVIII showed higher cytokine positive cells. All 3 treatments at the 250 IU/kg dose (FIG. 40C) elevated the percentage of cytokine positive cells, which indicated higher immunogenicity at this dose. Similar results were obtained for IL-4.

Figure 41:
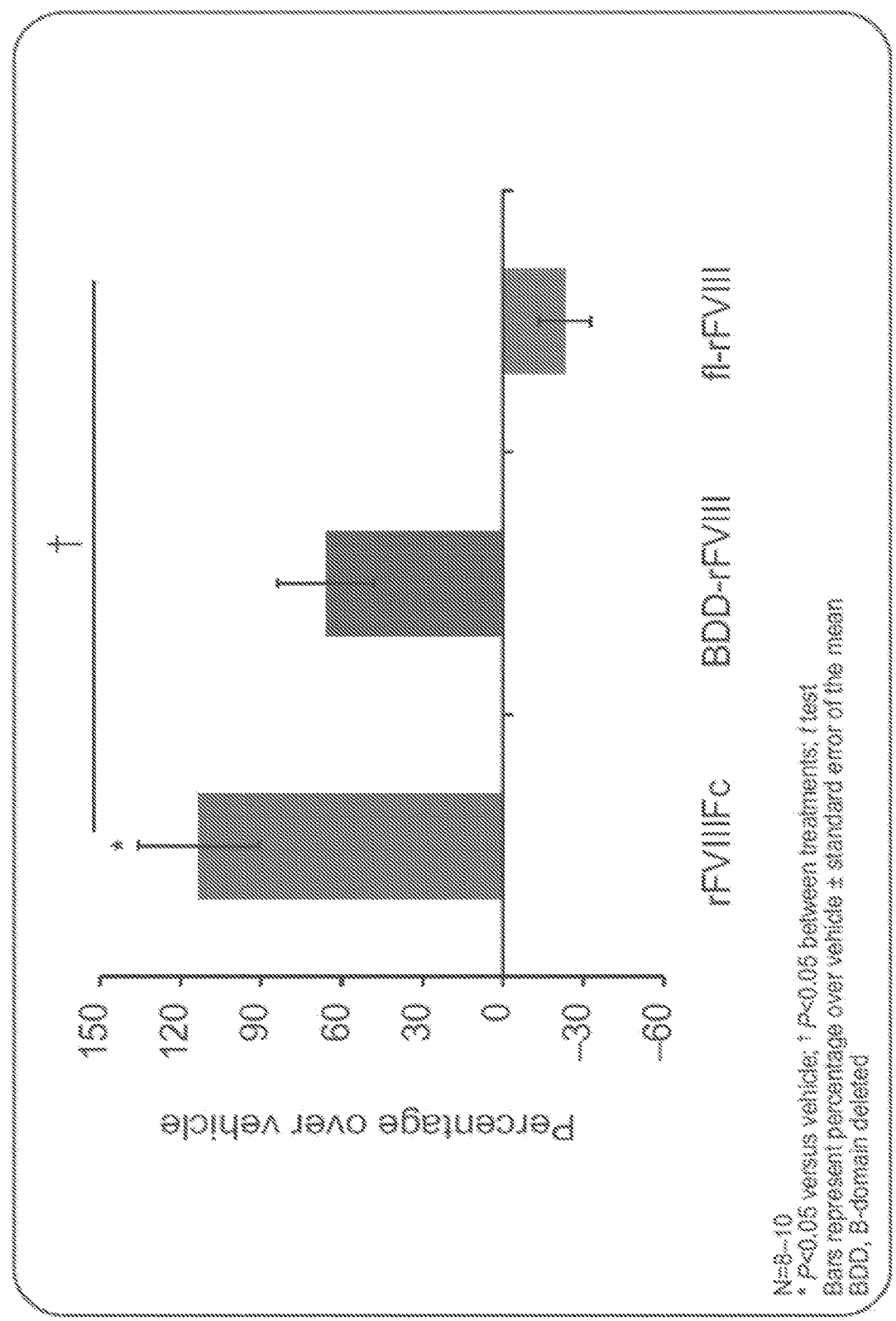

CD4/CD25/Foxp3 Triple Positive Cells (Markers for Treg Cells):

At the 100 IU/kg dose, the percentage increase of Treg cells over vehicle were significantly higher in the rFVIIIFc group (P<0.05) compared with BDD-rFVIII and fl-rFVIII groups (FIG. 41). Similar results were obtained for the 50 IU/kg of rFVIIIFc indicating that both the 50 and 100 IU/kg rFVIIIFc treatments can promote predominance of Treg cells and suppress immune responses to FVIII.

Real-Time Polymerase Chain Reaction for Tolerance-Related Cytokines:

Real Time PCR analysis for immuno tolerance related cytokines namely TGF-β (FIG. 42A), IL-10 (FIG. 42B) and IL-35 (IL-12a and EBI-3 subunits, shown respectively in FIGS. 42C and 42D) was carried out using RNA isolated from mice belonging to the 100 IU/kg treatment group. mRNA levels were upregulated for the tested cytokines in the rFVIIIFc group (P<0.05) compared with the other treatments at 100 IU/kg, which indicated the presence of splenocytes actively expressing tolerogenic cytokines thereby promoting an immunosuppressive microenvironment. mRNA expression immunotolerance markers Foxp3 (FIG. 42E), CD25 (FIG. 42F), CTLA-4 (FIG. 42G), and Indoleamine 2,3-dioxygenase (IDO-1) (FIG. 42H) were higher in total splenocytes from 100 IU/kg group FACS Analysis of PD-L1-PD-1 Pathway:

PD-L1 (CD274) on dendritic cells engage PD-1 (CD279) on T-cells to promote inhibitory pathways that suppress T-cell activation and proliferation, thereby leading to suppression of immune responses. Splenocytes from the 100 IU/kg group were stained for either surface CD11c and PD-L1 (FIG. 43A), or CD4 and PD-1 (FIG. 43B). At the 100 IU/kg dose, the percentage of dendritic cells positive for PD-L1 and the percentage of T-cells positive for PD-1 were higher in the animals receiving rFVIIIFc (P<−0.05) compared with those receiving BDD-FVIII and fl-rFVIII. This indicated positive regulation of immunosuppressive pathways at both dendritic cells and T-cells by rFVIIIFc.

Discussion

The experimental results shown above indicated that rFVIIIFc at doses of 50 and 100 IU/kg had low immunogenicity and promoted tolerance to FVIII, as demonstrated by:

(a) A lower level of pro-immunogenic cytokines (IL-2 and TNF-α) in CD4+ T-cells compared with other FVIII molecules;

(b) An up-regulation of regulatory T-cells and markers (Foxp3, CD25, PD-1, CTLA4) that are responsible for immune tolerance in rFVIIIFc-injected mice. The significance of Foxp3+ Treg and the role of CTLA4 in promoting tolerance to FVIII in haemophilia have been previously described (Cao et al., J. Thromb. Haemost. 7(S1):88-91 (2009); Astermark et al. J. Thromb. Haemost. 5:263-5 (2007)).

(c) A higher level of tolerogenic cytokines (Il-10, TGF-β, IL-35) in splenocytes of mice injected with rFVIII. These markers have been shown in several studies to be key immunoregulatory cytokines and major determinants of immuno-tolerance (Bi et al., Nat. Genet. 10:119-21 (1995)).

(d) An elevation of tolerogenic dendritic cell population (PD-L1, IDO-1, and decreased CD80) in mice following injection with rFVIIIFc.

Concurrently, rFVIIIFc-treated mice also showed lower or no antibodies to FVIII at doses of 50 and 100 IU/kg (Liu et al., WFH Abstract #FB-WE-04.2-5 (2012)) and resisted challenge with 250 IU/kg once tolerised with 50 IU/kg of rFVIIIFc.

Conclusions:

rFVIIIFc-treated mice showed lower or no antibodies to FVIII at doses of 50 and 100 IU/kg compared with traditional FVIII therapies. Based on T-cell and dendritic cell studies in mice, rFVIIIFc was found to be less immunogenic than traditional FVIII therapies and promoted tolerogenic pathways. rFVIIIFc upregulated key immunoregulatory cytokines in splenocytes of haemophilia A mice that are indicative of immunotolerance. Taken together these findings indicate the existence of a tolerogenic microenvironment in the spleen of mice injected with rFVIIIFc at low doses (50 and 100 IU/kg).

These studies have demonstrated for the first time that rFVIIIFc activates dendritic cell signaling, which is a crucial determinant of immunotolerance. These findings indicate the existence of functional immune tolerance to FVIII imparted by rFVIIIFc in haemophilia A mice.

Example 15

Evaluation of Antibody Responses to rFVIIIFc Compared to XYNTHA® and ADVATE® in Hemophilia a Mice Development of inhibitory antibodies to replacement FVIII occurs in 20-30% of previously untreated patients, being the most severe complication of hemophilia treatment. Immune tolerance induction (ITI), which entails frequent administration of FVIII, is currently used to treat patients who develop inhibitors. A subset of these patients, however, do not respond to ITI. See, e.g., Green, Haemophilia 17:831-838 (2011); Eckhardt et al. J. Thromb. Haemost. 9:1948-58 (2011); Cao et al., J. Thromb. Haemost. 7(S1):88-91 (2009). Recombinant FVIIIFc has a half-life approximately 1.6-fold longer than the half-life of rFVIII and it is currently in phase 2/3 clinical development. The experiments disclosed herein assess the immunogenicity and immune tolerance properties of rFVIIIFc compared with other rFVIII replacement proteins in hemophilia A (HemA) mice.

(a) Immunogenicity Comparison for rFVIIIFc, XYNTHA® and ADVATE® in HemA Mice:

Antibody Response: Four groups of HemA mice, with 9-12 HemA mice per group, were treated with 50 IU/kg, 100 IU/kg and 250 IU/kg doses of rFVIIIFc, XYNTHA®, ADVATE®, and vehicle control. Doses were administered at day 0, day 7, day 14, day 21, and day 35. Blood was drawn at day 0, day 14, day 21, day 28 and day 42 (FIG. 44).

rFVIIIFc induced a significantly lower antibody response at 50 IU/kg (FIG. 45) and at 100 IU/kg (FIG. 46) compared to XYNTHA® and ADVATE®. However, all FVIII proteins showed similar antibody response at 250 IU/kg (FIG. 47). Neutralizing antibody titers correlated with total binding antibody levels (FIG. 48).

(b) Immunogenicity Comparison for rFVIIIFc, XYNTHA® and ADVATE® in HemA Mice:

T-Cell Response Profiling: For T-cell response profiling in splenocytes, an additional dose of rFVIIIFc, XYNTHA®, ADVATE®, and vehicle control was administered at day 53. Spleens were collected at day 56 (FIG. 49). The results indicated that rFVIIIFc promotes predominance of CD4/CD25/Foxp3-positive Treg Cells (FIG. 50, right panel).

Summary:

Administration of rFVIIIFc resulted in significantly lower antibody response compared with XYNTHA® and ADVATE® at doses of 50 and 100 IU/kg. The tolerogenic profile following 50 and 100 IU/kg doses of rFVIIIFc indicated that rFVIIIFc can promote predominance of Treg cells and suppress immune response to FVIII (c) rFVIII Immune Tolerization Study:

To test whether repeated administration of rFVIIIFc can induce functional tolerance in vivo the following dosing regimen was adopted. HemA mice (8-10 wk old) were injected with 50 IU/kg of rFVIIIFc or vehicle every week for 4 weeks (on days 0, 7, 14, 21) followed by one injection on day 35. Starting day 49 these mice were challenged with weekly 250 IU/kg of rFVIIIFc to determine if the animals can tolerate high doses of rFVIIIFc. The challenge doses were administered on days 0, 7, 14, and 21 starting day 49 of the study (see FIG. 51). Blood samples were collected at specified time points to check for anti-FVIII antibodies using ELISA. As shown in FIG. 52, repeated dosing of rFVIIIFc led to statistically significant reduction in antibodies to rFVIIIFc when challenged at high doses of 250 IU/kg, while animals receiving vehicle had higher levels of antibodies upon challenge. This clearly indicates that repeated administration of rFVIIIFc at 50 IU/kg based on the dosing scheme followed can induce tolerance to higher doses of rFVIIIFc (250 IU/kg).

Conclusion:

At therapeutic doses, rFVIIIFc was found to be (1) less immunogenic compared with XYNTHA® and ADVATE®, and (2) capable of inducing immune tolerance to FVIII in HemA mice.

Currently, its being determined whether even lower doses of rFVIIIFc can lead to immune tolerization to higher doses of rFVIIIFc. In the present study, lower doses of rFVIIIFc, namely 25 IU/kg and 10 IU/kg, are being used during the tolerance induction phase. This will be followed by challenging with 250 IU/kg of rFVIIIFc and measurement of antibodies to FVIII as carried out for the previous study.

Example 16

Clearance Pathways of rFVIIIFc in Haemophilia A Mice

Long-lasting recombinant coagulation FVIII Fc fusion protein (rFVIIIFc) is currently in phase 3 clinical study for episodic and prophylactic treatment of individuals with haemophilia A. Compared with recombinant full-length FVIII (ADVATE®, Baxter Healthcare Corporation), rFVIIIFc has a 1.7-fold extended half-life and significantly decreased clearance in patients with haemophilia A. See, Powell et al., Blood 119:3031-7(2012). This improved pharmacokinetic (PK) profile is mediated through the interaction of Fc with neonatal Fc receptor (FcRn). See Dumont et al., Blood 119:3024-30 (2012). rFVIIIFc is comprised of a single B-domain deleted human coagulation FVIII attached directly to the Fc domain of human immunoglobulin G1, which is naturally recycled upon cellular uptake (endocytosis or pinocytosis) through interaction with FcRn (FIG. 53). Monocytic cells (macrophages and dendritic cells), including liver resident macrophages (Kupffer cells), are implicated in the clearance of von Willebrand factor (VWF) and FVIII (FIG. 54). See van Schooten et al. *Blood* 112(5):1704-12 (2008).

In order to elucidate the cell types involved in rFVIIIFc uptake, clearance, and FcRn-mediated recycling, we studied the impact of macrophage and Kupffer cell depletion on the clearance of rFVIIIFc in genetically engineered mouse models.

Materials and Methods

The clearance of rFVIIIFc and rFVIII (BDD) was compared in 3 knockout (KO) mouse models: (1) haemophilia A (FVIII KO), deficient in FVIII; (2) double KO (DKO) of FVIII and VWF, lacking expression of both FVIII and VWF; and (3) FcRn-KO, lacking expression of the FcRn. In all 3 models, macrophage and Kupffer cells were depleted with CLODROSOME® (Encapsula NanoSciences, Inc), which is a toxic ATP analogue (clodronate) encapsulated in liposomes that is specifically phagocytosed by macrophages and triggers apoptosis. See van Rooijen & Hendrikx, Methods Mol. Biol. 605:189-203 (2010).

Control mice in each group were treated with ENCAPOSOME® nontoxic liposomes (FIG. 55). A single intravenous dose of either FVIII or rFVIIIFc (125 or 250 IU/kg) was injected 24 hours after treatment with liposomes. Blood samples were collected by retroorbital or vena cava blood collection at specified time points (4 samples per time point).

Human FVIII activity in plasma samples was then measured by a FVIII chromogenic assay, and PK parameters were estimated with WINNONLIN® software (Pharsight Corp.) using a noncompartmental analysis model.

Kupffer cell and macrophage depletion was evaluated by immunohistochemical staining, and was quantified using Visiopharm software (Hoersholm, Denmark) or by reverse transcrition polymerase chain reaction (RT-PCR).

Results (a) Depletions of Macrophages and Kupffer Cells:

FIG. 56 shows a representative staining of liver sections with an antibody to Iba-1, a specific macrophage marker, 24 hours after control ENCAPSOME® (A, A') or CLODROSOME® (B, B') treatment of haemophilia A mice. A' and B' show the quantification masks highlighting the stained Kupffer cells (azure), total tissue area (navy blue), and empty areas (grey). Similar depletion profiles were obtained in other mouse strains. Quantitative analysis of positively stained areas showed that >90% of liver Kupffer cells were depleted and remained low for >3 days post CLODROSOME® treatment (n=4) compared with control ENCAPSOME-treated animals (FIG. 57). Circulating monocytic cells were also reduced by >50% within 24 hours of CLODROSOME® treatment, assessed by flow cytometric analysis of blood cells stained with a labeled antibody to F4/80+(n=4). Within 48 hours, depleted blood cells recovered (FIG. 57). Consistent with the observed depletion of macrophages in the liver, RT-PCR analysis of the expression of the macrophage marker epidermal growth factor module-containing mucin-like receptor 1 (Emr1) (F4/80) showed that CLODROSOME® treatment decreased Emr1 mRNA expression >95% in liver and lung in haemophilia A mice (FIG. 58). Emr1 is the designation used for the human protein. The mouse homolog is known as F4/80. Emr1 is a transmembrane protein present on the cell-surface of mature macrophages.

(b) Clearance of FVIII in Mouse Models:

In contrast to previously reported results that suggest Kupffer cells play a role in the clearance of both FVIII and VWF (van Schooten C J, et al. Blood. 112(5):1704-12 (2008)), Kupffer cell depletion did not cause the expected decrease in FVIII clearance in haemophilia A mice (FIG. 59). To the contrary, depletion of Kupffer cells in haemophilia A mice significantly increased the clearance of rFVIIIFc (FIG. 59). Similarly, in DKO mice, Kupffer cell depletion did not decrease FVIII clearance and significantly increased clearance of rFVIIIFc (FIG. 60). In FcRn-KO mice, Kupffer cell depletion did not affect the clearance of FVIII or rFVIIIFc (FIG. 61).

Conclusions:

Macrophage and Kupffer cell depletion in haemophilia A and DKO mice (deficient in FVIII and VWF) increased rFVIIIFc clearance, but did not decrease FVIII clearance, indicating that macrophage and Kupffer cells can account for much of the difference in clearance between FVIII and rFVIIIFc in these mice. In the absence of both VWF and FVIII (DKO mice), depletion of macrophages and Kupffer cells increased the clearance of rFVIIIFc to levels approaching that of FVIII.

The lack of effect of Kupffer cells depletion on FVIII clearance in either haemophilia A or DKO mice contrasted with previously published studies. See van Rooijen & Hendrikx, Methods Mol. Biol. 605:189-203 (2010). Macrophage and Kupffer cell depletion in FcRn-KO mice did not result in significant clearance differences between FVIII and rFVIIIFc, indicating a potential role of FcRn in macrophage-mediated recycling of rFVIIIFc.

Together, these studies indicated that rFVIIIFc was protected in a macrophage- and/or Kupffer cell-dependent manner and that a natural pathway in these cells can contribute to FcRn-mediated recycling of rFVIIIFc.

Example 17

Immune Tolerization to Pre-Existing Antibodies to Factor VIII

It is highly likely that patients that receive rFVIIIFc were previously on a different rFVIII therapy. About 30% of hemophilia A patients develop antibodies to FVIII, which is a major problem in current FVIII replacement therapy. Currently, the only approved approach to tolerize patients having FVIII inhibitors is to dose them with high doses of FVIII for an indefinite period of time, i.e., until the patient is tolerized. Thus, it is of interest to determine if low dose rFVIIIFc can reverse the immunogenicity of FVIII by inhibiting T and B cell signaling pathways and skewing towards tolerance.

In this study, hemA mice (8-10 wks old) will be injected weekly once for 5 weeks with either BDD-FVIII (XYNTHA®) or fl-FVIII (ADVATE®) at 50 IU/kg. Levels of anti-FVIII antibodies will be determined in blood samples drawn from these animals on specified days as indicated in the scheme. Following the induction of inhibitory antibodies, animals will be switched to injections with 50 IU/kg of rFVIIIFc weekly for 5 weeks. This will be the tolerization phase. Levels of anti-FVIII antibodies will be determined again from blood samples drawn as indicated. Following the tolerization phase, animals will be injected again with XYNTHA® or ADVATE® at 50 IU/kg for another four injections and blood samples drawn will be tested for anti-FVIII antibodies. In the event of successful tolerization, the second challenge with XYNTHA® or ADVATE® should not produce any antibodies to FVIII which may indicate the capability of rFVIIIFc to induce immunotolerance to FVIII.

Example 18

T-Cell Adoptive Immunotherapy and Transfer of Immune Tolerance

Regulatory T-cells (Tregs) are the master players in the induction and maintenance of peripheral tolerance to FVIII and other peptide therapeutics. One of the key studies used in determining the presence of functional immune tolerance is by transferring Treg cells isolated from tolerized animals to recipients, which are then challenged with higher doses of FVIII. The presence of functional transfer of tolerance is evidenced by lack of or lesser antibody production in the challenged recipient mice.

In this study, hemA mice (8-10 weeks old) will be tolerized by injecting 50 IU/kg of rFVIIIFc or vehicle every week for 4 weeks (on days 0, 7, 14, 21) followed by two injections on days 35 and 53. Plasma samples will be collected for determination of anti-FVIII antibody levels using ELISA. On day 56, mice with no antibodies will be euthanized and their spleens will be isolated. Splenocytes from these mice will be harvested and made into single cell suspensions using the splenocyte isolation kit (Miltenyi Biotec). Tregs from total splenocytes will be isolated using the CD4 CD25 murine Treg magnetic bead based isolation kit (Miltenyi Biotec). Isolated Tregs will be enumerated using a cell counter. An aliquot of the cell suspension will be fixed using 3% formalin for phenotypic analysis by FACS to determine the purity of the isolate. Tregs will then be injected into recipient mice on day 0 at $1 \times 10^6$ cells/mouse in 200 µL saline by IV.

Starting day 1 animals will be challenged with 250 IU/kg of rFVIIIFc followed by repeated injections weekly once on days 8, 15, 22, and 29. Blood samples will be collected on days 15, 22, 29 and 36 for plasma anti-FVIII antibody analysis using ELISA. In the event of successful transfer of tolerance, mice receiving Tregs from rFVIIIFc tolerized animals will not develop antibodies to FVIII whereas, mice injected with Tregs isolated from vehicle injected donor mice show the presence of anti-FVIII antibodies.

Example 19

Identification of Mechanisms of Immune Tolerance Induction by rFVIIIFc: Studies with Dendritic Cells and Macrophages One of the key features that distinguishes rFVIIIFc from other FVIII drug products is the presence of the Fc moiety which is a naturally occurring constituent. This could be one responsible factor that suppresses the immune response and drives an immune tolerance reaction. Fc molecules present in IgG and in rFVIIIFc are capable of interacting with the classical IgG Fc receptors and FcRn. Among the Fc receptors, the subtype FcγRIIb (FcγR2b) is an inhibitory receptor and delivers suppressive signals that curb the activation of cell types harboring that receptor. Fc receptors including FcRn are chiefly localized in antigen presenting cells (APC-dendritic cells, macrophages and B-cells), but not in T-cells. Therefore, it is possible that the rFVIIIFc could engage FcR2b and/or FcRn in these cells to skew towards a tolerogenic phenotype.

To ascertain whether rFVIIIFc engages FcR2b and/or FcRn in dendritic cells and macrophages to develop a tolerogenic phenotype, the following experiments will be conducted:

1. Identification of markers at the mRNA and cell surface levels (protein) in murine macrophage cell lines, splenic macrophages and splenic dendritic cells that are regulated by rFVIIIFc in comparison with FVIII alone or a mutant of FVIIIFc (N297A) which does not interact with Fc receptors.

2. Overexpression and knockdown of FcgR2b or FcRn in RAW 264.7 murine macrophage cell line and investigating the effects of rFVIIIFc on these receptors by studying downstream targets 3. Identification of the possible involvement of other pathways of importance such as TLR mediated signaling in the APC response to rFVIIIFc Example 20

Alternate Routes for Induction of Tolerance

Immune tolerance to rFVIIIFc may also be achieved via mucosal route. Two possible sites for inducing tolerance are the gastrointestinal mucosa and the respiratory mucosa. Oral tolerance to rFVIIIFc can be induced by either feeding animals or using oral gavages to deliver the molecule to the intestinal mucosa. The gut mucosa has specialized secondary lymphoid organs namely the Peyer's patches which contains antigen presenting cells (APC) that are important in regulatory immune responses. These APCs can process antigens and activate specific subsets of dendritic cells and Tregs which can travel to other sites in the body and program other cells of the immune system to suppress an immune response in the presence of antigen, in this case exogenously supplied FVIII. This phenomenon could be mediated by Fc interactions with FcRn and/or FcgR2b present on the APC of the gut mucosal immune system. Respiratory mucosa can be tolerized by inhalation of aerosols of rFVIIIFc which may operate based on the same mechanism as for the gut.

The ascertain whether immune tolerance can be achieve via mucosal route, XYNTHA® or ADVATE® will be administered orally or via aerosol to hemA mice. Following the induction of inhibitory antibodies, animals will be switched to rFVIIIFc. This will be the tolerization phase. Levels of anti-FVIII antibodies will be determined from blood samples drawn as indicated. Following the tolerization phase, animals will be injected again with XYNTHA® or ADVATE® and blood samples drawn will be tested for anti-FVIII antibodies. In the event of successful tolerization, the second challenge with XYNTHA® or ADVATE® should not produce any antibodies to FVIII which may indicate the capability of rFVIIIFc to induce immunotolerance to FVIII after mucosal administration.

Example 21

Immunotolerance to Other Clotting Factors

To ascertain whether immunotolerance can be conferred by Fc to clotting factor payloads other than FVIII, chimeric polypeptides comprising the FVIIa clotting factor fused to Fc (rFVIIaFc), or the FIX clotting factor fused to Fc (rFIXFc) are generated. Cloning, expression, and purification of rFVIIaFc and rFIXFc are performed according to methods known in the art. Biochemical, biophysical and pharmacokinetic characterization of rFVIIaFc and rFIXFc are conducted as disclosed in the examples above and/or using methods known in the art. The evaluation of antibody responses to rFVIIaFc and rFIXFc compared to commercial clotting factors and immunotolerance studies are performed as disclosed in the examples above. Chimeric polypeptides comprising a clotting factor payload and an Fc moiety such as rFIXFc or FVIIaFc can effectively induce immunotolerance to the unmodified clotting factor (i.e., FIX or FVII without an Fc portion).

Example 22

Transplacental Transfer of Immune Tolerance to FVIII Using rFVIIIFc

The objective of this study was to determine whether the administration of rFVIIIFc to pregnant mice could transfer the molecule to the fetus via the placenta (due to the interaction of the Fc portion with the FcRn receptor on placental cells), and whether the exposure of the fetal immune system to the rFVIIIFc at an early stage could lead to tolerance by programming the thymus to recognize FVIII as a self antigen and not to develop an immune reaction towards it.

Pregnant mice were infused with either one dose (6U) of rFVIIIFc or XYNTHA® intravenously by retro-orbital injection on day 16 of gestation or two doses (6U each) by tail vein injection on days 15 and 17 of gestation. The immunogenicity of XYNTHA® was evaluated in the pups born out of the immunized mothers, after pups had reached maturity (ages 6-9 weeks old). Day 16 of pregnancy was chosen because it coincided with the development of the autoimmune regulatory molecule, AIRE, which plays a crucial role in removing self-reactive T-cells from the thymus. The results showed that in the first experiment, that tested dosing of pregnant mice with a single infusion of rFVIIIFc or XYNTHA® at day 16 of gestation, pups born out of rFVIIIFc treated pregnant mice had statistically significantly lower Bethesda titers to XYNTHA®, compared to pups born out of XYNTHA® treated pregnant mice (FIG. 62). In the second experiment, that tested dosing of pregnant mice on d15 and d17 of gestation, pups born out of rFVIIIFc treated pregnant mice had statistically significantly lower Bethesda titers to XYNTHA®, compared to pups born out of control mothers and a trend for lower titers compared to pups born from mothers treated with XYNTHA® (FIG. 63)

The transplacental transfer of protein (rFVIIIFc) from maternal to the fetal circulation will be evaluated by detecting FVIII activity in pups born out of immunized mice. The actions at the T-cell level will be evaluated by T-cell profiling and Treg transfer studies from rFVIIIFc tolerized pups.

Example 23 rFVIIIFc Regulates Tolerogenic Markers in Antigen Presenting Cells

Materials and Methods:

Mice:

Hemophilia A (HemA) mice (C57BL/6) bearing a FVIII exon 16 knockout on a 129×B6 background (Bi, L., Lawler, A. M., Antonarakis, S. E., High, K. A., Gearhart, J. D., and Kazazian, H. H., Jr. 1995. Targeted disruption of the mouse factor VIII gene produces a model of haemophilia A. *Nat Genet* 10:119-121) were obtained from Dr. H. Kazazian (University of Pennsylvania, Philadelphia, Pa., USA) and maintained as breeding colonies at either Biogen Idec Hemophilia or Charles River Laboratory or Jackson Laboratories. All animal procedures used were approved by the Institutional Animal Care and Use Committee (IACUC) and performed based on guidelines from the Guide to the Care and Use of Laboratory Animals.

Antibodies and Reagents:

Antibodies used for staining and Flow Cytometry were obtained from BD Biosciences (Franklin Lakes, N.J., USA) or eBioscience (San Diego, Calif., USA). Antibodies used were directed against murine surface markers such as CD4 and PD-1 (T-helper cells), CD11c, CD80, and PD-L1 (dendritic cells), and CD25 (Treg cells), intracellular cytokines (IL-2, IL-4, TNF-α), and transcription factors (Foxp3). Reagents for intracellular staining for cytokines and transcription factors were purchased from BD Biosciences. Recombinant B-domain deleted FVIIIFc (rFVIIIFc) and recombinant B-domain deleted FVIII (rFVIII) were synthesized as in Peters et al. (Peters, R. T., Toby, G., Lu, Q., Liu, T., Kulman, J. D., Low, S. C., Bitonti, A. J., and Pierce, G. F. 2012. Biochemical and functional characterization of a recombinant monomeric Factor VIII-Fc fusion protein. *J. Thromb Haemost.* DOI: 10.1111/jth.12076).

Other Factor VIII drug substances namely rBDD FVIII XYNTHA® (Wyeth Pharmaceuticals, Philadelphia, Pa., USA), and full-length FVIII ADVATE® (Baxter Healthcare Corporation, Westlake Village, Calif., USA) were purchased and reconstituted according to manufacturers' guidelines.

Immunization/Tolerance Induction in Mice:

Three treatment groups consisting of 8-10 week old male HemA mice received intravenous doses of 50, 100, or 250 IU/kg, which were administered on days 0, 7, 14, 21, 35, and 53. Each treatment and dose level was administered to 10 mice. Blood samples were collected by retro-orbital bleeding on days 0 (pre-bleed), 14, 21, 28, and 42, and used for separating plasma and determining anti-FVIII antibody levels using ELISA. Animals were injected once more on day 53, euthanised on day 56 by $CO_2$ inhalation and spleens were dissected in sterile PBS. Splenocytes were separated using the mouse spleen dissociation kit and a gentle MACS dissociator (Miltenyi Biotec, Cologne, Germany). Single cell suspensions of splenocytes were either fixed in 3% formalin (Boston BioProducts) for FACS staining or stored in dissociation buffer for RNA isolation (Roche Applied Science, Indianapolis, Ind.). For immune tolerance testing studies, mice were initially injected with 50 IU/kg on days 0, 7, 14, 21, and 35. After confirming the absence of antibodies to FVIII on day 42, these mice were administered with 250 IU/kg of rFVIIIFc once weekly; i.e., days 49, 56, 63, and 70 (days 0, 7, 14, and 21 of rechallenge). Rechallenged animals were tested for anti-FVIII antibody levels on bleeds collected on days 14, 21, and 28.

Anti-FVIII Antibody ELISA:

The protocol followed was designed in house at Biogen Idec Hemophilia. Prior to the assay, all plasma samples were warmed to 56° C. in a water bath to inactivate residual coagulation factors introduced by the treatments and anti-coagulation enzymes that could break down the coated standards on the plate. On day 1, a 96 well, high binding microtiter plate (Thermo Immulon 2HB) was coated with 1 µg/ml (100 µl/well) B-domain deleted FVIII in 0.05M sodium carbonate, pH 9.6 and incubated overnight (12 to 18 hours) at 4° C. On the following day the supernatant was removed and the plate washed 4 times with PBST (phosphate buffered saline containing 0.05% Tween 20). The plate was then blocked with 200 per well of PBST containing 10% heat inactivated horse serum, pH 7.4 for 60 minutes at room temperature. The standard used for mouse IgG was a polyclonal pool of anti-FVIII monoclonal antibodies prepared by mixing equal amount of GMA8002 (A1), GMA8008 (C2), GMA8011(C1), GMA8015(A2), GMA8016 (A2), GMA8005 (A1/A3). All monoclonal antibodies were from Green Mountain Antibodies, Inc, Burlington, Vt. with the FVIII domain epitopes are shown in parenthesis. Mouse plasma test samples were diluted in blocking buffer and contained the same concentration of heated plasma as the standards. The blocking buffer was then removed and the diluted standards and samples were added at 100 µl/well in duplicates. The plate was incubated for 2 hours at 37° C. with shaking on an orbital shaker. After washing 4 times with PBST 100 µl/well of goat anti-mouse IgG-HRP, diluted 1:20000 in blocking buffer was added and incubated for 60 minutes at 37° C. with shaking on an orbital shaker. The plate was washed again 4 times with PBST, and then 100 µl/well of TMB was added and incubated at RT for 5 to 10 minutes. Results were read at OD 650 with a plate reader Bethesda Assay for Determining Neutralizing Antibody Titers:

This assay determined the titer of neutralizing anti-FVIII antibodies in a given plasma sample. Briefly, the assay was performed by mixing plasma samples with known concentrations of recombinant FVIII and incubation at 2 hours at 37° C. Residual FVIII activity in the mixture was then tested using a Coatest FVIII SP kit, in the presence of Factor IXa, Factor X, phospholipids and CaCl2. The activity of FVIII was calculated using a standard curve for FVIII activity plotted using rFVIII in the absence of any inhibitors.

FACS Staining:

T-cell and dendritic cell response profiling was conducted on isolated mouse splenocytes. Splenic lymphocytes and dendritic cells were stained for surface and intracellular targets. For surface staining, $1\times10^6$ total splenocytes were incubated with antibodies at appropriate concentrations. For intracellular staining, cells were permeabilised with BD Fix-Perm solution (BD Biosciences) followed by incubation with antibodies to cytokines in the same buffer. Foxp3 staining was carried out using antibody in Foxp3 staining buffer (BD Biosciences). Fluorescence intensity was recorded using a BD FACS Canto II and analysis performed using FLOWJO software. Lymphocytes were costained with CD4 and intracellular markers IL-2, TNF-α, and IL-4. Regulatory T cells (Treg) were stained for surface markers CD4 and CD25 followed by intracellular Foxp3. Splenocytes were stained for CD11c and PD-L1 (dendritic cells) or CD4 and PD-1 (CD4+ T-cells) to identify cells involved in the PD-L1-PD-1 pathway.

Real Time PCR and Real Time PCR Based Array Analysis:

Total RNA was isolated using an RNA isolation kit (Roche Applied Science, Indianapolis, Ind.) and reverse transcribed to cDNA (Qiagen, Hilden, Germany). Real time PCR primers for the tested genes were designed using the online algorithm available on the IDT technologies website (www.idtdna.com) and were purchased from IDT technologies (Coralville, Iowa). SYBR green-based real-time PCR was carried out using Quantitect system (Qiagen, Hilden, Germany) in an ABI 7900 Fast Block real-time PCR machine (Applied Biosystems, Foster City, Calif.). For real time PCR based arrays, 500 ng of total cDNA was mixed with SYBR green based qPCR master mix, and aliquoted onto 96-well plate array (PAMM047Z, T-cell Anergy and Immune Tolerance PCR Array; SA Biosciences, Frederick, Md., USA). Reactions were carried out with an ABI 7900 Fast Block real-time PCR machine (Applied Biosystems, Foster City, Calif.). Results were analysed using the 7500 software version 2.0.5 and the relative levels of gene transcripts were measured with endogenous housekeeping genes as control using the 2−ΔCt relative quantification method (Livak, K. J., and Schmittgen, T. D. 2001. Analysis of relative gene expression data using real-time quantitative PCR and the 2(−Delta Delta C(T)) Method. *Methods* 25:402-408.). The housekeeping genes used for normalization were GAPDH, HPRT, Hsp90ab, beta-actin, and GusB. For each sample average Ct values for the housekeeping genes were taken together and used to calculate the ΔCt. mRNAs that displayed threshold cycles (Ct)≥35 were excluded from the analysis.

T-Cell Proliferation and Determination of Interferon-γ (IFN-γ) Levels:

HemA mice (8-10 weeks old) were injected with FVIII drug substances once a week for 2 weeks. Seventy two hours post the second injection mice were euthanized and peritoneal macrophages were collected by lavage using sterile PBS. Splenic T-cells were isolated using magnetic bead based murine CD4+ T-cell isolation kit (Miltenyi Biotec, Germany). T-cells were labeled with 10 μM CFSE (Invitrogen, Carlsbad, Calif.) for 15 minutes in warm PBS and plated in 96 well ultra-low adhesion plates (Corning) along with peritoneal macrophages at a density of 1×10⁶ cells per ml for each. Cells were then incubated with 0.1, 1 and 10 nM of rFVIII or vehicle or CD3/CD28 microbeads (positive control; Miltenyi Biotec) in X-VIVO 15 medium (Lonza) containing co-stimulatory antibodies namely anti-CD28 and anti-CD49d (BD Biosciences), for 96 hours at 37° C. At the end of the incubation, IFNγ levels in the culture supernatant were measured using an ELISA kit from Meso Scale Devices (MSD). T-cell proliferation was determined by measuring CFSE fluorescence intensity (MFI) in T-cells gated based on forward and side scatters, using FACS (BD FACS CANTO II).

Statistical Analysis:

Statistical analysis of results were carried out either using unpaired student's T-test or Mann-Whitney's T-test. P-values <0.05 were considered to be significant.

Results:

Dendritic cells are professional antigen presenting cells and harbor key molecules and enzymes that are pivotal in skewing an immune response towards tolerance. Splenocytes from hemA mice injected with FVIII drug substances or vehicle were stained for CD11c and MHC Class II molecules to gate the dendritic cells. Splenic composition of dendritic cells expressing markers such as CD80, a surface marker upregulated in mature dendritic cells indicating more antigen presentation and CD274 (PD-L1), the ligand for the PD-1 receptor, were identified by co-staining with specific antibodies to these molecules. As shown in FIG. 63A, splenocytes from 100 IU/kg rFVIIIFc or BDD-FVIII injected HemA mice showed a significant decrease in the percentage of dendritic cells expressing CD80, suggesting an abundance of immature dendritic cells.

Although mice receiving fl-FVIII showed a decrease in the percentage of CD80+ dendritic cells compared to vehicle, it did not attain statistical significance (FIG. 64A). The trend was similar for mice receiving the 50 IU/kg dose of rFVIIIFc. At 250 IU/kg, all the three treatments showed no alterations in the percentage of CD80+ dendritic cells among the splenocytes.

Results from FACS analysis for splenic dendritic cells expressing CD274 (PD-L1), revealed that rFVIIIFc at 100 IU/kg enhanced the percentage of these cells compared to vehicle and other FVIII treatments (FIG. 64B). This molecule was also regulated at the mRNA level by rFVIIIFc as illustrated by real time PCR analysis (FIG. 64C). This suggests the rFVIIIFc regulates the PD-L1:PD-1 pathway, one of the key immunosuppressive pathways, thereby reducing the immunogenicity to FVIII. In addition to CD274, rFVIIIFc also upregulated mRNA levels of indoleamine 2,3-dioxygenase (IDO), a key enzyme that regulates T-cell proliferation and activation by affecting tryptophan metabolism (FIG. 64D).

Example 24 rFVIIIFc at Low Doses Enhances the Expression of Markers of Immune Tolerance and Anergy in Splenocytes Experimental procedures were conducted according to the Materials and Methods described in Example 23.

In order to identify markers of immune tolerance induced by rFVIIIFc, real time PCR based arrays focused on genes specific for immune tolerance and anergy (SA Biosciences) was employed. mRNA isolated from splenocytes obtained from mice injected with 50 and 250 IU/kg of rFVIIIFc and vehicle was used to identify novel response elements activated by this drug substance.

Candidates were identified based on their expression level (2-fold above or below vehicle), and the p-value based on student's T-test (<0.05). Relative expression of each gene was determined using the $2^{-\Delta ct}$ method (Livak, K. J., and Schmittgen, T. D. 2001. Analysis of relative gene expression data using real-time quantitative PCR and the 2(−Delta Delta C(T)) Method. *Methods* 25:402-408) after normalizing to the average Ct values of a set of 5 housekeeping genes (see Example 23, Materials and Methods).

Based on these criteria, array analysis performed revealed candidates that were preferentially regulated by rFVIIIFc at 50 IU/kg at the splenocyte level, in comparison to vehicle and 250 IU/kg injected mice (FIG. 65 and FIG. 66). These included statistically significant upregulation of tolerance specific genes such as Foxp3, CTLA-4, and CD25; anergy associated genes such as Egr2, Dgka, and CBL-B; genes belonging to the Tumor Necrosis Factor Superfamily (TNFRSF); prostaglandin synthase 2 (PTGS2) and prostaglandin E2 receptor (PTGER2) (see FIG. 66). Conversely some of the downregulated genes identified using this array are known pro-inflammatory molecules such as CCL3 and STAT3 (FIG. 66).

These results indicated the presence of tolerogenic pathways and a tolerogenic microenvironment within the splenocytes of animals receiving 50 IU/kg of rFVIIIFc. The gene expression profiles determined using the array will be validated using real time PCR with individual primer pairs for the identified candidates.

Example 25

CD4+ Splenocytes from 250 IU/Kg Group of Mice Proliferate and Produce High Levels of IFN-γ

Experimental procedures were conducted according to the Materials and Methods described in Example 23.

T-cell proliferation studies were employed to investigate factor VIII specific T-cell responses ex vivo. CD4+ T-cells isolated from mice receiving two weekly injections of either 50 or 250 IU/kg of rFVIIIFc, were labeled with CFSE and reconstituted with peritoneal macrophages (antigen presenting cells; APC) and incubated in the presence of B-domain deleted rFVIII at three concentrations, 0.1, 1, and 10 nM.

FACS analysis for proliferation based on CFSE dilution signals revealed that, T-cells from the group treated with 250 IU/kg of rFVIIIFc showed a dose dependent increase in proliferation, which was statistically significant at 10 nM (FIG. 67). In parallel, T-cells from mice treated with 50 IU/kg of rFVIIIFc did not show a significant increase in proliferation with escalating concentrations of rFVIII ex vivo compared to vehicle (FIG. 67).

IFN levels measured from the culture supernatants of these incubations revealed a similar profile matching the T-cell proliferation pattern, i.e., a dose dependent increase in secretion from T-cells derived from mice treated with 250 IU/kg of rFVIIIFc (FIG. 68A) whereas no changes in levels from T-cells from mice treated with 50 IU/kg of rFVIIIFc (FIG. 68B).

In order to dissect the mechanism(s) of action of rFVIIIFc in suppressing the immune response to FVIII, we employed two mutant constructs—one which does not bind to the Fcγ receptor (termed rFVIIIFc-N297A) and the other one which lacks binding the to the FcRn receptor (termed rFVIIIFc-IHH). These constructs were used to identify the interactions of the rFVIIIFc with one of these receptors in bringing about the immunosuppressive action. To this end, we tested the IFNγ secretion profile of T-cells derived from mice that received two weekly injections of rFVIIIFc-N297A at 250 IU/kg doses (FIG. 68C) and 50 IU/kg doses (FIG. 68D).

Side by side comparisons of IFNγ secretion from T-cells derived from 250 IU/kg of rFVIIIFc and rFVIIIFc-N297A revealed that the level of the cytokine was highly reduced in the T-cells from animals receiving the mutant, albeit significantly higher levels compared to vehicle. However, the levels of IFNγ from the 50 IU/kg group of the mutant protein did not show a significant difference from that of 50 IU/kg of rFVIIIFc. This suggests that the higher antibody production and T-cell proliferation observed at higher doses of rFVIIIFc might be a resultant of the interaction of the Fc with the Fcγ receptors which is abolished by the Fcγ non-binding mutant.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

TABLE 1

| Polynucleotide Sequences |
|---|
| A. B-Domain Deleted FVIIIFc<br>(i) B-Domain Deleted FVIIIFc Chain DNA Sequence (FVIII signal peptide underlined, Fc region in bold) (SEQ ID NO: 1, which encodes SEQ ID NO: 2) |
| 661 A TGCAAATAGA GCTCTCCACC TGCTTCTTTC |
| 721 TGTGCCTTTT GCGATTCTGC TTTAGTGCCA CCAGAAGATA CTACCTGGGT GCAGTGGAAC |
| 781 TGTCATGGGA CTATATGCAA AGTGATCTCG GTGAGCTGCC TGTGGACGCA AGATTTCCTC |
| 841 CTAGAGTGCC AAAATCTTTT CCATTCAACA CCTCAGTCGT GTACAAAAAG ACTCTGTTTG |
| 901 TAGAATTCAC GGATCACCTT TTCAACATCG CTAAGCCAAG GCCACCCTGG ATGGGTCTGC |
| 961 TAGGTCCTAC CATCCAGGCT GAGGTTTATG ATACAGTGGT CATTACACTT AAGAACATGG |
| 1021 CTTCCCATCC TGTCAGTCTT CATGCTGTTG GTGTATCCTA CTGGAAAGCT TCTGAGGGAG |
| 1081 CTGAATATGA TGATCAGACC AGTCAAAGGG AGAAAGAAGA TGATAAAGTC TTCCCTGGTG |
| 1141 GAAGCCATAC ATATGTCTGG CAGGTCCTGA AAGAGAATGG TCCAATGGCC TCTGACCCAC |
| 1201 TGTGCCTTAC CTACTCATAT CTTTCTCATG TGGACCTGGT AAAAGACTTG AATTCAGGCC |
| 1261 TCATTGGAGC CCTACTAGTA TGTAGAGAAG GGAGTCTGGC CAAGGAAAAG ACACAGACCT |
| 1321 TGCACAAATT TATACTACTT TTTGCTGTAT TTGATGAAGG GAAAAGTTGG CACTCAGAAA |

TABLE 1-continued

Polynucleotide Sequences

```
1381 CAAAGAACTC CTTGATGCAG GATAGGGATG CTGCATCTGC TCGGGCCTGG CCTAAAATGC

1441 ACACAGTCAA TGGTTATGTA AACAGGTCTC TGCCAGGTCT GATTGGATGC CACAGGAAAT

1501 CAGTCTATTG GCATGTGATT GGAATGGGCA CCACTCCTGA AGTGCACTCA ATATTCCTCG

1561 AAGGTCACAC ATTTCTTGTG AGGAACCATC GCCAGGCGTC CTTGGAAATC TCGCCAATAA

1621 CTTTCCTTAC TGCTCAAACA CTCTTGATGG ACCTTGGACA GTTTCTACTG TTTTGTCATA

1681 TCTCTTCCCA CCAACATGAT GGCATGGAAG CTTATGTCAA AGTAGACAGC TGTCCAGAGG

1741 AACCCCAACT ACGAATGAAA AATAATGAAG AAGCGGAAGA CTATGATGAT GATCTTACTG

1801 ATTCTGAAAT GGATGTGGTC AGGTTTGATG ATGACAACTC TCCTTCCTTT ATCCAAATTC

1861 GCTCAGTTGC CAAGAAGCAT CCTAAAACTT GGGTACATTA CATTGCTGCT GAAGAGGAGG

1921 ACTGGGACTA TGCTCCCTTA GTCCTCGCCC CCGATGACAG AAGTTATAAA AGTCAATATT

1981 TGAACAATGG CCCTCAGCGG ATTGGTAGGA AGTACAAAAA AGTCCGATTT ATGGCATACA

2041 CAGATGAAAC CTTTAAGACT CGTGAAGCTA TTCAGCATGA ATCAGGAATC TTGGGACCTT

2101 TACTTTATGG GGAAGTTGGA GACACACTGT TGATTATATT TAAGAATCAA GCAAGCAGAC

2161 CATATAACAT CTACCCTCAC GGAATCACTG ATGTCCGTCC TTTGTATTCA AGGAGATTAC

2221 CAAAGGTGT AAAACATTTG AAGGATTTTC CAATTCTGCC AGGAGAAATA TTCAAATATA

2281 AATGGACAGT GACTGTAGAA GATGGGCCAA CTAAATCAGA TCCTCGGTGC CTGACCCGCT

2341 ATTACTCTAG TTTCGTTAAT ATGGAGAGAG ATCTAGCTTC AGGACTCATT GGCCCTCTCC

2401 TCATCTGCTA CAAAGAATCT GTAGATCAAA GAGGAAACCA GATAATGTCA GACAAGAGGA

2461 ATGTCATCCT GTTTTCTGTA TTTGATGAGA ACCGAAGCTG GTACCTCACA GAGAATATAC

2521 AACGCTTTCT CCCCAATCCA GCTGGAGTGC AGCTTGAGGA TCCAGAGTTC CAAGCCTCCA

2581 ACATCATGCA CAGCATCAAT GGCTATGTTT TTGATAGTTT GCAGTTGTCA GTTTGTTTGC

2641 ATGAGGTGGC ATACTGGTAC ATTCTAAGCA TTGGAGCACA GACTGACTTC CTTTCTGTCT

2701 TCTTCTCTGG ATATACCTTC AAACACAAAA TGGTCTATGA AGACACACTC ACCCTATTCC

2761 CATTCTCAGG AGAAACTGTC TTCATGTCGA TGGAAAACCC AGGTCTATGG ATTCTGGGGT

2821 GCCACAACTC AGACTTTCGG AACAGAGGCA TGACCGCCTT ACTGAAGGTT TCTAGTTGTG

2881 ACAAGAACAC TGGTGATTAT TACGAGGACA GTTATGAAGA TATTTCAGCA TACTTGCTGA

2941 GTAAAAACAA TGCCATTGAA CCAAGAAGCT TCTCTCAAAA CCCACCAGTC TTGAAACGCC

3001 ATCAACGGGA ATAACTCGT ACTACTCTTC AGTCAGATCA AGAGGAAATT GACTATGATG

3061 ATACCATATC AGTTGAAATG AAGAAGGAAG ATTTTGACAT TTATGATGAG GATGAAAATC

3121 AGAGCCCCCG CAGCTTTCAA AAGAAAACAC GACACTATTT TATTGCTGCA GTGGAGAGGC

3181 TCTGGGATTA TGGGATGAGT AGCTCCCCAC ATGTTCTAAG AAACAGGGCT CAGAGTGGCA

3241 GTGTCCCTCA GTTCAAGAAA GTTGTTTTCC AGGAATTTAC TGATGGCTCC TTTACTCAGC

3301 CCTTATACCG TGGAGAACTA AATGAACATT TGGGACTCCT GGGGCCATAT ATAAGAGCAG

3361 AAGTTGAAGA TAATATCATG GTAACTTTCA GAAATCAGGC CTCTCGTCCC TATTCCTTCT

3421 ATTCTAGCCT TATTTCTTAT GAGGAAGATC AGAGGCAAGG AGCAGAACCT AGAAAAAACT

3481 TTGTCAAGCC TAATGAAACC AAAACTTACT TTTGGAAAGT GCAACATCAT ATGGCACCCA

3541 CTAAAGATGA GTTTGACTGC AAAGCCTGGG CTTATTTCTC TGATGTTGAC CTGGAAAAAG

3601 ATGTGCACTC AGGCCTGATT GGACCCCTTC TGGTCTGCCA CACTAACACA CTGAACCCTG

3661 CTCATGGGAG ACAAGTGACA GTACAGGAAT TTGCTCTGTT TTTCACCATC TTTGATGAGA
```

TABLE 1-continued

Polynucleotide Sequences

```
3721 CCAAAAGCTG GTACTTCACT GAAAATATGG AAAGAAACTG CAGGGCTCCC TGCAATATCC

3781 AGATGGAAGA TCCCACTTTT AAAGAGAATT ATCGCTTCCA TGCAATCAAT GGCTACATAA

3841 TGGATACACT ACCTGGCTTA GTAATGGCTC AGGATCAAAG GATTCGATGG TATCTGCTCA

3901 GCATGGGCAG CAATGAAAAC ATCCATTCTA TTCATTTCAG TGGACATGTG TTCACTGTAC

3961 GAAAAAAGA GGAGTATAAA ATGGCACTGT ACAATCTCTA TCCAGGTGTT TTTGAGACAG

4021 TGGAAATGTT ACCATCCAAA GCTGGAATTT GGCGGGTGGA ATGCCTTATT GGCGAGCATC

4081 TACATGCTGG GATGAGCACA CTTTTTCTGG TGTACAGCAA TAAGTGTCAG ACTCCCCTGG

4141 GAATGGCTTC TGGACACATT AGAGATTTTC AGATTACAGC TTCAGGACAA TATGGACAGT

4201 GGGCCCCAAA GCTGGCCAGA CTTCATTATT CCGGATCAAT CAATGCCTGG AGCACCAAGG

4261 AGCCCTTTTC TTGGATCAAG GTGGATCTGT TGGCACCAAT GATTATTCAC GGCATCAAGA

4321 CCCAGGGTGC CCGTCAGAAG TTCTCCAGCC TCTACATCTC TCAGTTTATC ATCATGTATA

4381 GTCTTGATGG GAAGAAGTGG CAGACTTATC GAGGAAATTC CACTGGAACC TTAATGGTCT

4441 TCTTTGGCAA TGTGGATTCA TCTGGGATAA ACACACAATAT TTTTAACCCT CCAATTATTG

4501 CTCGATACAT CCGTTTGCAC CCAACTCATT ATAGCATTCG CAGCACTCTT CGCATGGAGT

4561 TGATGGGCTG TGATTTAAAT AGTTGCAGCA TGCCATTGGG AATGGAGAGT AAAGCAATAT

4621 CAGATGCACA GATTACTGCT TCATCCTACT TTACCAATAT GTTTGCCACC TGGTCTCCTT

4681 CAAAAGCTCG ACTTCACCTC CAAGGGAGGA GTAATGCCTG GAGACCTCAG GTGAATAATC

4741 CAAAAGAGTG GCTGCAAGTG GACTTCCAGA AGACAATGAA AGTCACAGGA GTAACTACTC

4801 AGGGAGTAAA ATCTCTGCTT ACCAGCATGT ATGTGAAGGA GTTCCTCATC TCCAGCAGTC

4861 AAGATGGCCA TCAGTGGACT CTCTTTTTTC AGAATGGCAA AGTAAAGGTT TTTCAGGGAA

4921 ATCAAGACTC CTTCACACCT GTGGTGAACT CTCTAGACCC ACCGTTACTG ACTCGCTACC

4981 TTCGAATTCA CCCCCAGAGT TGGGTGCACC AGATTGCCCT GAGGATGGAG GTTCTGGGCT

5041 GCGAGGCACA GGACCTCTAC GACAAAACTC ACACATGCCC ACCGTGCCCA GCTCCAGAAC

5101 TCCTGGGCGG ACCGTCAGTC TTCCTCTTCC CCCCAAAACC CAAGGACACC CTCATGATCT

5161 CCCGGACCCC TGAGGTCACA TGCGTGGTGG TGGACGTGAG CCACGAAGAC CCTGAGGTCA

5221 AGTTCAACTG GTACGTGGAC GGCGTGGAGG TGCATAATGC CAAGACAAAG CCGCGGGAGG

5281 AGCAGTACAA CAGCACGTAC CGTGTGGTCA GCGTCCTCAC CGTCCTGCAC CAGGACTGGC

5341 TGAATGGCAA GGAGTACAAG TGCAAGGTCT CCAACAAAGC CCTCCCAGCC CCCATCGAGA

5401 AAACCATCTC CAAAGCCAAA GGGCAGCCCC GAGAACCACA GGTGTACACC CTGCCCCCAT

5461 CCCGGGATGA GCTGACCAAG AACCAGGTCA GCCTGACCTG CCTGGTCAAA GGCTTCTATC

5521 CCAGCGACAT CGCCGTGGAG TGGGAGAGCA ATGGGCAGCC GGAGAACAAC TACAAGACCA

5581 CGCCTCCCGT GTTGGACTCC GACGGCTCCT TCTTCCTCTA CAGCAAGCTC ACCGTGGACA

5641 AGAGCAGGTG GCAGCAGGGG AACGTCTTCT CATGCTCCGT GATGCATGAG GCTCTGCACA

5701 ACCACTACAC GCAGAAGAGC CTCTCCCTGT CTCCGGGTAA A
```

(ii) Fc DNA sequence (mouse IgK signal peptide underlined)
(SEQ ID NO: 3, which encodes SEQ ID NO: 4)

```
7981 ATGGA GACAGACACA

8041 CTCCTGCTAT GGGTACTGCT GCTCTGGGTT CCAGGTTCCA CTGGTGACAA AACTCACACA

8101 TGCCCACCGT GCCCAGCACC TGAACTCCTG GGAGGACCGT CAGTCTTCCT CTTCCCCCCA
```

TABLE 1-continued

Polynucleotide Sequences

8161 AAACCCAAGG ACACCCTCAT GATCTCCCGG ACCCCTGAGG TCACATGCGT GGTGGTGGAC

8221 GTGAGCCACG AAGACCCTGA GGTCAAGTTC AACTGGTACG TGGACGGCGT GGAGGTGCAT

8281 AATGCCAAGA CAAAGCCGCG GGAGGAGCAG TACAACAGCA CGTACCGTGT GGTCAGCGTC

8341 CTCACCGTCC TGCACCAGGA CTGGCTGAAT GGCAAGGAGT ACAAGTGCAA GGTCTCCAAC

8401 AAAGCCCTCC CAGCCCCCAT CGAGAAAACC ATCTCCAAAG CCAAAGGGCA GCCCCGAGAA

8461 CCACAGGTGT ACACCCTGCC CCCATCCCGC GATGAGCTGA CCAAGAACCA GGTCAGCCTG

8521 ACCTGCCTGG TCAAAGGCTT CTATCCCAGC GACATCGCCG TGGAGTGGGA GAGCAATGGG

8581 CAGCCGGAGA ACAACTACAA GACCACGCCT CCCGTGTTGG ACTCCGACGG CTCCTTCTTC

8641 CTCTACAGCA AGCTCACCGT GGACAAGAGC AGGTGGCAGC AGGGGAACGT CTTCTCATGC

8701 TCCGTGATGC ATGAGGCTCT GCACAACCAC TACACGCAGA AGAGCCTCTC CCTGTCTCCG

8761 GGTAAA

B. Full Length FVIIIFc
(i) Full Length FVIIIFc DNA Sequence (FVIII signal peptide underlined,
Fc region in bold) (SEQ ID NO: 5, which encodes SEQ ID NO: 6)

661 ATG CAAATAGAGC TCTCCACCTG

721 CTTCTTTCTG TGCCTTTTGC GATTCTGCTT TAGTGCCACC AGAAGATACT ACCTGGGTGC

781 AGTGGAACTG TCATGGGACT ATATGCAAAG TGATCTCGGT GAGCTGCCTG TGGACGCAAG

841 ATTTCCTCCT AGAGTGCCAA ATCTTTTCC ATTCAACACC TCAGTCGTGT ACAAAAAGAC

901 TCTGTTTGTA GAATTCACGG ATCACCTTTT CAACATCGCT AAGCCAAGGC CACCCTGGAT

961 GGGTCTGCTA GGTCCTACCA TCCAGGCTGA GGTTTATGAT ACAGTGGTCA TTACACTTAA

1021 GAACATGGCT TCCCATCCTG TCAGTCTTCA TGCTGTTGGT GTATCCTACT GGAAAGCTTC

1081 TGAGGGAGCT GAATATGATG ATCAGACCAG TCAAAGGGAG AAAGAAGATG ATAAAGTCTT

1141 CCCTGGTGGA AGCCATACAT ATGTCTGGCA GGTCCTGAAA GAGAATGGTC CAATGGCCTC

1201 TGACCCACTG TGCCTTACCT ACTCATATCT TTCTCATGTG GACCTGGTAA AGACTTGAA

1261 TTCAGGCCTC ATTGGAGCCC TACTAGTATG TAGAGAAGGG AGTCTGGCCA AGGAAAAGAC

1321 ACAGACCTTG CACAAATTTA TACTACTTTT TGCTGTATTT GATGAAGGGA AAAGTTGGCA

1381 CTCAGAAACA AAGAACTCCT TGATGCAGGA TAGGGATGCT GCATCTGCTC GGGCCTGGCC

1441 TAAAATGCAC ACAGTCAATG GTTATGTAAA CAGGTCTCTG CCAGGTCTGA TTGGATGCCA

1501 CAGGAAATCA GTCTATTGGC ATGTGATTGG AATGGGCACC ACTCCTGAAG TGCACTCAAT

1561 ATTCCTCGAA GGTCACACAT TTCTTGTGAG GAACCATCGC CAGGCGTCCT TGGAAATCTC-

1621 GCCAATAACT TTCCTTACTG CTCAAACACT CTTGATGGAC CTTGGACAGT TTCTACTGTT

1681 TTGTCATATC TCTTCCCACC AACATGATGG CATGGAAGCT TATGTCAAAG TAGACAGCTG

1741 TCCAGAGGAA CCCCAACTAC GAATGAAAAA TAATGAAGAA GCGGAAGACT ATGATGATGA

1801 TCTTACTGAT TCTGAAATGG ATGTGGTCAG GTTTGATGAT GACAACTCTC CTTCCTTTAT

1861 CCAAATTCGC TCAGTTGCCA AGAAGCATCC TAAAACTTGG GTACATTACA TTGCTGCTGA

1921 AGAGGAGGAC TGGGACTATG CTCCCTTAGT CCTCGCCCCC GATGACAGAA GTTATAAAAG

1981 TCAATATTTG AACAATGGCC CTCAGCGGAT TGGTAGGAAG TACAAAAAAG TCCGATTTAT

2041 GGCATACACA GATGAAACCT TTAAGACTCG TGAAGCTATT CAGCATGAAT CAGGAATCTT

2101 GGGACCTTTA CTTTATGGGG AAGTTGGAGA CACACTGTTG ATTATATTTA AGAATCAAGC

2161 AAGCAGACCA TATAACATCT ACCCTCACGG AATCACTGAT GTCCGTCCTT TGTATTCAAG

TABLE 1-continued

Polynucleotide Sequences

```
2221 GAGATTACCA AAAGGTGTAA AACATTTGAA GGATTTTCCA ATTCTGCCAG GAGAAATATT

2281 CAAATATAAA TGGACAGTGA CTGTAGAAGA TGGGCCAACT AAATCAGATC CTCGGTGCCT

2341 GACCCGCTAT TACTCTAGTT TCGTTAATAT GGAGAGAGAT CTAGCTTCAG GACTCATTGG

2401 CCCTCTCCTC ATCTGCTACA AAGAATCTGT AGATCAAAGA GGAAACCAGA TAATGTCAGA

2461 CAAGAGGAAT GTCATCCTGT TTTCTGTATT TGATGAGAAC CGAAGCTGGT ACCTCACAGA

2521 GAATATACAA CGCTTTCTCC CCAATCCAGC TGGAGTGCAG CTTGAGGATC CAGAGTTCCA

2581 AGCCTCCAAC ATCATGCACA GCATCAATGG CTATGTTTTT GATAGTTTGC AGTTGTCAGT

2641 TTGTTTGCAT GAGGTGGCAT ACTGGTACAT TCTAAGCATT GGAGCACAGA CTGACTTCCT

2701 TTCTGTCTTC TTCTCTGGAT ATACCTTCAA ACACAAAATG GTCTATGAAG ACACACTCAC

2761 CCTATTCCCA TTCTCAGGAG AAACTGTCTT CATGTCGATG GAAACCCAG GTCTATGGAT

2821 TCTGGGGTGC CACAACTCAG ACTTTCGGAA CAGAGGCATG ACCGCCTTAC TGAAGGTTTC

2881 TAGTTGTGAC AAGAACACTG GTGATTATTA CGAGGACAGT TATGAAGATA TTTCAGCATA

2941 CTTGCTGAGT AAAAACAATG CCATTGAACC AAGAAGCTTC TCCCAGAATT CAAGACACCC

3001 TAGCACTAGG CAAAAGCAAT TTAATGCCAC CACAATTCCA GAAAATGACA TAGAGAAGAC

3061 TGACCCTTGG TTTGCACACA GAACACCTAT GCCTAAAATA CAAATGTCT CCTCTAGTGA

3121 TTTGTTGATG CTCTTGCGAC AGAGTCCTAC TCCACATGGG CTATCCTTAT CTGATCTCCA

3181 AGAAGCCAAA TATGAGACTT TTTCTGATGA TCCATCACCT GGAGCAATAG ACAGTAATAA

3241 CAGCCTGTCT GAAATGACAC ACTTCAGGCC ACAGCTCCAT CACAGTGGGG ACATGGTATT

3301 TACCCCTGAG TCAGGCCTCC AATTAAGATT AAATGAGAAA CTGGGGACAA CTGCAGCAAC

3361 AGAGTTGAAG AAACTTGATT TCAAAGTTTC TAGTACATCA AATAATCTGA TTTCAACAAT

3421 TCCATCAGAC AATTTGGCAG CAGGTACTGA TAATACAAGT TCCTTAGGAC CCCCAAGTAT

3481 GCCAGTTCAT TATGATAGTC AATTAGATAC CACTCTATTT GGCAAAAAGT CATCTCCCCT

3541 TACTGAGTCT GGTGGACCTC TGAGCTTGAG TGAAGAAAAT AATGATTCAA AGTTGTTAGA

3601 ATCAGGTTTA ATGAATAGCC AAGAAAGTTC ATGGGGAAAA AATGTATCGT CAACAGAGAG

3661 TGGTAGGTTA TTTAAAGGGA AAAGAGCTCA TGGACCTGCT TTGTTGACTA AAGATAATGC

3721 CTTATTCAAA GTTAGCATCT CTTTGTTAAA GACAAACAAA ACTTCCAATA ATTCAGCAAC

3781 TAATAGAAAG ACTCACATTG ATGGCCCATC ATTATTAATT GAGAATAGTC CATCAGTCTG

3841 GCAAAATATA TTAGAAAGTG ACACTGAGTT TAAAAAAGTG ACACCTTTGA TTCATGACAG

3901 AATGCTTATG GACAAAAATG CTACAGCTTT GAGGCTAAAT CATATGTCAA ATAAAACTAC

3961 TTCATCAAAA AACATGGAAA TGGTCCAACA GAAAAAAGAG GGCCCCATTC CACCAGATGC

4021 ACAAAATCCA GATATGTCGT TCTTTAAGAT GCTATTCTTG CCAGAATCAG CAAGGTGGAT

4081 ACAAAGGACT CATGGAAAGA ACTCTCTGAA CTCTGGGCAA GGCCCCAGTC AAAGCAATT

4141 AGTATCCTTA GGACCAGAAA AATCTGTGGA AGGTCAGAAT TTCTTGTCTG AGAAAAACAA

4201 AGTGGTAGTA GGAAAGGGTG AATTTACAAA GGACGTAGGA CTCAAAGAGA TGGTTTTTCC

4261 AAGCAGCAGA AACCTATTTC TTACTAACTT GGATAATTTA CATGAAAATA ATACACACAA

4321 TCAAGAAAAA AAAATTCAGG AAGAAATAGA AAAGAAGGAA ACATTAATCC AAGAGAATGT

4381 AGTTTTGCCT CAGATACATA CAGTGACTGG CACTAAGAAT TTCATGAAGA ACCTTTTCTT

4441 ACTGAGCACT AGGCAAAATG TAGAAGGTTC ATATGACGGG GCATATGCTC CAGTACTTCA

4501 AGATTTTAGG TCATTAAATG ATTCAACAAA TAGAACAAAG AAACACACAG CTCATTTCTC
```

TABLE 1-continued

Polynucleotide Sequences

```
4561 AAAAAAGGG GAGGAAGAAA ACTTGGAAGG CTTGGGAAAT CAAACCAAGC AAATTGTAGA

4621 GAAATATGCA TGCACCACAA GGATATCTCC TAATACAAGC CAGCAGAATT TTGTCACGCA

4681 ACGTAGTAAG AGAGCTTTGA AACAATTCAG ACTCCCACTA GAAGAAACAG AACTTGAAAA

4741 AAGGATAATT GTGGATGACA CCTCAACCCA GTGGTCCAAA ACATGAAAC ATTTGACCCC

4801 GAGCACCCTC ACACAGATAG ACTACAATGA GAAGGAGAAA GGGGCCATTA CTCAGTCTCC

4861 CTTATCAGAT TGCCTTACGA GGAGTCATAG CATCCCTCAA GCAAATAGAT CTCCATTACC

4921 CATTGCAAAG GTATCATCAT TTCCATCTAT TAGACCTATA TATCTGACCA GGGTCCTATT

4981 CCAAGACAAC TCTTCTCATC TTCCAGCAGC ATCTTATAGA AAGAAAGATT CTGGGGTCCA

5041 AGAAAGCAGT CATTTCTTAC AAGGAGCCAA AAAAAATAAC CTTTCTTTAG CCATTCTAAC

5101 CTTGGAGATG ACTGGTGATC AAAGAGAGGT TGGCTCCCTG GGGACAAGTG CCACAAATTC

5161 AGTCACATAC AAGAAAGTTG AGAACACTGT TCTCCCGAAA CCAGACTTGC CCAAAACATC

5221 TGGCAAAGTT GAATTGCTTC CAAAAGTTCA CATTTATCAG AAGGACCTAT TCCCTACGGA

5281 AACTAGCAAT GGGTCTCCTG GCCATCTGGA TCTCGTGGAA GGGAGCCTTC TTCAGGGAAC

5341 AGAGGGAGCG ATTAAGTGGA ATGAAGCAAA CAGACCTGGA AAAGTTCCCT TTCTGAGAGT

5401 AGCAACAGAA AGCTCTGCAA AGACTCCCTC CAAGCTATTG GATCCTCTTG CTTGGGATAA

5461 CCACTATGGT ACTCAGATAC CAAAAGAAGA GTGGAAATCC CAAGAGAAGT CACCAGAAAA

5521 AACAGCTTTT AAGAAAAAGG ATACCATTTT GTCCCTGAAC GCTTGTGAAA GCAATCATGC

5581 AATAGCAGCA ATAAATGAGG GACAAAATAA GCCCGAAATA GAAGTCACCT GGGCAAAGCA

5641 AGGTAGGACT GAAAGGCTGT GCTCTCAAAA CCCACCAGTC TTGAAACGCC ATCAACGGGA

5701 AATAACTCGT ACTACTCTTC AGTCAGATCA AGAGGAAATT GACTATGATG ATACCATATC

5761 AGTTGAAATG AAGAAGGAAG ATTTTGACAT TTATGATGAG GATGAAAATC AGAGCCCCCG

5821 CAGCTTTCAA AAGAAAACAC GACACTATTT TATTGCTGCA GTGGAGAGGC TCTGGGATTA

5881 TGGGATGAGT AGCTCCCCAC ATGTTCTAAG AAACAGGGCT CAGAGTGGCA GTGTCCCTCA

5941 GTTCAAGAAA GTTGTTTTCC AGGAATTTAC TGATGGCTCC TTTACTCAGC CCTTATACCG

6001 TGGAGAACTA AATGAACATT TGGGACTCCT GGGGCCATAT ATAAGAGCAG AAGTTGAAGA

6061 TAATATCATG GTAACTTTCA GAAATCAGGC CTCTCGTCCC TATTCCTTCT ATTCTAGCCT

6121 TATTTCTTAT GAGGAAGATC AGAGGCAAGG AGCAGAACCT AGAAAAAACT TGTCAAGCC

6181 TAATGAAACC AAAACTTACT TTTGGAAAGT GCAACATCAT ATGGCACCCA CTAAAGATGA

6241 GTTTGACTGC AAAGCCTGGG CTTATTTCTC TGATGTTGAC CTGGAAAAAG ATGTGCACTC

6301 AGGCCTGATT GGACCCCTTC TGGTCTGCCA CACTAACACA CTGAACCCTG CTCATGGGAG

6361 ACAAGTGACA GTACAGGAAT TTGCTCTGTT TTTCACCATC TTTGATGAGA CCAAAAGCTG

6421 GTACTTCACT GAAAATATGG AAAGAAACTG CAGGGCTCCC TGCAATATCC AGATGGAAGA

6481 TCCCACTTTT AAAGAGAATT ATCGCTTCCA TGCAATCAAT GGCTACATAA TGGATACACT

6541 ACCTGGCTTA GTAATGGCTC AGGATCAAAG GATTCGATGG TATCTGCTCA GCATGGGCAG

6601 CAATGAAAAC ATCCATTCTA TTCATTTCAG TGGACATGTG TTCACTGTAC GAAAAAAGA

6661 GGAGTATAAA ATGGCACTGT ACAATCTCTA TCCAGGTGTT TTTGAGACAG TGGAAATGTT

6721 ACCATCCAAA GCTGGAATTT GGCGGGTGGA ATGCCTTATT GGCGAGCATC TACATGCTGG

6781 GATGAGCACA CTTTTTCTGG TGTACAGCAA TAAGTGTCAG ACTCCCCTGG GAATGGCTTC

6841 TGGACACATT AGAGATTTTC AGATTACAGC TTCAGGACAA TATGGACAGT GGGCCCCAAA
```

TABLE 1-continued

Polynucleotide Sequences

```
6901 GCTGGCCAGA CTTCATTATT CCGGATCAAT CAATGCCTGG AGCACCAAGG AGCCCTTTTC

6961 TTGGATCAAG GTGGATCTGT TGGCACCAAT GATTATTCAC GGCATCAAGA CCCAGGGTGC

7021 CCGTCAGAAG TTCTCCAGCC TCTACATCTC TCAGTTTATC ATCATGTATA GTCTTGATGG

7081 GAAGAAGTGG CAGACTTATC GAGGAAATTC CACTGGAACC TTAATGGTCT TCTTTGGCAA

7141 TGTGGATTCA TCTGGGATAA ACACAATAT TTTTAACCCT CCAATTATTG CTCGATACAT

7201 CCGTTTGCAC CCAACTCATT ATAGCATTCG CAGCACTCTT CGCATGGAGT TGATGGGCTG

7261 TGATTTAAAT AGTTGCAGCA TGCCATTGGG AATGGAGAGT AAAGCAATAT CAGATGCACA

7321 GATTACTGCT TCATCCTACT TTACCAATAT GTTTGCCACC TGGTCTCCTT CAAAAGCTCG

7381 ACTTCACCTC CAAGGGAGGA GTAATGCCTG AGACCTCAG GTGAATAATC CAAAAGAGTG

7441 GCTGCAAGTG GACTTCCAGA AGACAATGAA AGTCACAGGA GTAACTACTC AGGGAGTAAA

7501 ATCTCTGCTT ACCAGCATGT ATGTGAAGGA GTTCCTCATC TCCAGCAGTC AAGATGGCCA

7561 TCAGTGGACT CTCTTTTTTC AGAATGGCAA AGTAAAGGTT TTTCAGGGAA ATCAAGACTC

7621 CTTCACACCT GTGGTGAACT CTCTAGACCC ACCGTTACTG ACTCGCTACC TTCGAATTCA

7681 CCCCCAGAGT TGGGTGCACC AGATTGCCCT GAGGATGGAG GTTCTGGGCT GCGAGGCACA

7741 GGACCTCTAC GACAAAACTC ACACATGCCC ACCGTGCCCA GCTCCAGAAC TCCTGGGCGG

7801 ACCGTCAGTC TTCCTCTTCC CCCCAAAACC CAAGGACACC CTCATGATCT CCCGGACCCC

7861 TGAGGTCACA TGCGTGGTGG TGGACGTGAG CCACGAAGAC CCTGAGGTCA AGTTCAACTG

7921 GTACGTGGAC GGCGTGGAGG TGCATAATGC CAAGACAAAG CCGCGGGAGG AGCAGTACAA

7981 CAGCACGTAC CGTGTGGTCA GCGTCCTCAC CGTCCTGCAC CAGGACTGGC TGAATGGCAA

8041 GGAGTACAAG TGCAAGGTCT CCAACAAAGC CCTCCCAGCC CCCATCGAGA AAACCATCTC

8101 CAAAGCCAAA GGGCAGCCCC GAGAACCACA GGTGTACACC CTGCCCCCAT CCCGGGATGA

8161 GCTGACCAAG AACCAGGTCA GCCTGACCTG CCTGGTCAAA GGCTTCTATC CCAGCGACAT

8221 CGCCGTGGAG TGGGAGAGCA ATGGGCAGCC GGAGAACAAC TACAAGACCA CGCCTCCCGT

8281 GTTGGACTCC GACGGCTCCT TCTTCCTCTA CAGCAAGCTC ACCGTGGACA AGAGCAGGTG

8341 GCAGCAGGGG AACGTCTTCT CATGCTCCGT GATGCATGAG GCTCTGCACA ACCACTACAC

8401 GCAGAAGAGC CTCTCCCTGT CTCCGGGTAA A
          (ii) Fc (same sequence as A (ii) (SEQ ID NO: 3))]
```

TABLE 2

Polypeptide Sequences

A. B-Domain Deleted FVIII-Fc Monomer Hybrid (BDD FVIIIFc monomer dimer): created by coexpressing BDD FVIIIFc and Fc chains.
Construct = HC-LC-Fc fusion. An Fc expression cassette is cotransfected with BDDFVIII-Fc to generate the BDD FVIIIFc monomer-. For the BDD FVIIIFc chain, the Fc sequence is shown in bold; HC sequence is shown in double underline; remaining B domain sequence is shown in italics. Signal peptides are underlined.
i) B domain deleted FVIII-Fc chain (19 amino acid signal sequence underlined) (SEQ ID NO: 2)

MQIELSTCFFLCLLRFCFS
ATRRYYLGAVELSWDYMQSDLGELPVDARFPPRVPKSFPFNTSVVYKKTL
FVEFTDHLFNIAKPRPPWMGLLGPTIQAEVYDTVVITLKNMASHPVSLHA
VGVSYWKASEGAEYDDQTSQREKEDDKVFPGGSHTYVWQVLKENGPMASD
PLCLTYSYLSHVDLVKDLNSGLIGALLVCREGSLAKEKTQTLHKFILLFA
VFDEGKSWHSETKNSLMQDRDAASARAWPKMHTVNGYVNRSLPGLIGCHR
KSVYWHVIGMGTTPEVHSIFLEGHTFLVRNHRQASLEISPITFLTAQTLL
MDLGQFLLFCHISSHQHDGMEAYVKVDSCPEEPQLRMKNNEEAEDYDDDL
TDSEMDVVRFDDDNSPSFIQIRSVAKKHPKTWVHYIAAEEEDWDYAPLVL
APDDRSYKSQYLNNGPQRIGRKYKKVRFMAYTDETFKTREAIQHESGILG
PLLYGEVGDTLLIIFKNQASRPYNIYPHGITDVRPLYSRRLPKGVKHLKD
FPILPGEIFKYKWTVTVEDGPTKSDPRCLTRYYSSFVNMERDLASGLIGP
LLICYKESVDQRGNQIMSDKRNVILFSVFDENRSWYLTENIQRFLPNPAG
VQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNR
GMTALLKVSSCDKNTGDYYEDSYEDISAYLLSKNNAIEPRSFSQNPPVLK
RHQREITRTTLQSDQEEIDYDDTISVEMKKEDFDIYDEDENQSPRSFQKK
TRHYFIAAVERLWDYGMSSSPHVLRNRAQSGSVPQFKKVVFQEFTDGSFT
QFLYRGELNEHLGLLGPYIRAEVEDNIMVTFRNQASRPYSFYSSLISYEE
DQRGAEPRKNFVKPNETKTYFWKVQHHMAPTKDEFDCKAWAYFSDVDLE
KDVHSGLIGPLLVCHTNTLNPAHGRQVTVQEFALFFTIFDETKSWYFTEN
MERNCRAPCNIQMEDPTFKENYRFHAINGYIMDTLPGLVMAQDQRIRWYL
LSMGSNENIHSIHFSGHVFTVRKKEEYKMALYNLYPGVFETVEMLPSKAG

TABLE 2-continued

Polypeptide Sequences

IWRVECLIGEHLHAGMSTLFLVYSNECQTPLGMASGHIRDFQITASGQYG
QWAPKLARLHYSGSINAWSTEEPFSWIKVDLLAPMIIHGIKTQGARQKFS
SLYISQFIIMYSLDGKKWQTYRGNSTGTLMVFFGNVDSSGIKHNIFNPPI
IARYIRLHPTHYSIRSTLRMELMGCDLNSCSMPLGMESKAISDAQITASS
YFTNMFATWSPSKARLHLQGRSNAWRPQVNNPKEWLQVDFQKTMKVTGVT
TQGVKSLLTSMYVKEFLISSSGPDSHGQWTLFFQNGKVKVFQGNQDSFTPVV
NSLDPPLLTRYLRIHPQSWVHQIALRMEVLGCEAQDLY**DKTHTCPPCPAP
ELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEAL
HNHYTQKSLSLSPGK** ii) Fc chain (20 amino acid heterologous signal
peptide from mouse Igκ chain underlined)
(SEQ ID NO: 4)

METDTLLLWVLLLWVPGSTG
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK

B. Full length FVIIIFc monomer hybrid (Full length
FVIIIFc monomer dimer): created by coexpressing
FVIIIFc and Fc chains.
Construct = HC-B-LC-Fc fusion. An Fc expression
cassette is cotransfected with full length FVIII-
Fc to generate the full length FVIIIFc monomer.
For the FVIIIFc chain, the Fc sequence is shown
in bold; HC sequence is shown in double underline;
B domain sequence is shown in italics. Signal
peptides are underlined.
i) Full length FVIIIFc chain (FVIII signal peptide
underlined (SEQ ID NO: 6)

MQIELSTCFFLCLLRFCFS
ATRRYYLGAVELSWDYMQSDLGELPVDARFPPRVPKSFPFNTSVVYKKTL
FVEFTDHLFNIAKPRPPWMGLLGPTIQAEVYDTVVITLKNMASHPVSLHA
VGVSYWKASEGAEYDDQTSQREKEDDKVFPGGSHTYVWQVLKENGPMASD
PLCLTYSYLSHVDLVKDLNSGLIGALLVCREGSLAKEKTQTLHKFILLFA
VFDEGKSWHSETKNSLMQDRDAASARAWPKMHTVNGYVNRSLPGLIGCHR
KSVYWHVIGMGTTPEVHSIFLEGHTFLVRNHRQASLEISPITFLTAQTLL
MDLGQFLLFCHISSSHQHDGMEAYVKVDSCPEEPQLRMKNNEEAEDYDDDL
TDSEMDVVRFDDDNSPSFIQIRSVAKKHPKTWVHYIAAEEEDWDYAPLVL
APDDRSYKSQYLNNGPQRIGRKYKKVRFMAYTDETFKTREAIQHESGILG
PLLYGEVGDTLLIIFKNQASRPYNIYPHGITDVRPLYSRPLPKGVKHLKD
FPILPGEIFKYKWTVTVEDGPTKSDPRCLTRYYSSFVNMERDLASGLIGP
LLICYKESVDQRGNQIMSDKRNVILFSVFDENRSWYLTENIQRFLPNPAG
VQLEDPEFQASNIMHSINGYVFDSLQLSVCLHEVAYWYILSIGAQTDFLS

VFFSGYTFKHKMVYEDTLTLFPFSGETVFMSMENPGLWILGCHNSDFRNR
GMTALLKVSSCDKNTGDYYEDSYEDISAYLLSKNNAIEPRSFSQNSRHPS
TRQKQFNATTIPENDIEKTDPWFAHRTPMPKIQNVSSSDLLMLLRQSPTP
HGLSLSDLQEAKYETFSDDPSPGAIDSNNSLSEMTHFRPQLHHSGDMVFT
PESGLQLRLNEKLGTTAATELKKLDFKVSSTSNNLISTIPSDNLAAGTDN
TSSLGPPSMPVHYDSQLDTTLFGKKSSPLTESGGPLSLSEENNDSKLLES
GLMNSQESSSWGKNVSSTESGRLFKGKRAHGPALLTKDNALFKVSISLLKT
NKTSNNSATNRKTHIDGPSLLIENSPSVWQNILESDTEFKKVTPLIHDRM
LMDKNATALRLNHMSNKTTSSKNMEMVQQKKEGPIPPDAQNPDMSFFKML
FLPESARWIQRTHGKNSLNSGQGPSPKQLVSLGPEKSVEGQNFLSEKNKV
VVGKGEFTKDVGLKEMVFPSSRNLFLTNLDNLHENNTHNQEKKIQEEIEK
KETLIQENVVLPQIHTVTGTKNFMKNLFLLSTRQNVEGSYDGAYAPVLQD
FRSLNDSTNRTKKHTAHFSKKGEEENLEGLGNQTKQIVEKYACTTRISPN
TSQQNFVTQRSKRALKQFRLPLEETELEKRIIVDDTSTQWSKNMKHLTPS
TLTQIDYNEKEKGAITQSPLSDCLTRSHSIPQANRSPLPIAKVSSFPSIR
PIYLTRVLFQDNSSHLPAASYRKKDSGVQESSHFLQGAKKNNLSLAILTL
EMTGDQREVGSLGTSATNSVTYKKVENTVLPKPDLPKTSGKVELLPKVHI
YQKDLFPTETSNGSPGHLDLVEGSLLQGTEGAIKWNEANRPGKVPFLRVA
TESSAKTPSKLLDPLAWDNHYGTQIPKEEWKSQEKSPEKTAFKKKDTILS
LNACESNHAIAAINEGQNKPEIEVTWAKQGRTERLCSQNPPVLKRHQREI
TRTTLQSDQEEIDYDDTISVEMKKEDFDIYDEDENQSPRSFQKKTRHYFI
AAVERLWDYGMSSSPHVLRNRAQSGSVPQFKKVVFQEFTDGSFTQPLYRG
ELNEHLGLLGPYIRAEVEDNIMVTFRNQASRPYSFYSSLISYEEDQRQGA
EPRKNFVKPNETKTYFWKVQHHMAPTKDEFDCKAWAYFSDVDLEKDVHSG
LIGPLLVCHTNTLNPAHGRQVTVQEFALFPTIFDETKSWYFTENMERNCR
APCNIQMEDPTFKENYRFHAINGYIMDTLPGLVMAQDQRIRWYLLSMGSN
ENIHSIHFSGHVFTVRKKEEYKMALYNLYPGVFETVEMLPSKAGIWRVEC
LIGEHLHAGMSTLFLVYSNKCQTPLGMASGHIRDFQITASGQYGQWAPKL
ARLHYSGSINAWSTKEPFSWIKVDLLAPMIIHGIKTQGARQKFSSLYISQ
FIIMYSLDGKKWQTYRGNSTGTLMVFFGNVDSSGIKHNFNPPIIARYIR
LHPTHYSIRSTLRMELMGCDLNSCSMPLGMESKAISDAQITASSYFTNMF
ATWSPSKARLHLQGRSNAWRPQVNNPKEWLQVDFQKTMKVTGVTTQGVKS
LLTSMYVKEFLISSSQDGHQWTLFFQNGKVKVFQGNQDSFTPVVNSLDPP
LLTRYLRIHPQSWVHQIALRMEVLGCEAQDLY**DKTHTCPPCPAPELLGGP
SVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQ
KSLSLSPGK** ii) Fc chain (20 amino acid heterologous signal
peptide from mouse Igκ chain underlined)
(SEQ ID NO: 4)

METDTLLLWVLLLWVPGSTG
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK

---

What is claimed is:

1. A method of inhibiting development of an inhibitor of a clotting factor in a subject in need thereof, wherein the subject is a fetus, the method comprising administering to the mother of the subject a chimeric polypeptide comprising a Factor VIII ("FVIII") portion and an Fc portion,
wherein the subject has a mutation in a FVIII gene, and wherein the FVIII portion consists essentially of or consists of the A2 domain of FVIII, the C2 domain of FVIII, or both the A2 domain and the C2 domain of FVIII.

2. The method of claim 1, wherein the chimeric polypeptide is a FVIII monomer dimer hybrid.

3. The method of claim 1, wherein the subject has a genetic polymorphism associated with decreased CTLA-4.

4. The method of claim 1, wherein the subject has a genetic polymorphism associated a mutation in DR15 or DQB0602 MHC Class II molecules.

5. The method of claim 1, wherein the chimeric polypeptide comprises one or more half-life extending moieties in addition to the Fc portion.

6. The method of claim 1, wherein the chimeric polypeptide is administered intravenously.

7. The method of claim 1, wherein the subject has severe hemophilia.

8. The method of claim 1, wherein the subject has a relative who has previously developed an inhibitory immune response.

9. The method of claim 1, wherein the subject has a genetic polymorphism associated with increased TNF-α.

10. The method of claim 1, wherein the subject has a genetic polymorphism associated with increased IL10.

11. The method of claim 1, wherein the Fc portion is identical to amino acids 1458 to 1683 of SEQ ID NO:2 or amino acids 2352 to 2577 of SEQ ID NO:6.

12. The method of claim 1, wherein the chimeric polypeptide is in the form of a hybrid comprising a second polypeptide in association with the chimeric polypeptide, wherein the second polypeptide consists essentially of an Fc.

13. The method of claim 1, wherein the chimeric polypeptide is administered at a dose of 10-100 IU/kg.

14. The method of claim 1, wherein said administration decreases the incidence of spontaneous bleeding.

* * * * *